(12) United States Patent
Takenouchi et al.

(10) Patent No.: US 6,960,573 B2
(45) Date of Patent: Nov. 1, 2005

(54) VITAMIN $D_3$ DERIVATIVE AND TREATING AGENT FOR INFLAMMATORY RESPIRATORY DISEASE USING SAME

(75) Inventors: Kazuya Takenouchi, Tokyo (JP); Qingzhi Gao, Tokyo (JP); Kenji Manabe, Tokyo (JP); Ryo Sogawa, Tokyo (JP); Yasuhiro Takano, Tokyo (JP); Seiichi Ishizuka, Tokyo (JP)

(73) Assignee: Teijin Limited, Tokyo (JP)

( * ) Notice: Subject to any disclaimer, the term of this patent is extended or adjusted under 35 U.S.C. 154(b) by 486 days.

(21) Appl. No.: 10/035,217

(22) Filed: Jan. 4, 2002

(65) Prior Publication Data

US 2002/0103173 A1 Aug. 1, 2002

Related U.S. Application Data

(62) Division of application No. 09/830,167, filed as application No. PCT/JP99/05826 on Oct. 22, 1999, now Pat. No. 6,531,460.

(30) Foreign Application Priority Data

| Oct. 23, 1998 | (JP) | 10-302321 |
|---|---|---|
| Dec. 21, 1998 | (JP) | 10-362827 |
| Dec. 22, 1998 | (JP) | 10-365207 |
| Dec. 22, 1998 | (JP) | 10-365208 |
| Dec. 22, 1998 | (JP) | 10-365209 |

(51) Int. Cl.[7] ............. C07D 401/00; C07D 307/00; A61K 31/34; A61K 31/335; A61K 31/36
(52) U.S. Cl. ............. 514/167; 514/167; 514/449; 514/450; 514/451; 514/460; 514/461; 549/292; 549/295; 549/273; 549/266; 549/321
(58) Field of Search ............. 514/167; 552/653; 549/295, 266, 292, 321

(56) References Cited

U.S. PATENT DOCUMENTS

| 5,354,872 A | 10/1994 | Conrow ............. 549/313 |
| 5,583,125 A | 12/1996 | Steinmeyer et al. ......... 514/167 |
| 5,604,257 A | 2/1997 | Tabe et al. ................. 514/460 |
| 5,719,297 A | 2/1998 | Tabe et al. ................. 549/323 |
| 5,986,112 A | 11/1999 | Tabe et al. ................. 549/324 |
| 6,177,586 B1 | 1/2001 | Tabe et al. ................. 556/489 |

FOREIGN PATENT DOCUMENTS

| EP | 619305 | 10/1994 |
| GB | 2 260 904 A | 5/1993 |
| JP | 7-173133 | 7/1995 |
| JP | 11-49747 | 2/1999 |
| WO | 98/58909 | 12/1998 |

OTHER PUBLICATIONS

Ishizuka et al. (DN 107:52924; HCAPLUS, abstract of J. Biol. Chem. (1987), 262 (15), 7165–70).*
XP 002226140, Abstract, JP 10/087495, Apr. 7, 1998.
XP 002226141, Abstract, JP 08/092098, Apr. 9, 1996.

(Continued)

Primary Examiner—Sabiha Qazi
(74) Attorney, Agent, or Firm—Sughrue Mion, PLLC

(57) ABSTRACT

Compounds expressed by the following general formula (1),

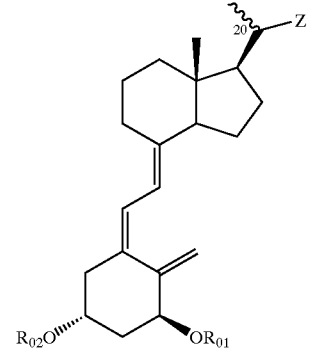

(1)

[wherein, $R_{01}$ and $R_{02}$ are each independently a hydrogen atom or a protecting group for a hydroxyl group; Z is one out of the following formulae (1-1), (1-2), (1-3), (1-4) and (1-5)].

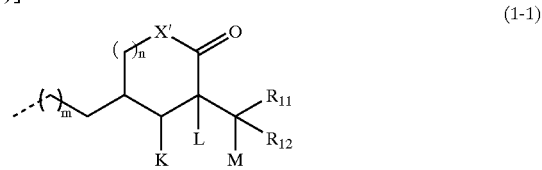

(1-1)

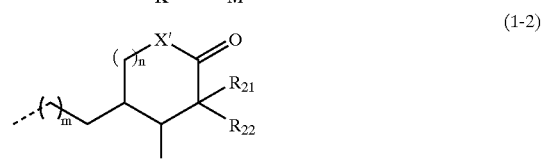

(1-2)

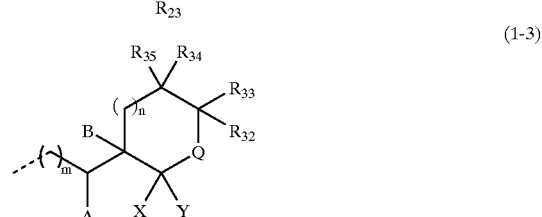

(1-3)

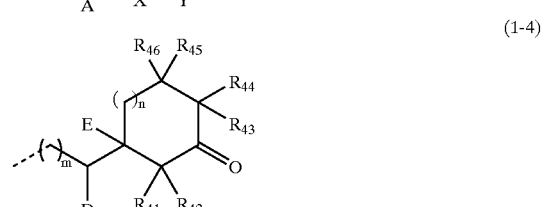

(1-4)

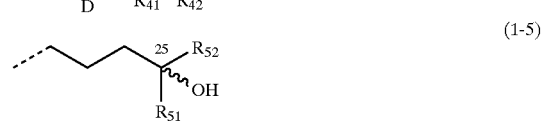

(1-5)

The compounds can be used as active ingredients of treating agents for inflammatory respiratory diseases, malignant tumors, rheumatoid arthritis, osteoporosis, diabetes mellitus, hypertension, alopecia, acne, psoriasis, dermatitis, hypercalcemia, hypoparathyroidism and metabolic disorder of cartilage.

9 Claims, No Drawings

OTHER PUBLICATIONS

Patent Abstracts of Japan, Publication No. 57–149224, Publication date Sep. 14, 1982, abstract.
Patent Abstracts of Japan, Publication No. 56–026820, Publication date Mar. 16, 1981, abstract.
Patent Abstracts of Japan, Publication No. 63–107928, Publication date May 12, 1988, abstract.
Patent Abstracts of Japan, Publication No. 62–026223, Publication date Feb. 4, 1987, abstract.
Patent Abstracts of Japan, Publication No. 05–294834, Publication date Nov. 9, 1993, abstract.
Patent Abstracts of Japan, Publication No. 07–291868, Publication date Nov. 7, 1995, abstract.
The Journal of Clinical Investigation, vol. 64, No. 1, Jul. 1979, pp. 218–225, "Evidence that Increased Circulating 1ω25–Dihydroxyvitamin D is the Probable Cause for Abnormal Calcium Metabolism in Sarcoidosis", Norman H. Bell et al.
Cell Calcium, vol. 16, 1994, pp. 112–122, "Activation of phosphoinositide metabolism by parathyroid hormone in growth plate chondrocytes", M. J. Zuscik et al.

Calcified Tissue International, vol. 50, 1992, pp. 61–66, "Differential Effects of Parathyroid Hormone on Chick Growth Plate and Articular Chondrocytes", Ian D. Crabb et al.

Endocrinology, vol. 118, No. 6, 1986, pp. 2445–2449, "Parathyroid Hormone Stimulates the Proliferation of Cells Derived from Human Bone", B. R. MacDonald et al.

The Journal of Clinical Investigation, vol. 83, Jan. 1989, pp. 60–65, "Insulin–like Growth Factor I Mediates Selective Anabolic Effects of Parathyroid Hormone in Bone Cultures", Ernesto Canalis et al.

J. Org. Chem., vol. 48, 1983, pp. 4433–4436, "Total Synthesis of 1ω25(R)–Dihydroxy Vitamin $D_3$ 26,23(S)–Lactone (Calcitriol Lactone), a Natural Metabolite of Vitamin $D_3$", Peter M. Wovkulich et al.

Abstract, WO94/07853.

* cited by examiner

VITAMIN D₃ DERIVATIVE AND TREATING AGENT FOR INFLAMMATORY RESPIRATORY DISEASE USING SAME

This is a Divisional application of Ser. No. 09/830,167, filed Apr. 23, 2000, now U.S. Pat. No. 531,460 is incorporated herein by reference, which is the National Stage of International Application No. PCT/JP99/05826, filed Oct. 22, 1999.

TECHNICAL FIELD

The present invention relates to vitamin $D_3$ derivatives useful as pharmaceutical products or pharmaceutically permissible solvates thereof, treating agents using same and pharmaceutical compositions containing same. More particularly, the invention relates to 1α-hydroxyvitamin $D_3$ derivatives having neutrophihc infiltration-suppressing activity and antagonistic effect to vitamin $D_3$ or pharmaceutically permissible solvates thereof, treating agents for inflammatory respiratory diseases and diseases attributable to the overactivity of vitamin $D_3$ containing same as active ingredients and pharmaceutical compositions containing same.

BACKGROUND ART

An active vitamin $D_3$ derivative has calcium absorption-stimulating activity in the small intestine, and activities such as the control of bone resorption and osteogenesis in the bones, and it is used as a treating agent for diseases caused by various kinds of calcium metabolism disorders. In recent years, immunoregulatory activity, cell proliferation inhibitory activity and cell differentiation inducting activity have been found besides these activities. For example, applications to a treating agent for malignant tumor (JP-A 57-149224 (hereinafter, JP-A means Japanese unexamined patent publication)), a treating agent for rheumatoid arthritis (JP-A 56-26820), an antialiergic agent (JP-A 63-107928, English Patent Publication No. 2260904 (GB 2260904-A)), a treating agent for psoriasis (JP-A 3-68009), a treating agent for diseases attributable to thromboxane $A_2$ production (JP-A 5-294834), a treating agent for eczema and dermatitis (JP-A. 7-291868), etc., are being studied.

Respiratory tract infection is a disease which is established when pathogens invade into the respiratory tract by getting over its infection preventing mechanisms, and the treatment is mainly based on the improvement of respiratory tract clearance by using a bronchodilator, an expectorant, etc. But, in the case of acute exacerbation with infection, the main treatment is the use of a strong antibacterial agent against phlogogenic bacteria. However, most underlying diseases constantly becomes worse when acute exacerbation is repeated. Further, current treatments, which depend on antibacterial agents in the extreme, are under reconsideration owing to the emergence of resistant bacteria such as MRSA.

Recently, the usefulness of a low-dose long administration of erythromycin for a chronic lower airway infectious disease has been reported, and it attracts medical attention. A chronic lower respiratory infectious disease is a generic name for bacterial infections observed in chronic bronchitis, diffuse panbronchiolitis, bronchiectasis, etc., (sometimes, it includes bronchial asthma, chronic pulmonary emphysema, tuberculosis sequela, etc., accompanied by infection). Although these are different in the name of disease, it is known that all of the diseases take common morbid states such as purulent sputum in large amount, fatigue dyspnea and hypoxemia. Regarding the working mechanism of erythromycin, it is estimated that erythromycin's function does not based simply on its antibacterial activity, namely, erythromycin acts not on bacteria themselves, and it is understood that erythromycin acts rather on inflammatory cells which accumulate on the airway accompanying the bacteria, especially acts on neutrophils. That is, neutrophils are considered to infiltrate into tissues by the various kinds of stimulation caused by the infection to release protease as well as activated oxygen, and these substances cause epithelium damage, the trouble of ciliary movement and mucosa hypersecretion to exert a bad influence upon respiratory physiological effect, and erythromycin acts on these processes. Based on such consideration, a medicine, which suppresses the pulmonary tissue infiltration of neutrophils or suppresses the activity of neutrophils, can be useful as a treating agent for inflammatory dyspnea, for example, chronic lower airway infectious disease.

On the other hand, when the control of vitamin D production becomes abnormal due to diseases, etc. and the intracorporeal concentration increases to express physiological effect excessively, various diseases attributable to the excess of the vitamin D are developed. For example, it is known that, in sarcoidosis, vitamin D is excessively produce by a tumorigenic macrophage-like cell (J. Clinical Invest., 64, 218–225 (1979)), and as a result, hypercalcemia is developed. For the treatment of the disease, a glucocorticoid is mainly used, but the long term administration of a large amount of the glucocorticoid causes adverse reaction. On the other hand, vitamin D is known to exhibit its physiological effect via intracellular vitamin D receptors, and thereby a vitamin $D_3$ antagonist, which is specific to the expression of effect via receptor, is supposed to be effective in order to suppress the excessively developed vitamin D activity.

Incidentally, an active vitamin $D_3$ controls the amount of production of parathyroid hormone (henceforth, this may be referred to as PTH) in a living body, and the amount of production of PTH is lowered by the increase of the production of the active vitamin $D_3$. Thereby, it is thought that the use of a vitamin $D_3$ antagonist corrects the decrease of PTH production attributable to the increase of active vitamin $D_3$ production, and further can accelerate the production of PTH. It is known that various diseases are caused by the decrease of PTH production, and one of the examples is hypoparathyroidism. The administration of PTH is considered to be ideal for the treatment of the disease; however, an orally administrable PTH preparation has not been developed yet. On the other hand, a vitamin $D_3$ antagonist is orally administrable, and thereby, the antagonist is supposed to be useful as an ideal treating agent for hypoparathyroidism.

Further, there are reports that PTH has effects on the growth and the differentiation of a cartilage cell, and the biosynthesis of cartilaginous matrix (Cellular and Calcium, 16, 112–122 (1994), and Calcified Tissue International, 50, 61–66 (1992)), on an osteoblast growth stimulating activity (Endocrinology, 118, 2445–2449 (1986)), on a collagen biosynthesis stimulating activity (J. Clin. Invest., 83, 60–65 (1989)) and the like. These reports show that PTH can become effective treating agents for metabolic disorder of cartilage and metabolic disorder of bone, and actually, a clinical investigation on osteogenesis is progressing by using an intramuscular injection preparation. However, an intramuscular injection preparation has such problems that the half life is short, and that hyperostosis, which is supposedly related to a transient increase in the intracorporeal concentration of PTH, is caused. On the other hand, a vitamin $D_3$ antagonist is orally administrable, and thereby it is supposed that the antagonist can solve these problems, and can be useful as an ideal treating agent for metabolic disorder of cartilage and that of bone.

Prior arts of the compound of the present invention are shown below.

The International Patent Publication WO95/33716 shows that compounds having an α-methyl lactone structure or an α-methylene lactone structure as the side chain of vitamin $D_3$ have an osteogenesis stimulation activity. However, the compounds disclosed by the present invention do not include the above-mentioned compounds, and further there is no description nor suggestion regarding that the compounds described in the publication have a neutrophilic infiltration suppressing activity or an antagonistic effect to vitamin $D_3$.

U.S. Patent Publication, U.S. Pat. No. 5,354,872 describes the method for the production of compounds having an α-hydroxy lactone structure or an α-hydroxy-α-alkyl lactone structure as the side chain of vitamin $D_3$; however, the compounds disclosed by the present invention do not include the above-mentioned compounds, and further there is no description nor suggestion regarding that the compounds described in the above-mentioned publication have a neutrophilic infiltration suppressing activity or an antagonistic effect to vitamin $D_3$.

J. Org. Chem., 48, 4433–4436 (1983), U.S. Patent Publication, U.S. Pat. No. 5,604,257 and the like describe compounds having an α-hydroxy-α-methyl lactone structure as the side chain of vitamin $D_3$, and the publication suggests an application as a treating agent for hypercalcemia, cancer, osteoporosis and the like. However, the compounds disclosed by the present invention do not include the above-mentioned compounds, and further there is neither description nor suggestion regarding that the compounds described in the above-mentioned literature and publication have a neutrophilic infiltration suppressing activity or an antagonistic effect to vitamin $D_3$.

International Patent Publication WO95/33716 describes that compounds having a carboxyl group or an ester group as a substituent at the 25-position of the side chain of vitamin $D_3$ have an osteogenesis stimulation activity. However, these compounds are clearly different from the compounds of the present invention having an amide group, an alkylcarbonyl group or a hydroxyalkyl group as a substituent at the 25-position of the side chain of vitamin $D_3$, and further there is no description nor suggestion regarding that the compounds described in the publication have a neutrophilic infiltration suppressing activity or an antagonistic effect to vitamin $D_3$.

International Patent Publication WO94/07853 describes that compounds having a carboxyl group, an ester group, an amide group, a thioester group or a cyano group as a substituent at the 25-position of vitamin $D_3$ have a cell differentiation inducting activity. However, the compounds disclosed by the publication have such a carboxyl group, an ester group, an amide group, a thioester group or a cyano group, and at the same time, a carbonyl group, a chlorine atom, a fluorine atom, a trifluoromethyl group or an alkyl group as the substituents at the 25-position of vitamin $D_3$, and they have a hydroxyl group or an alkoxy group at the 24-position, and further the bonding between the 22-position and the 23-position is a double bond. The compounds of the present invention have an amide group, an alkylcarbonyl group or a hydroxyalkyl group, and at the same time, a hydroxy group as the substituents at the 25-position, and the 24-position has no substituent, and the bonding between the 22-position and the 23-position is a single bond, and they are clearly different from the compounds described in the publication. Further, there is no description nor suggestion regarding that the compounds described in the publication have a neutrophilic infiltration suppressing activity or an antagonistic effect to vitamin $D_3$.

DISCLOSURE OF THE INVENTION

It is an object of the present invention to provide new vitamin $D_3$ derivatives having suppressing effect on neutrophilic infiltration and effective as treating agents for inflammatory respiratory diseases.

Another object of the present invention is to provide new vitamin $D_3$ derivatives having antagonistic effect to vitamin $D_3$ and effective as a treating agent for diseases attributable to the overactivity of vitamin $D_3$.

Still another object of the present invention is to provide methods for treating inflammatory respiratory diseases using these vitamin $D_3$ derivatives as active ingredients.

Yet another object of the present invention is to provide methods for treating diseases attributable to the overactivity of vitamin $D_3$ using these vitamin $D_3$ derivatives as active ingredients.

A further object of the present invention is to provide pharmaceutical compositions containing these vitamin $D_3$ derivatives as active ingredients.

According to the present invention, the above objects of the present invention are achieved by vitamin $D_3$ derivatives expressed by the following general formula [1] or pharmaceutically permissible solvates thereof,

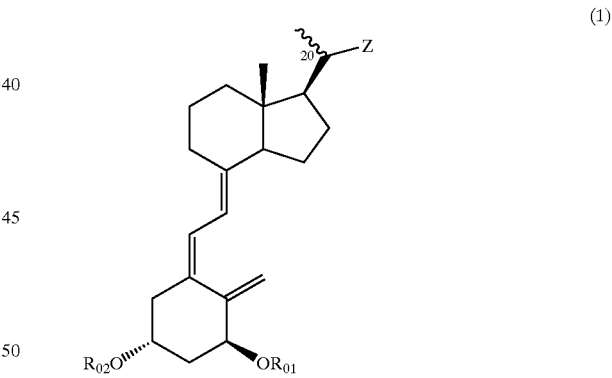

{wherein, $R_{01}$ and $R_{02}$ are each independently a hydrogen atom, a trimethylsilyl group, a triethylsilyl group, a t-butyldimethylsilyl group, an acetyl group, a methoxymethyl group or a tetrahydro-4H-pyran-2-yl group;

Z is one out of the following formulae (1-1), (1-2), (1-3), (1-4) or (1-5),

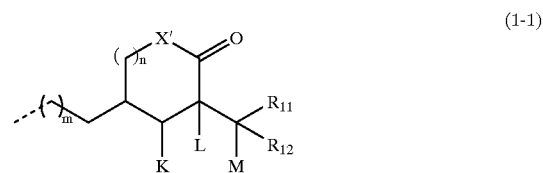

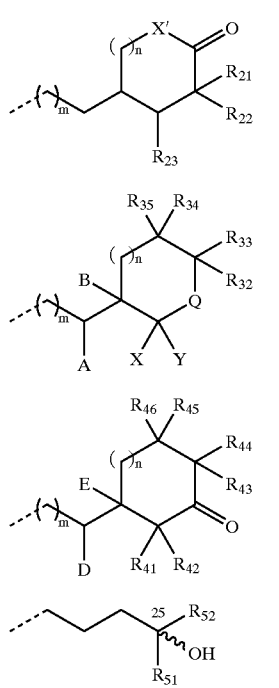

[in the above formulae (1-1) to (1-5), m is an integer of 0 to 2;

n is an integer of 0 to 2;

X' is an oxygen atom or NH;

$R_{11}$ and $R_{12}$ are identical to or different from each other, and express a hydrogen atom or a $C_1$–$C_4$ alkyl group;

K, L and M take each a hydrogen atom; M is a hydrogen atom, and K and L together express a single bond and express a double bond in cooperation with the single bond already shown in the formula; or K is a hydrogen atom, and L and M together express a single bond and express a double bond in cooperation with the single bond already shown in the formula;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or $R_{21}$ and $R_{22}$ together may express a $C_3$–$C_6$ cyclic alkyl group in cooperation with the carbon atom to which they are bonded;

Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and E express each a hydrogen atom, D is a hydroxy group and E expresses a hydrogen atom, D and E together express a single bond and express a double bond in cooperation with the single bond already shown in the formula, or E and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a C–$C_4$ alkyl group which may be substituted with a hydroxyl group, a $C_2$–$C_5$ acyloxy group or a $C_1$–$C_4$ alkyloxy group;

$R_{51}$ expresses —CONR$_{511}$R$_{512}$, —COR$_{513}$ or —C(OH)R$_{514}$R$_{515}$, wherein R$_{511}$ and R$_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and R$_{513}$, R$_{514}$ and R$_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{44}$, and $R_{45}$ and $R_{46}$ are both hydroxy groups, both alkyloxy groups, or a hydroxy group and an alkyloxy group, (b) a compound expressed by the above formula (1) in which Z is the following formula (1-6),

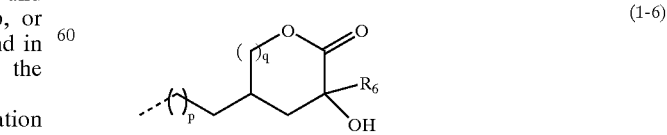

(wherein, p and q are each 0 or the integer 1; $R_6$ is a hydrogen atom or a $C_1$–$C_4$ alkyl group), and (c) a compound of the following formula (2),

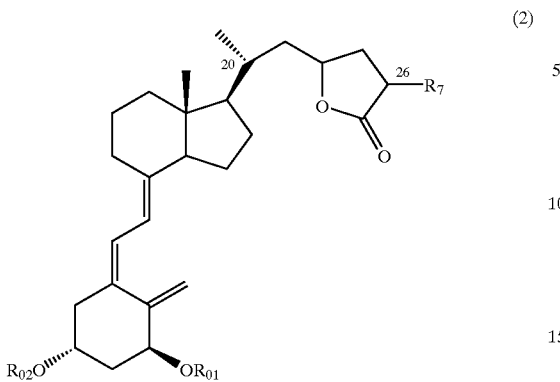

(2)

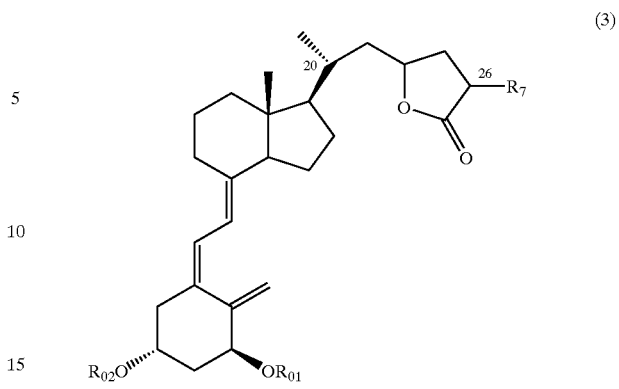

(3)

(wherein, $R_{01}$ and $R_{02}$ are defined in the same manner as in the above formula (1); the configuration of the carbon atom at the 20-position is (R)-configuration; $R_7$ is a methyl group or a methylene group; when $R_7$ is a methylene group, the bond between $R_7$ and the carbon atom at the 26-position is double bond)}.

When the structure of a compound of the above formula (1) has an asymmetric carbon, the configuration of the asymmetric carbon may be either (S)-configuration or (R)-configuration as far as it is not especially specified, further, when L and M, A and B, D and E, or E and $R_{41}$ together form a double bond, the configuration of the double bond may be either (E)-configuration or (Z)-configuration, and furthermore, the present invention includes mixtures of these various isomers at an arbitrary ratio.

In addition, according to the present invention, above objects of the present invention are achieved by therapeutic methods for inflammatory respiratory diseases using above vitamin $D_3$ derivatives or pharmaceutically permissible solvates thereof in therapeutically effective amounts as active ingredients.

Further, according to the present invention, above objects of the present invention are achieved by therapeutic methods for diseases attributable to the overactivity of vitamin $D_3$ using the above vitamin $D_3$ derivatives or pharmaceutically permissible solvates thereof in therapeutically effective amounts as active ingredients.

Further, according to the present invention, the above objects of the present invention are achieved by pharmaceutical compositions consisting of the above vitamin $D_3$ derivatives or pharmaceutically permissible solvates thereof, and pharmaceutically permissible supports.

Furthermore, the above objects of the present invention are achieved by treating agents for inflammatory respiratory diseases containing vitamin $D_3$ derivatives expressed by the following general formula (3) or pharmaceutically permissible solvates thereof in therapeutically effective amounts as active ingredients, (wherein, $R_{01}$, $R_{02}$ and $R_7$ are defined in the same manner as in the above formula (2)).

BEST MODE FOR CARRYING OUT THE INVENTION

Terms used in the present invention are defined as follows.

The term "$C_2$–$C_5$ acyloxy group" expresses a normal, branched or cyclic aliphatic hydrocarbon carbonyloxy group having a carbon number of 2 to 5. Concrete examples of the group include acetoxy, propionyloxy, butyryloxy, isobutyryloxy, valeryloxy, isovaleryloxy, pivaloyloxy, cyclopropylcarbonyloxy, cyclopropylacetoxy and cyclobutylcarbonyloxy groups, etc.

The term "$C_1$–$C_4$ alkyloxy group" expresses a normal, branched or cyclic aliphatic hydrocarbon oxy group having a carbon number of 1 to 4. Concrete examples of the group include methoxy, ethoxy, propoxy, butoxy, isopropoxy, isobutoxy, s-butoxy, t-butoxy and cyclopropylmethyloxy groups, etc.

The term "$C_1$–$C_4$ alkyloxycarbonyl group" expresses a normal, branched or cyclic aliphatic hydrocarbon oxycarbonyl group having a carbon number of 1 to 4. Concrete examples of the group include methoxycarbonyl, ethoxycarbonyl, propoxycarbonyl, butoxycarbonyl, isopropoxycarbonyl, isobutoxycarbonyl, s-butoxycarbonyl, t-butoxycarbonyl and cyclopropylmethyloxycarbonyl groups, etc.

The term "$C_3$–$C_6$ cyclic alkyl group" expresses a cyclic aliphatic hydrocarbon group having a carbon number of 3 to 6. Concrete examples of the group include cyclopropyl, methylcyclopropyl, cyclobutyl, cyclopentyl and cyclohexyl groups, etc.

The term "nitrogen-containing $C_3$–$C_8$ alkyl ring" expresses an aliphatic hydrocarbon ring which has a carbon number of 3 to 8 and contains a nitrogen atom in a ring. Concrete examples of the ring include aziridine, azetidine, pyrrolidine, imidazolidine, pyrazolidine, piperidine and piperazine rings, etc.

The term "$C_1$–$C_4$ alkyl group which may be substituted with a hydroxy group, a $C_2$–$C_5$ acyloxy group or a $C_1$–$C_4$ alkyloxy group" expresses a normal, branched or cyclic aliphatic hydrocarbon group having a carbon number of 1 to 4 whose arbitrary position may be substituted with a hydroxy group, an acyloxy group having a carbon number of 2 to 5 or an alkyloxy group having a carbon number of 1 to 4. Examples of the group include methyl, ethyl, propyl, isopropyl, cyclopropyl, butyl, isobutyl, s-butyl, t-butyl, cyclopropylmethyl, cyclobutyl, hydroxymethyl, hydroxyethyl, hydroxypropyl, hydroxybutyl, acetoxymethyl, propionyloxymethyl, butyryloxymethyl, acetoxyethyl, propionyloxyethyl, butyryloxyethyl, acetoxypropyl, propionyloxypropyl, butyryloxypropyl, methoxymethyl, ethoxymethyl, methoxyethyl, ethoxyethyl, methoxypropyl and ethoxypropyl groups, etc.

In the above formula (1), $R_{01}$ and $R_{02}$ are each independently a hydrogen atom, a trimethylsilyl group, a triethylsilyl group, a t-butyldimethylsilyl group, an acetyl group, a methoxymethyl group or tetrahydro-4H-pyran-2-yl. Among these groups, the case where both of $R_{01}$ and $R_{02}$ are hydrogen atoms, trimethylsilyl groups, triethylsilyl groups or t-butyldimethylsilyl groups is preferable, and further the case where they are hydrogen atoms is the most preferable.

In the above formula (1), Z expresses one of the above-mentioned formulae (1-1), (1-2), (1-3), (1-4) and (1-5).

In the above formula (1), m is an integer of 0 to 2, and 0 or 1 is especially preferable.

In the above formula (1), n is an integer of 0 to 2, and 0 or 1 is especially preferable.

In the above formula (1), X' is an oxygen atom or NH, and an oxygen atom is especially preferable.

In the above formula (1), $R_{11}$ and $R_{12}$ are identical to or different from each other, and they express a hydrogen atom or a $C_1$–$C_4$ alkyl group. A hydrogen atom, a methyl group or an ethyl group is especially preferable.

In the above formula (1), K, L and M are all hydrogen atoms; M is a hydrogen atom, and K and L together express a single bond and express a double bond in cooperation with the single bond already shown in the formula; or K is a hydrogen atom, and L and M together express a single bond and express a double bond in cooperation with the single bond already shown in the formula. The cases where M is a hydrogen atom, and K and L together express a single bond and express a double bond in cooperation with the single bond already shown in the formula; and K is a hydrogen atom, and L and M together express a single bond and express a double bond in cooperation with the single bond already shown in the formula are especially preferable. Further, the case where K is a hydrogen atom, and L and M together express a single bond and express a double bond in cooperation with the single bond already shown in the formula is the most preferable.

In the above formula (1), $R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group, a $C_1$–$C_4$ alkyl group which may be substituted with a hydroxyl group, a $C_2$–$C_5$ acyloxy group or a $C_1$–$C_4$ alkyloxy group; or $R_{21}$ and $R_{22}$ together may express a $C_3$–$C_6$ cyclic alkyl group in cooperation with the carbon atom to which they are bonded. Among them, the case where $R_{21}$ and $R_{22}$ are identical to or different from each other, and they are a hydrogen atom, a hydroxyl group or a $C_1$–$C_4$ alkyl group, or $R_{21}$ and $R_{22}$ together express a $C_3$–$C_6$ cyclic alkyl group in cooperation with the carbon atom to which they are bonded is preferable. Further, the case where $R_{21}$ and $R_{22}$ are a hydrogen atom, a hydroxyl group, a methyl group, an ethyl group or an n-propyl group, or both the members together form a cyclopropyl group in cooperation with the carbon atom to which they are bonded is especially preferable. In addition, $R_{23}$ is preferably a hydrogen atom or a hydroxyl group.

Preferable examples of the combination of $R_{21}$, $R_{22}$ and $R_{23}$ include (a) $R_{21}$, $R_{22}$ and $R_{23}$ are all hydrogen atoms, (b) $R_{21}$ and $R_{22}$ are methyl groups, and $R_{23}$ is a hydrogen atom, (c) the combination of $R_{21}$ and $R_{22}$ is the case where they are a methyl group and a hydroxyl group, and $R_{23}$ is a hydrogen atom, (d) the combination of $R_{21}$ and $R_{22}$ is the case where they are a methyl group and a hydroxyl group, and $R_{23}$ is a hydroxyl group and (e) $R_{21}$ and $R_{22}$ together form a cyclopropyl group in cooperation with the carbon atom to which they are bonded, and $R_{23}$ is a hydrogen atom.

In the above formula (1), Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group, or a $C_1$–$C_4$ alkyl group which may be substituted with a hydroxy group, a $C_2$–$C_5$ acyloxy group or a $C_1$–$C_4$ alkyloxy group. Among them, $R_{31}$ is especially preferably a hydrogen atom, a hydroxyl group or, a $C_1$–$C_4$ alkyl group which may be substituted with a hydroxy group, a $C_2$–$C_5$ acyloxy group or a $C_1$–$C_4$ alkyloxy group. Further, $R_{31}$ is the most preferably a hydrogen atom, a hydroxyl group or a methyl group.

In the above formula (1), $R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group. Among them, a hydrogen atom or a $C_1$–$C_4$ alkyl is preferable, and further a hydrogen atom is the most preferable.

In the above formula (1), A and B are identical to or different from each other, and they express a hydrogen atom or a hydroxyl group, or both the members together express a single bond and form a double bond in cooperation with the single bond already shown in the formula. Among them, the case where A and B are both hydrogen atoms, A is a hydroxyl group and B is a hydrogen atom, or they together express a single bond and form a double bond in cooperation with the single bond already shown in the formula is preferable.

In the above formula (1), X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group. Especially the case where X and Y together express a carbonyl group in cooperation with the carbon atom to which they are bonded is preferable.

In the above formula (1), $R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group. In addition, both the members together express a $C_1$–$C_5$ alkylidene group, or they together express a $C_3$–$C_6$ cyclic alkyl group in cooperation with the carbon atom to which they are bonded. Especially, the case where they express hydrogen atoms, or both the members together express a methylene group is preferable.

In the above formula (1), $R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group, or a $C_1$–$C_4$ alkyl group which may be substituted with a hydroxyl group, a $C_2$–$C_5$ acyloxy group or a $C_1$–$C_4$ alkyloxy group. In addition, both the members together express a $C_1$–$C_5$ alkylidene group, or they together express a $C_3$–$C_6$ cyclic alkyl group in cooperation with the carbon atom to which they are bonded. Especially, the case where they express hydrogen atoms, or both the members together express a methylene group is preferable.

In the above formula (1), $R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group. Especially, the case where they are a hydrogen atom, a hydroxyl group, a methyl group or an ethyl group, and further the case where they are hydrogen atoms is the most preferable.

In the above formula (1), D and E both express hydrogen atoms, D is a hydroxy group and E expresses a hydrogen atom, or D and E together express a single bond and express a double bond in cooperation with the single bond already shown in the formula. In addition, E and $R_{41}$ together express a single bond and express a double bond in cooperation with the single bond already shown in the formula, wherein D expresses a hydrogen atom or a hydroxy group, and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group. Especially, the case where D and E both are hydrogen atoms, D and E together express a single bond and express a double bond in cooperation with the single bond already shown in the formula, or D is a hydrogen atom, and E and $R_{41}$ together express a single bond and express a double bond in cooperation with the single bond already shown in the formula is preferable.

In the above formula (1), $R_{51}$ expresses —$CONR_{511}R_{512}$, —$COR_{513}$ or —$C(OH)R_{514}R_{515}$. Herein, $R_{511}$ and $R_{512}$ are identical to or different from each other, and they are a hydrogen atom or a $C_1$–$C_4$ alkyl, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group. Especially, $R_{51}$ is preferably —$CONR_{511}R_{512}$ or —$COR_{513}$. In addition, $R_{511}$ and $R_{512}$ are preferably a methyl group or an ethyl group, or both the members together express an aziridine, pyrrolidine, piperidine or morpholino ring in cooperation with the nitrogen atom to which they are bonded. $R_{513}$, $R_{514}$ and $R_{515}$ are preferably a methyl group or an ethyl group.

In the above formula (1), $R_{52}$ expresses a methyl group, an ethyl group, a trifluoromethyl group or a pentafluoroethyl group. Especially, a methyl group is preferable.

Vitamin $D_3$ derivatives of the present invention can be optionally converted into pharmaceutically permissible solvates thereof. Examples of such a solvent include water, methanol, ethanol, propyl alcohol, isopropyl alcohol, butanol, t-butanol, acetonitrile, acetone, methyl ethyl ketone, chloroform, ethyl acetate, diethyl ether, t-butyl methyl ether, benzene, toluene, DMF, DMSO, etc. Especially, water, methanol, ethanol, propyl alcohol, isopropyl alcohol, acetonitrile, acetone, methyl ethyl ketone and ethyl acetate may be cited as preferable examples.

Preferable concrete examples of the vitamin $D_3$ derivative of the present invention expressed by the above formula (1) are shown in Tables 1-1-1, 1-2-1, 1-3-1, 1-3-2, 1-4-1, 1-4-2 and 1-5-1. Further, in these compounds, when an asymmetric carbon is included in the structure of a compound, the configuration of the asymmetric carbon can be either (S)-configuration or (R)-configuration as far as it is not especially specified. When L and M, A and B, D and E, or E and $R_{41}$ together form a double bond, the configuration of the double bond includes both (E)-configuration and (Z)-configuration. In addition, for the convenience of reading, a subscript is written in a normal size in a table, for example, "$CH_2$" is written as "CH2".

TABLE 1-1-1

Structure of Compound: formula (1), Z = (1-1)

| Comp. No. | R01, R02 | X' | m | n | R11, R12 | K, L, M |
|---|---|---|---|---|---|---|
| 1101(*) | H, H | oxygen atom | 0 | 0 | H, H | K=H, L,M=double bond |
| 1102 | H, H | oxygen atom | 0 | 0 | H, Me | K=H, L,M=double bond |
| 1103 | H, H | oxygen atom | 0 | 0 | H, Et | K=H, L,M=double bond |
| 1104 | H, H | oxygen atom | 0 | 0 | Me, Me | K=H, L,M=double bond |
| 1105 | H, H | oxygen atom | 0 | 0 | Me, Et | K=H, L,M=double bond |
| 1106 | H, H | oxygen atom | 0 | 0 | Et, Et | K=H, L,M=double bond |
| 1107 | H, H | oxygen atom | 0 | 0 | H, H | K,L=double bond, M=H |
| 1108 | H, H | oxygen atom | 0 | 0 | H, Me | K,L=double bond, M=H |
| 1109 | H, H | oxygen atom | 0 | 0 | H, Et | K,L=double bond, M=H |
| 1110 | H, H | oxygen atom | 0 | 0 | Me, Me | K,L=double bond, M=H |
| 1111 | H, H | oxygen atom | 0 | 0 | Me, Et | K,L=double bond, M=H |
| 1112 | H, H | oxygen atom | 0 | 0 | Et, Et | K,L=double bond, M=H |
| 1113(*) | H, H | oxygen atom | 0 | 0 | H, H | K,L,M=H |
| 1114 | H, H | oxygen atom | 0 | 0 | H, Me | K,L,M=H |
| 1115 | H, H | oxygen atom | 0 | 0 | H, Et | K,L,M=H |
| 1116 | H, H | oxygen atom | 0 | 0 | Me, Me | K,L,M=H |
| 1117 | H, H | oxygen atom | 0 | 0 | Me, Et | K,L,M=H |
| 1118 | H, H | oxygen atom | 0 | 0 | Et, Et | K,L,M=H |
| 1119 | H, H | oxygen atom | 0 | 1 | H, H | K=H, L,M=double bond |
| 1120 | H, H | oxygen atom | 0 | 1 | H, Me | K=H, L,M=double bond |
| 1121 | H, H | oxygen atom | 0 | 1 | H, Et | K=H, L,M=double bond |
| 1122 | H, H | oxygen atom | 0 | 1 | Me, Me | K=H, L,M=double bond |
| 1123 | H, H | oxygen atom | 0 | 1 | Me, Et | K=H, L,M=double bond |
| 1124 | H, H | oxygen atom | 0 | 1 | Et, Et | K=H, L,M=double bond |
| 1125 | H, H | oxygen atom | 0 | 1 | H, H | K,L=double bond, M=H |
| 1126 | H, H | oxygen atom | 0 | 1 | H, Me | K,L=double bond, M=H |
| 1127 | H, H | oxygen atom | 0 | 1 | H, Et | K,L=double bond, M=H |
| 1128 | H, H | oxygen atom | 0 | 1 | Me, Me | K,L=double bond, M=H |

TABLE 1-1-1-continued

Structure of Compound: formula (1), Z = (1-1)

| Comp. No. | R01, R02 | X' | m | n | R11, R12 | K, L, M |
|---|---|---|---|---|---|---|
| 1129 | H, H | oxygen atom | 0 | 1 | Me, Et | K,L=double bond, M=H |
| 1130 | H, H | oxygen atom | 0 | 1 | Et, Et | K,L=double bond, M=H |
| 1201 | H, H | oxygen atom | 1 | 0 | H, H | K=H, L,M=double bond |
| 1202 | H, H | oxygen atom | 1 | 0 | H, Me | K=H, L,M=double bond |
| 1203 | H, H | oxygen atom | 1 | 0 | H, Et | K=H, L,M=double bond |
| 1204 | H, H | oxygen atom | 1 | 0 | Me, Me | K=H, L,M=double bond |
| 1205 | H, H | oxygen atom | 1 | 0 | Me, Et | K=H, L,M=double bond |
| 1206 | H, H | oxygen atom | 1 | 0 | Et, Et | K=H, L,M=double bond |
| 1207 | H, H | oxygen atom | 1 | 1 | H, H | K=H, L,M=double bond |
| 1208 | H, H | oxygen atom | 1 | 1 | H, Me | K=H, L,M=double bond |
| 1209 | H, H | oxygen atom | 1 | 1 | H, Et | K=H, L,M=double bond |
| 1210 | H, H | oxygen atom | 1 | 1 | Me, Me | K=H, L,M=double bond |
| 1211 | H, H | oxygen atom | 1 | 1 | Me, Et | K=H, L,M=double bond |
| 1212 | H, H | oxygen atom | 1 | 1 | Et, Et | K=H, L,M=double bond |
| 1301 | H, H | NH | 0 | 0 | H, H | K=H, L,M=double bond |
| 1302 | H, H | NH | 0 | 0 | H, Me | K=H, L,M=double bond |
| 1303 | H, H | NH | 0 | 0 | H, Et | K=H, L,M=double bond |
| 1304 | H, H | NH | 0 | 0 | Me, Me | K=H, L,M=double bond |
| 1305 | H, H | NH | 0 | 0 | Me, Et | K=H, L,M=double bond |
| 1306 | H, H | NH | 0 | 0 | Et, Et | K=H, L,M=double bond |
| 1307 | H, H | NH | 0 | 1 | H, H | K=H, L,M=double bond |
| 1308 | H, H | NH | 0 | 1 | H, Me | K=H, L,M=double bond |
| 1309 | H, H | NH | 0 | 1 | H, Et | K=H, L,M=double bond |
| 1310 | H, H | NH | 0 | 1 | Me, Me | K=H, L,M=double bond |
| 1311 | H, H | NH | 0 | 1 | Me, Et | K=H, L,M=double bond |
| 1312 | H, H | NH | 0 | 1 | Et, Et | K=H, L,M=double bond |

(*)In the formula (1), a compound having (R)-configuration at the 20-position is excluded.

TABLE 1-2-1

Structure of Compound: formula (1), Z = (1-2)

| Comp. No. | R01, R02 | X' | m | n | R21, R22 | R23 |
|---|---|---|---|---|---|---|
| 2101 | H, H | oxygen atom | 0 | 0 | H, H | H |
| 2102 | H, H | oxygen atom | 0 | 0 | Me, Me | H |
| 2103 | H, H | oxygen atom | 0 | 0 | Et, Et | H |
| 2104 | H, H | oxygen atom | 0 | 0 | Me, OH | OH |
| 2105 | H, H | oxygen atom | 0 | 0 | (CH2)2 | H |
| 2106 | H, H | oxygen atom | 0 | 1 | H, H | H |
| 2107 | H, H | oxygen atom | 0 | 1 | Me, Me | H |
| 2108 | H, H | oxygen atom | 0 | 1 | Et, Et | H |
| 2109 | H, H | oxygen atom | 0 | 1 | Me, OH | H |
| 2110 | H, H | oxygen atom | 0 | 1 | Me, OH | OH |
| 2111 | H, H | oxygen atom | 0 | 1 | (CH2)2 | H |
| 2201 | H, H | NH | 0 | 0 | H, H | H |
| 2202 | H, H | NH | 0 | 0 | Me, Me | H |
| 2203 | H, H | NH | 0 | 0 | Et, Et | H |
| 2204 | H, H | NH | 0 | 0 | Me, OH | H |
| 2205 | H, H | NH | 0 | 0 | Me, OH | OH |
| 2206 | H, H | NH | 0 | 0 | (CH2)2 | H |
| 2207 | H, H | NH | 0 | 1 | H, H | H |
| 2208 | H, H | NH | 0 | 1 | Me, Me | H |
| 2209 | H, H | NH | 0 | 1 | Et, Et | H |
| 2210 | H, H | NH | 0 | 1 | Me, OH | H |
| 2211 | H, H | NH | 0 | 1 | Me, OH | OH |
| 2212 | H, H | NH | 0 | 1 | (CH2)2 | H |
| 2301 | H, H | oxygen atom | 1 | 0 | H, H | H |
| 2302 | H, H | oxygen atom | 1 | 0 | Me, Me | H |
| 2303 | H, H | oxygen atom | 1 | 0 | Et, Et | H |
| 2304 | H, H | oxygen atom | 1 | 0 | Me, OH | OH |
| 2305 | H, H | oxygen atom | 1 | 0 | (CH2)2 | H |

TABLE 1-3-1

Structure of Compound: formula (1), Z = (1-3)

| Comp. No. | R01, R02 | Q | m | n | A, B | X, Y | R31 | R32, R33 | R34, R35 |
|---|---|---|---|---|---|---|---|---|---|
| 3101 | H, H | >C(-F)-R31 | 0 | 0 | double bond | carbonyl | H | H, H | H, H |
| 3102 | H, H | >C(-F)-R31 | 1 | 0 | double bond | carbonyl | H | H, H | H, H |
| 3103 | H, H | >C(-F)-R31 | 0 | 1 | double bond | carbonyl | H | H, H | H, H |
| 3104 | H, H | >C(-F)-R31 | 1 | 1 | double bond | carbonyl | H | H, H | H, H |
| 3105 | H, H | >C(-F)-R31 | 0 | 0 | double bond | carbonyl | Me | H, H | H, H |
| 3106 | H, H | >C(-F)-R31 | 1 | 0 | double bond | carbonyl | Me | H, H | H, H |
| 3107 | H, H | >C(-F)-R31 | 0 | 1 | double bond | carbonyl | Me | H, H | H, H |
| 3108 | H, H | >C(-F)-R31 | 1 | 1 | double bond | carbonyl | Me | H, H | H, H |
| 3109 | H, H | >C(-F)-R31 | 0 | 0 | double bond | carbonyl | Et | H, H | H, H |
| 3110 | H, H | >C(-F)-R31 | 1 | 0 | double bond | carbonyl | Et | H, H | H, H |

TABLE 1-3-1-continued

Structure of Compound: formula (1), Z = (1-3)

| Comp. No. | R01, R02 | Q | m | n | A, B | X, Y | R31 | R32, R33 | R34, R35 |
|---|---|---|---|---|---|---|---|---|---|
| 3111 | H, H | >C(-F)-R31 | 0 | 1 | double bond | carbonyl | Et | H, H | H, H |
| 3112 | H, H | >C(-F)-R31 | 1 | 1 | double bond | carbonyl | Et | H, H | H, H |
| 3113 | H, H | >C(-F)-R31 | 0 | 0 | double bond | carbonyl | OH | H, H | H, H |
| 3114 | H, H | >C(-F)-R31 | 1 | 0 | double bond | carbonyl | OH | H, H | H, H |
| 3115 | H, H | >C(-F)-R31 | 0 | 1 | double bond | carbonyl | OH | H, H | H, H |
| 3116 | H, H | >C(-F)-R31 | 1 | 1 | double bond | carbonyl | OH | H, H | H, H |
| 3201 | H, H | >C(-F)-R31 | 0 | 0 | A=OH, B=H | carbonyl | H | H, H | H, H |
| 3202 | H, H | >C(-F)-R31 | 1 | 0 | A=OH, B=H | carbonyl | H | H, H | H, H |
| 3203 | H, H | >C(-F)-R31 | 0 | 1 | A=OH, B=H | carbonyl | H | H, H | H, H |
| 3204 | H, H | >C(-F)-R31 | 1 | 1 | A=OH, B=H | carbonyl | H | H, H | H, H |
| 3205 | H, H | >C(-F)-R31 | 0 | 0 | A=OH, B=H | carbonyl | Me | H, H | H, H |
| 3206 | H, H | >C(-F)-R31 | 1 | 0 | A=OH, B=H | carbonyl | Me | H, H | H, H |
| 3207 | H, H | >C(-F)-R31 | 0 | 1 | A=OH, B=H | carbonyl | Me | H, H | H, H |
| 3208 | H, H | >C(-F)-R31 | 1 | 1 | A=OH, B=H | carbonyl | Me | H, H | H, H |
| 3209 | H, H | >C(-F)-R31 | 0 | 0 | A=OH, B=H | carbonyl | Et | H, H | H, H |
| 3210 | H, H | >C(-F)-R31 | 1 | 0 | A=OH, B=H | carbonyl | Et | H, H | H, H |
| 3211 | H, H | >C(-F)-R31 | 0 | 1 | A=OH, B=H | carbonyl | Et | H, H | H, H |
| 3212 | H, H | >C(-F)-R31 | 1 | 1 | A=OH, B=H | carbonyl | Et | H, H | H, H |
| 3301 | H, H | >C(-F)-R31 | 0 | 0 | A=H, B=H | carbonyl | H | H, H | H, H |
| 3302 | H, H | >C(-F)-R31 | 1 | 0 | A=H, B=H | carbonyl | H | H, H | H, H |
| 3303 | H, H | >C(-F)-R31 | 0 | 1 | A=H, B=H | carbonyl | H | H, H | H, H |
| 3304 | H, H | >C(-F)-R31 | 1 | 1 | A=H, B=H | carbonyl | H | H, H | H, H |
| 3305 | H, H | >C(-F)-R31 | 0 | 0 | A=H, B=H | carbonyl | Me | H, H | H, H |
| 3306 | H, H | >C(-F)-R31 | 1 | 0 | A=H, B=H | carbonyl | Me | H, H | H, H |
| 3307 | H, H | >C(-F)-R31 | 0 | 1 | A=H, B=H | carbonyl | Me | H, H | H, H |
| 3308 | H, H | >C(-F)-R31 | 1 | 1 | A=H, B=H | carbonyl | Me | H, H | H, H |
| 3309 | H, H | >C(-F)-R31 | 0 | 0 | A=H, B=H | carbonyl | Et | H, H | H, H |
| 3310 | H, H | >C(-F)-R31 | 1 | 0 | A=H, B=H | carbonyl | Et | H, H | H, H |
| 3311 | H, H | >C(-F)-R31 | 0 | 1 | A=H, B=H | carbonyl | Et | H, H | H, H |
| 3312 | H, H | >C(-F)-R31 | 1 | 1 | A=H, B=H | carbonyl | Et | H, H | H, H |

TABLE 1-3-2

Structure of Compound: formula (1), Z = (1-3)

| Comp. No. | R01, R02 | Q | m | n | A, B | X, Y | R31 | R32, R33 | R34, R35 |
|---|---|---|---|---|---|---|---|---|---|
| 3401 | H, H | >N-R31 | 0 | 0 | double bond | carbonyl | H | H, H | H, H |
| 3402 | H, H | >N-R31 | 1 | 0 | double bond | carbonyl | H | H, H | H, H |
| 3403 | H, H | >N-R31 | 0 | 1 | double bond | carbonyl | H | H, H | H, H |
| 3404 | H, H | >N-R31 | 1 | 1 | double bond | carbonyl | H | H, H | H, H |
| 3405 | H, H | >N-R31 | 0 | 0 | double bond | carbonyl | Me | H, H | H, H |
| 3406 | H, H | >N-R31 | 1 | 0 | double bond | carbonyl | Me | H, H | H, H |
| 3407 | H, H | >N-R31 | 0 | 1 | double bond | carbonyl | Me | H, H | H, H |
| 3408 | H, H | >N-R31 | 1 | 1 | double bond | carbonyl | Me | H, H | H, H |
| 3409 | H, H | >N-R31 | 0 | 0 | double bond | carbonyl | Et | H, H | H, H |
| 3410 | H, H | >N-R31 | 1 | 0 | double bond | carbonyl | Et | H, H | H, H |
| 3411 | H, H | >N-R31 | 0 | 1 | double bond | carbonyl | Et | H, H | H, H |
| 3412 | H, H | >N-R31 | 1 | 1 | double bond | carbonyl | Et | H, H | H, H |
| 3413 | H, H | >N-R31 | 0 | 0 | double bond | carbonyl | OH | H, H | H, H |
| 3414 | H, H | >N-R31 | 1 | 0 | double bond | carbonyl | OH | H, H | H, H |
| 3415 | H, H | >N-R31 | 0 | 1 | double bond | carbonyl | OH | H, H | H, H |
| 3416 | H, H | >N-R31 | 1 | 1 | double bond | carbonyl | OH | H, H | H, H |
| 3501 | H, H | >N-R31 | 0 | 0 | A=OH, B=H | carbonyl | H | H, H | H, H |
| 3502 | H, H | >N-R31 | 1 | 0 | A=OH, B=H | carbonyl | H | H, H | H, H |
| 3503 | H, H | >N-R31 | 0 | 1 | A=OH, B=H | carbonyl | H | H, H | H, H |
| 3504 | H, H | >N-R31 | 1 | 1 | A=OH, B=H | carbonyl | H | H, H | H, H |
| 3505 | H, H | >N-R31 | 0 | 0 | A=OH, B=H | carbonyl | Me | H, H | H, H |
| 3506 | H, H | >N-R31 | 1 | 0 | A=OH, B=H | carbonyl | Me | H, H | H, H |
| 3507 | H, H | >N-R31 | 0 | 1 | A=OH, B=H | carbonyl | Me | H, H | H, H |
| 3508 | H, H | >N-R31 | 1 | 1 | A=OH, B=H | carbonyl | Me | H, H | H, H |
| 3509 | H, H | >N-R31 | 0 | 0 | A=OH, B=H | carbonyl | Et | H, H | H, H |
| 3510 | H, H | >N-R31 | 1 | 0 | A=OH, B=H | carbonyl | Et | H, H | H, H |
| 3511 | H, H | >N-R31 | 0 | 1 | A=OH, B=H | carbonyl | Et | H, H | H, H |
| 3512 | H, H | >N-R31 | 1 | 1 | A=OH, B=H | carbonyl | Et | H, H | H, H |
| 3513 | H, H | >N-R31 | 0 | 0 | A=OH, B=H | carbonyl | OH | H, H | H, H |
| 3514 | H, H | >N-R31 | 1 | 0 | A=OH, B=H | carbonyl | OH | H, H | H, H |
| 3515 | H, H | >N-R31 | 0 | 1 | A=OH, B=H | carbonyl | OH | H, H | H, H |
| 3516 | H, H | >N-R31 | 1 | 1 | A=OH, B=H | carbonyl | OH | H, H | H, H |
| 3601 | H, H | >N-R31 | 0 | 0 | A=H, B=H | carbonyl | H | H, H | H, H |
| 3602 | H, H | >N-R31 | 1 | 0 | A=H, B=H | carbonyl | H | H, H | H, H |
| 3603 | H, H | >N-R31 | 0 | 1 | A=H, B=H | carbonyl | H | H, H | H, H |

TABLE 1-3-2-continued

Structure of Compound: formula (1), Z = (1-3)

| Comp. No. | R01, R02 | Q | m | n | A, B | X, Y | R31 | R32, R33 | R34, R35 |
|---|---|---|---|---|---|---|---|---|---|
| 3604 | H, H | >N-R31 | 1 | 1 | A=H, B=H | carbonyl | H | H, H | H, H |
| 3605 | H, H | >N-R31 | 0 | 0 | A=H, B=H | carbonyl | Me | H, H | H, H |
| 3606 | H, H | >N-R31 | 1 | 0 | A=H, B=H | carbonyl | Me | H, H | H, H |
| 3607 | H, H | >N-R31 | 0 | 1 | A=H, B=H | carbonyl | Me | H, H | H, H |
| 3608 | H, H | >N-R31 | 1 | 1 | A=H, B=H | carbonyl | Me | H, H | H, H |
| 3609 | H, H | >N-R31 | 0 | 0 | A=H, B=H | carbonyl | Et | H, H | H, H |
| 3610 | H, H | >N-R31 | 1 | 0 | A=H, B=H | carbonyl | Et | H, H | H, H |
| 3611 | H, H | >N-R31 | 0 | 1 | A=H, B=H | carbonyl | Et | H, H | H, H |
| 3612 | H, H | >N-R31 | 1 | 1 | A=H, B=H | carbonyl | Et | H, H | H, H |

TABLE 1-4-1

Structure of Compound: formula (1), Z = (1-4)

| Comp. No. | R01, R02 | m | n | D, E | E, R41 | R41, R42 | R43, R44 | R45, R46 |
|---|---|---|---|---|---|---|---|---|
| 4101 | H, H | 0 | 0 | D=H, E=H | — | H, H | H, H | H, H |
| 4102 | H, H | 0 | 0 | D=H, E=H | — | H, H | methylene | H, H |
| 4103 | H, H | 0 | 0 | D=H, E=H | — | H, OH | methylene | H, H |
| 4104 | H, H | 0 | 0 | D=H, E=H | — | H, Me | methylene | H, H |
| 4105 | H, H | 0 | 0 | D=H, E=H | — | OH, Me | methylene | H, H |
| 4106 | H, H | 0 | 0 | D=H, E=H | — | Me, Me | methylene | H, H |
| 4107 | H, H | 0 | 0 | D=H, E=H | — | methylene | H, H | H, H |
| 4108 | H, H | 0 | 0 | D=H, E=H | — | methylene | H, OH | H, H |
| 4109 | H, H | 0 | 0 | D=H, E=H | — | methylene | H, Me | H, H |
| 4110 | H, H | 0 | 0 | D=H, E=H | — | methylene | OH, Me | H, H |
| 4111 | H, H | 0 | 0 | D=H, E=H | — | methylene | Me, Me | H, H |
| 4201 | H, H | 0 | 0 | double bond | — | H, OH | H, H | H, H |
| 4202 | H, H | 0 | 0 | double bond | — | H, OH | H, Me | H, H |
| 4203 | H, H | 0 | 0 | double bond | — | OH, Me | H, H | H, H |
| 4204 | H, H | 0 | 0 | double bond | — | OH, Me | H, Me | H, H |
| 4205 | H, H | 0 | 0 | double bond | — | methylene | H, H | H, H |
| 4301 | H, H | 0 | 0 | D=H | double bond | R42=H | H, H | H, H |
| 4302 | H, H | 0 | 0 | D=H | double bond | R42=H | H, OH | H, H |
| 4303 | H, H | 0 | 0 | D=H | double bond | R42=H | H, Me | H, H |
| 4304 | H, H | 0 | 0 | D=H | double bond | R42=H | OH, Me | H, H |
| 4305 | H, H | 0 | 0 | D=H | double bond | R42=H | Me, Me | H, H |
| 4306 | H, H | 0 | 0 | D=H | double bond | R42=OH | H, H | H, H |
| 4307 | H, H | 0 | 0 | D=H | double bond | R42=OH | H, OH | H, H |
| 4308 | H, H | 0 | 0 | D=H | double bond | R42=OH | H, Me | H, H |
| 4309 | H, H | 0 | 0 | D=H | double bond | R42=OH | OH, Me | H, H |
| 4310 | H, H | 0 | 0 | D=H | double bond | R42=OH | Me, Me | H, H |
| 4311 | H, H | 0 | 0 | D=H | double bond | R42=Me | H, H | H, H |
| 4312 | H, H | 0 | 0 | D=H | double bond | R42=Me | H, OH | H, H |
| 4313 | H, H | 0 | 0 | D=H | double bond | R42=Me | H, Me | H, H |
| 4314 | H, H | 0 | 0 | D=H | double bond | R42=Me | OH, Me | H, H |
| 4315 | H, H | 0 | 0 | D=H | double bond | R42=Me | Me, Me | H, H |

TABLE 1-4-2

Structure of Compound: formula (1), Z = (1-4)

| Comp. No. | R01, R02 | m | n | D, E | E, R41 | R41, R42 | R43, R44 | R45, R46 |
|---|---|---|---|---|---|---|---|---|
| 4401 | H, H | 0 | 1 | D=H, E=H | — | H, H | H, H | H, H |
| 4402 | H, H | 1 | 0 | D=H, E=H | — | H, H | H, H | H, H |
| 4403 | H, H | 1 | 1 | D=H, E=H | — | H, H | H, H | H, H |
| 4404 | H, H | 0 | 1 | D=H, E=H | — | H, H | methylene | H, H |
| 4405 | H, H | 1 | 0 | D=H, E=H | — | H, H | methylene | H, H |
| 4406 | H, H | 1 | 1 | D=H, E=H | — | H, H | methylene | H, H |
| 4407 | H, H | 0 | 1 | D=H, E=H | — | methylene | H, H | H, H |
| 4408 | H, H | 1 | 0 | D=H, E=H | — | methylene | H, H | H, H |
| 4409 | H, H | 1 | 1 | D=H, E=H | — | methylene | H, H | H, H |
| 4501 | H, H | 0 | 1 | double bond | — | H, OH | H, H | H, H |
| 4502 | H, H | 1 | 0 | double bond | — | H, OH | H, H | H, H |
| 4503 | H, H | 1 | 1 | double bond | — | H, OH | H, H | H, H |
| 4504 | H, H | 0 | 1 | double bond | — | OH, Me | H, H | H, H |
| 4505 | H, H | 1 | 0 | double bond | — | OH, Me | H, H | H, H |
| 4506 | H, H | 1 | 1 | double bond | — | OH, Me | H, H | H, H |
| 4601 | H, H | 0 | 1 | D=H | double bond | R42=H | H, H | H, H |

TABLE 1-4-2-continued

Structure of Compound: formula (1), Z = (1-4)

| Comp. No. | R01, R02 | m | n | D, E | E, R41 | R41, R42 | R43, R44 | R45, R46 |
|---|---|---|---|---|---|---|---|---|
| 4602 | H, H | 1 | 0 | D=H | double bond | R42=H | H, H | H, H |
| 4603 | H, H | 1 | 1 | D=H | double bond | R42=H | H, H | H, H |
| 4604 | H, H | 0 | 1 | D=H | double bond | R42=OH | H, H | H, H |
| 4605 | H, H | 1 | 0 | D=H | double bond | R42=OH | H, H | H, H |
| 4606 | H, H | 1 | 1 | D=H | double bond | R42=OH | H, H | H, H |

TABLE 1-5-1

Structure of Compound: formula (1), Z = (1-5)

| Comp. No. | R01, R02 | R52 | R51 | R511, R512 | R513 | R514, R515 |
|---|---|---|---|---|---|---|
| 5101 | H, H | Me | CONR511R512 | H, H | — | — |
| 5102 | H, H | Me | CONR511R512 | Me, Me | — | — |
| 5103 | H, H | Me | CONR511R512 | Et, Et | — | — |
| 5104 | H, H | Me | CONR511R512 | CH2 | — | — |
| 5105 | H, H | Me | CONR511R512 | (CH2)4 | — | — |
| 5106 | H, H | Me | CONR511R512 | (CH2)5 | — | — |
| 5107 | H, H | Me | COR513 | — | Me | — |
| 5108 | H, H | Me | COR513 | — | Et | — |
| 5109 | H, H | Me | C(OH)R514R515 | — | — | Me, Me |
| 5110 | H, H | Me | C(OH)R514R515 | — | — | Et, Et |
| 5201 | H, H | Et | CONR511R512 | H, H | — | — |
| 5202 | H, H | Et | CONR511R512 | Me, Me | — | — |
| 5203 | H, H | Et | CONR511R512 | Et, Et | — | — |
| 5204 | H, H | Et | CONR511R512 | CH2 | — | — |
| 5205 | H, H | Et | CONR511R512 | (CH2)4 | — | — |
| 5206 | H, H | Et | CONR511R512 | (CH2)5 | — | — |
| 5207 | H, H | Et | COR513 | — | Me | — |
| 5208 | H, H | Et | COR513 | — | Et | — |
| 5209 | H, H | Et | C(OH)R514R515 | — | — | Me, Me |
| 5210 | H, H | Et | C(OH)R514R515 | — | — | Et, Et |

In addition, preferable concrete examples of the compound expressed by the formula (3) used in the present invention include compounds whose $R_{01}$ and $R_{02}$ are hydrogen atoms, and $R_7$ is a methylene group, and compounds whose $R_{01}$ and $R_{02}$ are hydrogen atoms, and $R_7$ is a methyl group. Further, when a compound of the examples has an asymmetric carbon in its structure, the configuration of the carbon includes both (S)-configuration and (R)-configuration as far as it is not especially specified.

A vitamin $D_3$ derivative expressed by the above formula (1) can be produced by subjecting a compound expressed by the following formula (4) and an ene-yne compound expressed by the following formula (5) to a coupling reaction in the presence of a palladium catalyst, for example, as shown by Trost, et al. (J. Am. Chem. Soc., 114, 9836–9845 (1992)) (Scheme 1).

Scheme 1

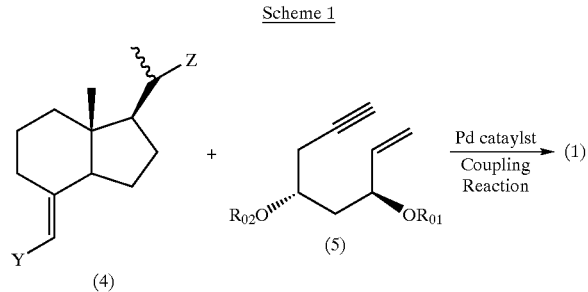

(in the above formulae (4) and (5), Z, $R_{01}$ and $R_{02}$ are defined in the same manner as in the above formula (1), and Y is an iodine atom or a bromine atom).

As the palladium catalyst in the coupling reaction, for example, a mixture of a 0- or 2-valent organic palladium compound and a trisubstituted phosphorus compound [molar ratio is (1:1) to (1:10)] is used. Examples of the palladium compound may include tetrakis(triphenylphosphine)palladium, tris(dibenzylideneacetone)palladium, tris(dibenzylideneacetone)palladium chloroform and palladium acetate. Further, examples of the trisubstituted phosphorus compound include triphenylphospline, tributylphosphine, etc. As the palladium catalyst of the combination of both the components, the combinations of tris(dibenzylideneacetone)palladium and triphenylphosphine, and tris(dibenzylideneacetone)palladium chloroform and triphenylphosphine [molar ratio of (1:1) to (1:10)] are preferable. Further, an organic palladium compound is used in the range of 1 to 100 mol %, preferably 5 to 30 mol % based on a compound expressed by the above formula (4). In order to produce an active palladium, a trisubstituted phosphorus compound is used in an amount of 1 to 10 equivalents to an organic palladium compound.

Herein, a compound expressed by the above formula (4) and an ene-yne compound expressed by the above formula (5) perform stoichiometrically equimolar reaction, but in order to surely complete the reaction, it is preferable that one component, which is commonly easier in availability, is used in a little excess than the other.

Examples of the organic solvent to be used in the coupling reaction include a hydrocarbon solvent such as hexane or toluene, an ether solvent such as tetrahydrofuran or dioxane, a water-soluble solvent such as N,N-dimethylformamide or acetonitrile, a mixed solvent of them, etc., and they are preferably used after sufficient deaeration. As the reaction temperature, a temperature ranging from room temperature to the boiling temperature of the solvent is commonly used. The reaction time depends on the reaction solvent and the reaction temperature used in the reaction, and it is commonly preferable that the reaction is continued until either the compound expressed by the above formula (4) or the ene-yne compound expressed by the above formula (5) disappears, when determined by using an analytical means such as thin layer chromatography. Further, it is preferable that the reaction is carried out, for example, in the presence of a base such as triethylamine or diisopropylamine for trapping hydrogen chloride, besides a palladium catalyst. As for the amount of the base used for the reaction, one equivalent or more based on a compound expressed by the above formula (4) is preferable, and optionally, the base may be used as the solvent at the same time.

A compound expressed by the above formula (4) (Z=(1-1); n=0), (Z=(1-2); n=0), (Z=(1-3)) or (Z=(1-4)) which is used as a raw material in the above-mentioned Scheme 1 can be produced from an aldehyde compound expressed by the following formula (6), for example, as shown in the following Scheme 2.

Scheme 2

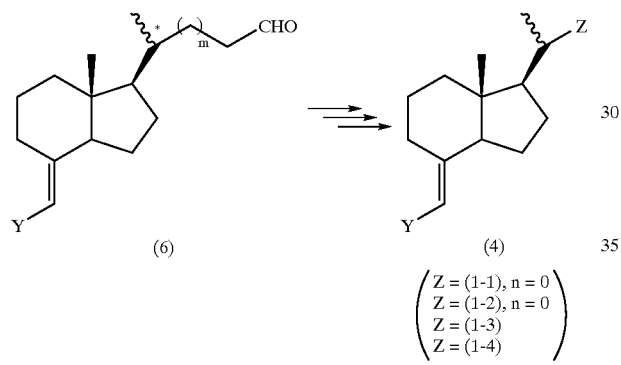

(in the above formula (6), m and Z are defined in the same manner as in the above formula (1), and Y is a bromine atom or an iodine atom).

The aldehyde compound (6) which is used in the reaction and in which the carbon atom marked with an asterisk * has (R)-configuration, and m is 0, 1 or 2 can be produced, for example, by combining known processes as shown the following in Schemes 3, 4 and 5.

Scheme 3

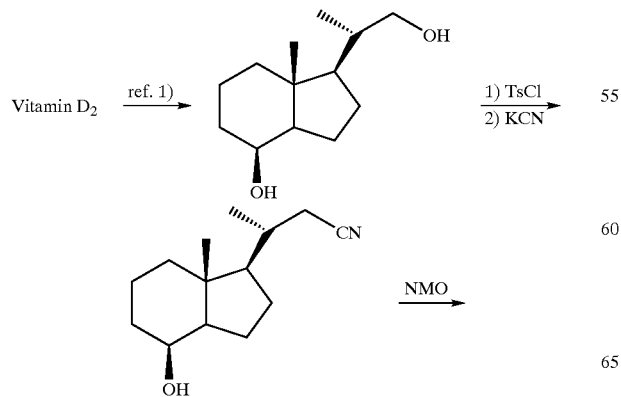

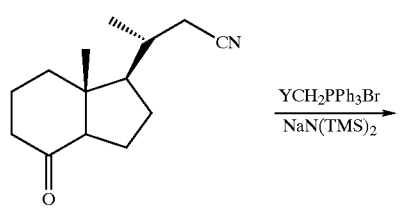

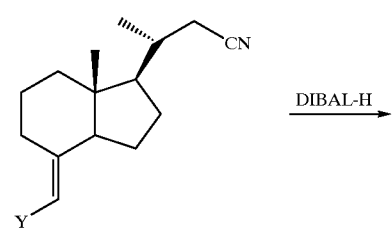

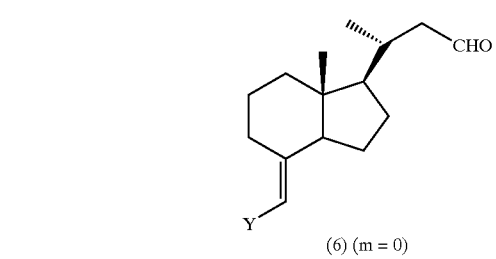

ref. 1) J. Org. Chem., 1986, 51, 1264.

Scheme 4

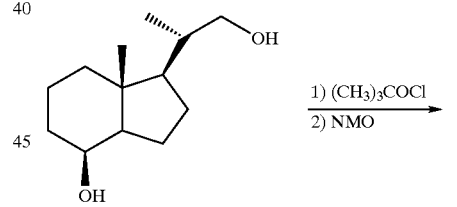

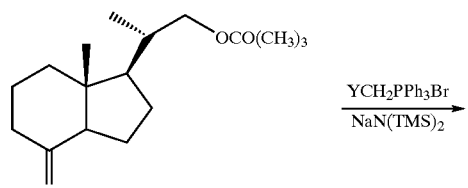

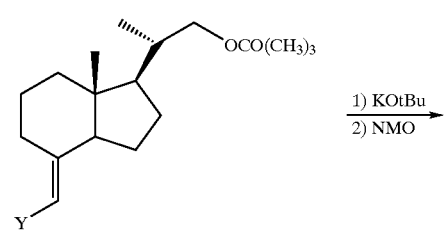

Scheme 5
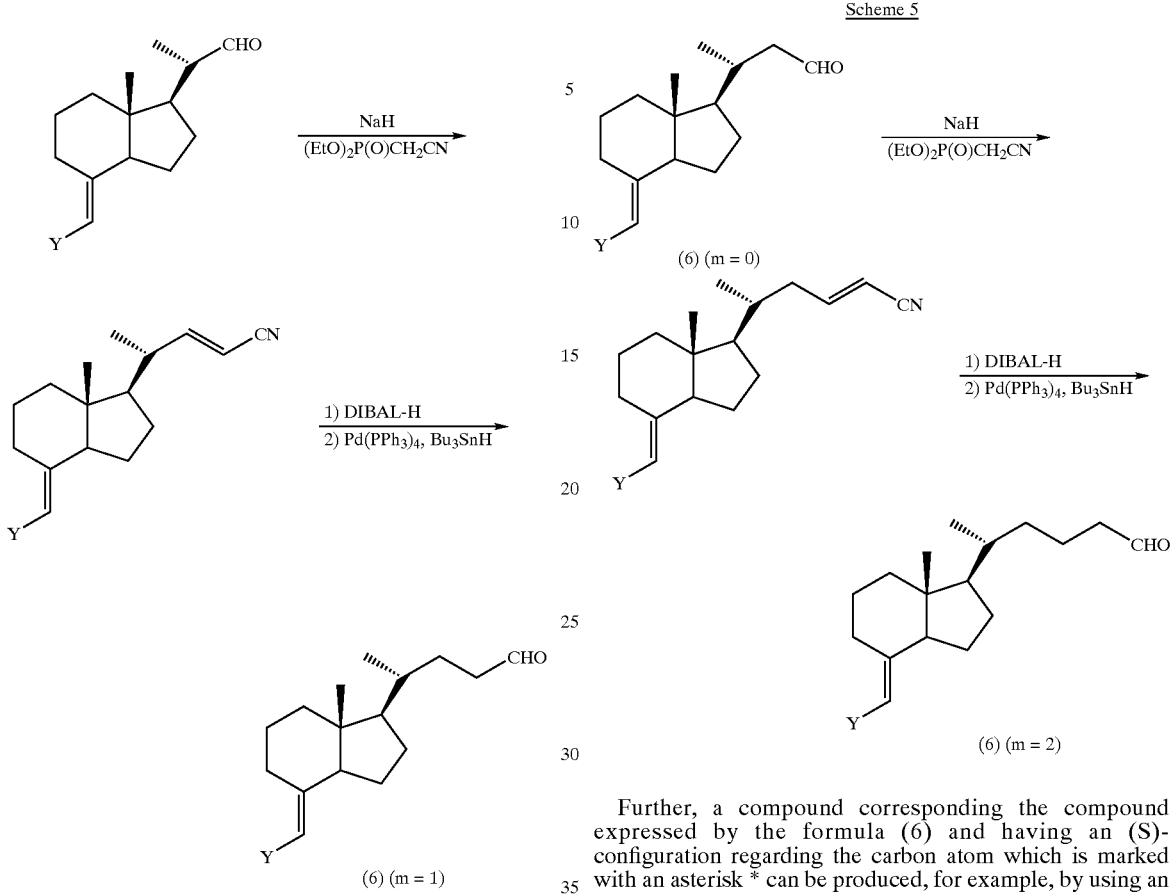
Further, a compound corresponding the compound expressed by the formula (6) and having an (S)-configuration regarding the carbon atom which is marked with an asterisk * can be produced, for example, by using an intermediate aldehyde obtained by Scheme 4 through a process shown by the following Scheme 6.
Scheme 6
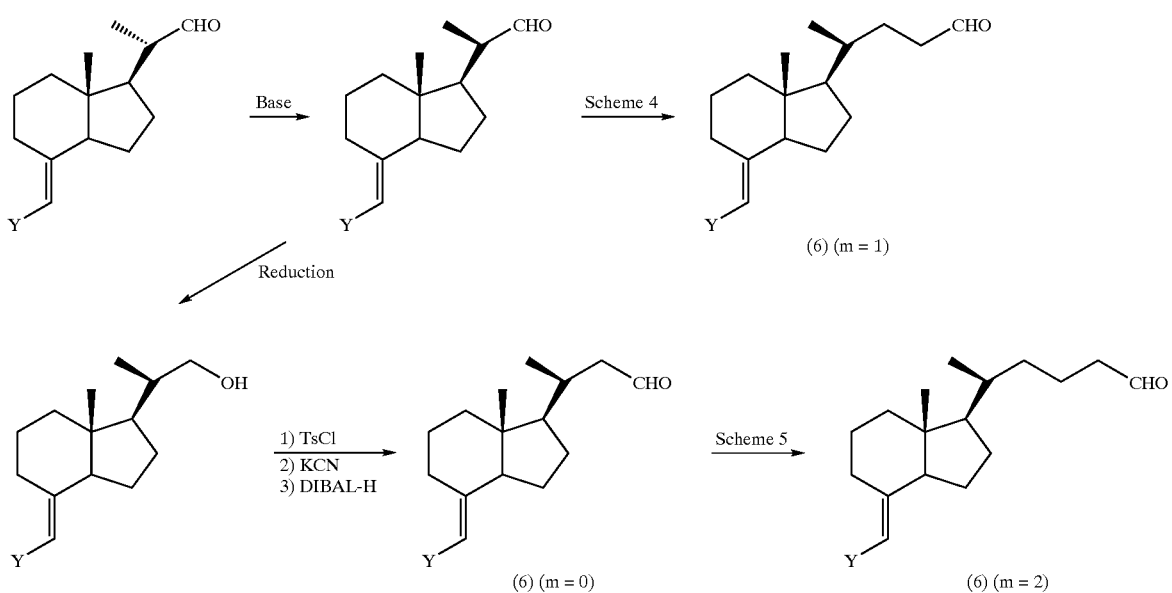

A compound expressed by the above formula (4) (Z=(1-1); X'=oxygen atom; n=0) can be produced, for example, through a process shown by the following Scheme 7 or 8 by using an aldehyde compound (6) obtained through the process shown above.
Scheme 7
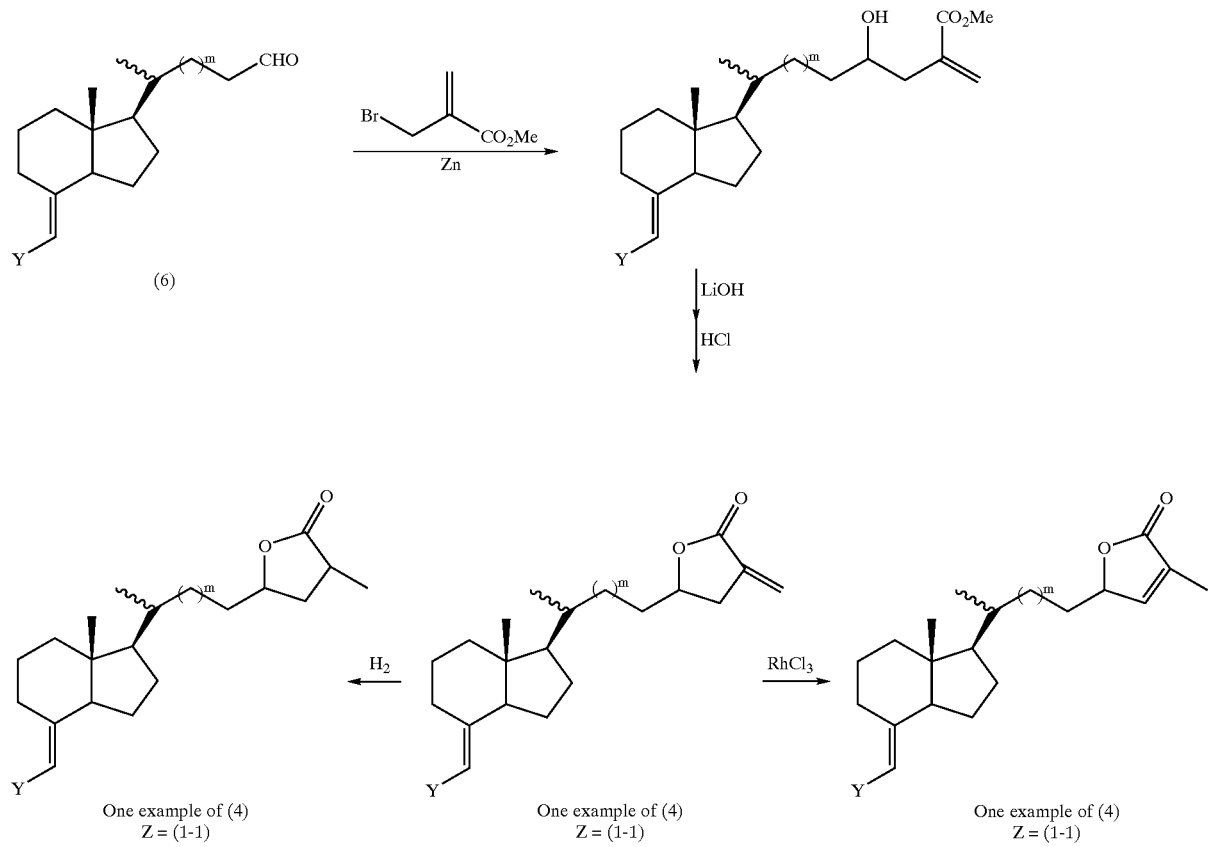
Scheme 8
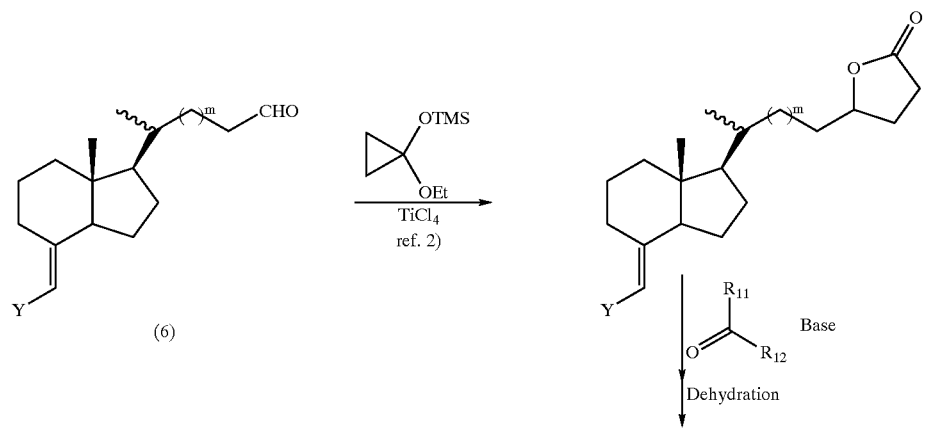

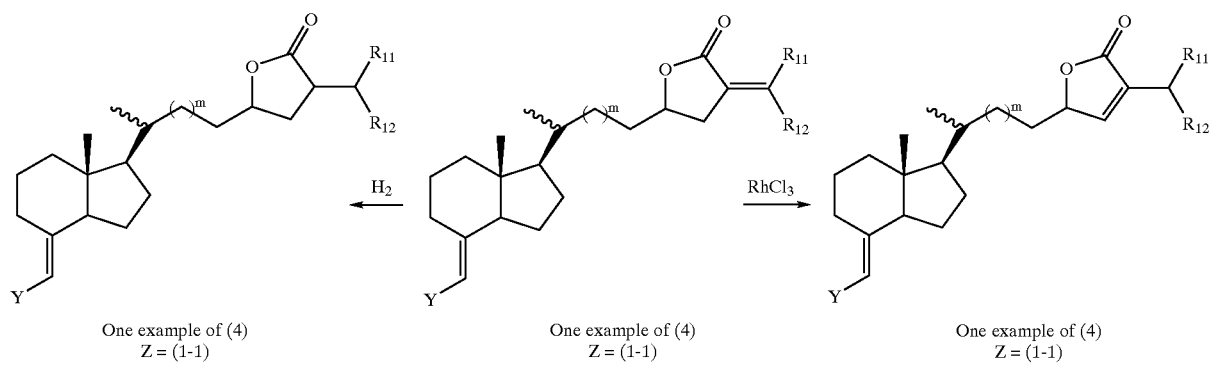
ref. 2) J. Am. Chem. Soc., 1977, 99, 7360.
Further, a compound expressed by the above formula (4) (Z=(1-1); X'=NH; n=0) can be produced, for example, through a process shown by the following Scheme 9 or 10.
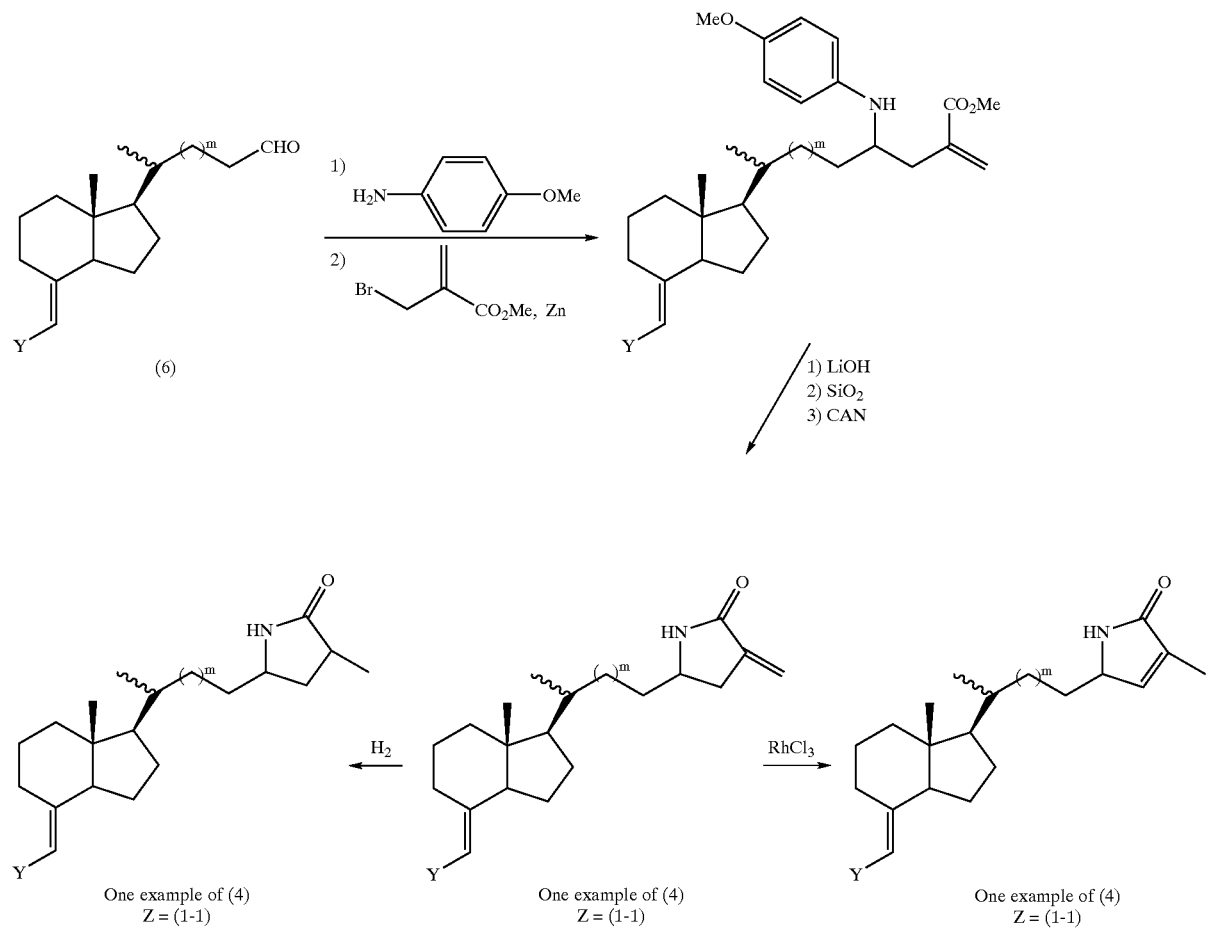
Scheme 9

Scheme 10
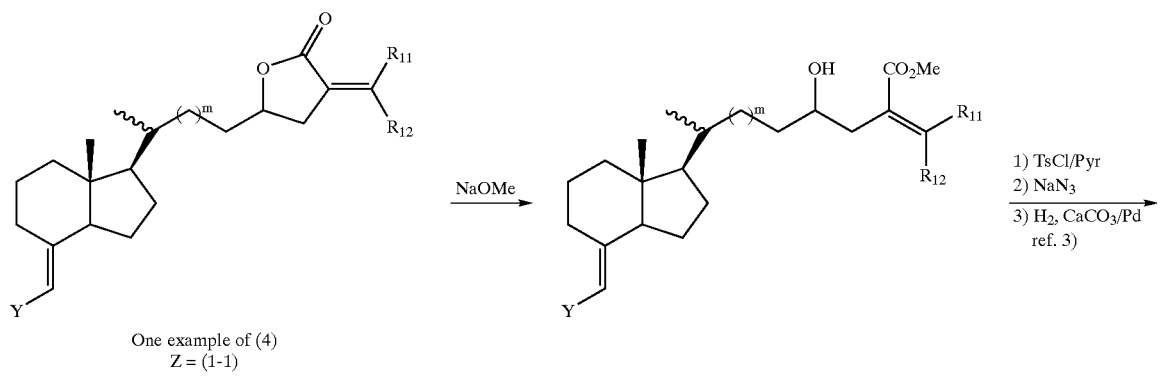
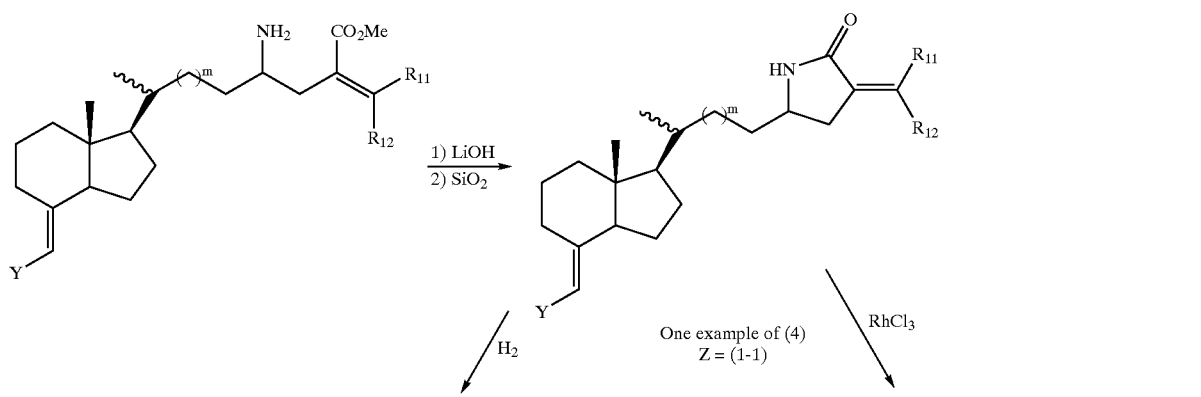
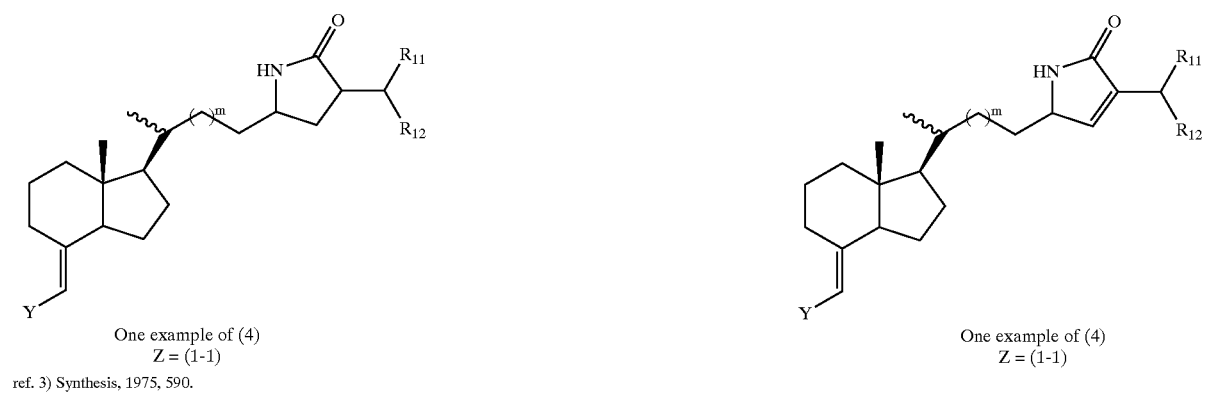
ref. 3) Synthesis, 1975, 590.
Further, a compound expressed by the above formula (4) (Z=(1-2); X'=oxygen atom; n=0) can be produced, for example, through a process shown by the following Scheme 11.

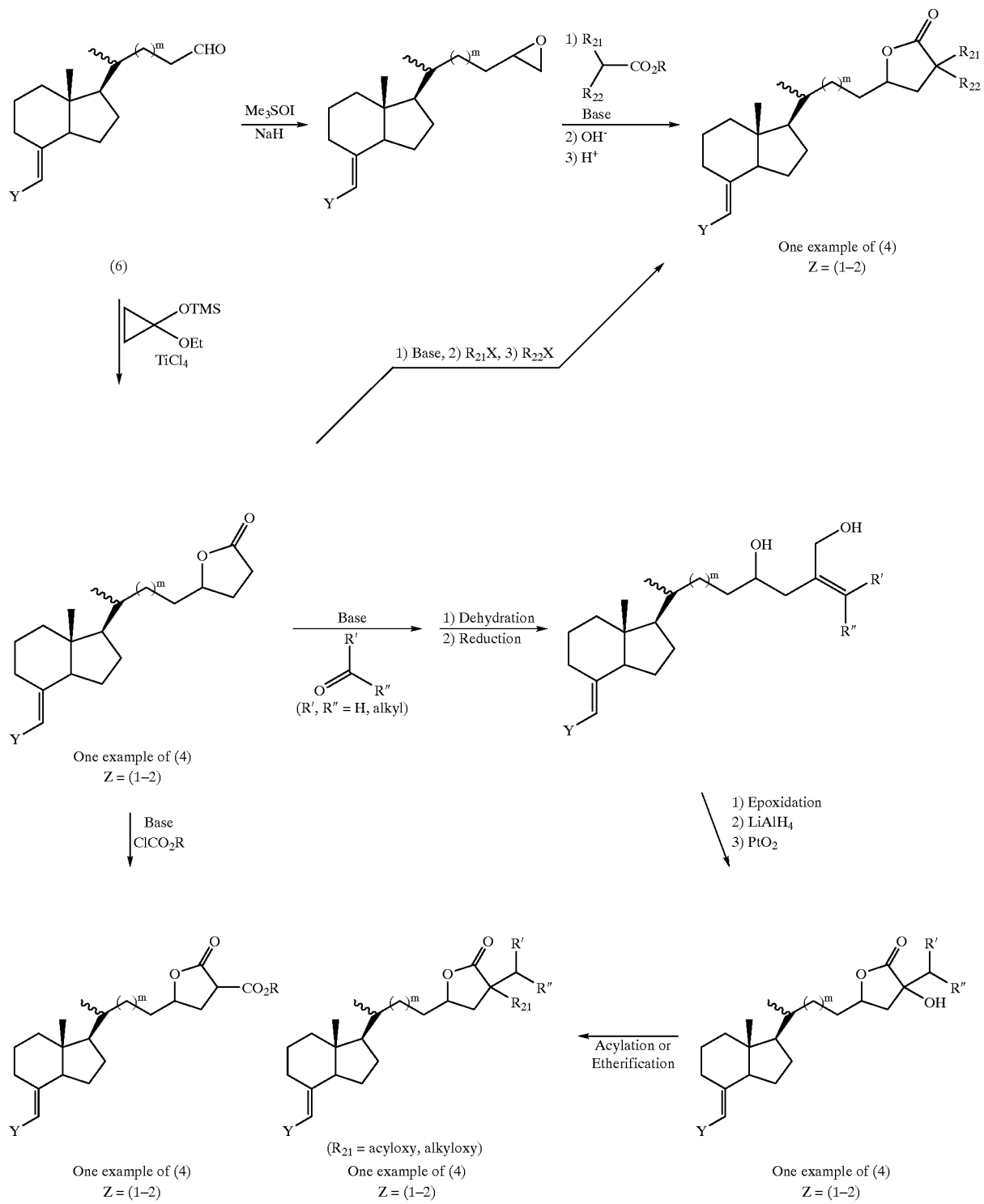
Scheme 11

Further, a compound expressed by the above formula (4) (Z=(1-2); X'=NH; n=0) can be produced, for example, through a process shown by the following Scheme 12.

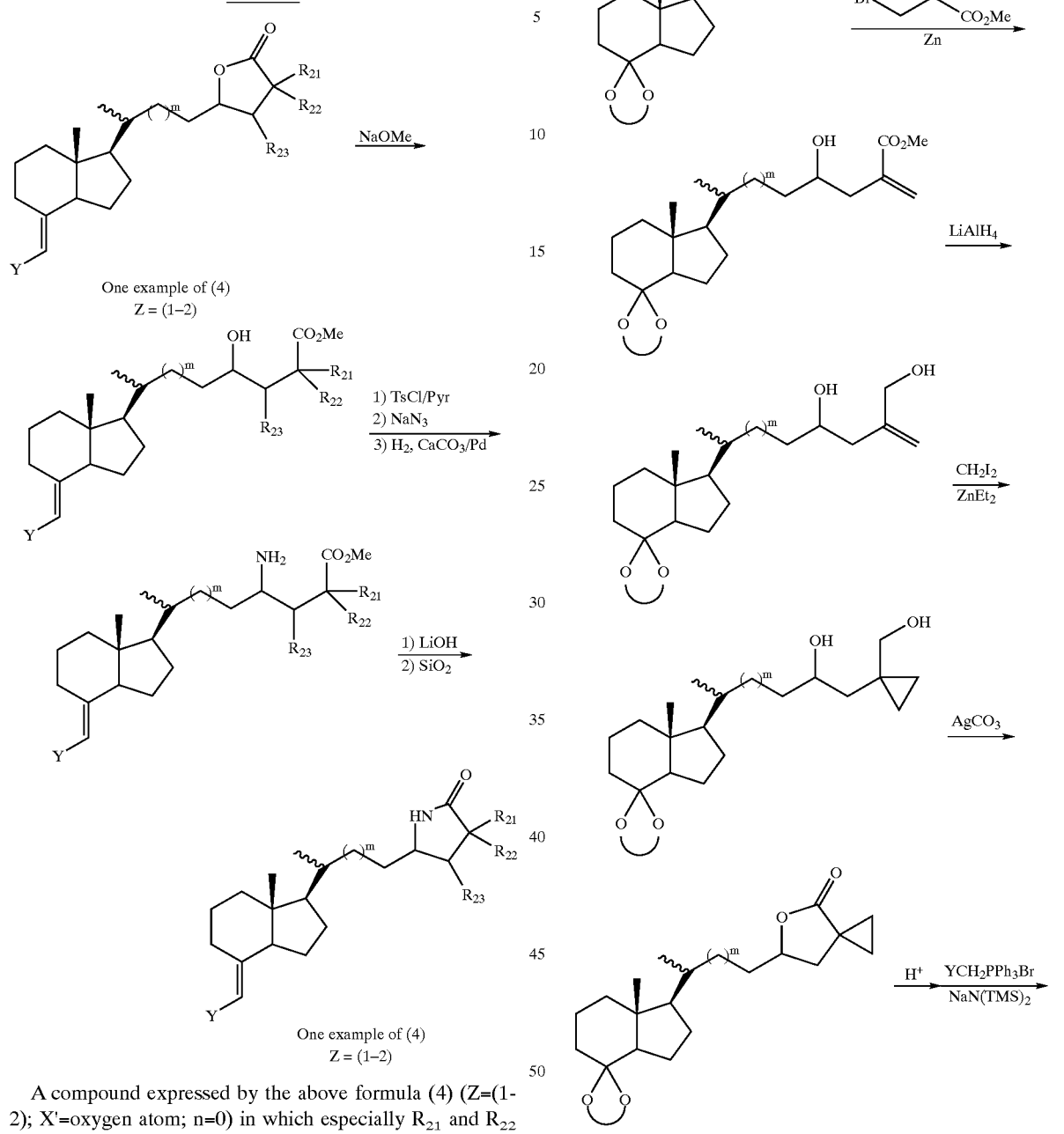

A compound expressed by the above formula (4) (Z=(1-2); X'=oxygen atom; n=0) in which especially $R_{21}$ and $R_{22}$ together form a cyclopropane ring in cooperation with the carbon atom to which they are bonded can be produced, for example, through a process shown by the following Scheme 13.

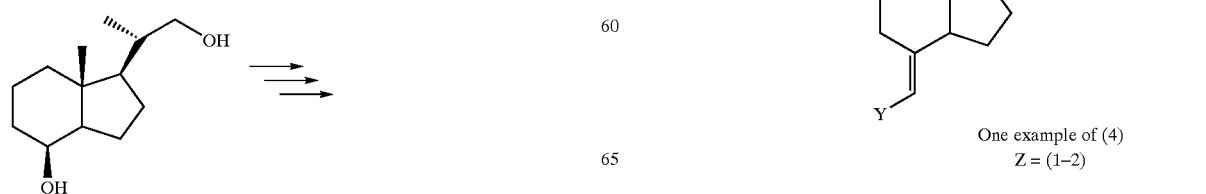

Further, a compound expressed by the above formula (4) (Z=(1-3) or (1-4)) can be derived from a compound (6) by using reactions shown by the below-mentioned Schemes 28 to 33.

A compound expressed by the above formula (4) (Z=(1-1); n=1 or 2) or (Z=(1-2); n=1 or 2), which is used as a raw material in the above Scheme 1, can be produced, for example, by deriving a compound (8) from a compound (7) through the protection of the hydroxy group and oxidation, obtaining a compound (9) through the construction of a ring structure by a below-mentioned process, subsequently deprotecting the protected hydroxyl group, and oxidizing and halomethylating the hydroxy group as shown in the following Scheme 14.

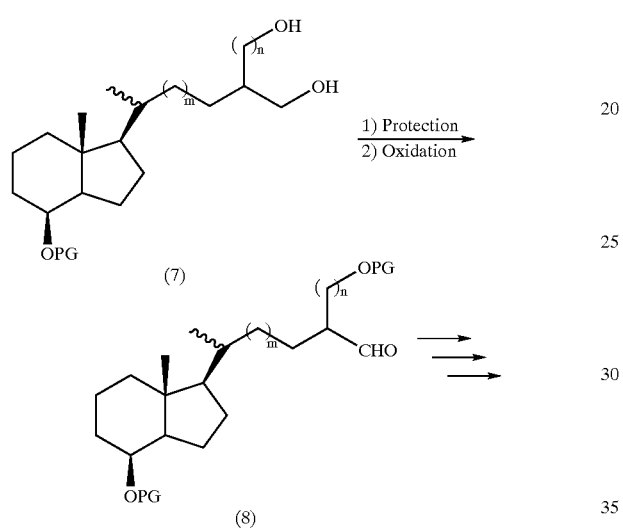

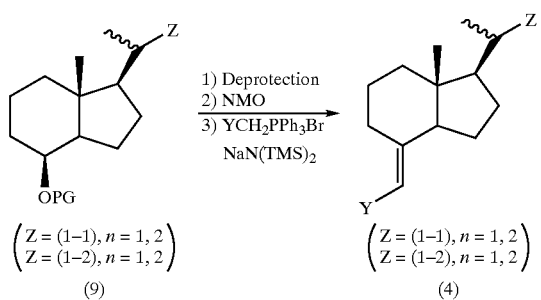

(in the above formulae (4), (7), (8) and (9), m and Z are defined in the same manner as in the above formula (1); Y is a bromine or iodine atom; n is an integer of 1 or 2; PG is a protecting group for a hydroxy group).

The compound (7) used in the Scheme 14 whose m is 1, 2 or 3 can be produced, for example, from an aldehyde compound (10) obtained from an intermediate of the above-mentioned Schemes 3 to 6 by combining known processes as shown in the following Scheme 15.

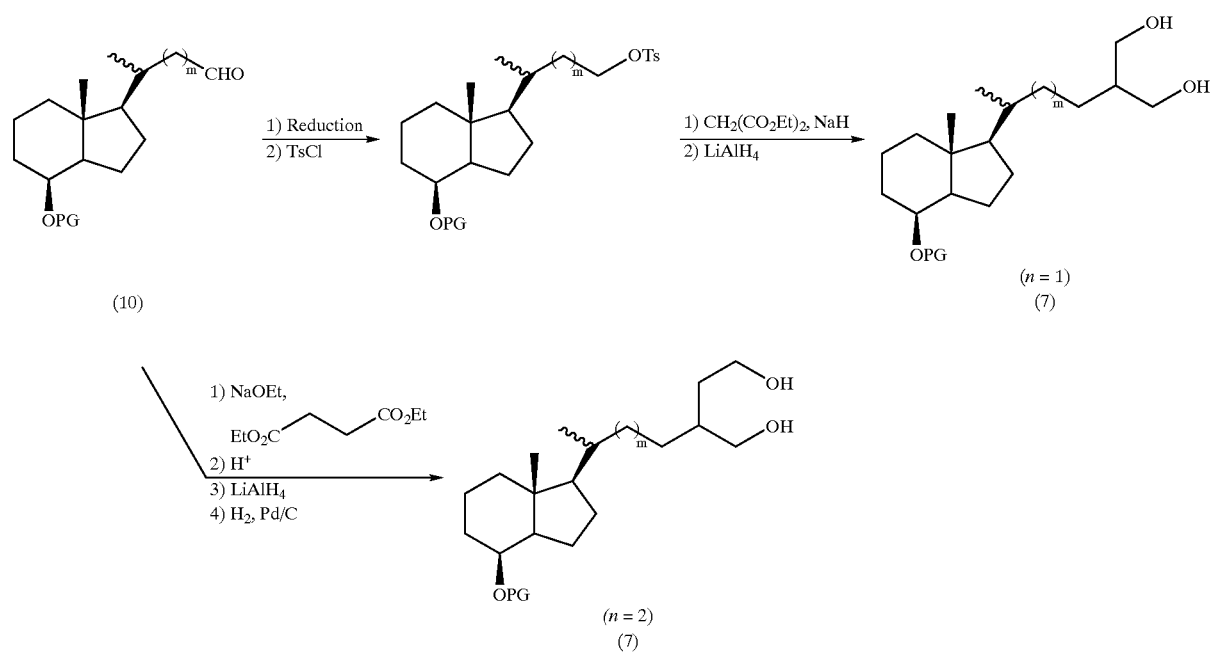

A compound expressed by the above formula (9) (Z=(1-1); X'=oxygen; n=1 or 2) can be produced, for example, by using a compound (8), which is obtained by the above-mentioned process, through the process shown by the following Scheme 16, 17 or 18.
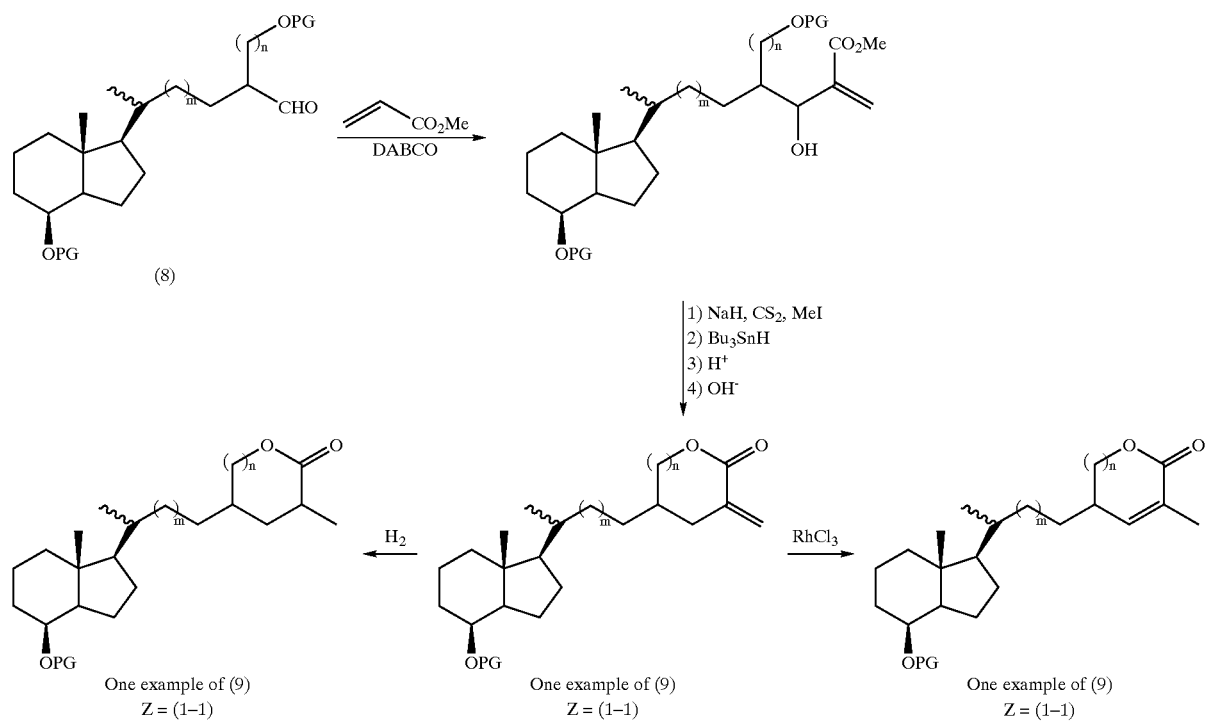
Scheme 16
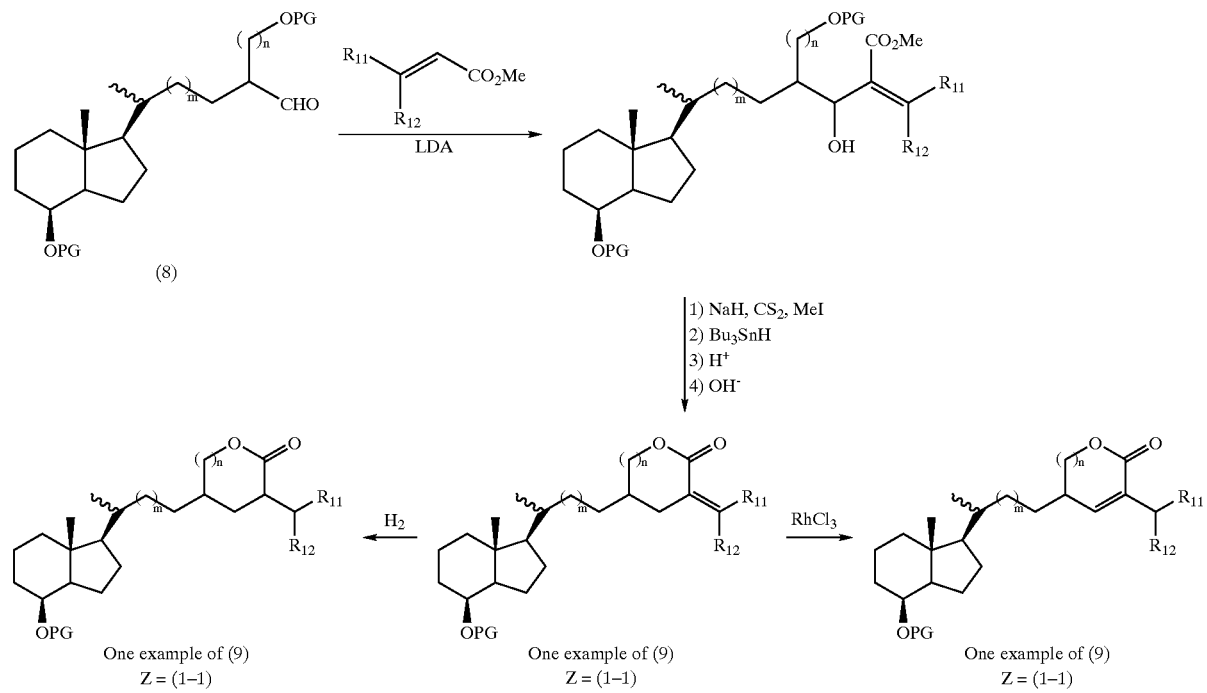
Scheme 17

Scheme 18
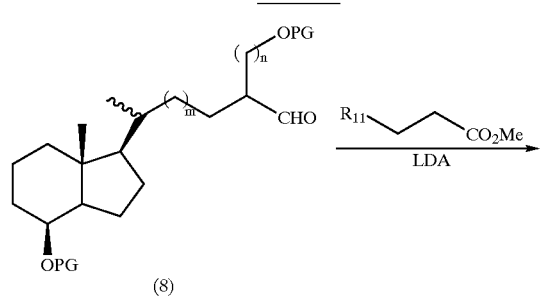
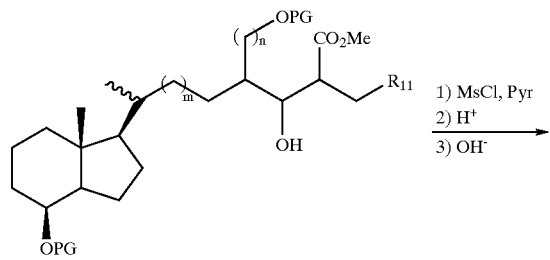
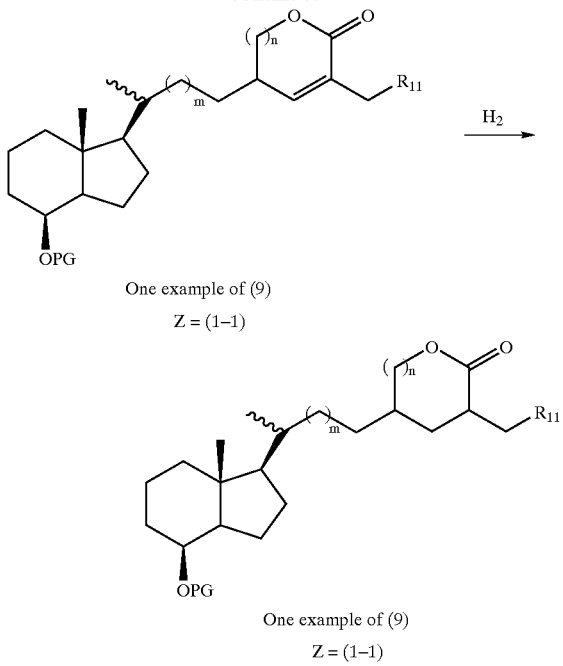
One example of (9)
Z = (1-1)
One example of (9)
Z = (1-1)
Further, a compound expressed by the above formula (4) (Z=(1-1); X'=NH; n=1 or 2) can be produced, for example, through the process shown by the following Scheme 19, 20 or 21.
Scheme 19
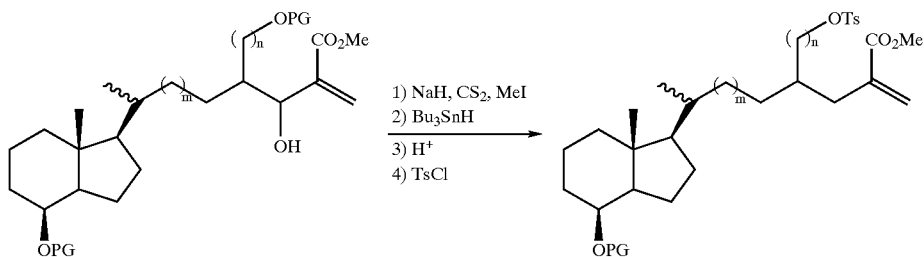
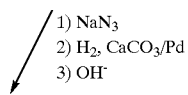
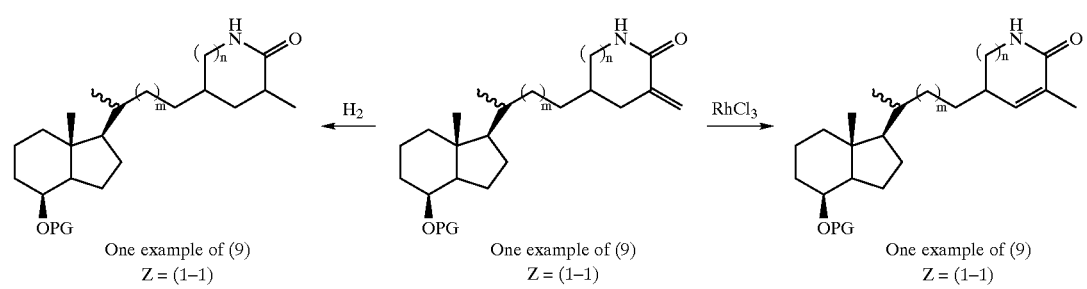
One example of (9)
Z = (1-1)
One example of (9)
Z = (1-1)
One example of (9)
Z = (1-1)

Scheme 20
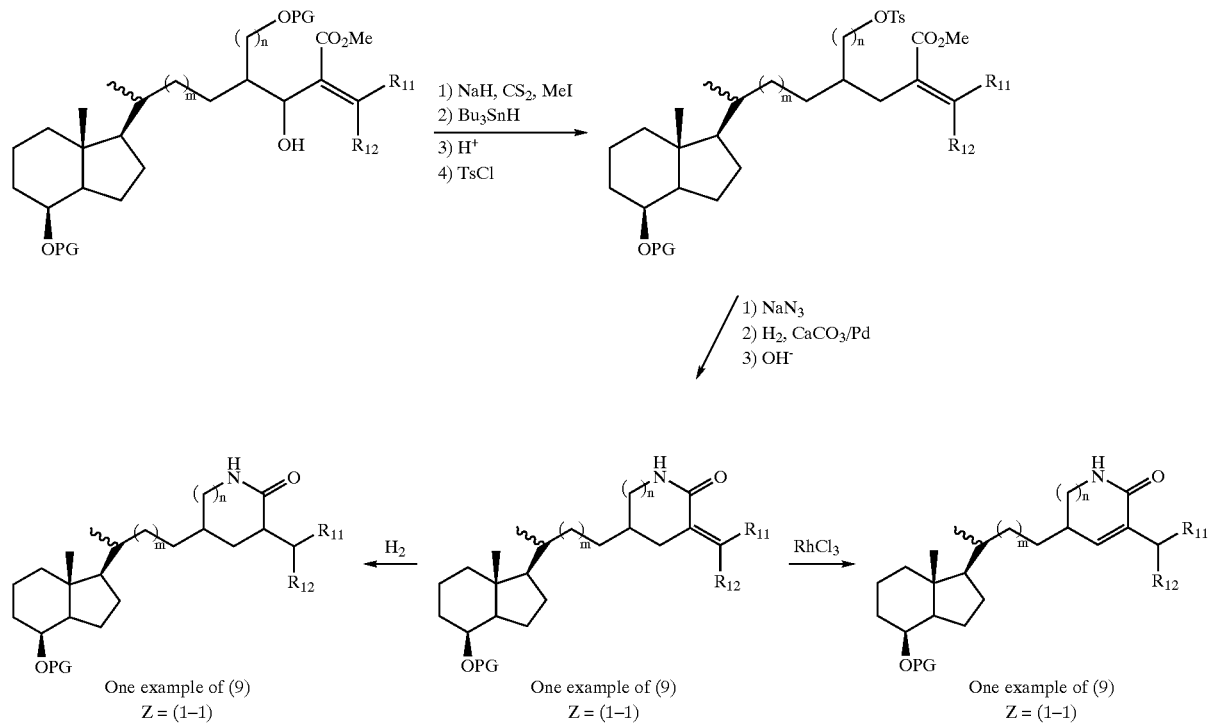
Scheme 21
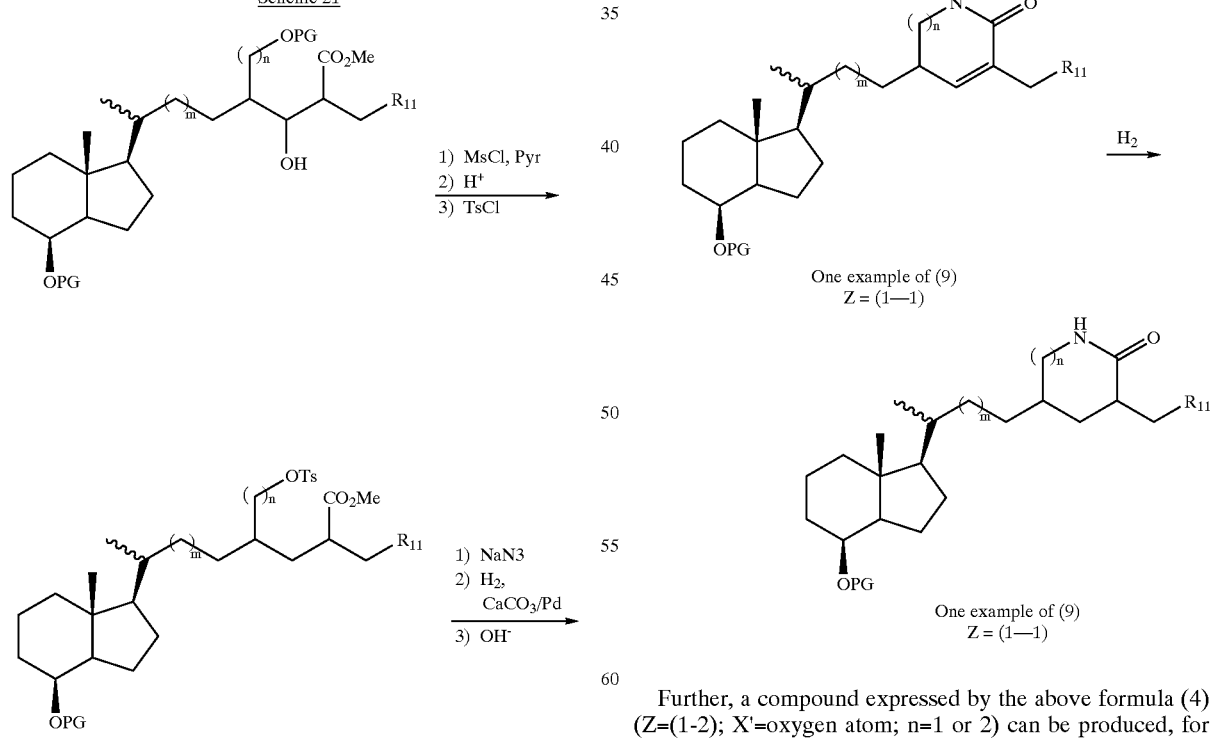
Further, a compound expressed by the above formula (4) (Z=(1-2); X'=oxygen atom; n=1 or 2) can be produced, for example, through the process shown by the following Scheme 22 or 23. Yet, the dioxolanone compound (11), which is used in Scheme 22, can be obtained by a known method (for example, Seebach, et al., Tetrahedron, 40, 1313 (1984)).

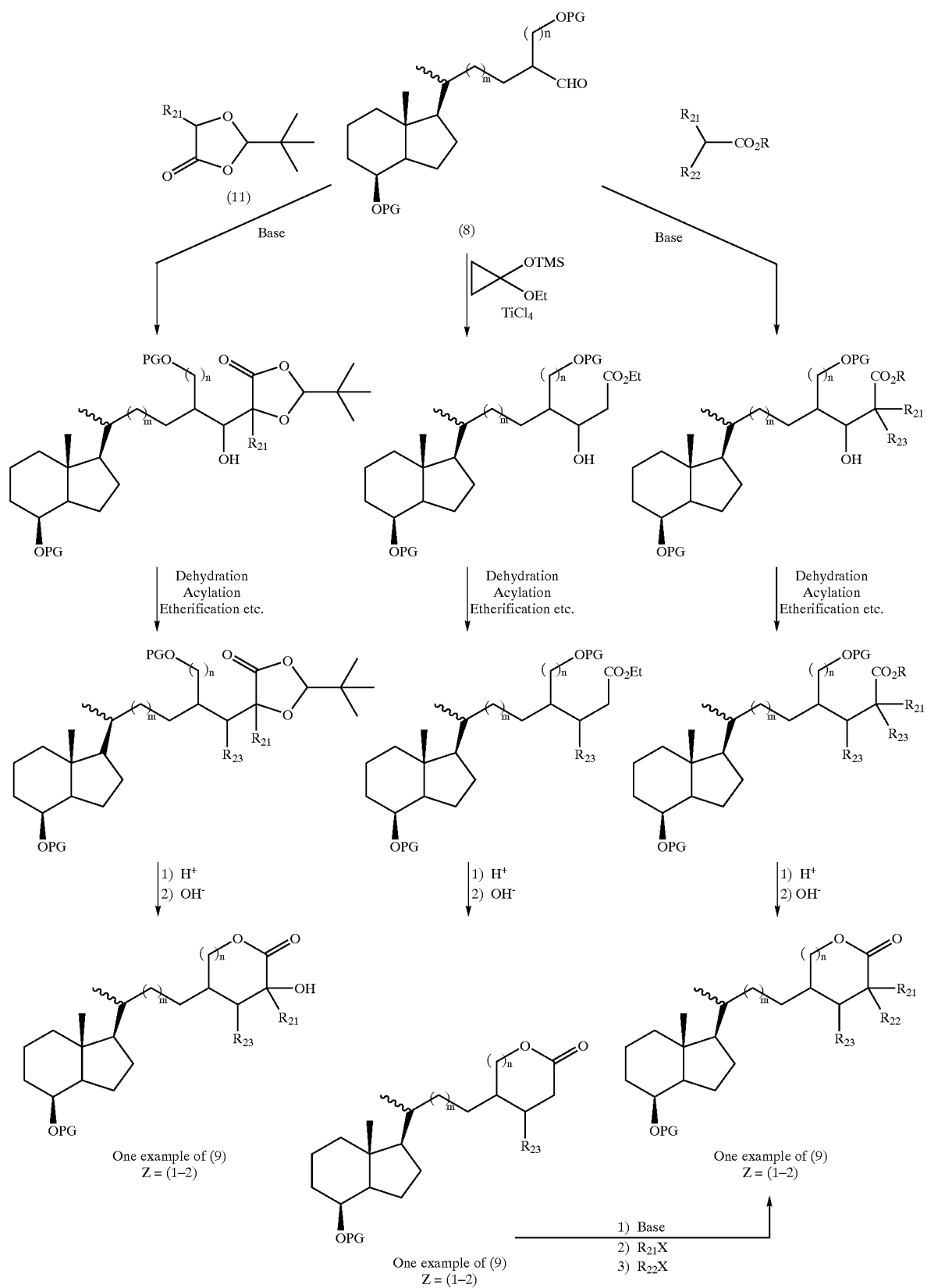

Scheme 23
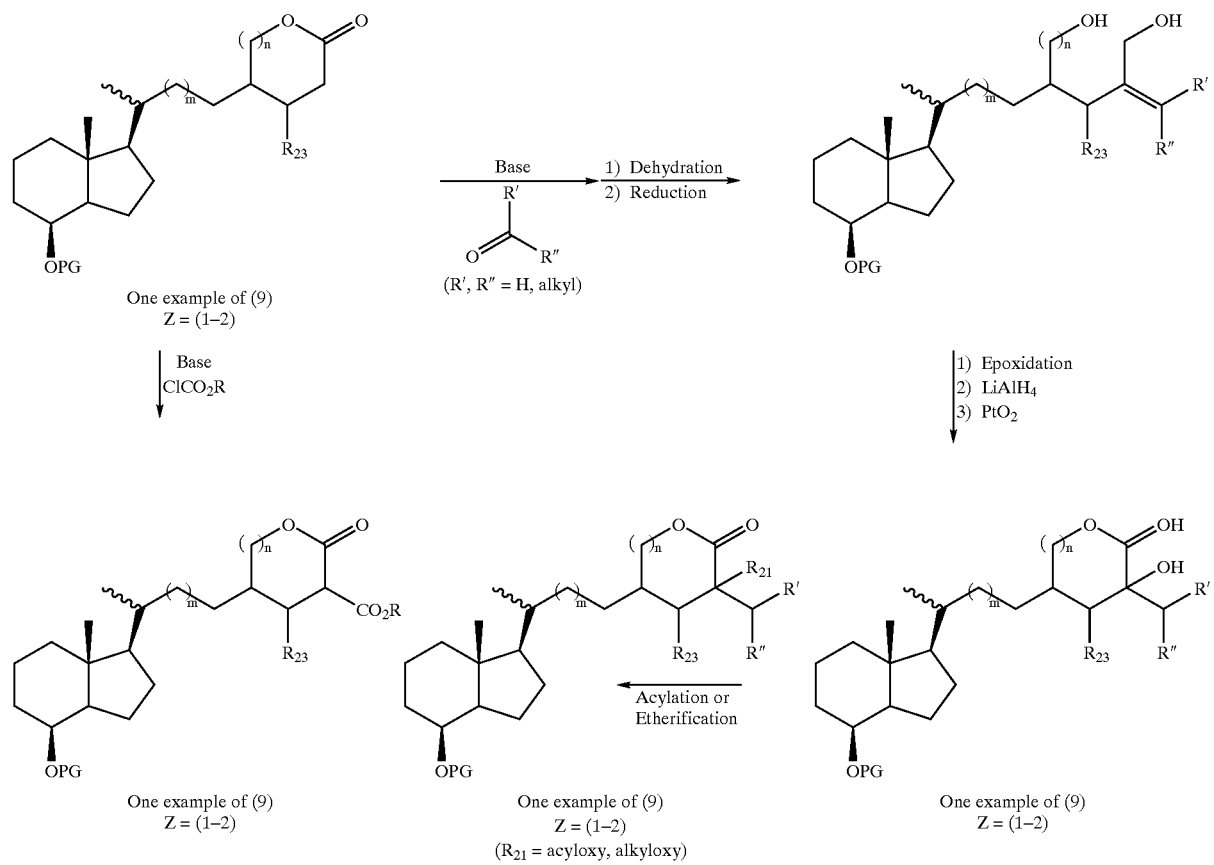
Further, a compound expressed by the above formula (4) (Z=(1-2); X'=NH; n=1 or 2) can be produced, for example, through the process shown by the following Scheme 24.
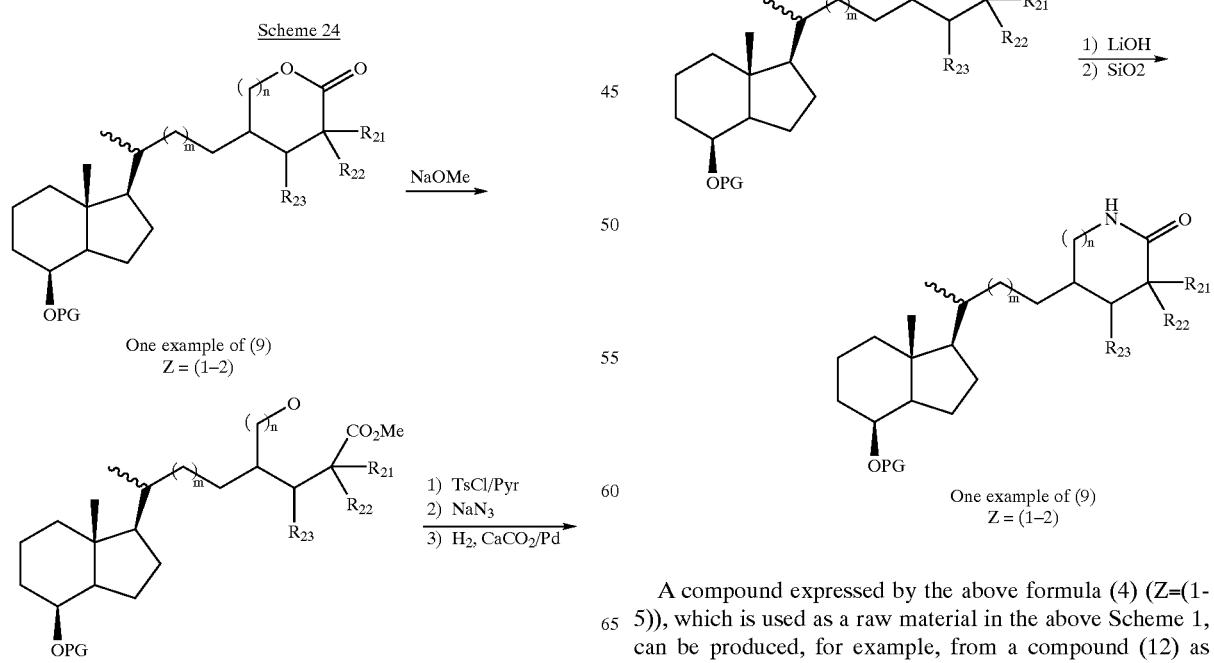
A compound expressed by the above formula (4) (Z=(1-5)), which is used as a raw material in the above Scheme 1, can be produced, for example, from a compound (12) as shown in the following Scheme 25.

Scheme 25
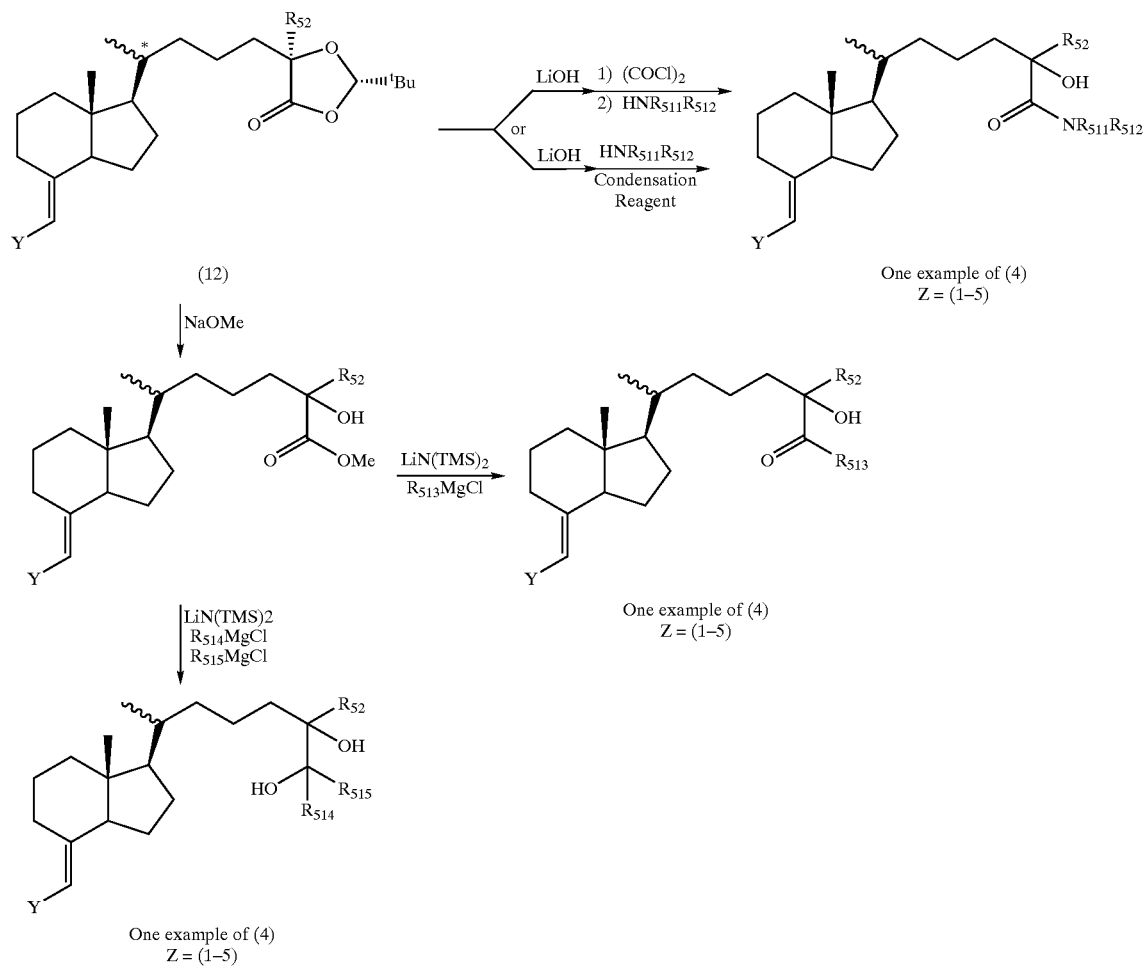
Further, a compound corresponding the compound (12), which is used in the preceding process and whose asymmetric center marked by an asterisk * has (R)-configuration, can be produced, for example, through combining known processes as shown in the following Scheme 26.
Scheme 26
-continued
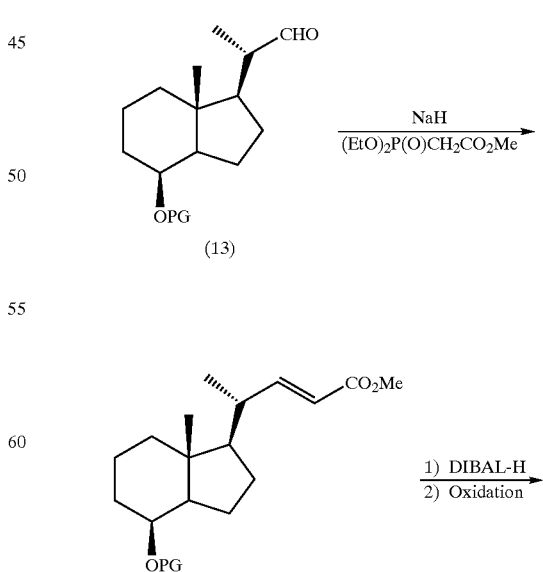

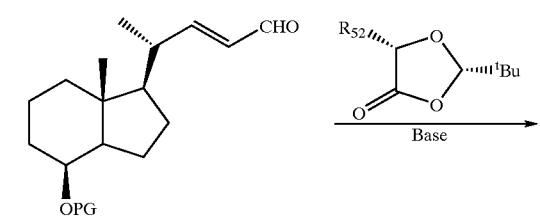

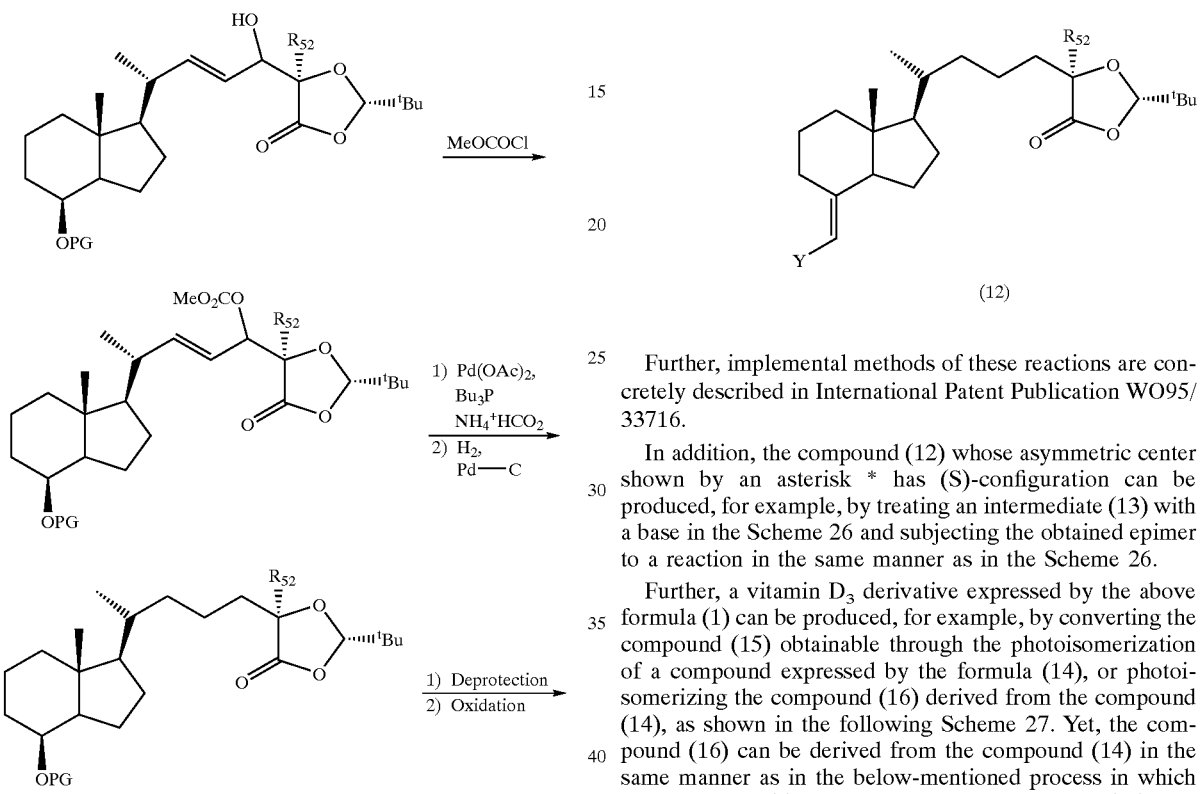

Further, implemental methods of these reactions are concretely described in International Patent Publication WO95/33716.

In addition, the compound (12) whose asymmetric center shown by an asterisk * has (S)-configuration can be produced, for example, by treating an intermediate (13) with a base in the Scheme 26 and subjecting the obtained epimer to a reaction in the same manner as in the Scheme 26.

Further, a vitamin $D_3$ derivative expressed by the above formula (1) can be produced, for example, by converting the compound (15) obtainable through the photoisomerization of a compound expressed by the formula (14), or photoisomerizing the compound (16) derived from the compound (14), as shown in the following Scheme 27. Yet, the compound (16) can be derived from the compound (14) in the same manner as in the below-mentioned process in which the compound (1) is derived from the compound (15).

Scheme 27

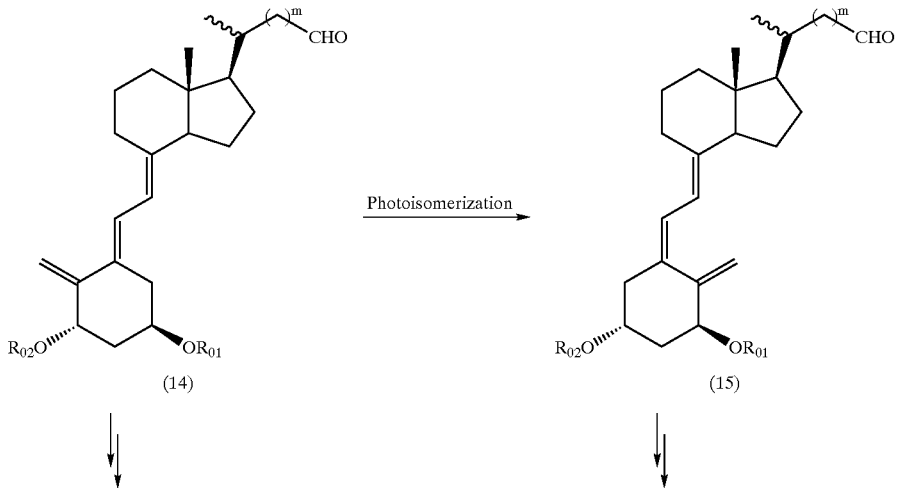

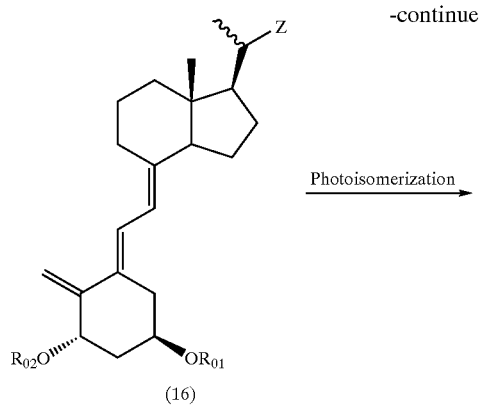
(16)
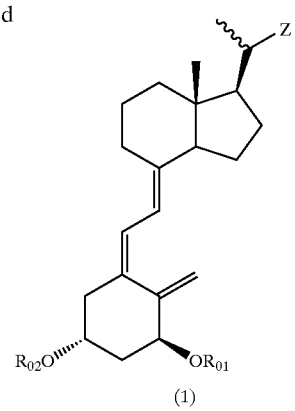
(1)
(in the formulae (1), (14), (15) and (16) of Scheme 27, m, Z, $R_{01}$ and $R_{02}$ are defined in the same manner as in the above formula (1)).
The compound (15) can be converted to the compound (1) (Z=(1-3)), for example, by subjecting the compound (15) and the compound (17) to aldol reaction and optionally further combining dehydration, reduction, hydrogenation and others as shown in the following Scheme 28.
Scheme 28
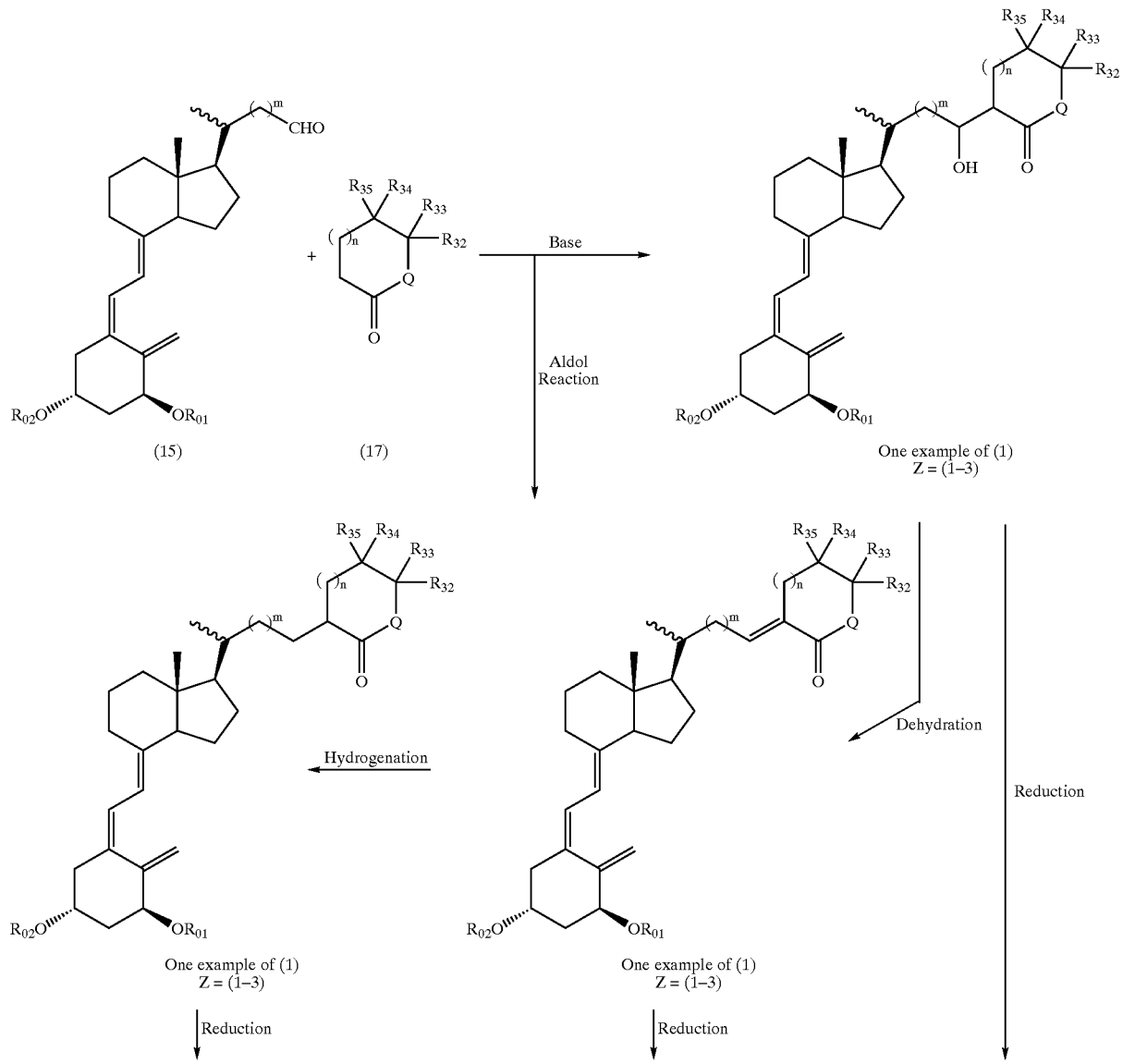

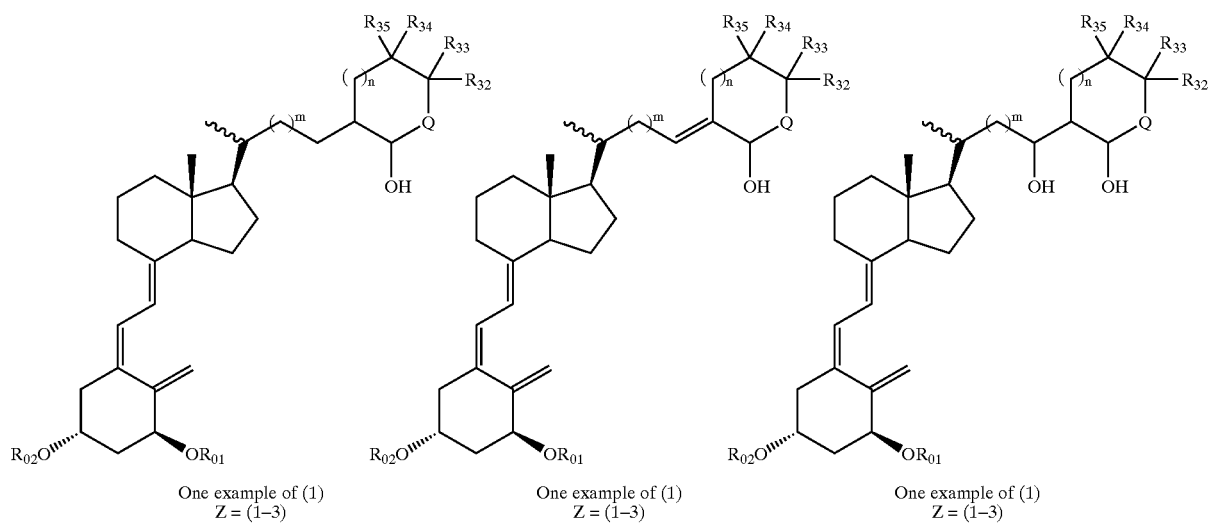

One example of (1)
Z = (1–3)

One example of (1)
Z = (1–3)

One example of (1)
Z = (1–3)

Examples of the base catalyst in the above aldol reaction can include an inorganic base catalyst such as potassium carbonate, lithium hydroxide, sodium hydroxide, potassium hydroxide, calcium hydroxide or sodium hydride, an organic base catalyst such as 1,8-diazabicyclo[5.4.0]undecene (DBU), and an organo metallic base catalyst such as lithium diisopropylamide, lithium hexamethyldisilylamide or sodium hexamethyldisilylamide. Among them, sodium hydroxide, potassium hydroxide, lithium diisopropylamide or lithium hexamethyldisilylamide can be cited as a preferable example. The amount of the base catalyst to be used is 0.1–10 equivalents, preferably 0.5–3 equivalents based on the aldehyde to be used as a raw material. Further, an additive for stimulating the reaction may be added to the reaction system as required. Here, an aldehyde expressed by the above formula (15) carries out stoichiometrically equimolar reaction with a compound expressed by the above formula (17), but it is preferable that one component, which is easier in availability is used in a little excess than the other for certainly completing the reaction.

Examples of the organic solvent to be used in the aldol reaction include an alcoholic solvent such as methanol or ethanol, a halogen containing solvent such as methylene chloride, chloroform or carbon tetrachloride, a hydrocarbon solvent such as hexane or toluene, an ether solvent such as tetrahydrofuran or dioxane, a water-soluble solvent such as N,N-dimethylformamide or acetonitrile, a mixed solvent of them, etc. The solvent can be selected considering the solubilities and the reactivities of the compounds. As for reaction temperature, a temperature in the range from −78° C. to the boiling point of the solvent is generally used. A reaction time depends on the base catalyst, the reaction solvent and the reaction temperature used. It is commonly preferable that the reaction is continued until either the compound expressed by the above formula (17) or the aldehyde expressed by the above formula (15) disappears when determined by using an analytical means such as thin layer chromatography.

Examples of the dehydrating agent to be used in the dehydration reaction include an acid such as potassium hydrogensulfate, oxalic acid, p-toluenesulfonic acid, iodine or anhydrous copper sulfate, a halogenating agent such as thionyl chloride or phosphoric acid chloride, a sulfonating agent such as methanesulfonyl chloride, etc. The agent is used in an amount of 1–10 equivalents, preferably 1–5 equivalents based on the raw material.

In the reductive reaction, sodium borohydride-cesium chloride, diisobutylaluminum hydride (DIBAH), 9-borabicyclo[3.3.1]nonane (9-BBN), lithium n-butylborohydride, K-Selectride®, tri-isobutylaluminium, etc., may be used.

In the hydrogenation, sodium borohydride, $Na_2S_2O_4$, NaHTe, tri-n-butyltin hydride, K-Selectride® or sodium aluminum hydride-cuprous chloride, or Birch reduction, etc., is applicable.

Further, the compound (15) can be converted to the compound (1) (Z=(1-3); Q is >C(—F)—$R_{31}$) by carrying out aldol reaction between the compound (15) and a compound (18), and subsequently subjecting the obtained ketone to silylation-enolation followed by fluorization as shown in the following Scheme 29.

Scheme 29
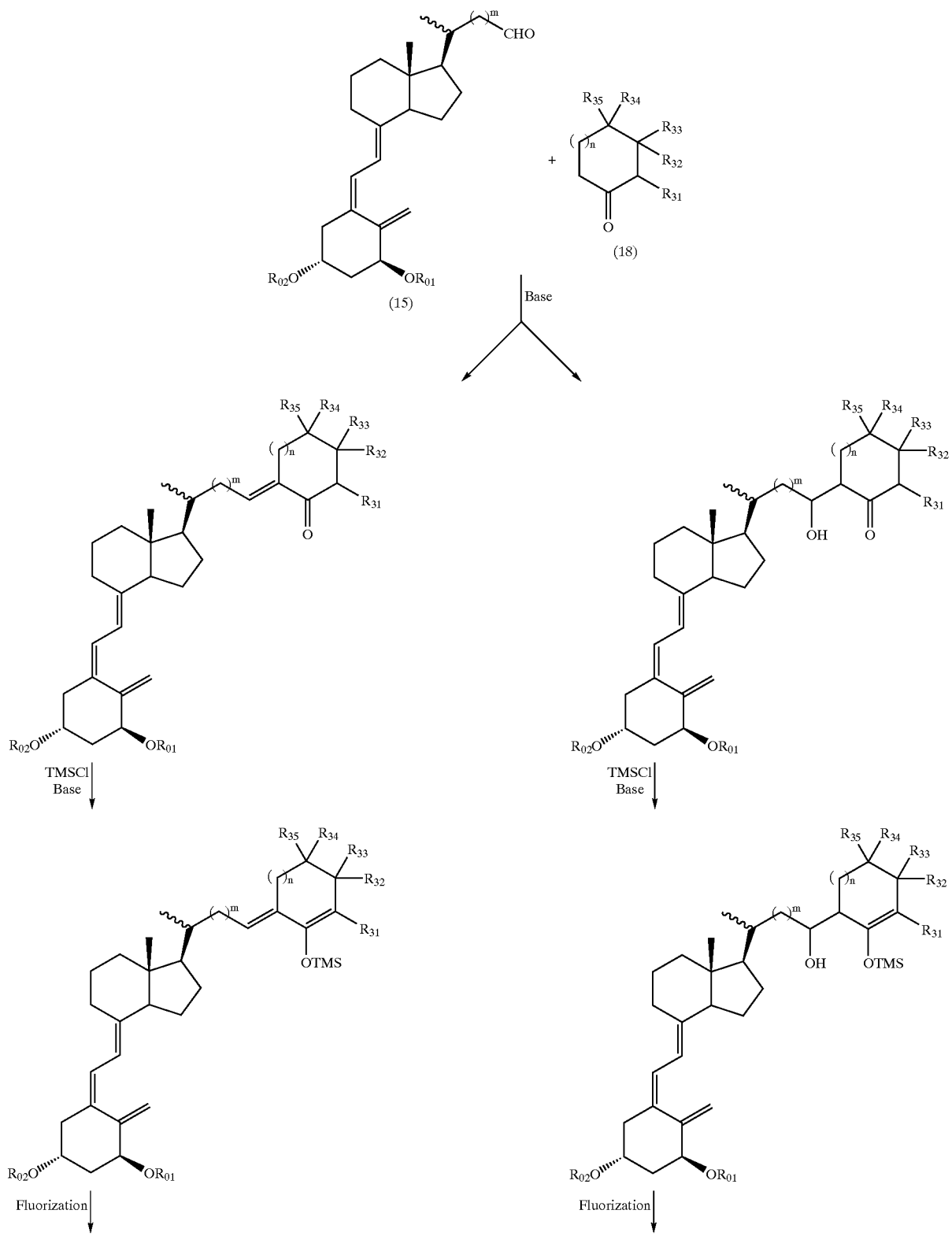

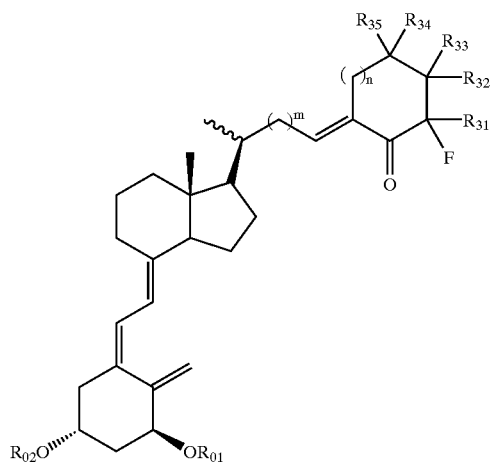

One example of (1)
Z = (1–3), Q = >C(-F)-R31

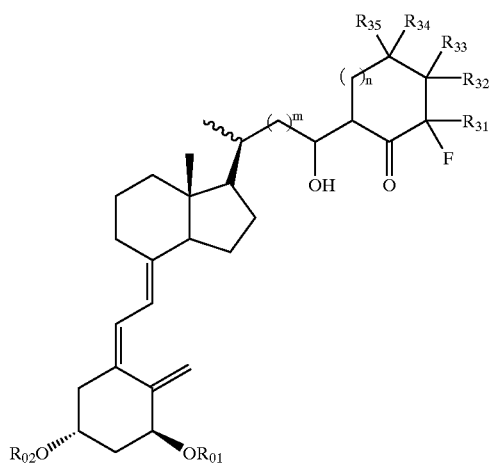

One example of (1)
Z = (1–3), Q = >C(-F)-R31

Examples of a fluorinating agent used in the fluorination include N-fluoropyridinium triflate, N-fluoropyridinium trifluoromethanesulfonate, N-fluoro-2,4,6-trimethylpyridinium triflate, N-fluoro-3,5-dichloropyridinium triflate, N-fluoro-2,6-dichloropyridinium triflate, N-fluoro-4,6-dimethylpyridinium-2-sulfonate, N-fluoro-4-methylpyridinium-2-sulfonate, N-fluoro-6-(trifluoromethyl)pyridinium-2-sulfonate, N-fluoro-4,6-bis(trifluoromethyl)pyridinium-2-sulfonate, $CsSO_4F$, $XeF_2$, $CF_3OF$, $CH_3CO_2F$, etc.

The compound (15) can be converted to the compound (1) (Z=(1-4); $R_{41}$=D=E=hydrogen atom), for example, by subjecting the compound (15) to reduction, halogenation, halogen-metal exchange reaction, metal-metal exchange reaction and 1,4-addition as shown in the following Scheme 30.

Scheme 30

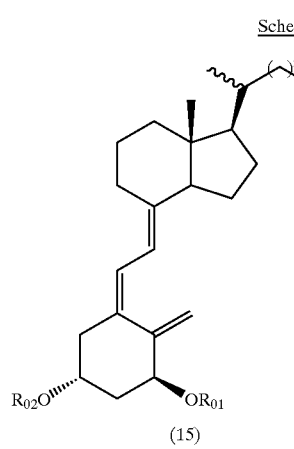

(15)

1) Reduction
2) Halogenation
3) Halogen-metal exchange
4) Metal-metal exchange

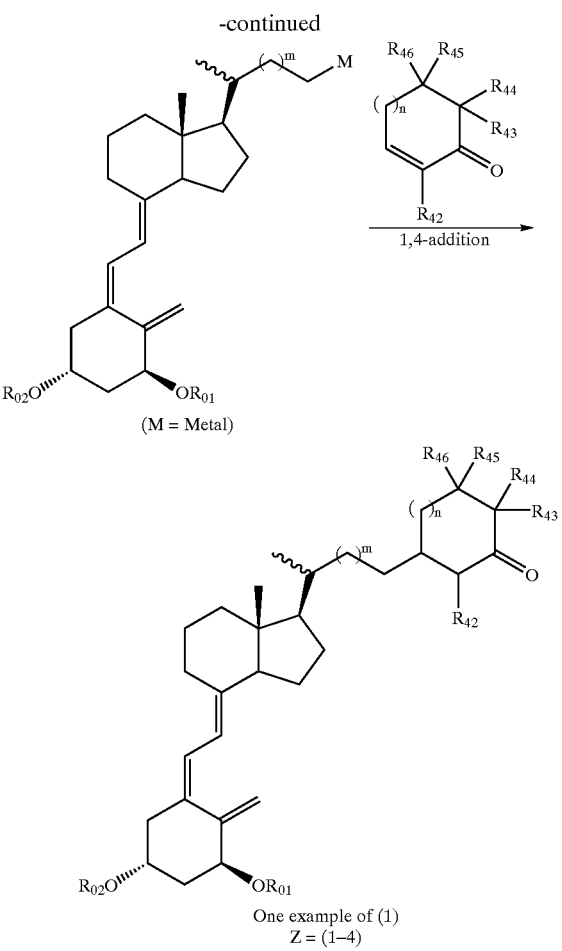

(M = Metal)

1,4-addition

One example of (1)
Z = (1–4)

The above reduction can be carried out, for example, by reducing the compound with a hydride reagent such as sodium borohydride or lithium aluminumhydride.

The halogenation can be carried out, for example, with the combination of carbon tetrabromide or carbon tetrachloride, and triphenylphosphine.

Examples of the metal reagent used in the above-mentioned metal-halogen exchange reaction include butyllithium, magnesium metal, samarium diiodide, etc., and it is used in an amount of 1–5 equivalents based on the raw material.

The metal-metal exchange reaction is optionally carried out successively after the metal-halide exchange reaction, and the metal-metal exchange reaction is performed, for example, by using copper iodide, copper bromide, an adequate complex of the copper halide, copper cyanide or the like.

In the 1,4-addition, an additive can be used, and the additive is, for example, a silylating agent such as trimethylsilyl triflate or chlorotrimethylsilane, a ligating compound such as hexamethylphosphoric triamide (HMPA) or triphenylphosphine, or a combination of these compounds. Especially, the combination of chlorotrimethylsilane and HMPA is cited as a preferable additive.

The metal-halogen exchange reaction, metal-metal exchange reaction and 1,4-addition in the above Scheme 30 are preferably carried out successively in a single reaction system without performing after-treatments.

Out of the compounds (1) (Z=(1-4)) obtained in the above Scheme 30, a compound in which $R_{42}$ is a hydrogen atom and/or $R_{43}$ and $R_{44}$ are both hydrogen atoms can be converted to a compound (1) (Z=(1-4)) having a methylene group at the α-position to the carbonyl group by further methylenating it in one step or two steps as shown in the following Scheme 31.

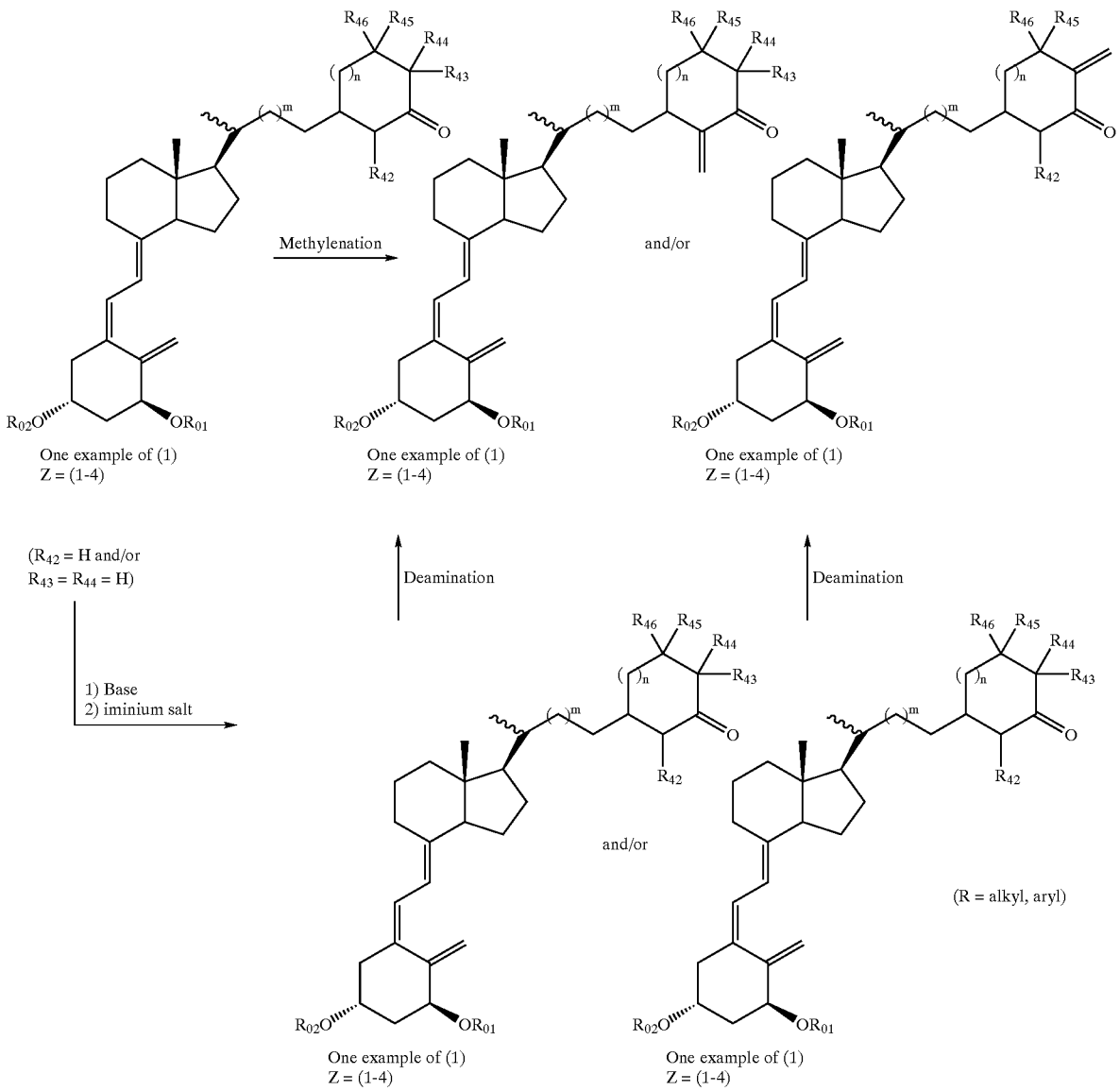

Scheme 31

In order to carry out the methylenation in one step, for example, N-methylanilinium trifluoroacetate and paraformaldehyde can be used.

Yet, the two-step methylenation can be carried out by adding an iminium salt followed by deamination. In this reaction, examples of the base include potassium tert-butoxide, sodium hydride, potassium hydride, sodium ethoxide, lithium diisopropylamide, lithium hexamethyldisilylamide, etc., and examples of the iminium salt include N,N-dimethyl(methylene)ammonium iodide, N,N-dimethyl(methylene)ammonium trifluoroacetic acid, etc. Further, the iminium salt may be generated in the reaction system from a secondary amine, and formaldehyde or its equivalent.

The deamination is carried out by heat treatment, conversion to an ammonium salt or the like.

Further, the compound (15) can be converted to a compound (1) (Z=(1-4); $R_{41}$=D=E=hydrogen atom) or (Z=(1-4); D=hydrogen atom, and E and $R_{41}$ together express a single bond and express a double bond in cooperation with the single bond already shown in the formula), for example, via the enol ether (19) which is obtained by coupling the compound (15) with an unsaturated enone as shown in the following Scheme 32.

Scheme 32

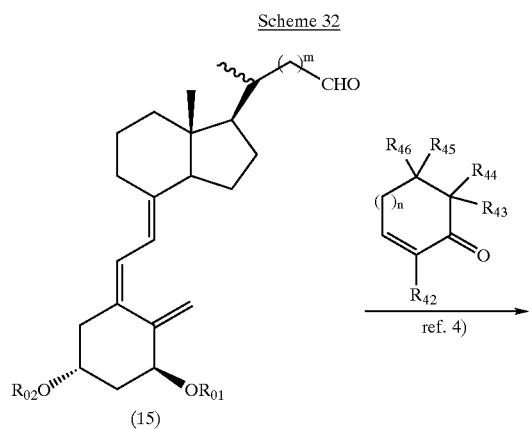

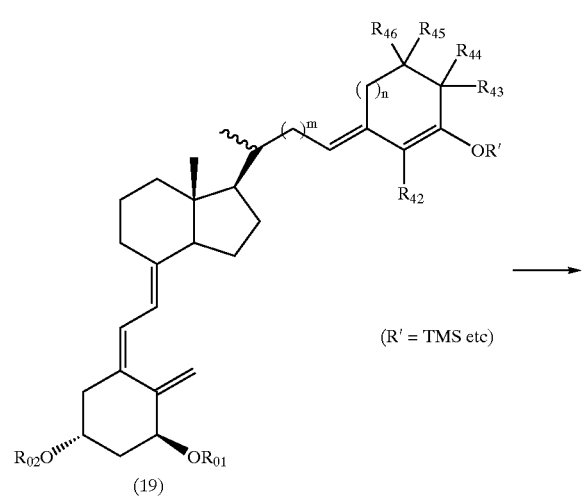

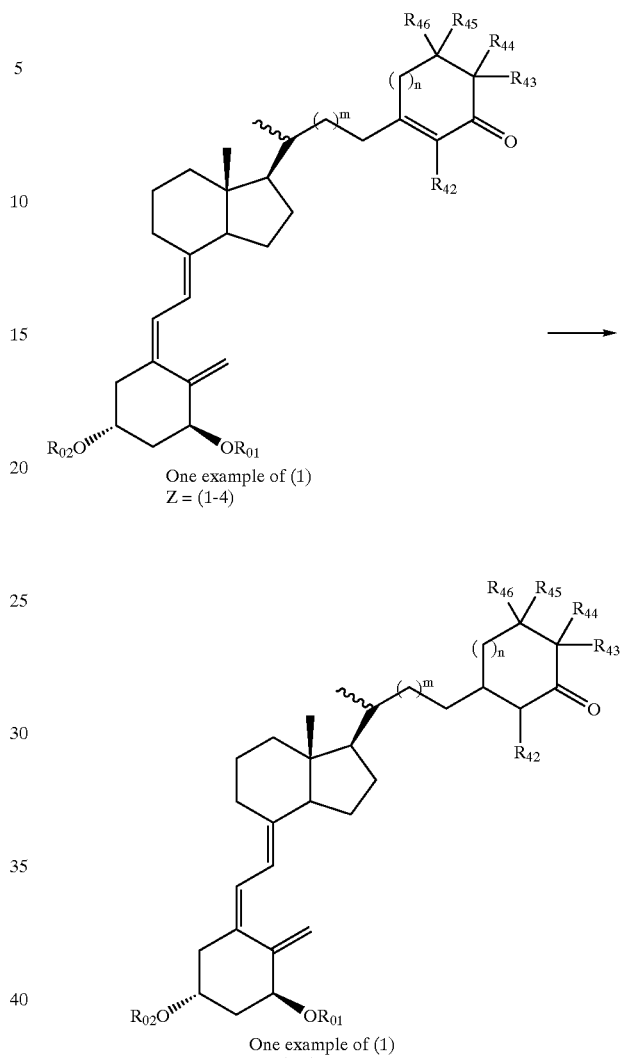

ref. 4) J. Org. Chem., 1986, 51, 3400-3402.

The coupling reaction and the conversion of the compound (19) to the compound (1) in the above Scheme 32 can be carried out by known processes.

Further, the compound (15) can be converted to the compound (1) (Z=(1-4); both D and E are hydrogen atoms, D is a hydroxyl group and E is a hydrogen atom, or D and E together express a single bond and express a double bond in cooperation with the single bond already shown in the formula; the combination of $R_{41}$ and $R_{42}$ is (a hydrogen atom and a hydroxyl group), (a hydrogen atom and a $C_2$–$C_5$ acyloxy group), (a $C_1$–$C_4$ alkyl group which may be substituted with a hydroxyl group, a $C_2$–$C_5$ acyloxy group or a $C_1$–$C_4$ alkyloxy group, and a hydroxy group) or (a $C_1$–$C_4$ alkyl group which may be substituted with a hydroxyl group, a $C_2$–$C_5$ acyloxy group or a $C_1$–$C_4$ alkyloxy group, and a $C_2$–$C_5$ acyloxy group)), for example, by carrying out aldol reaction between the aldehyde (15) and a cycloalkanone (20) whose carbonyl group at the α-position to the ketone is protected by acetal, and subsequently optionally carrying out dehydration, reduction or reaction with an organometallic reagent, acetal deprotection, and the like as shown in the following Scheme 33.
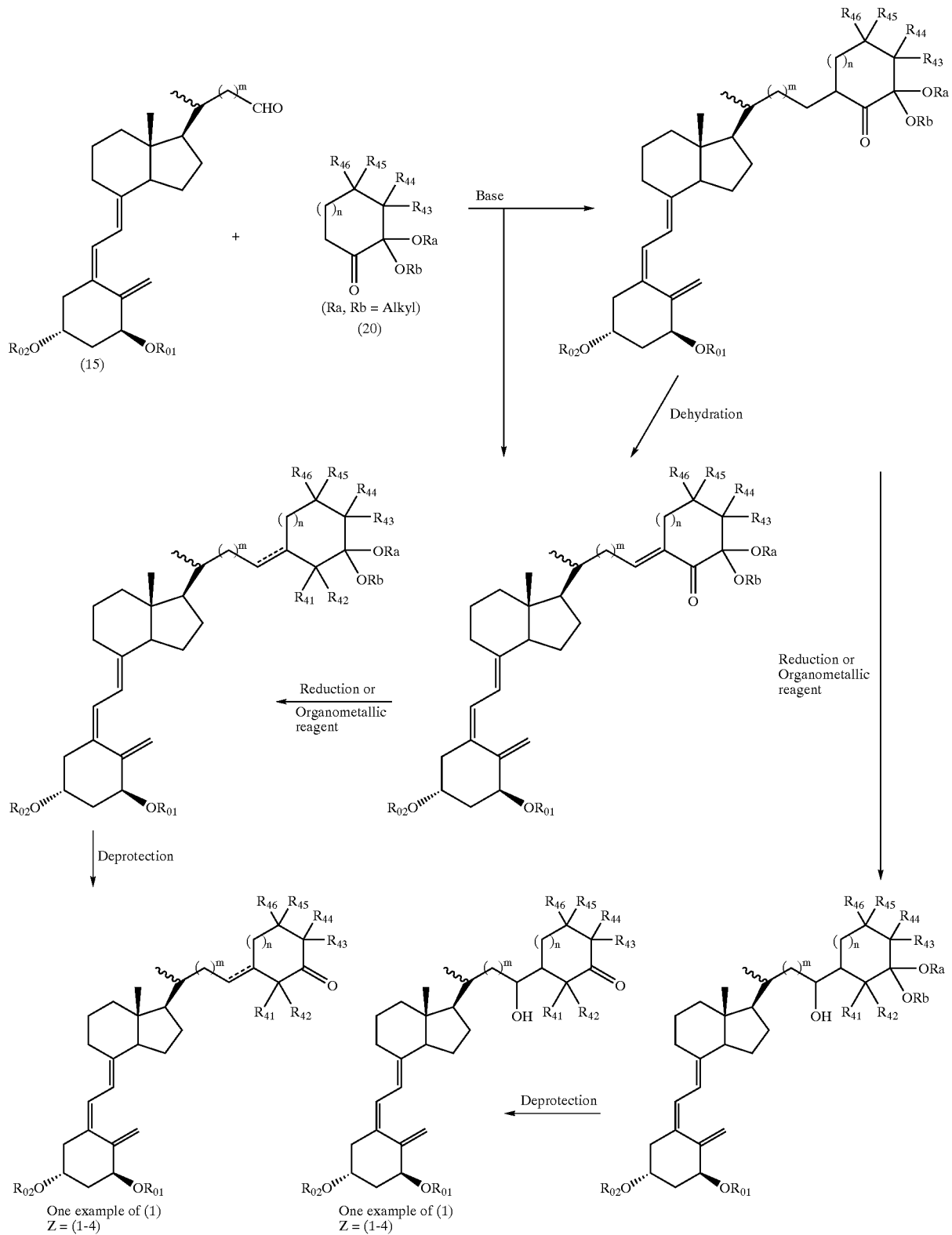

The above-mentioned aldol reaction, dehydration and reduction can be carried out under the conditions of the above Scheme 28.

Examples of the organometallic reagent used in the reaction with an organometallic reagent include an organolithium compound, a Grignard reagent, an organocerium reagent and the like.

The removal of the acetal group in deprotection can be carried out by using toluenesulfonic acid, trifluoroacetic acid, sulfuric acid, toluenesulfonic acid-pyridine complex or the like as a catalyst.

The conversion of the compound (15) to the compound (1) (z=(1-1), (1-2) or (1-5)) also can be achieved by using reactions shown in the above Schemes 2 to 26.

The aldehyde expressed by the above formula (14) can be produced, for example, in a manner shown the following Schemes 34 and 35. That is, the compound (14) in which m is 0, 1 or 2 can be produce by using the compound (21) obtainable from vitamin $D_2$ through a known process (International Patent Publication WO90/09991; Tetrahedron, 20, 4609–4619 (1987)) as a raw material.

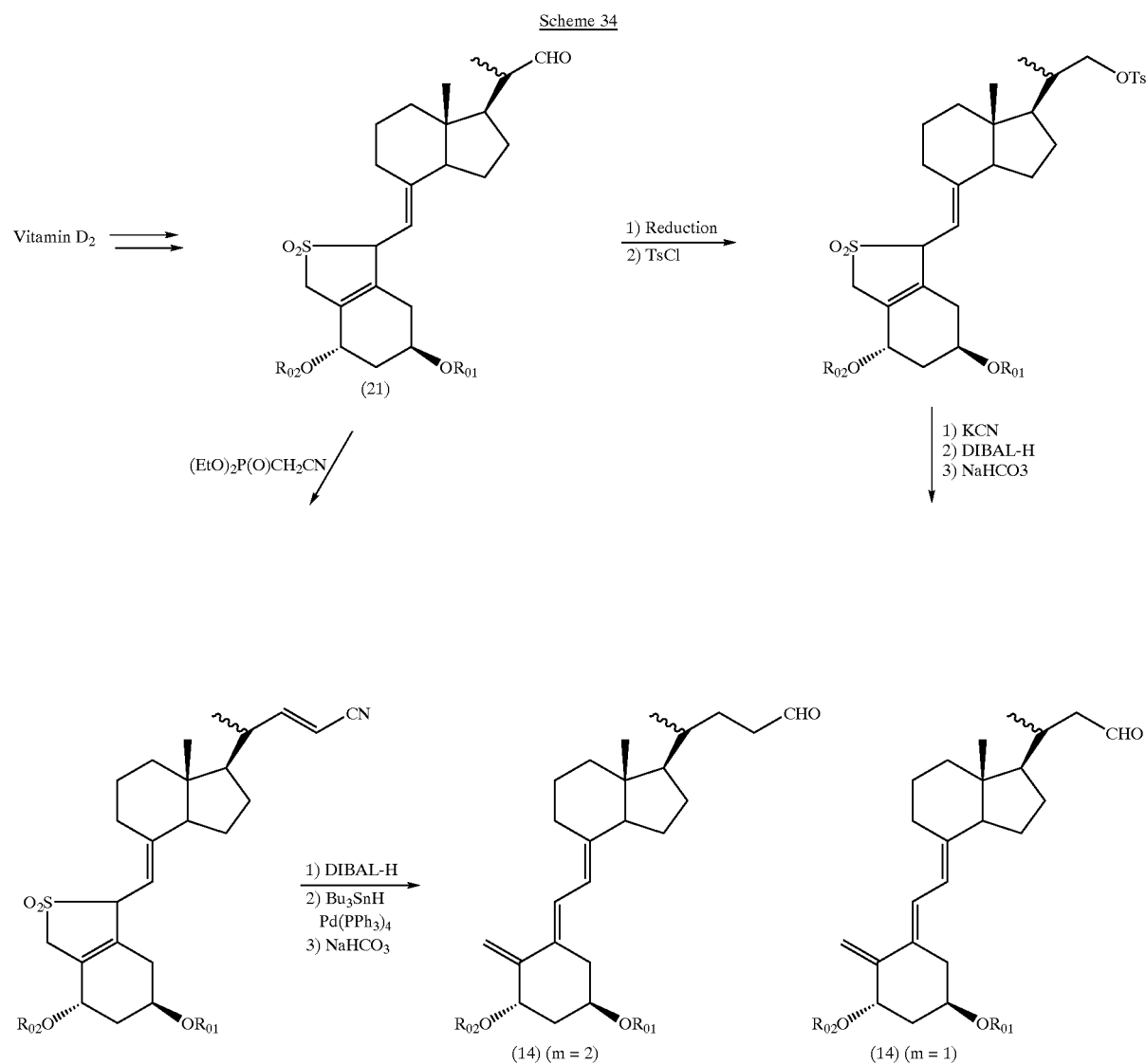

Scheme 35

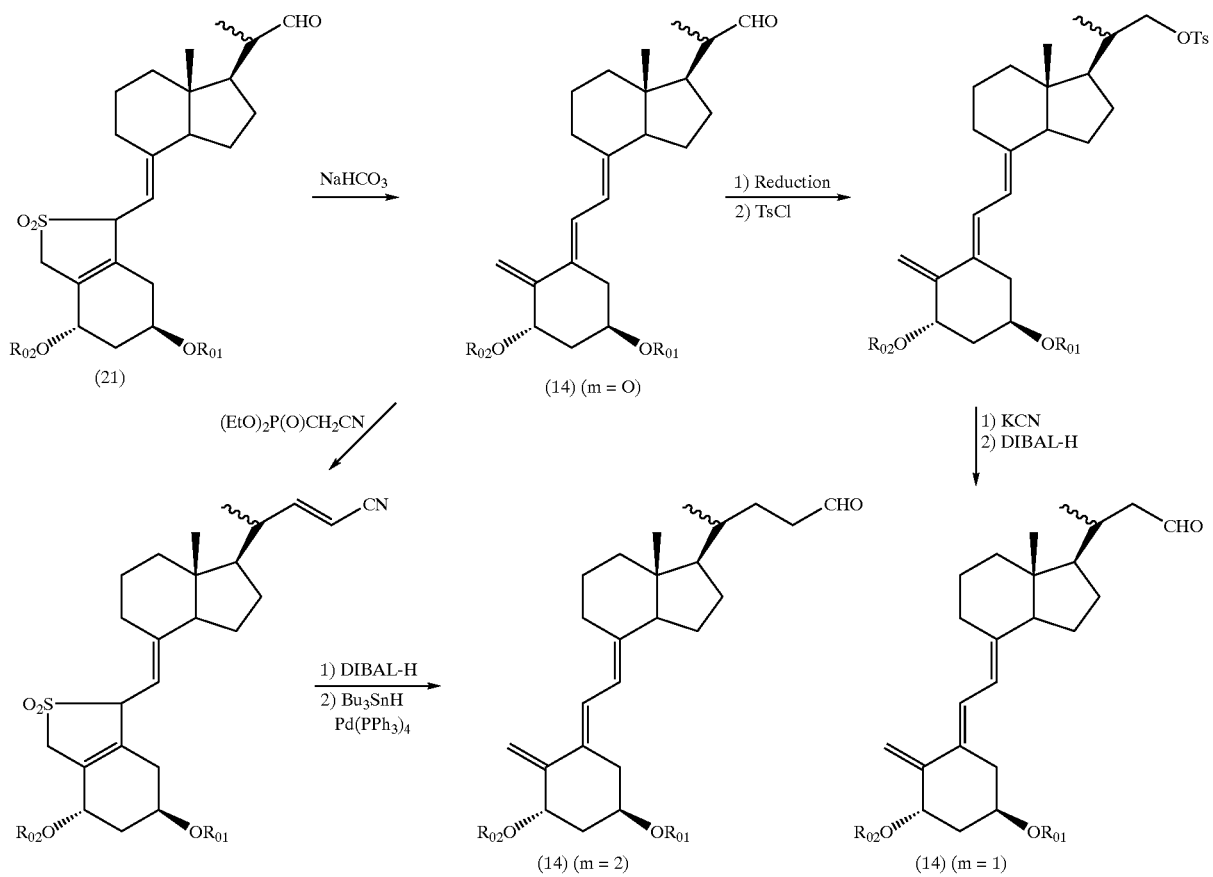

The compound of the above formula (1) which is obtained through a process shown above can be converted to a vitamin $D_3$ derivative of the above formula (1) whose $R_{01}$ and $R_{02}$ are hydrogen atoms, by carrying out deprotection reaction, as required.

The deprotection reaction can be carried out as shown below. When $R_{01}$ and $R_{02}$ are acetyl groups, common alkali hydrolysis, or a treatment with potassium cyanide, ammonium-methanol or the like can be used. When $R_{01}$ and $R_{02}$ are methoxymethyl groups or tetrahydro-4H-pyran-2-yl groups, the reaction can be carried out under acidic conditions, for example, by using hydrochloric acid, acetic acid, trifluoroacetic acid or the like, or pyridinium, p-toluenesulfonate (PPTS), $LiBF_4$ or the like. When $R_{01}$ and $R_{02}$ are trimethylsilyl groups, triethylsilyl groups or t-butyldimethylsilyl groups, the reaction can be carried out according to a known method (for example, Caverly, Tetrahedron, 20, 4609–4619 (1987)), and as the deprotecting agent, for example, tetrabutylammonium fluoride, pyridinium p-toluenesulfonate, hydrogen fluoride, etc., may be used. Examples of the organic solvent to be used in the reaction include a halogen-containing solvent such as methylene chloride, chloroform or carbon tetrachloride, a hydrocarbon solvent such as hexane or toluene, an ether solvent such as tetrahydrofuran or dioxane, a water-soluble solvent such as N,N-dimethylformamide or acetonitrile, a mixed solvent of them, etc. The solvent may be selected in consideration of the solubility and the reactivity of the compound. The reaction temperature generally ranges from −20° C. to the boiling point of the solvent. The reaction time depends on the dehydrating agent, deprotecting agent, reaction solvent and reaction temperature used, and it is commonly preferable that the reaction is continued until the starting material disappears when determined by using an analytical means such as thin layer chromatography.

Further, the above deprotection reaction may be carried out by using a reagent consisting of a combination of an alkali metal salt of tetrafluoroboric acid and a mineral acid, especially in the case where $R_{01}$ and $R_{02}$ are trimethylsilyl groups, triethylsilyl groups or t-butyldimethylsilyl groups. As the alkali metal salt of tetrafluoroboric acid, lithium tetrafluoroborate, sodium tetrafluoroborate or potassium tetrafluoroborate may be used, and as the mineral acid, hydrochloric acid, sulfuric acid, etc., may be used. It is preferable that the alkali metal salt of tetrafluoroboric acid is used in an amount of 1–3 equivalents based on the hydroxyl group to be deprotected, and the mineral acid is used in an amount of 0.05–3 equivalents. To the reaction solvent, reaction temperature and reaction time, the same conditions as in the above deprotection reaction may be applied. Especially, acetonitrile and methylene chloride are preferable as the solvent, the reaction temperature is preferably from 0° C. to room temperature, and the reaction time is preferably from 10 min to about 1 hr.

Further, vitamin $D_3$ derivatives expressed by the above formula (3) can be produced through a known process, for example, the process described in International Patent Publication WO95/33716.

Thus obtained vitamin $D_3$ derivatives can be optionally converted into pharmaceutically permissible solvates shown above.

Furthermore, the present invention provides treating agents for inflammatory respiratory diseases containing vitamin $D_3$ derivatives expressed by the above formula (1) or (3), or pharmaceutically permissible solvates thereof in therapeutically effective amounts and also methods for treating the diseases using the agents.

Preferable examples of the inflammatory respiratory diseases to be objective of the treating agents or the treating methods of the present invention include one or not less than two kinds of inflammatory respiratory diseases selected from a group consisting of acute upper airway infection, chronic sinusitis, allergic rhinitis, chronic lower airway infection, pulmonary emphysema, pneumonia, bronchial asthma, tuberculosis sequela, acute airway distress syndrome, cystic fibrosis and pulmonary fibrosis.

As an inflammatory respiratory disease which is objective of the present invention, we can select especially one or not less than two kinds of acute upper airway infections from a group consisting of, for example, common cold, acute pharyngitis, acute rhinitis, acute sinusitis, acute tonsillitis, acute pharyngitis, acute epiglottitis and acute bronchitis, or one or not less than two kinds of chronic lower airway infections from a group consisting of, for example, chronic bronchitis, diffuse panbronchiolitis and bronchiectasis.

Further, the present invention provides agents containing a vitamin $D_3$ derivative expressed by the above formula (1) or a pharmaceutically permissible solvate thereof in a pharmaceutically effective amount for treating diseases selected from a group consisting of malignant tumors, rheumatoid arthritis, osteoporosis, diabetes mellitus, hypertension, alopecia, acne, psoriasis and dermatitis and methods for treating a group of the diseases using the treating reagents.

Furthermore, the present invention provides agents containing a vitamin $D_3$ derivative expressed by the above formula (1) which is a compound having an antagonistic effect to vitamin $D_3$ in a pharmaceutically effective amount for treating diseases selected from a group consisting of hypercalcemia attributable to excess vitamin $D_3$, hypoparathyroidism and metabolic disorder of cartilage, and methods for treating a group of the diseases using the treating reagents. The hypercalcemia attributable to excess vitamin $D_3$ means, for example, a disease such as sarcoidosis caused by the overproduction of vitamin $D_3$ in tumorigenic macrophage-like cells or lymphocyte cells of a malignant lymphoma patient, or vitamin $D_3$ toxipathy caused by the megadose of vitamin $D_3$. The hypoparathyroidism is, for example, idiopathic or postoperative hypoparathyroidism caused by the depression of PTH production, or the like. The metabolic disorder of cartilage is, for example, a disease in which cartilage components are decomposed and decreased due to the lowering of the biosynthesis ability or the damage of collagen, proteoglucan, etc., in cartilage cells or substrates. Examples of the disease may include osteoarthritis, rheumatoid arthritis, rheumatic fever, etc.

Treating agents for various diseases of the present invention can be administered orally, or parentally through intravenous, subcutaneous, intramuscular, percutaneous, intranasal or intrarectal route or the like, or by inhalation.

Dosage forms for oral administration include tablets, pills, powders, granules, liquids, suspensions, syrups, capsules, etc.

The tablets are formulated according to a conventional process by using additives consisting of an excipient such as lactose, starch, calcium carbonate, crystalline cellulose or silicic acid; a binder such as carboxymethylcellulose, methylcellulose, calcium phosphate or polyvinylpyrrolidone; a disintegrator such as sodium alginate, sodium bicarbonate, sodium laurylsulfate or stearic acid monoglyceride; a humectant such as glycerin; an absorbent such as kaolin or colloidal silica; a lubricant such as talc or granular boric acid, etc.

The pills, powders and granules are prepared by conventional processes also using additives similar to those mentioned above.

Liquid preparations such as the liquids, suspensions and syrups can be formulated also according to conventional processes. As a carrier, for example, a glycerol ester such as tricaprylin, triacetin or an iodized poppy oil fatty acid ester; water; an alcohol such as ethanol; or an oily base such as liquid paraffin, coconut oil, soybean oil, sesame oil or corn oil is used.

The capsules are formulated by filling a powdery, granular or liquid pharmaceutical composition, or the like, in gelatin capsules, or the like.

Dosage forms for intravenous, subcutaneous and intramuscular administration include injections in the forms of sterilized aqueous solutions, non-aqueous solutions, etc. In an aqueous solution, for example, a physiological saline solution or the like is used as a solvent. In a non-aqueous solution, for example, propylene glycol, polyethylene glycol, a vegetable oil such as olive oil, an organic ester which is acceptable for injection such as ethyl oleate or an iodized poppy oil fatty acid ester, or the like is used as a solvent. To the pharmaceutical preparations for injection are optionally added an isotonizing agent, a preservative, a humectant agent, an emulsifier, a dispersant, a stabilizer, etc., and the preparation may be sterilized by applying an adequate treatment such as filtration through a bacterium-retaining filter, blending of a germicide or irradiation. Also, the preparation may be prepared as an aseptic solid preparation which is used by dissolving in sterilized water or a sterilized solvent for injection just prior to use.

Further, a compound of the present invention may be used in the form of a clathrate compound prepared by using α, β or γ-cyclodextrin, a methylated cyclodextrin, or the like. The compound may be used also as an injection of lipoid form.

Dosage forms for percutaneous administration preparations include ointments, creams, lotions, solutions, etc.

Examples of the base of an ointment include a fatty acid such as castor oil, olive oil, sesame oil or safflower oil; lanolin; white, yellow or hydrophilic vaseline; wax; a higher alcohol such as oleyl alcohol, isostearyl alcohol, octyldodecanol or hexyldecanol; a glycol such as glycerin, diglycerin, ethylene glycol, propylene glycol, sorbitol or 1,3-butanediol; etc. Further, as a solubilizing agent for a compound of the present invention, ethanol, dimethyl sulfoxide, polyethylene glycol, etc., may be compounded. Optionally, a preservative such as a paraoxybenzoic acid ester, sodium benzoate, salicylic acid, sorbic acid or boric acid; an antioxidant such as butylhydroxyanisole or dibutylhydroxytoluene; etc., may be added.

Further, in order to stimulate percutaneous absorption in an ointment, an absorption promoter such as diisopropyl adipate, diethyl sebacate, ethyl caproate or ethyl laurate may be compounded. Also, for stabilization, a compound of the present invention may be used in the form of a clathrate compound prepared by using α, β or γ-cyclodextrin, a methylated cyclodextrin, etc. An ointment can be prepared by a conventional process.

In the creams, dosage forms of oil-in-water type are preferable with the aim of stabilizing compounds of the present invention. Further, the above-mentioned fatty oil, higher alcohol, glycol, or the like may be used as the base of a cream, and diethylene glycol, propylene glycol, sorbitan mono fatty acid ester, polysorbate 80, sodium laurylsulfate, or the like may be used as the emulsifier of a cream. Further, the above-mentioned preservative, antioxidant, or the like may be added, as necessary. Furthermore, as in the case of ointment, a compound of the present invention can be used in the form of a clathrate compound prepared by using a cyclodextrin or a methylcyclodextrin. A cream can be prepared according to a conventional process.

Examples of the lotions include a suspension-type lotion, an emulsion-type lotion and a solution-type lotion. The suspension-type lotion is prepared by using a suspending agent such as sodium alginate, traganth or sodium carboxymethylcellulose, and optionally by adding an antioxidant, a preservative, etc.

The emulsion-type lotion is prepared according to a conventional process by using an emulsifier such as sorbitan mono fatty acid ester, polysorbate 80 or sodium laurylsulfate. A compound of the present invention can be dissolved in an alcohol such as ethanol, and optionally an antioxidant, a preservative, or the like is added.

Besides the above-mentioned dosage forms, pastas, poultices, aerosols, etc., may be cited. Pharmaceutical preparations having these dosage forms can be prepared according to conventional processes.

Pharmaceutical preparations for intranasal administration are supplied in the form of a liquid or powdery composition. As the base of the liquid preparation, water, saline, a phosphate buffer solution, an acetate buffer solution, or the like is used, and the liquid preparation may contain further a surfactant, an antioxidant, a stabilizer, a preservative and/or a thickener. As the base for the powdery preparation, a water-absorbent base is preferable. Examples of the water-absorbent base include polyacrylate salts such as sodium polyacrylate, potassium polyacrylate and ammonium polyacrylate; cellulose lower-alkyl ethers such as methylcellulose, hydroxyethylcellulose, hydroxypropylcellulose and sodium carboxymethylcellulose; and polyethylene glycol, polyvinyl pyrrolidone, amylose, pullulan, etc., which are easily soluble in water. Further, they include cellulose compounds such as crystalline cellulose, α-cellulose and cross-linked sodium carboxymethylcellulose; starch compounds such as hydroxypropyl starch, carboxymethyl starch, cross-linked starches, amylose, amylopectin and pectin; proteins such as gelatin, casein and sodium caseinate; gums such as gum arabic, tragacanth gum and glucomannan; and polyvinylpolypyrrolidone, cross-linked polyacrylic acid and salts thereof, cross-linked polyvinyl alcohols, etc., which are scarcely soluble in water. These compounds may be used alone or in mixtures of two or more thereof. The powdery preparation may be further compounded with an antioxidant, a coloring agent, a preservative, a disinfectant, an antiseptic, etc. These liquid and powdery preparations can be applied, for example, by using a spraying device, etc.

For intrarectal administration, ordinary suppositories such as gelatin soft capsule are used.

Further, for inhalation, a powdery or liquid composition prepared by using an active ingredient of a vitamin $D_3$ derivative of the present invention alone or in combination with an adequate biocompatible vehicle can be administered to disease sites using an applicator such as a spraying device, a nebulizer or an atomizer, Alternatively, an active ingredient may be administered to disease sites by using a pMDI (volumetric sprayer) in which a suspension or solution prepared by suspending or dissolving the active ingredient in a spraying agent for aerosol such as alternative flon is filled. Furthermore, the ingredient is dissolved in an ethanol aqueous solution, the solution is filled in an adequate sprayer, and thus, it can be administered to disease sites.

A pharmaceutically effective dose of an active ingredient of the present invention depends on administration route, age and sex of the patient and the conditions of the disease, but it is ordinarily about 0.001–100 μg per day, preferably about 0.01–50 μg per day, and administration frequency is ordinarily 1–3 time per day. The pharmaceutical preparation is preferably prepared so as to meet these conditions.

Further, treating agents of the present invention for various kinds of diseases can be administered in combination with conventional medicines.

Effectiveness for inflammatory respiratory diseases of vitamin $D_3$ derivatives expressed by the above formula (1) of the present invention has been demonstrated by experiments using lipopolysaccharide (LPS)-induced pneumonia hamsters, which are widely used as an inflammatory pulmonary disease model, as shown concretely in the below-mentioned examples. That is, it has been found that compounds of the present invention significantly suppress LPS-induced pneumonia by intra-respiratory tract administration or oral administration.

Effectiveness of vitamin $D_3$ derivatives expressed by the above formula (1) of the present invention for diseases attributable to the vitamin $D_3$ overactivity has been demonstrated based on the parameter of differentiation-inducing effect on HL-60 cells, as concretely shown in the below-mentioned examples. That is, the compound of the present invention specifically suppresses the differentiation of HL-60 cells induced by an active vitamin $D_3$ (1α,25-dihydroxyvitamin $D_3$), and accordingly it becomes clear that the compound of the present invention acts as an antagonist to vitamin $D_3$. Other vitamin $D_3$ derivatives expressed by the above formula (1) and having antagonistic effect to vitamin $D_3$ also can be screened by a similar evaluation system to that used in experimental examples.

On the other hand, it has been clarified that the blood calcium level-elevation effects of compounds of the present invention is extremely reduced compared with that of 1α,25-dihydroxyvitamin $D_3$ although the generally most worried side effect of active vitamin $D_3$ compounds is the elevation of calcium level in blood. For example, the blood calcium level-elevation effects of compounds of the present invention in oral administration to rats, which are compared with that of 1 α,25-dihydroxyvitamin $D_3$, are as shown below:

Compound No. 3105c, 1/>100
Compound No.3405, 1/>100
Compound No. 5102, 1/259
Compound No. 5107, 1/11.

From the above results, it is thought that in vitamin $D_3$ derivatives expressed by the above formula (1), the separation of the development concentrations for anti-inflammatory effect and antagonistic effect to vitamin $D_3$ from that for blood calcium level elevation effect has been achieved, and side effect will not be generated.

Thus, treating agents containing vitamin $D_3$ derivatives expressed by the above formula (1) as active ingredients can be considered to be effective for inflammatory respiratory diseases or diseases attributable to the overactivity of vitamin $D_3$.

By the way, it has been reported that an active vitamin $D_3$ has various effects on cell metabolism. Examples of such reports include the stimulation of maturation and differentiation of cell (Tanaka, et al., Biochem. J., 204, 713–719 (1982); Amento, et al., J. Clin. Invest., 73, 731–739 (1984); Colston, et al., Endocrinology, 108, 1083–1086 (1981); Abeetl, et al., Proc. Natl. Acad. Sci., 78, 4990–4994 (1981)) and immunosuppression effect such as interleukin-2 production inhibition (Rigbi, Immunology Today, 9, 54–58 (1988)). In addition, also immunology synergistic effect has been detected, and the stimulation of the production of bactericidal oxygen metabolites and the stimulation of leukocyte chemotactic response have been discovered.

It has been recognized that also vitamin $D_3$ derivatives expressed by the above formula (1) have the cell differentiation-inducing effect as mentioned above. This fact demonstrates that vitamin $D_3$ derivatives expressed by the above formula (1) have possibilities of therapies in various fields including, for example, malignant tumor, psoriasis, rheumatoid arthritis, inflammatory diseases such as dermatitis and autoimmune diseases, and other therapies associated with supplementary agents in chemotherapy of infectious diseases (especially, bacterial, viral or fungus) and other therapies associated with mononuclear phagocyte.

Further, it is expected that vitamin $D_3$ derivatives expressed by the above formula (1) are also effective for the treatment of hypertension, the treatment of diabetes mellitus, the stimulation of hair growth and the treatment of acne, for which an active vitamin $D_3$ is effective as shown by the following reports: the treatment of hypertension (Lind, et al., Acta Med. Scand., 222, 423–427 (1987)), the treatment of diabetes mellitus (Inomata, et al., Bone Mineral, 1, 187–192 (1986)), the stimulation of hair growth (Lancet, March 4, 478 (1989)) and the treatment of acne (Malloy, et al., Tricontinental Meeting for Investigative Dermatology, Washington, 1989).

Some of vitamin $D_3$ derivatives of the present invention expressed by the above formula (1) are very high in bonding capacity to 1 α,25-dihydroxyvitamin $D_3$ receptor, i.e. they have bonding capacities ranging from same degree to about 1/50 of 1α,25-dihydroxyvitamin $D_3$, and high vitamin $D_3$-like effects can be expected. In other words, compounds of the present invention are expected to be effective as an osteoporosis treating agent based on bone metabolism maintaining effect characteristic to an active vitamin $D_3$.

EXAMPLES

The present invention will be explained further in detail henceforth with examples, while the present invention is not restricted by the examples. The compound numbers in every example correspond to the compound numbers shown in the above-mentioned Tables 1-1-1, 1-2-1,1-3-1,1-3-2,1-4-1,1-4-2 and 1-5-1. A compound number having an alphabet shows a stereoisomer of the compound.

Reference Example 1
Production of Compound (6) (m=O; Y=Br)

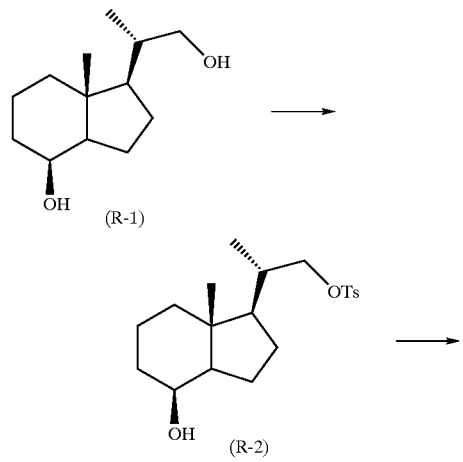

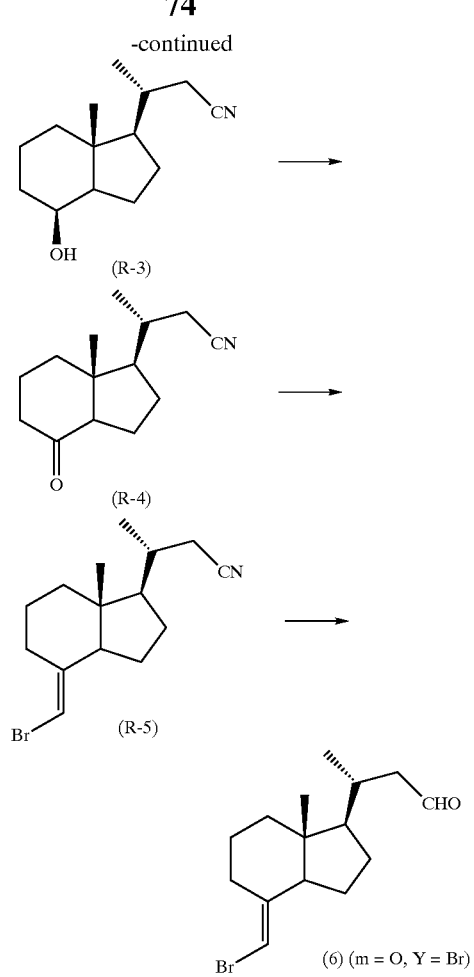

(1) The (R-1) (10.0 g, 47.1 mmol), which can be obtained from vitamin $D_2$ through a known process (for example, J. Org. Chem., 51, 1264–1269 (1986)), was dissolved in dry pyridine (30 ml), p-toluenesulfonyl chloride (10.8 g, 56.5 mmol) was added, and the mixture was stirred for 2.5 hr at room temperature. The reaction mixture was extracted three times with ethyl acetate after the addition of 2N hydrochloric acid (200 ml). The combined organic layers were washed with a saturated sodium bicarbonate aqueous solution and with brine, dried over anhydrous sodium sulfate and concentrated to obtain a crude product of (R-2).

(2) The above-obtained crude product of (R-2) was dissolved in DMF (60 ml), potassium cyanide (15.3 g, 235.5 mmol) and 18-crown-6 (1.24 g, 4.7 mmol) were added, and the mixture was stirred overnight at 100° C. The reaction mixture was extracted twice with ethyl acetate after the addition of water. The combined organic layers were washed with a saturated sodium bicarbonate aqueous solution and with brine, dried over anhydrous sodium sulfate and concentrated. The residue was purified by silica gel column chromatography (hexane:ethyl acetate=5:1 to 4:1) to obtain (R-3) (6.50 g, 62% yield).

(3) The above-obtained (R-3) (6.50 g, 29.4 mmol) was dissolved in acetone (80 ml), and the solution was stirred for 15 min at room temperature after the addition of a spatula of anhydrous magnesium sulfate. To the solution were added N-methylmorpholine-N-oxide (5.16 g, 44.0 mmol) and dichlorotris(triphenylphosphine)ruthenium (II) (141 mg, 0.15 mmol), and the mixture was stirred for 21 hr. Further, to the reaction mixture were added N-methylmorpholineoxide (3.4 g, 29.4 mmol) and dichlorotris(triphenylphosphine)ruthenium (II) (300 mg, 0.31 mmol), and the mixture was stirred for 3 hr at room temperature. The reaction mixture was concentrated, and the residue was extracted twice with ethyl acetate after 120 ml of 0.2N-hydrochloric acid was added. The combined organic layers were washed with brine, dried over anhydrous sodium sulfate and concentrated. The residue was purified by silica gel column chromatography (hexane:ethyl acetate=5:1 to 4:1) to obtain (R-4) (5.92 g, 92% yield).

(4) (Bromomethyl)triphenylphosphonium bromide (12.3 g) was suspended in dry THF (270 ml), the suspension was cooled to −40° C. A sodium hexamethyldisilazide solution (27.4 ml, 1M, 27.4 mmol) in THF was added dropwise, and the mixture was stirred for 45 min at the same temperature (Solution A). The above-obtained (R-4) (2.0 g, 9.12 mmol) was dissolved in dry THF (20 ml) in another container, and the solution was cooled with ice. The above-obtained Solution A was added dropwise over 1 hr, and the mixture was stirred further for 2.5 hr under cooling with ice. The reaction mixture was extracted twice with ethyl acetate after a saturated ammonium chloride aqueous solution was added. The combined organic layers were washed with brine, dried over anhydrous magnesium sulfate and concentrated. The residue was purified by silica gel column chromatography (hexane:ethyl acetate=40:1 to 10:1) to obtain (R-5) (1.23 g, 46% yield).

$^1$H NMR (CDCl$_3$) δ: 0.59 (s, 3 H), 1.18 (d, J=6 Hz, 3 H), 2.21–2.35 (m, 2 H), 2.86–2.91 (m, 1 H), 5.67 (s, 1 H).

(5) The above-obtained (R-5) (1.23 g, 4.15 mmol) was dissolved in dry dichloromethane (70 ml), and the solution was cooled to −75° C. A diisobutylaluminum hydride solution (6.2 ml, 1.01M, 6.2 mmol) in toluene was added dropwise, and the mixture was stirred for 1.5 hr at the same temperature. The reaction mixture was warmed up to room temperature after methanol (2 ml) was added. Water (10 ml), a saturated sodium sulfate aqueous solution (10 ml) and 6N-hydrochloric acid (5 ml) were added, and the mixture was stirred for 30 min. The precipitated solids were removed by celite filtration, and the filtrate was extracted twice with dichloromethane. The combined organic layers were washed with a saturated sodium bicarbonate aqueous solution and with brine, dried over anhydrous magnesium sulfate and concentrated. The residue was purified by silica gel column chromatography (hexane:ethyl acetate=80:3) to obtain (6) (m=0; Y=Br) (0.93 g, 75% yield).

Reference Example 2
Production of Compound (6) (m=1, Y=Br)

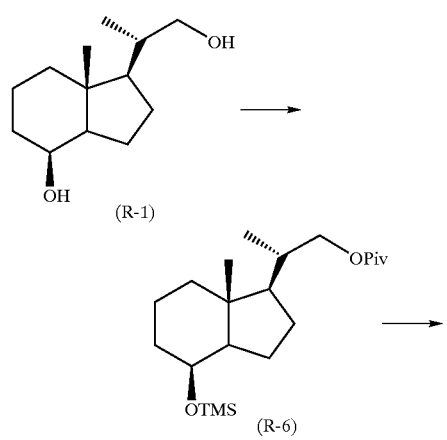

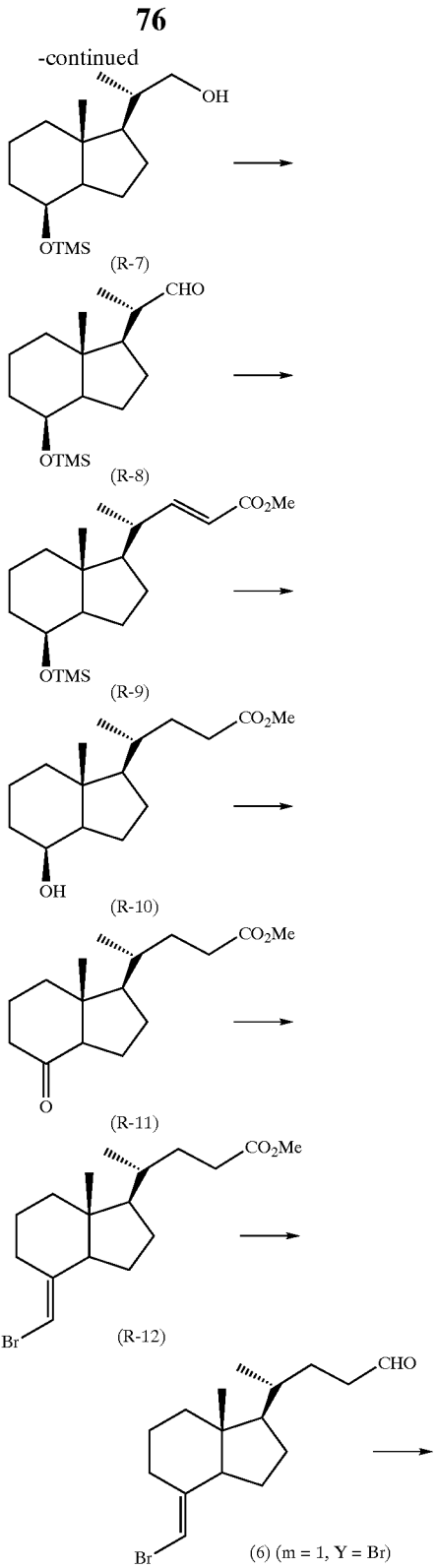

(1) The (R-1) (10.05 g), which can be obtained from vitamin D$_2$ through a known process (for example, J. Org. Chem., 51, 1264–1269 (1986)), was dissolved in pyridine (80 ml), and the solution was cooled to 0° C. Trimethylcacetyl chloride (6.1 ml) was added, and the mixture was stirred for 1 hr. Subsequently, trimethylsilyl chloride (6.6 ml) was added, and the mixture was stirred further 1 hr. The reaction mixture was poured into ice-water and extracted with ether. The combined organic layers were washed successively with a saturated potassium hydrogensulfate solution, water and brine, dried over anhydrous sodium sulfate and concentrated to obtain a crude product of (R-6).

(2) An ether solution of the above-obtained (R-6) was added dropwise to a suspension of potassium t-butoxide (21.2 g) and water (2 ml) in ether (270 ml) at 0° C. The mixture was warmed up to room temperature and stirred overnight. The reaction mixture was poured into ice-water and extracted with ether. The combined organic layers were washed with brine, subsequently dried over anhydrous magnesium sulfate and concentrated. The residue was purified by silica gel column chromatography (hexane: ethyl acetate=9:1) to obtain (R-7) (12.86 g, 96% yield).

$^1$H NMR (CDCl$_3$) δ: 0.05 (s, 9 H), 0.90 (s, 3 H), 1.02 (d, J=6.6 Hz, 3 H), 1.10–1.96 (m, 13 H), 3.36 (dd, J=6.9, 10.6 Hz, 1 H), 3.63 (dd, J=3.3, 10.6 Hz, 1 H), 4.00 (br., 1 H).

(3) The above-obtained (R-7) was treated in the same manner as in the conversion from (R-3) to (R-4) in Reference Example 1 to obtain (R-8).

$^1$H NMR (CDCl$_3$) δ: 0.06 (s, 9 H), 0.93 (s, 3 H), 1.09 (d, J=6.5 Hz, 3 H), 1.24–1.83 (m, 12 H), 2.31–2.41 (m, 1 H), 4.02 (br., 1 H), 9.58 (d, J=3.2 Hz, 1 H).

(4) Into a toluene solution (70 ml) of the above-obtained (R-8) (3.46 g) was added methyl (triphenylphosphoranylidene)acetate (12.24 g), and the mixture was heated and refluxed overnight. After insoluble matter was filtered off, the filtrate was evaporated, and the residue was purified by silica gel column chromatography (hexane:ethyl acetate=30:1) to obtain (R-9) (3.88 g, 94% yield).

$^1$H NMR (CDCl$_3$) δ: 0.05 (s, 9 H), 0.92 (s, 3 H), 1.06 (d, J=6.3 Hz, 3 H), 1.11–1.96 (m, 12 H), 2.21–2.30 (m, 1 H), 3.72 (s, 3 H), 3.99 (br., 1 H), 5.74 (d, J=15.5 Hz, 1 H), 6.84 (dd, J=8.9, 15.5 Hz, 1 H).

(5) The above-obtained (R-9) (2.08 g) was dissolved in methanol (10 ml) and ethyl acetate (5 ml). The air of the reaction system was substituted with hydrogen after the addition of a drop of concentrated hydrochloric acid and palladium-carbon (about 100 mg). The mixture was stirred overnight at room temperature in this state, and subsequently the reaction mixture was filtered, and the filtrate was concentrated. The residue was purified by silica gel column chromatography (hexane ethyl acetate=4:1) to obtain (R-10) (1.58 g, 96% yield).

$^1$H NMR (CDCl$_3$) δ: 0.90 (d, J=6.6 Hz, 3 H), 0.93 (s, 3 H), 1.05–2.42 (m, 17 H), 3.66 (s, 3 H), 4.08 (d, J=3.0 Hz, 1 H).

(6) Pyridinium dichromate (PDC) (3.64 g) was dissolved in dimethylformamide (20 ml), and the solution was cooled to 0° C. A dimethylformamide solution (5 ml) of the above-obtained (R-10) (1.29 g) was added dropwise, and the mixture was stirred for 2 hr in this state. The reaction mixture was poured into a suspension of silica gel in a mixed solvent of hexane and ethyl acetate(2:1), the mixture was filtered through celite, and the filtrate was concentrated. The residue was purified by silica gel column chromatography (hexane:ethyl acetate=8:1 to 4:1) to obtain (R-11) (1.24 g, 97% yield).

$^1$H NMR (CDCl$_3$) δ: 0.64 (s, 3 H), 0.96 (d, J=4.6 Hz, 3 H), 1.26–2.48 (m, 17 H), 3.67 (s, 3 H).

(7) The above-obtained (R-11) was treated in the same manner as in the conversion from (R-4) to (R-5) in Reference Example 1 to obtain (R-12) (50% yield).

$^1$H NMR (CDCl$_3$) δ: 0.56 (s, 3 H), 0.93 (d, J=6.3 Hz, 3 H), 1.21–2.04 (m, 14 H), 2.23–2.42 (m, 2 H), 2.84–2.90 (m, 1 H), 3.66 (s, 3 H), 5.64 (d, J=1.7 Hz, 1 H).

(8) Into a methylene chloride solution (5 ml) of the above-obtained (R-12) (292 mg) was added a diisobutylaluminum hydride solution (1 ml, 0.93M) in hexane at −78° C. After the mixture was stirred for 30 min, methanol (2 ml) was added, and the resultant mixture was well stirred. After the addition of a saturated ammonium aqueous solution, the reaction mixture was warmed up to room temperature, and extracted with ethyl acetate. The combined organic layers were washed serially with a saturated sodium bicarbonate aqueous solution, water and brine, dried over anhydrous sodium sulfate, and concentrated. The residue was purified by silica gel column chromatography (hexane:ethyl acetate= 25:1) to obtain the compound (6) (m=1, Y=Br) (243 mg, 91% yield).

$^1$H NMR (CDCl$_3$) δ: 0.57 (s, 3 H), 0.94 (d, J=6.3 Hz, 3 H), 1.26–2.05 (m, 16 H), 2.36–2.54 (m, 1 H), 2.85–2.90 (m, 1 H), 5.65 (d, J=1.7 Hz, 1 H), 9.78 (t, J=1.8 Hz, 1 H).

Reference Example 3

Production of Compounds (R-17) and (R-18) (an example of Compound (8) (m=0; n=1))

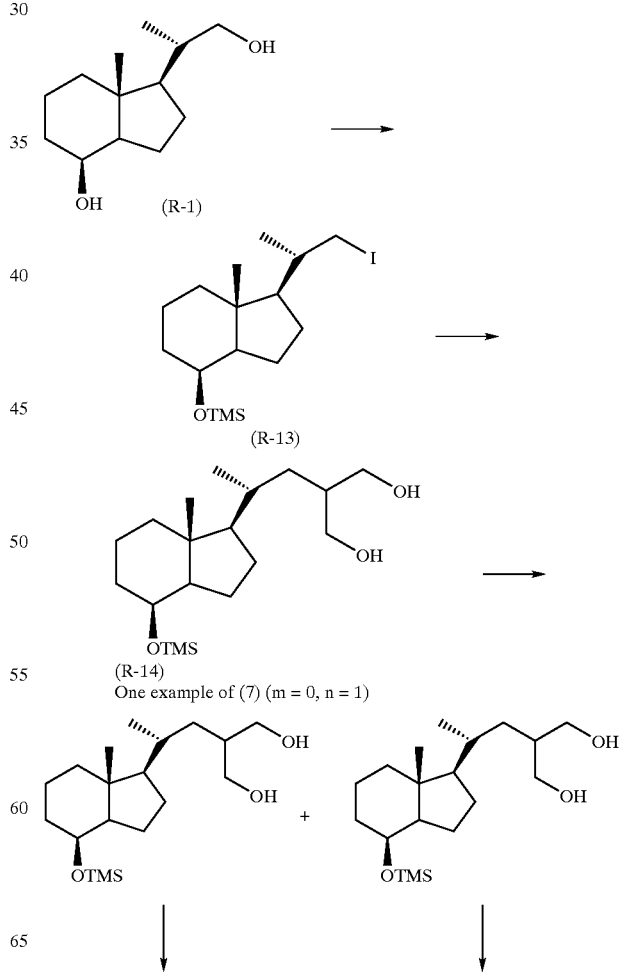

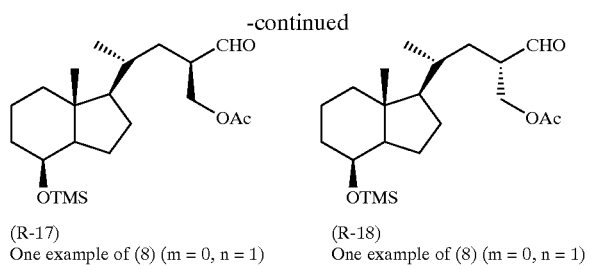

(R-17)
One example of (8) (m = 0, n = 1)

(R-18)
One example of (8) (m = 0, n = 1)

(1) The (R-1) (3 g), which can be obtained from vitamin D$_2$ through a known process (J. Org. Chem., 51, 1264–1269 (1986)), was dissolved in pyridine (15 ml), to the solution was added p-toluenesulfonyl chloride (3.2 g) at room temperature, and the mixture was stirred for 2 hr. Chlorotrimethylsilane was added dropwise at room temperature in a nitrogen atmosphere, and the mixture was stirred further for 20 min. The reaction mixture was extracted with ethyl acetate after the addition of a saturated sodium bicarbonate aqueous solution. The combined organic layers were washed with brine and concentrated. The residue was dissolved in acetone (30 ml), sodium iodide (2.5 g) was added, and the mixture was heated and refluxed for 5 hr. The reaction mixture was cooled to room temperature, and extracted with ethyl acetate after the addition of a saturated sodium thiosulfate aqueous solution. The combined organic layers were dried over anhydrous sodium sulfate and concentrated. The residue was purified by silica gel column chromatography (hexane:ethyl acetate=5:1) to obtain (R-13) (4.7 g, 85% yield).

$^1$H NMR (CDCl$_3$) δ: 0.05 (s, 9 H), 0.87 (s, 3 H), 0.95 (d, J=5.6 Hz, 3 H), 1.00–2.00 (m, 13 H), 3.12 (dd, J=5.3, 9.6 Hz, 1 H), 3.27 (dd, J=2.3, 9.6 Hz, 1 H), 3.93 (d, J=2.6 Hz, 1 H).

(2) Sodium hydride (320 mg) was suspended in toluene (50 ml), and the suspension was cooled with ice. Diethyl malonate (1.2 ml) was added dropwise, and the mixture was warmed up to room temperature and stirred for about 30 min. A toluene solution (10 ml) of the above-obtained (R-13) (2.1 g) was added, and the mixture was stirred for 10 hr under heating and refluxing. The reaction mixture was extracted with ethyl acetate after the addition of a saturated ammonium chloride aqueous solution. The combined organic layers were dried over anhydrous magnesium sulfate and concentrated. The residue was dissolved in THF (20 ml), and the solution was cooled with ice. A diisobutylaluminum hydride solution (10 ml, 0.93M) in toluene was added dropwise, and the mixture was warmed up to room temperature and stirred for about 4 hr. The reaction mixture was extracted with ethyl acetate after the addition of a saturated ammonium chloride aqueous solution. The combined organic layers were dried over anhydrous magnesium sulfate and concentrated. The residue was purified by silica gel column chromatography (hexane:ethyl acetate=1:1) to obtain (R-14) (0.94 g, 81% yield).

$^1$H NMR (CDCl$_3$) δ: 0.00 (s, 9 H), 0.84 (s, 3 H), 0.88 (d, J=6.6 Hz, 3 H), 0.60–1.90 (m, 16 H), 2.12 (br., 2 H), 3.50–3.82 (m, 4 H), 3.93 (br., 1 H).

(3) The above-obtained (R-14) (171 mg) was dissolved in isopropyl ether (2 ml), lipase PS (10 mg) and further vinyl acetate (69 μl) were added, and the mixture was stirred for 12 hr at room temperature. The reaction mixture was filtered with a glass filter, and the filtrate was concentrated. The residue was purified by silica gel column chromatography (hexane:ethyl acetate=3:1) to obtain (R-15) (83 mg, 43%) and (R-16) (83 m g, 43% yield).

Diastereomer 1 ((R-15) or (R-16))

$^1$H NMR (CDCl$_3$) δ: 0.00 (s, 9 H), 0.84 (s, 3 H), 0.86 (d, J=6.3 Hz, 3 H), 0.80–2.00 (m, 17 H), 2.03 (s, 3 H), 3.44 (br., 2 H), 3.94–4.24 (m, 2 H), 3.93 (br., 1 H).

Diastereomer 2 ((R-15) or (R-16))

$^1$H NMR (CDCl$_3$) δ: 0.00 (s, 9 H), 0.84 (s, 3 H), 0.86 (d, J=6.3 Hz, 3 H), 0.70–2.00 (m, 17 H), 2.03 (s, 3 H), 3.40–3.60 (br., 2 H), 3.94 (br., 1 H), 4.05 (br., 1 H).

(4) The above-obtained (R-15) (84 mg) was dissolved in toluene (10 ml), to the solution were added methyl allylcarbonate (3 ml) and further dichlorotris-(triphenylphosphine) ruthenium (21 mg), and the mixture was stirred for 3 hr under heating and refluxing. Brine was added to the reaction mixture, and the water layer was extracted with ethyl acetate. The combined organic layers were dried over anhydrous magnesium sulfate and concentrated. The residue was purified by silica gel column chromatography (hexane:ethyl acetate=4:1) to obtain (R-17) (64 mg, 75%).

$^1$H NMR (CDCl$_3$) δ: 0.00 (s, 9 H), 0.82 (s, 3 H), 0.88 (d, J=6.3 Hz, 3 H), 0.80–2.00 (m, 16 H), 1.99 (s, 3 H), 3.94 (br., 1 H), 4.00–4.30 (m, 2 H), 9.57 (d, J=3.3 Hz, 1H).

(5) The above-obtained (R-16) was treated in the same manner as in Reference Example 3 (4) to obtain (R-18) (70% yield).

$^1$H NMR (CDCl$_3$) δ: 0.00 (s, 9 H), 0.84 (s, 3 H), 0.88 (d, J=6.3 Hz, 3 H), 0.80–2.00 (m, 16 H), 1.99 (s, 3 H), 3.94 (br., 1 H), 4.15–4.30 (m, 2 H), 9.61 (d, J=1.7 Hz, 1 H).

Reference Example 4

Production of Compound (R-23) (one example of Compound (8) (m=0; n=1))

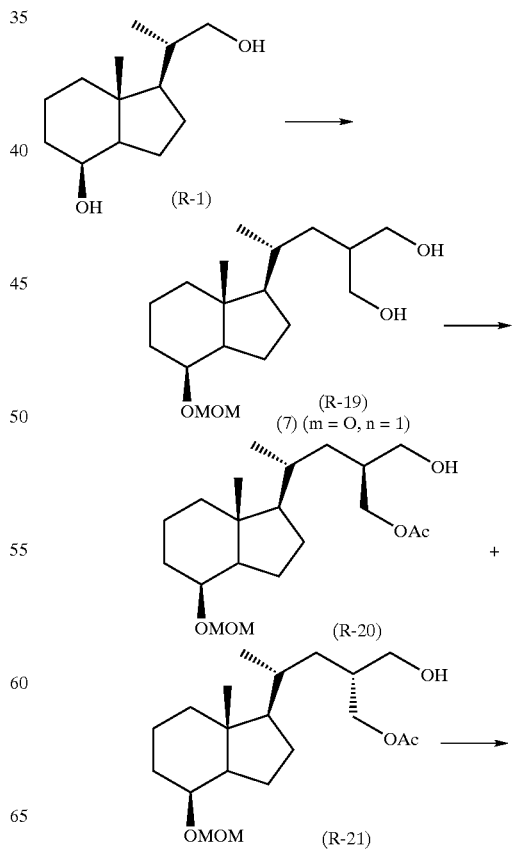

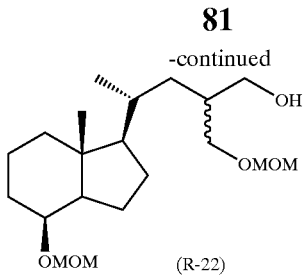

(R-22)

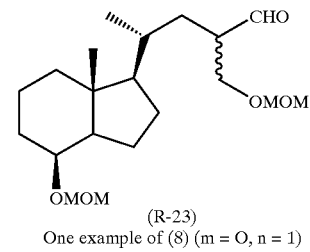

(R-23)
One example of (8) (m = O, n = 1)

(1) Employing substantially the same processes as in Reference Examples 3 (1) and (2), but using chloromethyl methyl ether in place of chlorotrimethylsilane, the (R-1) was converted to (R-19) (77% yield).

$^1$H NMR (CDCl$_3$) δ: 0.83 (s, 3 H), 0.86 (d, J=6.6 Hz, 3 H), 0.60–2.00 (m, 16 H), 3.28 (s, 3 H), 3.30–3.90 (m, 4 H), 3.77 (br., 1 H), 4.46 (d, J=6.6 Hz, 1 H), 4.57 (d, J=6.6 Hz, 1 H).

(2) In the same manner as in Reference Example 3 (3), the above-obtained (R-19) was treated to obtain (R-20) (49% yield) and (R-21) (49% yield).

Diastereomer 1 ((R-20) or (R-21))

$^1$H NMR (CDCl$_3$) δ: 0.90 (s, 3 H), 0.92 (d, J=6.6 Hz, 3 H), 0.70–2.00 (m, 16 H), 2.07 (s, 3 H), 3.35 (s, 3 H), 3.47 (dd, J=6.3, 11.2 Hz, 1 H), 3.63 (dd, J=3.3, 11.2 Hz, 1 H), 3.84 (d, J=2.6 Hz, 1 H), 4.0–4.15 (m, 2 H), 4.53 (d, J=6.6 Hz, 1 H), 4.64 (d, J=6.6 Hz, 1 H).

Diastereomer 2 ((R-20) or (R-21))

$^1$H NMR (CDCl$_3$) δ: 0.90 (s, 3 H), 0.93 (d, J=6.6 Hz, 3 H), 0.80–2.00 (m, 16 H), 2.07 (s, 3 H), 3.35 (s, 3 H), 3.40–3.50 (m, 2 H), 3.84 (d, J=2.3 Hz, 1 H), 4.01 (dd, J=6.5, 11.2 Hz, 1 H), 4.53 (d, J=6.6 Hz, 1 H), 4.64 (d, J=6.6 Hz, 1 H).

(3) The above-obtained mixture (5.7 g) of (R-20) and (R-21) was dissolved in diisopropylethylamine (15 ml) in a nitrogen atmosphere, chloromethyl methyl ether (1.8 ml) was added dropwise under cooling with ice, and the mixture was stirred overnight in this state. The reaction mixture was extracted with ethyl acetate after the addition of 1N hydrochloric acid. The combined organic layers were dried over anhydrous magnesium sulfate and concentrated. The residue was dissolved in a mixed solvent of methanol and water (4:1) (50 ml), a 4N lithium hydroxide aqueous solution was added, and the mixture was stirred for 2 hr at room temperature. The reaction mixture was extracted with ethyl acetate after the addition of 1N hydrochloric acid. The organic layers were dried over anhydrous magnesium sulfate and concentrated. The residue was purified by silica gel column chromatography (hexane:ethyl acetate=2:1 to an ethyl acetate single solvent) to obtain (R-22) (4.72 g, 83%). The sample is a mixture of stereoisomers based on the asymmetric point to which MOMOCH$_2$ group is bound.

$^1$H NMR (CDCl$_3$) δ: 0.89 (s, 3 H), 0.93 (d, J=6.6 Hz, 3 H), 3.35 (s, 3 H), 3.38 (s, 3 H), 3.40–3.70 (m, 2 H), 3.84 (d, J=2.6 Hz, 1 H), 4.55 (d, J=6.9 Hz, 1 H), 4.64 (d, J=6.9 Hz, 1 H).

(4) The above-obtained (R-22) was treated in the same manner as in Reference Example 3 (4) to obtain (R-23) (76% yield). The sample is a mixture of stereoisomers based on the asymmetric point to which MOMOCH$_2$ group is bound.

$^1$H NMR (CDCl$_3$) δ: 0.87 (s, 3 H), 0.90 (s, 3 H), 0.92 (d, J=6.6 Hz, 3 H), 1.00–2.00 (m, 16 H), 3.33 (s, 3 H), 3.35 (s, 3 H), 3.55–3.75 (m, 2 H), 3.85 (br., 1 H), 4.40–4.70 (m, 2 H), 9.65 (d, J=3.3 Hz, 1 H), 9.71 (d, J=2.2 Hz, 1 H).

Reference Example 5

Production of Compound (14) (m=2)

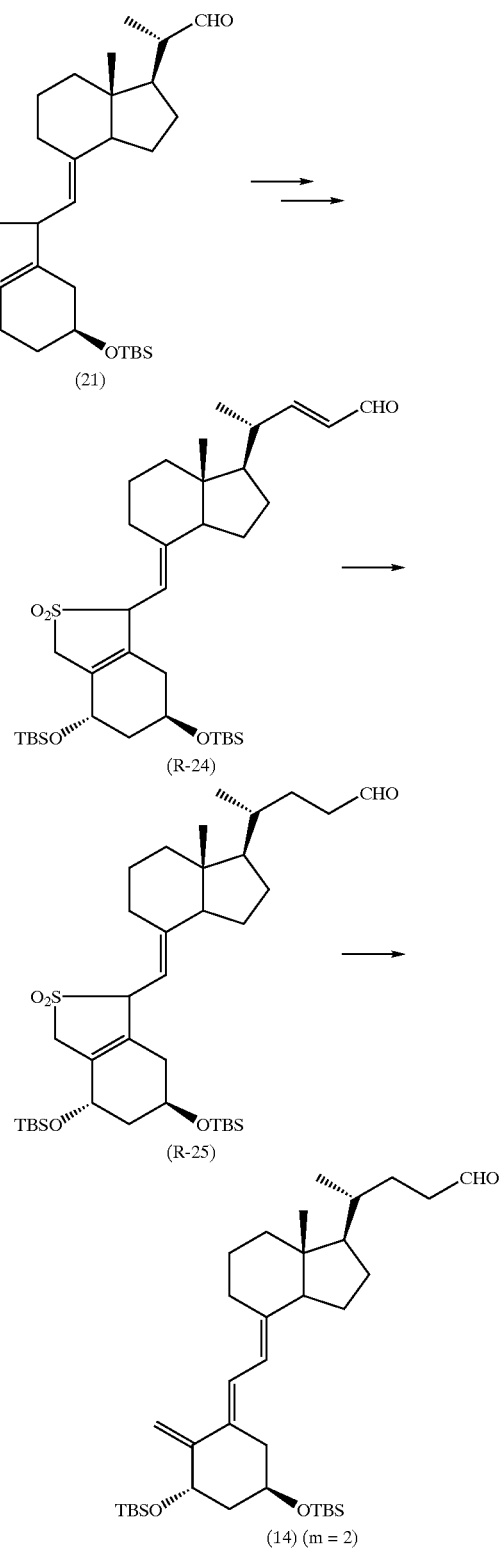

(1) Sodium hydride (220 mg, 60% in oil, 5.5 mmol) was suspended in dry THF (60 ml) in a nitrogen atmosphere, and the suspension was cooled with ice. A dry THF solution (10 ml) of diethyl cyanomethyl phosphonate (0.97 ml, 6 mmol) was added dropwise, and the mixture was stirred for 15 min in this state. To the reaction mixture was added dropwise a dry THF solution (10 ml) of the (21) (3.2 g, 5 mmol), which can be obtained through a known process (International Patent Publication WO90/09991; Tetrahedron, 20, 4609–4619 (1987)), and the mixture was stirred for 30 min under cooling with ice. This reaction mixture was extracted with ethyl acetate after the addition of a saturated ammonium chloride aqueous solution. The combined organic layers were dried over anhydrous magnesium sulfate and concentrated. The residue was dissolved in dry dichloromethane (60 ml), and the solution was cooled to −78° C. A diisobutylaluminum hydride solution (7.4 ml, 1.01 M, 7.5 mmol) in toluene was added dropwise, and subsequently the mixture was stirred for 1.5 hr at the same temperature. The reaction mixture was extracted with ethyl acetate after the addition of a saturated ammonium chloride aqueous solution. The combined organic layers were dried over anhydrous magnesium sulfate and concentrated. The residue was purified by silica gel column chromatography (hexane:ethyl acetate=4:1) to obtain (R-24) (2.8 g, 87% yield).

(2) The above-obtained (R-24) (1.0 g, 1.51 mmol) was dissolved in dry toluene (20 ml) in a nitrogen atmosphere, to the solution were added tetrakis(triphenylphosphine)palladium (0) (62 mg, 0.054 mmol) and subsequently tributyltin hydride (2.0 ml, 7.55 mmol), and the mixture was stirred for 1 hr at room temperature. The reaction mixture was concentrated, and the residue was purified by silica gel column chromatography (hexane:ethyl acetate=20:1 to 5:1) to obtain (R-25) (0.6 g, 60% yield).

(3) The above-obtained (R-25) (580 mg, 0.87 mmol) was dissolved in ethanol (30 ml), and sodium bicarbonate (0.73 g, 8.7 mmol) was added, and the mixture was stirred for 3 hr at 80° C. The reaction mixture was filtered, and the filtrate was concentrated. The residue was purified by silica gel column chromatography (hexane:ethyl acetate=8:1) to obtain (14) (m=2) (454 m g, 87% yield).

Reference Example 6

Production of Compound (R-27)

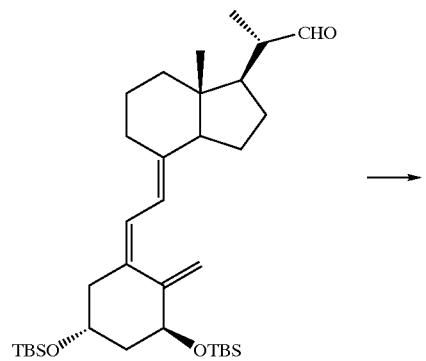

(15) (m = O)

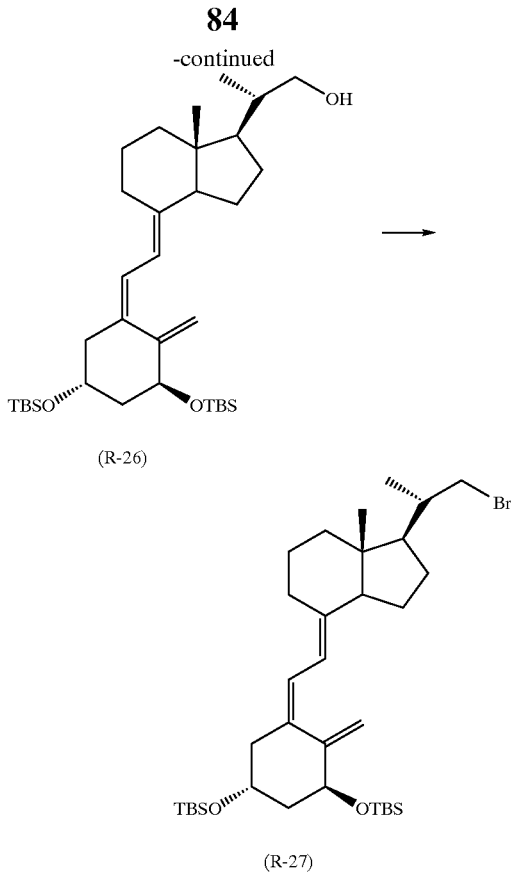

(1) The Compound (15) (m=O) (620 mg, 1.08 mmol), which can be obtained through a known process (International Patent Publication WO90/09991; Tetrahedron, 20, 4609–4619 (1987)), was dissolved in methanol (20 ml), and the solution was cooled to 0° C. To the solution was added sodium borohydride (80.6 mg, 2.13 mmol) in three divisions every 15 min, and subsequently, the mixture was stirred for 15 min. The reaction mixture was extracted with ethyl acetate after the addition of water. The combined organic layers were washed with brine, dried over anhydrous sodium sulfate and concentrated. The residue was purified by silica gel column chromatography (hexane:ethyl acetate=9:1) to obtain (R-26) (429 m g, 60% yield).

$^1$H NMR (CDCl$_3$) δ: 0.06 (s, 12 H), 0.56 (s, 3 H), 0.85 (s, 18 H), 1.05 (d, J=7 Hz, 3 H), 2.1–1.2 (m, 18 H), 2.22 (dd, J=7, 13 Hz, 1 H), 2.43 (br., 1 H), 2.82 (br., 1 H), 3.39 (dd, J=3, 9 Hz, 1 H), 3.65 (dd, J=3, 10 Hz, 1 H), 4.19 (m, 1 H) 4.37 (m, 1 H), 4.86 (d, J=3 Hz, 1 H), 5.18 (d, J=3 Hz, 1 H), 6.02 (d, J=11 Hz, 1 H), 6.24 (d, J=11 Hz, 1 H).

(2) The above-obtained (R-26) (223 mg, 0.388 mmol) and carbon tetrabromide (161 mg, 0.485 mmol) were dissolved in dichloromethane (1 ml), and the solution was cooled to 0° C. Triphenylphosphine (153 mg, 0.582 mmol) was added, and the mixture was stirred for 3 min. The reaction mixture was concentrated, the residue was washed with a mixed solvent (30 ml) of ethyl acetate and hexane (3:1), and only the soluble portion was purified by silica gel column chromatography (hexane:ethyl acetate=19:1) to obtain (R-27) (196 m g, 82% yield).

$^1$H-NMR (CDCl$_3$) δ: 0.06 (s, 12 H), 0.56 (s, 3 H), 0.88 (s, 18 H), 1.06 (d, 3 H, J=7 Hz), 2.1–1.2 (m, 17 H), 2.20 (dd, J=7, 13 Hz, 1 H), 2.45 (br., 1 H), 2.82 (br., 1 H), 3.36 (dd, J=3, 9 Hz, H), 3.50 (dd, J=3, 10 Hz, 1 H), 4.18 (m, 1 H), 4.37 (m, 1 H), 4.86 (d, J=3 Hz, 1 H), 5.17 (d, J=3 Hz, 1 H), 6.02 (d, J=1 Hz, 1 H), 6.23 (d, J=11 Hz, 1 H).

Example 1-1
Production of Compounds No. 1207a and No. 1207b

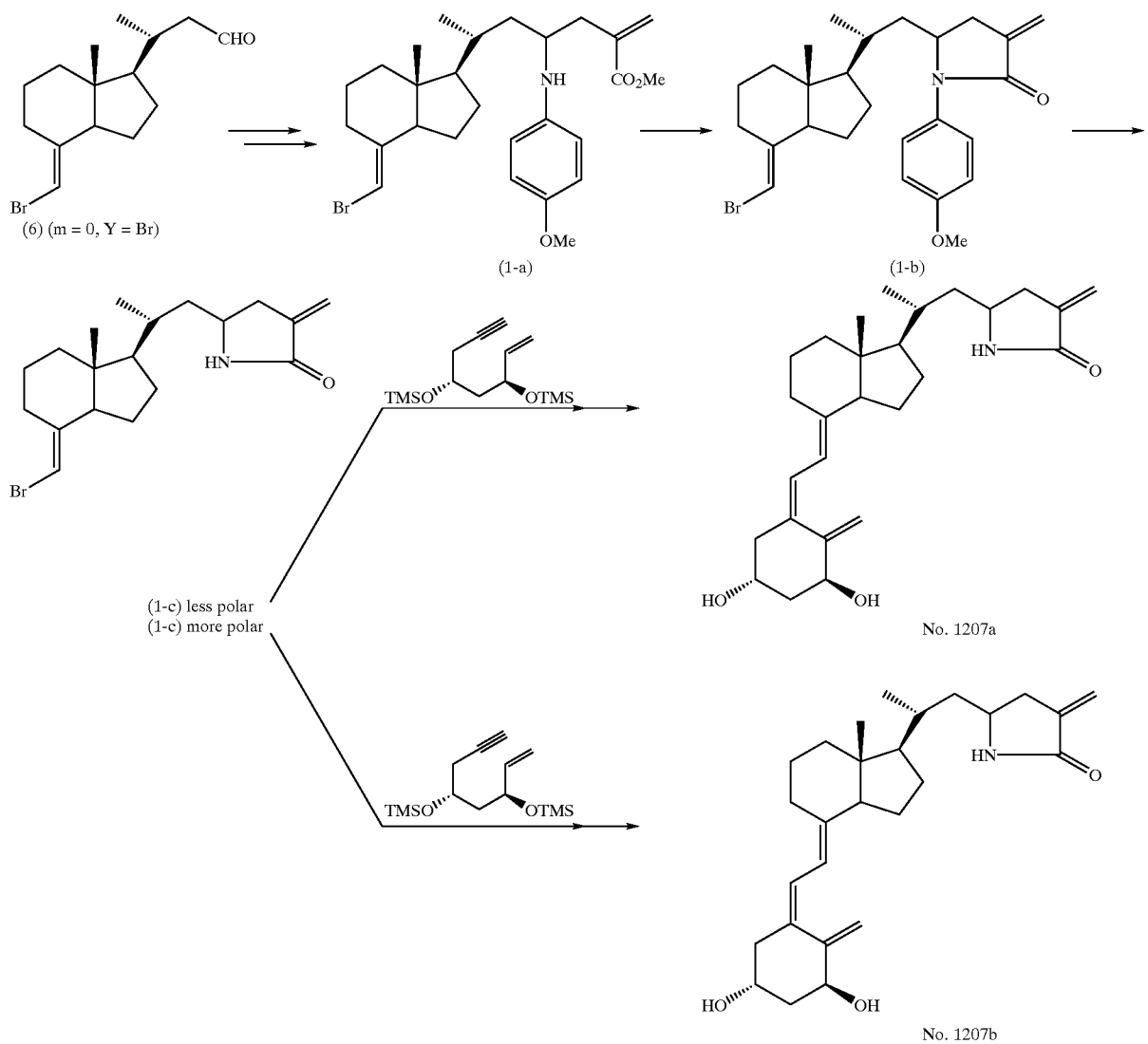

(1) In a nitrogen atmosphere, the (6) (m=0; Y=Br) (629 mg, 2.10 mmol), which can be obtained through the process of Reference Example 1, was dissolved in dry THF (4 ml), and the solution was cooled with ice. A dry THF solution (4 ml) of anhydrous magnesium sulfate (304 mg, 2.52 mmol) and 4-methoxyaniline (263 mg, 2.10 mmol) was added, and the mixture was stirred for 4 hr under cooling with ice. Zinc powder (washed with hydrochloric acid) (206 mg, 3.15 mmol) and methyl 2-bromomethyleneacrylate (376 mg, 2.10 mmol) were added, and the mixture was stirred for 2.5 hr under cooling with ice. The reaction mixture was extracted with ethyl acetate after the addition of a saturated ammonium chloride aqueous solution. The combined organic layers were washed with brine, dried and concentrated. The obtained residue was purified by silica gel column chromatography (hexane:ethyl acetate=20:1 to 12:1) to obtain (1-a) (803 mg, 76% yield). The sample is a mixture of stereoisomers based on the asymmetric point on the lactam ring. The ratio of the diastereomers is 1.4/1.

$^1$H NMR (CDCl$_3$) δ: 0.53 & 0.58 (s, 3 H), 0.90 & 1.06 (d, J=6.4 Hz, 3 H), 1.17–1.70 (m, 7 H), 1.85–2.06 (m, 6 H), 2.15–2.36 (m, 1 H), 2.58–2.88 (m, 2 H), 3.12 (br., 1 H), 3.58 (br., 2 H), 3.74 (s, 3 H), 3.75 (s, 3 H), 5.53 & 5.60 (s, 1 H), 5.64 (s, 1 H), 6.18 (s, 3 H), 6.52 (d, J=8.9 Hz, 1 H), 6.62 (d, J=9.1 Hz, 1 H), 7.73–7.79 (m, 2 H).

(2) The above-obtained (1-a) (400 mg, 0.79 mmol) was dissolved in a mixed solvent of THF (4 ml) and methanol (6 ml), a 4N lithium hydroxide solution (1.0 ml, 3.96 mmol) was added, and the mixture was stirred for 4.5 hr at room temperature and further for 1.5 hr at 50° C. The reaction mixture was extracted with ethyl acetate after the adjustment of pH of the reaction mixture to about 5 by adding a 10% citric acid aqueous solution. The combined organic layers were washed with brine, dried and concentrated to obtain 455 mg of a residue. Out of the residue, 100 mg was dissolved in dry toluene (3 ml), to the solution were added silica gel (400 mg) and molecular sieve 3A (200 mg), and the mixture was stirred for 4 hr at 105° C. The reaction mixture was filtered with a glass filter, the insoluble matter was washed with methanol, and filtrate and washings were combined and concentrated. The residue was purified by silica gel column chromatography (hexane:ethyl acetate=

3:1) to obtain (1-b) (50 mg, 59% yield, diastereomer ratio=1.4:1). The remaining portion (355 mg) of that residue was treated in the same manner to convert to (1-b). The total of both the products was 217 mg (58% yield). The sample is a mixture of stereoisomers based on the asymmetric point on the lactam ring.

$^1$H NMR (CDCl$_3$) δ: 0.41 & 0.58 (s, 3 H), 0.92 & 0.97 (d, J=6.4 Hz, 3 H), 1.04–2.00 (m, 14 H), 2.47–2.58 (m, 1 H), 2.81–2.86 (m, 1 H), 3.00–3.17 (m, 1 H), 3.81 (s, 1 H), 4.11–4.23 (m, 1 H), 5.40 (s, 1 H), 5.61 & 5.64 (s, 1 H), 6.09 (d, J=2.8 Hz, 1 H), 6.93 (d, J=8.4 Hz, 2 H), 7.32 & 7.34 (d, J=8.6 Hz, 2 H).

(3) The above-obtained (1-b) (167 mg, 0.35 mmol) was dissolved in acetonitrile (5 ml), and the solution was cooled with ice. An aqueous solution (4 ml) of ammonium cerium nitrate (581 mg, 1.06 mmol) was added dropwise, and the mixture was stirred for 40 min under cooling with ice. The reaction mixture was extracted with ethyl acetate after the addition of water, a saturated sodium bicarbonate aqueous solution and a saturated sodium sulfite aqueous solution. The combined organic layers were washed with brine, dried and concentrated. The obtained residue was combined to the residue which was obtained from a separate starting raw material (1-b) (50 mg) by treating in the same manner, and they were purified by silica gel column chromatography (hexane:ethyl acetate=2:1 to 1:1) to obtain both of (1-c) less polar compound (68 mg, 40% yield) and (1-c) more polar compound (44 mg, 26%). These are stereoisomers based on the asymmetric point on the lactam ring.

(1-c) Less Polar Compound $^1$H NMR (CDCl$_3$) δ: 0.58 (s, 3 H), 1.00 (d, J=6.4 Hz, 3 H), 1.15–1.37 (m, 4 H), 1.39–1.71 (m, 7 H), 1.80–2.17 (m, 3 H), 2.32–2.42 (m, 1 H), 2.85–2.89 (m, 1 H), 3.01 (ddt, J=2.5, 7.8, 17.0 Hz, 1 H), 3.72–3.81 (m, 1 H), 5.32 (s, 1 H), 5.64 (s, 1 H), 5.95 (t, J=2.8 Hz, 1 H), 7.39 (br., 1 H).

(1-c) More Polar Compound $^1$H NMR (CDCl$_3$) δ: 0.58 (s, 3 H), 0.99 (d, J=6.1 Hz, 3 H), 1.17–1.72 (m, 11 H), 1.80–2.07 (m, 3 H), 2.36–2.46 (m, 1 H), 2.85–3.02 (m, 2 H), 3.70–3.79 (m, 1 H), 5.35 (s, 1 H), 5.65 (d, J=1.7 Hz, 1 H), 5.98 (t, J=2.5 Hz, 1 H), 6.57 (br., 1 H).

(4) In a nitrogen atmosphere, triphenylphosphine (10.7 mg, 41 μmol) and tris(dibenzylideneacetone)dipalladium(0)-chloroform adduct (7.1 mg, 6.8 μmol) were dissolved in dry toluene (0.75 ml), and the solution was stirred for 20 min at room temperature in a nitrogen atmosphere. The above-obtained (1-c) less polar compound (25 mg, 68 μmol) and a diisopropylethylamine solution (0.75 ml) of (3S),(5R)-3,5-bis(trimethylsilyloxy)-1-octen-7-yne (39 mg, 136 μmol) were added, and the mixture was stirred for 6 hr at 100° C. The reaction mixture was extracted with ethyl acetate after the addition of a saturated potassium hydrogensulfate aqueous solution. The combined organic layers were washed with a saturated sodium bicarbonate aqueous solution and with brine, dried and concentrated to obtain a crude coupled body. This was dissolved in acetonitrile (3 ml), to the solution was added lithium tetrafluoroborate (33 mg, 352 μmol), subsequently a 1N sulfuric acid-acetonitrile solution (106 μmol, 106 μl) under cooling with ice, and the mixture was stirred for 20 min in this state. The reaction mixture was extracted with ethyl acetate after the addition of a saturated sodium bicarbonate aqueous solution. The combined organic layers were washed with brine, dried and concentrated. The residue was purified by silica gel column chromatography (hexane:ethyl acetate=2:1 to 1:1, and to hexane ethyl acetate:methanol=3:3:1). The above process was repeated using the raw material, (1-c) less polar compound (43 mg, 117 μmol), and the product was combined to the above-obtained product. The combined products were purified by HPLC fractionation (column, ODS; acetonitrile:water=45:55) to obtain Compound No. 1207a (3.3 mg, 4.2% yield).

$^1$H NMR (CDCl$_3$) δ: 0.56 (s, 3 H), 0.99 (d, J=6.4 Hz, 3 H), 1.18–1.75 (m, 13 H), 1.75–2.02 (m, 5 H), 2.28–2.44 (m, 2 H), 2.57–2.62 (m, 1 H), 2.80–2.85 (m, 1 H), 2.97–3.07 (m, 1 H), 3.73–3.80 (m, 1 H), 4.23 (br., 1 H), 4.43 (br., 1 H), 5.00 (s, 1 H), 5.34 (s, 2 H), 5.99 (t, J=3.0 Hz, 1 H), 6.02 (d, J=11.5 Hz, 1 H), 6.14 (s, 1 H), 6.37 (d, J=11.1 Hz, 1 H).

(5) The same operation was carried out by using (1-c) more polar compound (44 mg, 120 μmol) as a raw material to obtain Compound No. 1207b (2.7 mg, 5.3% yield).

$^1$H NMR (CDCl$_3$) δ: 0.57 (s, 3 H), 0.99 (d, J=6.1 Hz, 3 H), 1.17–1.74 (m, 13 H), 1.88–2.03 (m, 5 H), 2.32 (dd, J=6.7 and 13.3 Hz, 1 H), 2.37–2.46 (m, 1 H), 2.57–2.63 (m, 1 H), 2.80–2.85 (m, 1 H), 2.92–3.02 (m, 1 H), 3.70–3.78 (m, 1 H), 4.23 (br., 1 H), 4.43 (br., 1 H), 5.00 (s, 1 H), 5.32–5.34 (m, 2 H), 5.71 (br.s, 1 H), 5.99 (t, J=2.8 Hz, 1 H), 6.02 (d, J=12.2 Hz, 1 H), 6.38 (d, J=10.9 Hz, 1 H).

Example 1-2

Production of Compound No. 1107a

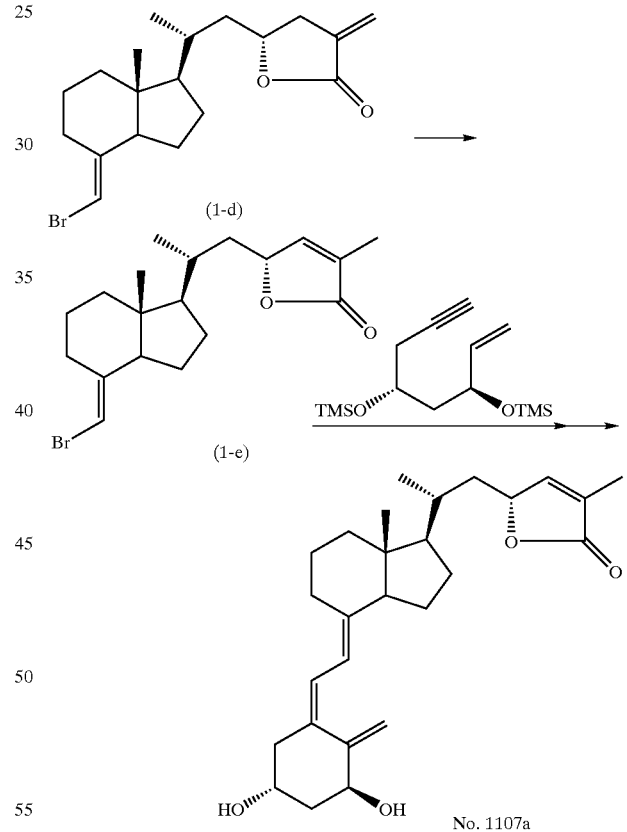

(1) Into an ethanol solution (5 ml) of the (1-d) (27 mg, 73.5 μmol) produced according to the method described in International Patent Publication WO95/33716 was added rhodium chloride (1 mg), and the mixture was stirred overnight at 80° C. The reaction mixture was evaporated, and the residue was purified by silica gel column chromatography to obtain (1-e) (23.5 mg, 87% yield).

$^1$H NMR (CDCl$_3$) δ: 0.59 (s, 3 H), 0.70–3.00 (m, 15 H, 1.06 (d, J=6.5 Hz, 3 H), 1.90 (s, 3 H), 2.80–2.90 (m, 1 H), 4.93–4.99 (m, 1 H), 5.64 (s, 1 H), 6.99 (t, J=1.6 Hz, 1H).

(2) Triphenylphosphine (13.7 mg, 52 μmol) and tris(dibenzylideneacetone)dipalladium (0)-chloroform adduct (9 mg, 8.6 μmol) were dissolved in dry toluene (1.0 ml), and the solution was stirred for 15 min in a nitrogen atmosphere. The above-obtained (1-e) (23.5 mg, 64 μmol) and a diisopropylethylamine solution (1.0 ml) of (3S),(5R)-3,5-bis(trimethylsilyloxy)-1-octen-7-yne (49.5 mg, 174 μmol) were added, and the mixture was stirred overnight at 90° C. The reaction mixture was extracted with ethyl acetate after the addition of 1N hydrochloric acid. The combined organic layers were washed with a saturated sodium bicarbonate aqueous solution and with brine, dried and concentrated. The residue was roughly purified by a short column of silica gel. The obtained crudely purified coupled body was dissolved in THF (3 ml), and a 1N TBAF solution in THF was added dropwise at 0° C. The mixture was stirred for 30 min at room temperature in this state, and then the reaction mixture was extracted with ethyl acetate after the addition of a saturated sodium bicarbonate aqueous solution. The combined organic layers were washed with brine, dried and concentrated. The residue was purified by silica gel column chromatography. The sample was purified by HPLC fractionation (column, ODS; acetonitrile water=40:60) to obtain Compound No. 1107a (7.9 mg, 29% yield).

$^1$H NMR (CDCl$_3$) δ: 0.57 (s, 3 H), 0.60–3.00 (m, 19 H), 1.06 (d, J=4.5 Hz, 3 H), 1.91 (s, 3 H), 4.23 (br., 1 H), 4.43 (br., 1 H), 4.90–5.01 (m, 1 H), 5.00 (s, 1 H), 5.33 (s, 1 H), 6.01 (d, J=7.8 Hz, 1 H), 6.37 (d, J=7.8 Hz, 1 H), 6.99 (d, J=1.0 Hz, 1 H).

Example 1-3
Production of Compound No. 1107b (1-g):
$^1$H NMR (CDCl$_3$) δ: 0.59 (s, 3 H), 0.70–3.00 (m, 15 H), 1.06 (d, J=5.1 Hz, 3 H), 1.90 (s, 3 H), 2.80–2.90 (m, 1 H), 4.93–4.99 (m, 1 H), 5.64 (s, 1 H), 7.06 (t, J=1.6 Hz, 1 H).
No. 1107b:
$^1$H NMR (CDCl$_3$) δ: 0.56 (s, 3 H), 0.60–3.00 (m, 19 H), 0.97 (d, J=4.1 Hz, 3 H), 1.87 (s, 3 H), 4.23 (br., 1 H), 4.43 (br., 1 H), 4.94 (br, 1 H), 5.00 (s, 1 H), 5.32 (s, 1 H), 6.00 (d, J=7.6 Hz, 1 H), 6.37 (d, J=7.6 Hz, 1 H), 7.06 (d, J=1.0 Hz, 1H).

Example 1-4
Production of Compounds No. 1104a and 1104b

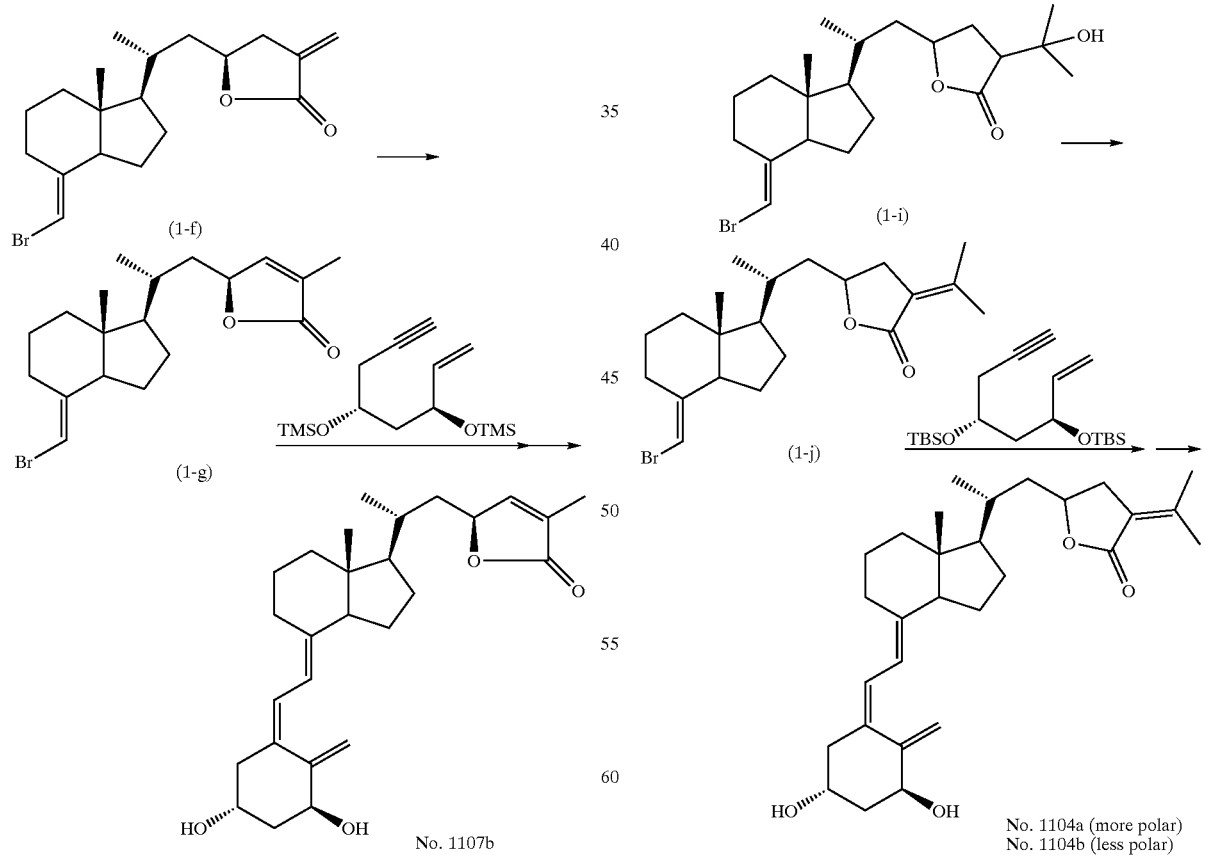

(1) By using the (1-f) which was produced in the method described in International Patent Publication WO95/33716, the same processes as in Example 1-2 were carried out.

(1) In a nitrogen atmosphere, the (6) (m=0; Y=Br) (0.51 g, 1.70 mmol), which can be produced according to the method of Reference Example 1, was dissolved in dry methylene chloride (5 ml), and the solution was cooled to −70° C. Titanium tetrachloride (0.64 g, 3.41 mmol) was added, and further a dry methylene chloride solution (3 ml) of (1-(ethoxycyclopropyl)oxy)trimethylsilane (0.59 g, 3.41 mmol) was added dropwise. The mixture was subsequently stirred at −70° C. for 1 hr, under cooling with ice for 1.5 hr and at room temperature for 1.5 hr. The reaction mixture was extracted with ethyl acetate after the addition of water. The combined organic layers were washed with brine, dried and concentrated. The residue was dissolved in dry THF (4 ml), a TBAF solution (1.0 ml, 1M, 1.0 mmol) in THF was added, and the mixture was stirred for 1 hr at room temperature. The reaction mixture was extracted with ethyl acetate after the addition of a saturated potassium hydrogensulfate aqueous solution. The combined organic layers were washed with brine, dried and concentrated. The residue was purified by silica gel column chromatography (hexane:ethyl acetate= 20:1 to 5:1) to obtain (1-h) (357 mg, 59% yield). The sample is a mixture of stereoisomers based on the asymmetric point on the lactone ring.

$^1$H NMR (CDCl$_3$) δ: 0.58, 0.58 (s, 3 H), 1.00–1.04 (m, 3 H), 1.20–2.05 (m, 15 H), 2.29–2.38 (m, 1 H), 2.49–2.57 (m, 2 H), 2.85–2.90 (m, 1 H), 4.54–4.62 (m, 1 H), 5.66 (s, 1 H).

MS: m/e 355.3 (M+1)$^+$ (2) In a nitrogen atmosphere, diisopropylamine (93 mg, 0.91 mmol) was dissolved in dry THF (3 ml), and the solution was cooled to −30° C. An n-butyllithium solution (0.57 ml, 1.47 M, 0.84 mmol) in hexane was added, and the reaction mixture was cooled to −70° C. A dry THF solution (3 ml) of the above-obtained (1-h) (250 mg, 0.704 mmol) was added dropwise, and the mixture was stirred for 1 hr at −70° C. without raising the temperature. A dry THF solution (2 ml) of acetone (49 mg, 0.84 mmol) was added, and the mixture was stirred for 2 hr while slowly warming up (final temperature of −35° C.). The reaction mixture was extracted with ethyl acetate after the addition of a saturated ammonium chloride aqueous solution. The combined organic layers were washed with brine, dried and concentrated. The residue was purified by silica gel column chromatography (hexane:ethyl acetate=10:1 to 3:1) to obtain (1-i) (226 mg, 78% yield). The sample is a mixture of stereoisomers based on the asymmetric point on the lactone ring.

$^1$H NMR (CDCl$_3$) δ: 0.58 (s, 3 H), 1.01–1.04 (m, 3 H), 1.22–2.07 (m, 13 H), 1.26–1.32 (m, 6 H), 2.19–2.28 (m, 2 H), 2.31–2.45 (m, 1 H), 2.72–2.80 (m, 1 H), 2.86–2.89 (mn, 1 H), 3.41, 3.62 (br., 1 H), 4.57–4.75 (m, 1 H), 5.65 (s, 1 H).

MS: m/e 413.3 (M+1)$^+$ (3) The above-obtained (1-i) (226 mg, 0.55 mmol) was dissolved in dry methylene chloride (5 ml), and dimethylaminopyridine (334 mg, 2.73 mmol) was added. The solution was cooled with ice, methanesulfonyl chloride (125 mg, 1.09 mmol) was added, and the mixture was stirred overnight at room temperature. The reaction mixture was extracted with ethyl acetate after the addition of water. The combined organic layers were washed with brine, dried and concentrated. The residue was purified by silica gel column chromatography (hexane:ethyl acetate=20:1 to 10:1) to obtain (1-j) (179 mg, 83% yield). The sample is a mixture of stereoisomers based on the asymmetric point on the lactone ring.

$^1$H NMR (CDCl$_3$) δ: 0.58 (s, 3 H), 1.00–1.03 (m, 3 H), 1.22–1.81 (m, 11 H), 1.86, 1.86 (s, 3 H), 1.94–2.04 (m, 3 H), 2.25 (s, 3 H), 2.37–2.43 (m, 1 H), 2.84–2.93 (m, 2 H), 4.46–4.51 (m, 1 H), 5.64 (s, 1 H).

MS: m/e 395.3 (M+1)$^+$ (4) By employing substantially the same process as in Example 1-1 (4), but using (3S),(5R)-3,5-bis(t-butyldimethylsilyloxy)-1-octen-7-yne in place of (3S),(5R)-3,5-bis(trimethylsilyloxy)-1-octen-7-yne, the raw material (1-i) (209 mg, 0.529 mmol) was converted to a coupled body (313 mg, 87% yield) and No. 1104a.

The Coupling Body $^1$H NMR (CDCl$_3$) δ: 0.06 (s, 6 H), 0.06 (s, 6 H), 0.55–0.57 (m, 3 H), 0.87 (m, 6 H), 0.88 (m, 12 H), 1.01–1.03 (m, 3 H), 1.23–2.04 (m, 17 H), 1.87 (s, 3 H), 2.25 (s, 3 H), 2.3–2.5 (m, 2 H), 2.8–3.0 (m, 2 H), 4.19 (br., 1 H), 4.37 (br., 1 H), 4.46–4.51 (m, 1 H), 4.86 (s, 1 H), 5.18 (s, 1 H), 6.02 (d, J=11.1 Hz, 1 H), 6.24 (d, J=11.1 Hz, 1 H).

MS: m/e 683.8 (M+1)$^+$ (5) After the removal of the protection groups, the No. 1104a was subjected to HPLC fractionation (column:ODS; acetonitrile:water=65:35) to separately collect two kinds of isomers, the more polar compound (31.5 mg, 15% yield) and the less polar compound (23.5 mg, 11% yield). These compounds are isomers based on the asymmetric point on the lactone ring.

More Polar Compound, No. 1104a $^1$H NMR (CDCl$_3$) δ: 0.57 (s, 3 H), 1.02 (d, J=6.1 Hz, 3 H), 1.18–2.04 (m, 18 H), 1.87 (s, 3 H), 2.25 (t, J=2.0 Hz, 3 H), 2.28–2.45 (m, 2 H), 2.56–2.61 (m, 1 H), 2.80–2.85 (m, 1 H), 2.96 (dd, J=7.6, 15.8 Hz, 1 H), 4.20–4.25 (m, 1 H), 4.41–4.54 (m, 2 H), 4.99 (s, 1 H), 5.33 (s, 1 H), 6.02 (d, J=11.4 Hz, 1 H), 6.37 (d, J=11.2 Hz, 1 H).

MS: m/e 455.5 (M+1)$^+$

Less Polar Compound, No. 1104b $^{11}$H NMR (CDCl$_3$) δ: 0.57 (s, 3 H), 1.01 (d, J=6.1 Hz, 3 H), 1.16–1.36 (m, 4 H), 1.43–2.05 (m, 14 H), 1.86 (s, 3 H), 2.25 (t, J=2.0 Hz, 3 H), 2.30–2.44 (m, 2 H), 2.57–2.62 (m, 1 H), 2.80–2.85 (m, 1 H), 2.98 (dd, J=7.6, 15.8 Hz, 1 H), 4.21–4.26 (m, 1 H), 4.41–4.45 (m, 1 H), 4.49–4.58 (m, 1 H), 5.00 (s, 1 H), 5.33 (t, J=1.7 Hz, 1 H), 6.02 (d, J=11.2 Hz, 1 H), 6.37 (d, J=11.2 Hz, 1 H).

MS: m/e 455.5 (M+1)$^+$

Example 1-5

Production of Compound No. 1125

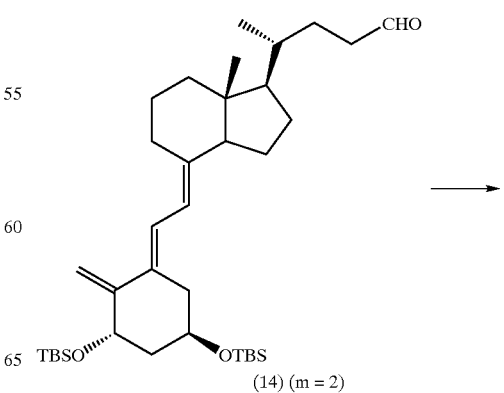

(14) (m = 2)

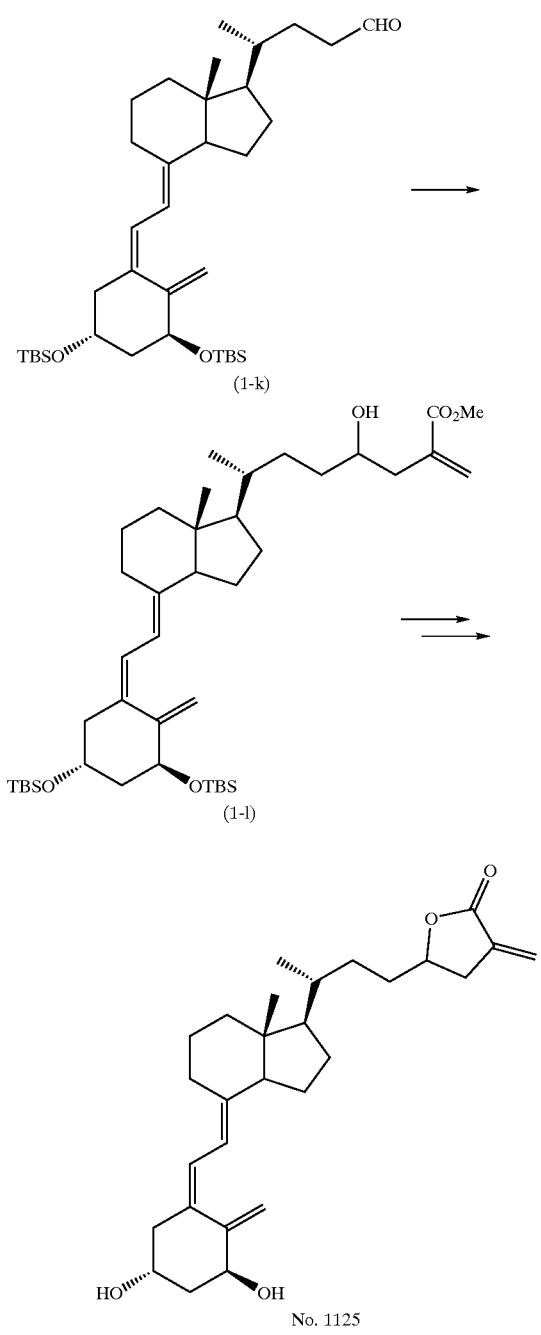

2.15–2.3 (m, 1 H), 2.42–2.47 (m, 2 H), 4.19 (br., 1 H), 4.38 (br., 1 H), 4.86 (s, 1 H), 5.17 (s, 1 H), 6.02 (d, J=12.0 Hz, 1 H), 6.23 (d, J=12.0 Hz, 1 H), 9.78 (s, 1 H).

(2) The above-obtained (1-k) (141 mg, 0.235 mmol) was dissolved in THF (3 ml), and the solution was cooled with ice. Methyl bromomethylacrylate (63 mg, 0.35 mmol), zinc powder (washed with hydrochloric acid) (23 mg, 0.35 mmol) and a saturated ammonium chloride aqueous solution (0.4 ml) were added, and the mixture was stirred for 1 hr in this state and further for 1 hr at room temperature. The reaction mixture was extracted with ethyl acetate after the addition of water. The combined organic layers were washed with brine, dried and concentrated. The residue was purified by silica gel column chromatography (hexane:ethyl acetate= 40:1 to 10:1) to obtain (1-l) (139 mg, 85% yield). The sample is a mixture of stereoisomers based on the asymmetric point to which the hydroxyl group is bound.

$^1$H NMR (CDCl$_3$) δ: 0.06 (s, 6 H), 0.06 (s, 6 H), 0.53 (s, 3 H), 0.87–0.95 (m, 3 H), 0.88 (s, 18 H), 1.23–2.9 (m, 24 H), 3.69–3.76 (br., 1 H), 3.77 (s, 3 H), 4.19 (br., 1 H), 4.37 (br., 1 H), 4.87 (d, J=2.5 Hz, 1 H), 5.17 (s, 1 H), 5.67 (s, 1 H), 6.02 (d, J=11.1 Hz, 1 H), 6.23 (d, J=10.4 Hz, 1 H), 6.26 (s, 1 H).

MS: m/e 701.8 (M+1)$^+$ (3) The above-obtained (1-l) (117 mg, 0.167 mmol) was dissolved in dry THF (2 ml), and the solution was cooled with ice. A TBAF solution (0.15 ml, 1N, 0.15 mmol) in THF was added, and the mixture was stirred for 30 min in this state. The reaction mixture was extracted twice with ethyl acetate after the addition of a saturated potassium hydrogensulfate aqueous solution. The combined organic layers were washed with brine, dried and concentrated. The residue was dissolved in a mixed solvent of acetonitrile (2 ml) and methylene chloride (1 ml), and the solution was cooled with ice. Lithium tetrafluoroborate (47 mg, 0.5 mmol) and a 1N sulfuric acid-acetonitrile solution (150 ml, 150 mmol) were added, and the mixture was stirred for 20 min in this state. The reaction mixture was extracted twice with ethyl acetate after the addition of a saturated sodium bicarbonate aqueous solution. The combined organic layers were washed with brine, dried and concentrated to obtain a residue. The (1-l) (22 mg) was treated in the same manner as described above to obtain a residue, and this was combined to the above-obtained one. The combined residue was treated with silica gel column chromatography (hexane:ethyl acetate=2:1 to hexane:ethyl acetate:methanol=3:3:1) to obtain a crudely purified product (64 mg), and this was further purified by HPLC fractionation (column, ODS; acetonitrile:water= 60:40) to obtain Compound No. 1125 (17.5 mg, 24% yield). The sample is a mixture of isomers based on the asymmetric point on the lactone ring.

(1) The (14) (m=2) (185 mg, 0.308 mmol) which was obtained in Reference Example 5 and anthracene (55 mg, 0.308 mmol) were dissolved in dry toluene 5 ml, and nitrogen gas was blown into the solution for 25 min at room temperature. Subsequently, the solution was sealed tightly and irradiated with light (mercury lamp, 100 W) for 1.5 hr. The reaction mixture was concentrated. After the addition of ethanol (5 ml), the residue was filtered to remove insoluble matter. The filtrate was evaporated, and the residue was purified by preparative TLC (hexane:ethyl acetate=5:1) to obtain (1-k) (143 mg, 77% yield).

$^1$H NMR (CDCl$_3$) δ: 0.06 (s, 12 H), 0.53 (s, 3 H), 0.81–0.95 (m, 3 H), 0.88 (s, 18 H), 1.23–2.05 (m, 17 H), $^1$H NMR (CDCl$_3$) δ: 0.55 (s, 3 H), 0.95 (d, J=6.3 Hz, 3 H), 1.03–2.06 (m, 20 H), 2.31 (dd, J=6.8, 13.4 Hz, 1 H), 2.52–2.61 (m, 2 H), 2.80–2.85 (m, 1 H), 3.00–3.10 (m, 1 H), 4.22 (br., 1 H), 4.44 (br., 2 H), 5.00 (s, 1 H), 5.33 (s, 1 H), 5.62 (t, J=2.5 Hz, 1 H), 6.02 (d, J=11.4 Hz, 1 H), 6.23 (t, J=2.5 Hz, 1 H), 6.38 (d, J=11.2 Hz, 1 H).

MS: m/e 441.5 (M+1)$^+$

Example 2-1

Production of Compound No. 2109a

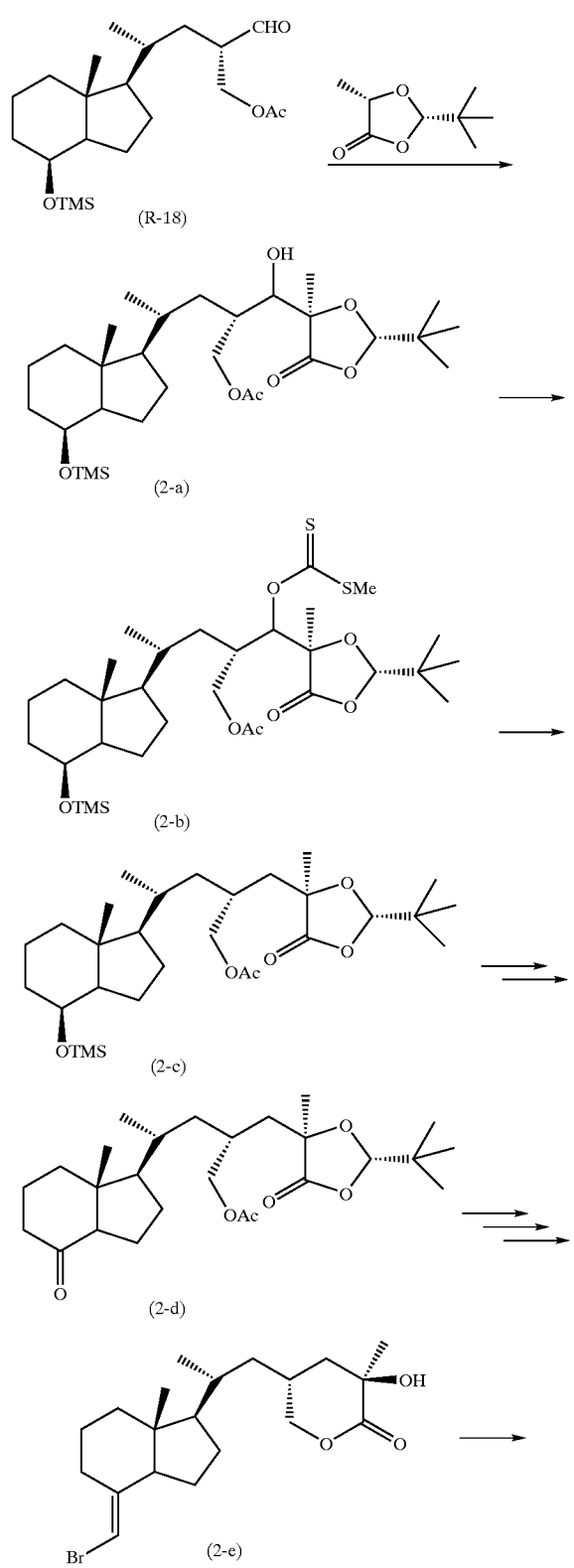

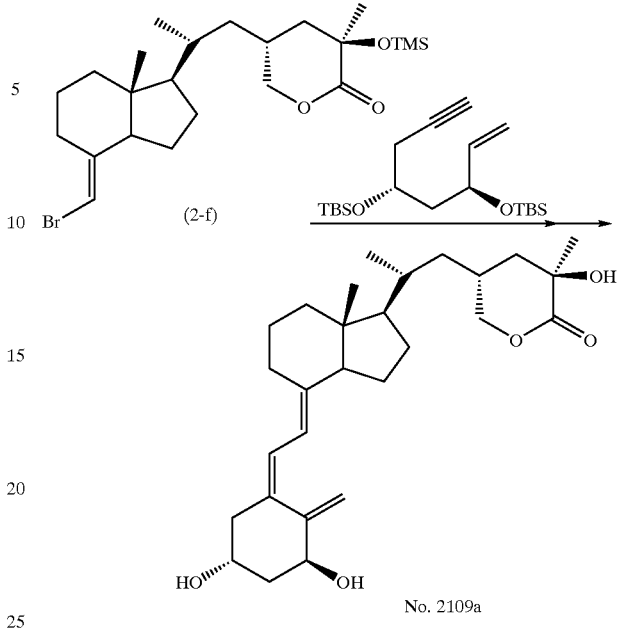

(1) In a nitrogen atmosphere, diisopropylamine (0.15 ml) was dissolved in dry THF (5 ml), and the solution was cooled to 0° C. An n-butyllithium solution (1.63 M) in hexane was added, and the mixture was stirred for 20 min in this state. The solution was cooled to −78° C., a THF solution (3 ml) of a dioxolanone compound (169 mg), which can be obtained by a known process (for example, Seebach, et al., Tetrahedron, 40, 1313 (1984)), was slowly added, and the mixture was stirred for 30 min at the temperature. A dry THF solution (2 ml) of the (R=18) (90 mg) obtained by Reference Example 3 was added, and the mixture was stirred for 1 hr at −78° C. The reaction mixture was extracted with ethyl acetate after the addition of a saturated ammonium chloride aqueous solution (20 ml). The combined organic layers were dried and concentrated. The residue was purified by silica gel column chromatography (hexane:ethyl acetate= 4:1) to obtain (2-a) (92 mg, 75% yield).

$^1$H NMR (CDCl$_3$) δ: 0.00 (s, 9 H), 0.70–2.00 (m, 16 H), 0.91 (s, 9 H), 1.00 (s, 3 H), 1.03 (s, 3 H), 1.44 (d, J=2.0 Hz, 3 H), 2.00 (s, 3 H), 2.44 (d, J=5.6 Hz, 1 H), 3.56 (d, J=6.0 Hz, 1 H), 3.80 (d, J=4.0 Hz, 1 H), 3.94 (br., 1 H), 4.00–4.40 (m, 1 H).

(2) The above-obtained (2-a) (58 mg) was dissolved in DMF (5 ml), 1,5-diazabicyclo[4,3,0]non-5-ene (0.066 ml), carbon disulfide (0.06 ml) and methane iodide (0.06 ml) were added, and the mixture was stirred for 20 min at room temperature. The reaction mixture was concentrated, and the residue was purified by silica gel column chromatography (hexane:ethyl acetate=10:1) to obtain (2-b) (33 mg, 50% yield).

$^1$H NMR (CDCl$_3$) δ: 0.00 (s, 9 H), 0.70–2.00 (m, 22 H), 0.89 (s, 9 H), 1.48 (s, 3 H), 2.00 (s, 3 H), 2.54 (s, 3 H), 3.80 (dd, J=8.3, 11.2 Hz, 1 H), 3.92 (br., 1 H), 4.77 (dd, J=4.0; 11.2 Hz, 1 H), 5.22 (s, 1 H), 6.18 (s, 1 H).

(3) In a nitrogen atmosphere, the above-obtained (2-b) (33 mg) was dissolved in dry toluene (6 ml), and a tributyltin hydride solution (1 ml, 0.93 M) in toluene was added, and the mixture was stirred for 30 min at 70° C. To the reaction mixture were added a saturated ammonium chloride aqueous solution (10 ml) and acetonitrile (15 ml), and the organic phase was separated from the inorganic phase. The organic layers were combined and washed with hexane (20 ml) and concentrated. The residue was purified by silica gel column chromatography (hexane:ethyl acetate=10:1) to obtain (2-c) (27 mg, 100% yield).

$^1$H NMR (CDCl$_3$) δ: 0.00 (s, 9 H), 0.70–2.00 (m, 18 H), 0.85 (s, 9 H), 0.90 (s, 9 H), 1.23 (s, 3 H), 1.40 (s, 3 H), 2.00 (s, 3 H), 3.80 (dd, J=6.9, 10.9 Hz, 1 H), 3.94 (br., 1 H), 4.05 (cd, J=5.0, 10.9 Hz, 1 H), 5.16 (s, 1 H).

(4) The above-obtained (2-c) (153 mg) was dissolved in 1,2-dimethoxyethane (8 ml), water (2 ml) and one drop of conc. sulfuric acid were added, and the mixture was stirred for 30 min at room temperature. The reaction mixture was extracted with ethyl acetate after the addition of a saturated sodium bicarbonate aqueous solution (10 ml). The combined organic layers were dried and concentrated to obtain a crude product whose TMS group had been removed. In a nitrogen atmosphere, the crude product was dissolved in dry toluene (8 ml), to the solution were added methyl allylcarbonate (2 ml) and tetrakis(triphenylphosphine)ruthenium hydride (14 mg), and the mixture was heated and refluxed for 2 hr. The reaction mixture was cooled down to room temperature and evaporated. The residue was purified by silica gel column chromatography (hexane:ethyl acetate=2:1) to obtain (2-d) (130 mg, 98% yield).

$^1$H NMR (CDCl$_3$) δ: 0.63 (s, 3 H), 0.70–2.00 (m, 17 H), 0.94 (s, 9 H), 0.99 (d, J=5.6 Hz, 3 H), 1.46 (s, 3 H), 2.06 (s, 3 H), 2.40 (m, 1 H), 3.99–4.08 (m, 2 H), 5.14 (s, 1H).

(5) In a nitrogen atmosphere, (bromomethyl)triphenylphosphonium bromide (1.3 g) was dissolved in dry THF (10 ml), and the solution was cooled to −78° C. A sodium bis(trimethylsilyl)amide solution (2.9 ml, 1M, 2.9 mmol) in THF was added, and the mixture was stirred for 1 hr in this state. A dry THF solution (5 ml) of the above-obtained (2-d) (130 mg) was added, and the mixture was stirred for 1 hr at −78° C. and subsequently stirred overnight while the mixture was warmed up slowly to room temperature. The reaction mixture was extracted with ethyl acetate after the addition of 1N hydrochloric acid (10 ml). The combined organic layers were dried and concentrated to obtain a crude product of a bromomethylene-substituted compound. The crude product was dissolved in a mixed solvent of methanol (3 ml) and water (1 ml), and the solution was stirred for 20 min at room temperature after the addition of 4N lithium hydroxide aqueous solution (0.5 ml). The reaction mixture was further stirred for 1 hr at room temperature after it was neutralized to pH 3 with conc. hydrochloric acid. The reaction mixture was extracted with ethyl acetate after the addition of a saturated sodium bicarbonate aqueous solution (20 ml). The combined organic layers were dried and concentrated, and the obtained residue was purified by silica gel column chromatography (hexane:ethyl acetate=5:1) to obtain (2-e) (35 mg, 30% yield).

$^1$H NMR (CDCl$_3$) δ: 0.70–2.00 (m, 18 H), 0.58 (s, 3 H), 0.99 (d, J=6.3 Hz, 3 H), 1.49 (s, 3 H), 2.81–2.88 (m, 1 H), 3.93 (t, J=10.9 Hz, 1 H), 4.38–4.45 (m, 1 H), 5.64 (s, 1 H).

(6) In a nitrogen atmosphere, the above-obtained (2-e) (17 mg) was dissolved in pyridine (5 ml), and trimethylsilyl chloride (0.5 ml) was added, and the mixture was stirred for 15 min at room temperature. The reaction mixture was extracted with ethyl acetate after the addition of a saturated ammonium chloride aqueous solution (10 ml). The combined organic layers were dried and concentrated, and the obtained residue was purified by silica gel column chromatography (hexane:ethyl acetate=15:1) to obtain (2-f) (25 mg, 74% yield).

$^1$H NMR (CDCl$_3$) δ: 0.00 (s, 9 H), 0.70–2.00 (m, 15 H), 0.42 (s, 3 H), 1.31 (s, 3 H), 1.43 (s, 3 H), 2.10–2.30 (m, 1 H), 2.40 (m, 1H), 2.60–2.80 (m, 1 H), 3.78–3.85 (m, 1 H), 4.30–4.50 (m, 1 H), 5.49 (s, 1 H).

(7) In a nitrogen atmosphere, triphenylphosphine (8 mg) and tris(benzylideneacetone)palladium (0)-chloroform adduct (6 mg) were dissolved in a mixed solvent of anhydrous toluene (0.5 ml) and diisopropylethylamine (0.5 ml), and the solution was stirred for 15 min at room temperature. The above-obtained (2-f) (25 mg) and (3S),(5R)-3,5-bis(t-butyldimethylsilyloxy)-1-octen-7-yne (39 mg) were dissolved in a mixed solvent of anhydrous toluene (0.5 ml) and diisopropylethylamine (0.5 ml), the solution was added to the above-obtained palladium catalyst solution, and the mixture was stirred for 3 hr at 100° C. The reaction mixture was extracted with ethyl acetate after the addition of 1N hydrochloric acid (5 ml). The combined organic layers were dried and concentrated, and the obtained residue was roughly purified by silica gel short column chromatography (hexane:ethyl acetate=20:1 to 10:1) to obtain a crude product of a coupled body. The crude product was dissolved in a mixed solvent of dimethoxyethane (8 ml) and water (2 ml), and the solution was stirred for 48 hr at room temperature after the addition of a drop of conc. sulfuric acid. The reaction mixture was extracted with ethyl acetate after the addition of a saturated sodium bicarbonate aqueous solution (10 ml). The combined organic layers were dried and concentrated, and the obtained residue was purified by silica gel column chromatography (hexane:ethyl acetate=1:3) to obtain Compound No. 2109a (5 mg, 46% yield).

$^1$H NMR (CDCl$_3$) δ: 0.55 (s, 3 H), 0.93 (d, J=6.6 Hz, 3 H), 1.10–3.50 (m, 22 H), 1.49 (s, 3 H), 3.88 (t, J=10.9 Hz, 1 H), 4.08 (br., 1 H), 4.35–4.45 (m, 2 H), 5.00 (s, 1 H), 5.32(s, 1H), 6.02 (d, J=11.2 Hz, 1 H), 6.37 (d, J=11.2 Hz, 1 H).

Example 2-2

Production of Compound No. 2109b

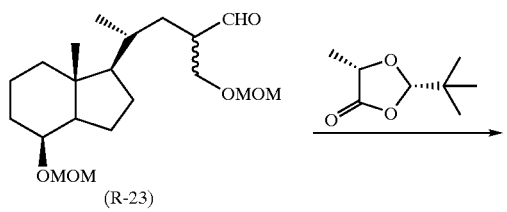

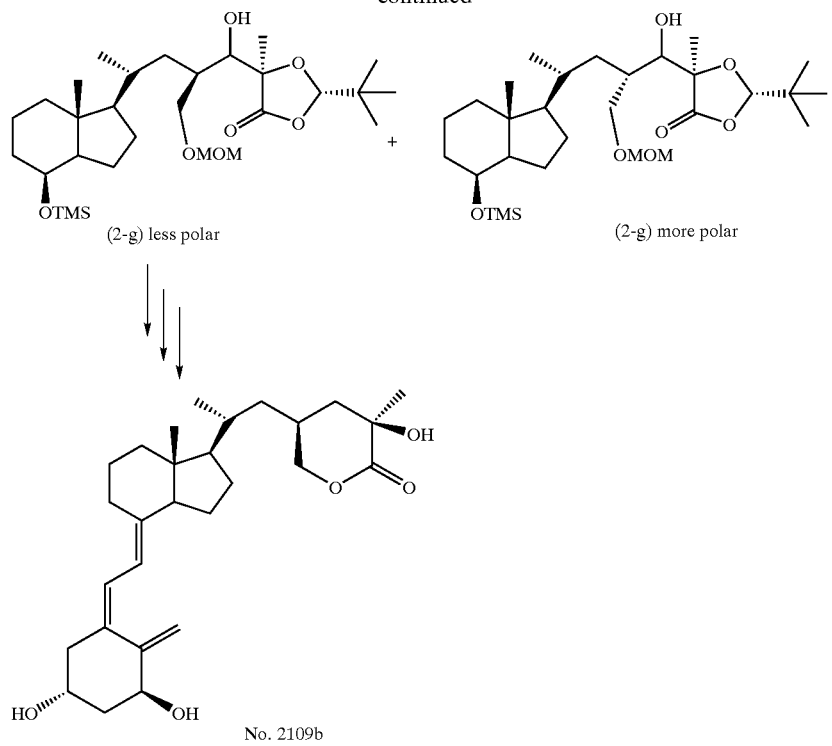

(2-g) less polar     (2-g) more polar

No. 2109b (1) The (R-23) (3.5 g, 9.8 mmol) obtained in Reference Example 4 was treated in the same manner as in Example 2-1 (1) to obtain (2-g) less polar compound (1.8 g, 36% yield) and (2-g) more polar compound (1.24 g, 24% yield). These compounds are stereoisomers.

(2) The above-obtained (2-g) lower compound was treated in the same manner as in Example 2-1 (2) to (7) to obtain No. 2109b.

$^1$H NMR (CDCl$_3$) δ: 0.55 (s, 3 H), 0.93 (d, J=6.6 Hz, 3 H), 1.10–3.50 (m, 18 H), 1.43 (s, 3 H), 2.30 (dd, J=6.6, 12.4 Hz, 1 H), 2.60 (dd, J=4.4, 14.6 Hz, 1 H), 2.76 (dd, J=4.4, 14.6 Hz, 1 H), 3.08 (s, 1 H), 3.94 (t, J=10.8 Hz, 1 H), 4.20–4.36 (m, 2 H), 4.43 (m, 1 H), 5.00 (s, 1 H), 5.32(s, 1H), 6.02 (d, J=11.3 Hz, 1 H), 6.37 (d, J=11.2 Hz, 1 H).

Example 2-3
Production of Compound No. 2109c

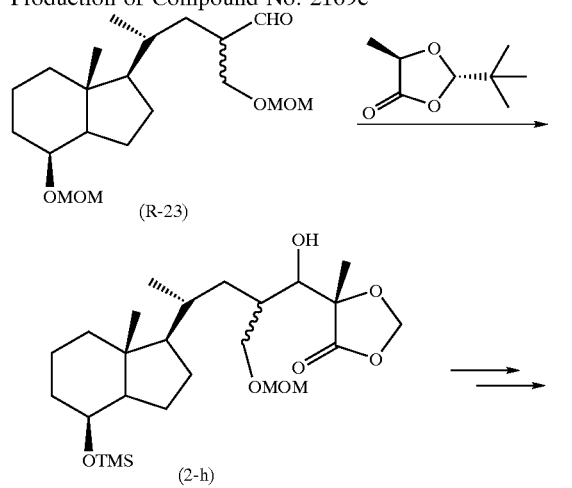

(R-23)

(2-h)

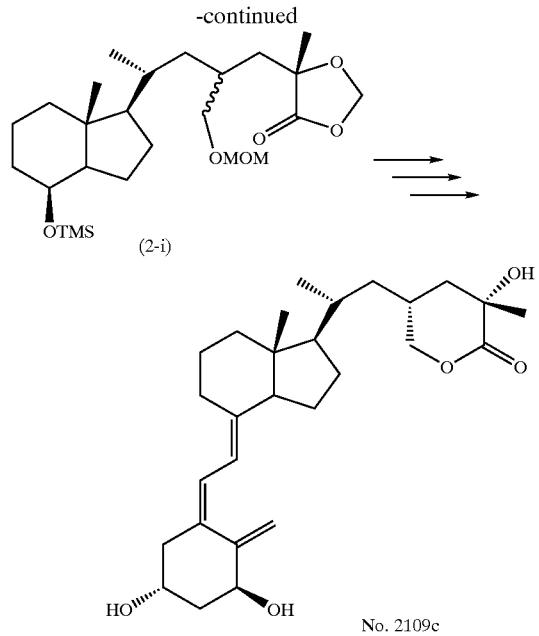

(2-i)

No. 2109c (1) By using the (R-23) obtained in Reference Example 4 and the shown dioxolan compound, the same process as in Example 2-1 (1) was carried out to obtain (2-h). The sample is a mixture of stereoisomers based on the asymmetric point to which MOMOCH$_2$ group is bound.

(2) By using the above-obtained (2-h), the same processes as in Example 2-1 (2) and (3) were carried out to obtain (2-i). These two steps of reactions proceeded only on the isomer which had a shown configuration based on the asymmetric point to which MOMOCH$_2$ group was bound. After the second stage reaction, the objective product was purified by silica gel column chromatography to obtain an optically pure (2-i).

(3) The above-obtained (2-i) was treated in the same manner as in Example 2-1 (4) to (7) to obtain No. 2109c.

$^1$H NMR (CDCl$_3$) δ: 0.56 (s, 3 H), 0.95 (d, J=6.3 Hz, 3 H), 1.00–3.20 (m, 22 H), 1.61 (s, 3 H), 3.94 (t, J=11.3 Hz, 1 H), 4.11–4.30 (m, 1 H), 4.24 (br., 1 H), 4.42 (br., 1 H), 4.99 (br., 1 H), 5.33 (br., 1 H), 6.01 (d, J=11.3 Hz, 1 H), 6.37 (d, J=11.3 Hz, 1 H).

Example 2-4

Production of Compound No. 2110a

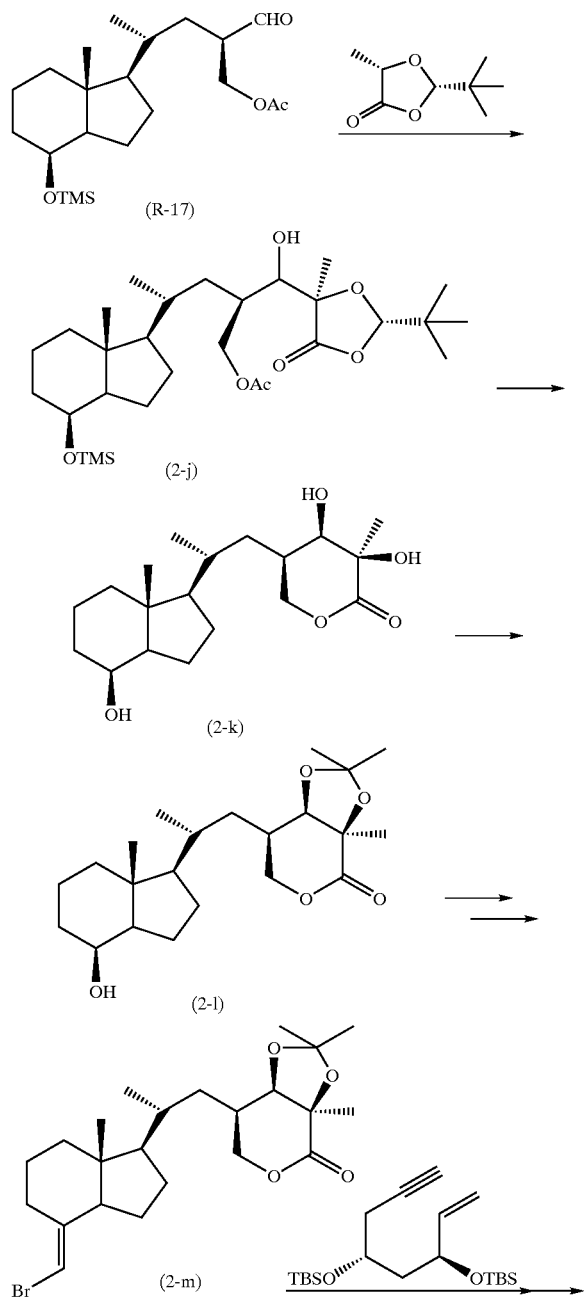

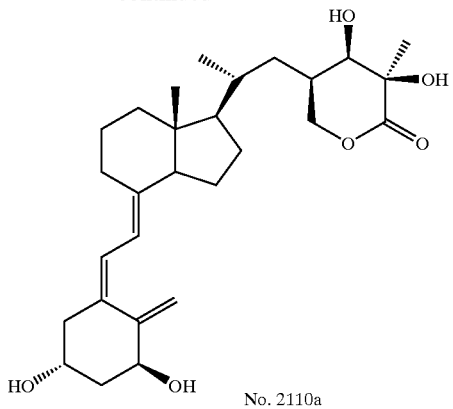

No. 2110a (1) The (R-17) obtained in Reference Example 3 was treated in the same manner as in Example 2-1 (1) to obtain (2-j).

(2) The above-obtained (2-j) (400 mg) was dissolved in a mixed solvent of methanol (15 ml) and water (5 ml), and the solution was stirred for 2 hr at room temperature after the addition of a 4N lithium hydroxide aqueous solution (2 ml). The reaction mixture was stirred further for 1 hr at room temperature after it was acidified to pH 2 by using conc. hydrochloric acid. The reaction mixture was extracted with ethyl acetate after the addition of water (10 ml). The combined organic layers were dried and concentrated, and the obtained residue was purified by silica gel column chromatography (hexane:ethyl acetate=1:2) to obtain (2-k) (170 mg, 67% yield).

(3) The above-obtained (2-k) (170 mg) was dissolved in 2,2-dimethoxypropane (2 ml), and the solution was stirred for 2 days at room temperature after the addition of one drop of conc. hydrochloric acid. The reaction mixture was extracted with ethyl acetate after the addition of a saturated sodium bicarbonate aqueous solution (10 ml). The combined organic layers were dried and concentrated, and the obtained residue was purified by silica gel column chromatography (hexane:ethyl acetate=3:1 to 1:1) to obtain (2-1) (120 mg, 63% yield).

$^1$H NMR (CDCl$_3$) δ: 0.96 (d, J=6.2 Hz, 3 H), 0.97 (s, 3 H), 1.00–2.30 (m, 16 H), 1.42 (s, 6 H), 4.01(br., 1 H), 4.00–4.15 (m, 2 H), 4.33 (t, J=10.8 Hz, 1 H).

(4) In a nitrogen atmosphere, the (2-1) (120 mg) was dissolved in dichloromethane (5 ml), and the solution was stirred for 6 hr at room temperature after the addition of pyridinium chlorochromate (PDC) (237 mg). The reaction mixture was filtered through celite, the filtrate was concentrated to obtain a crude product of a ketone. In a nitrogen atmosphere, (bromomethylitriphenylphosphonium bromide (689 mg) was suspended in dry THF (5 ml), and the suspension was cooled to −60° C. A sodium bis (trimethylsilyl)amide solution (1.54 ml, 1M, 1.54 mmol) in dry THF was added, and the mixture was stirred for 1 hr in this state. The solution was cooled to −78° C., and a dry THF solution (5 ml) of the above ketone crude body (130 mg) was added. The mixture was stirred for 1 hr in this state, and subsequently it was stirred overnight while the reaction mixture was slowly warmed up to room temperature. The reaction mixture was extracted with ethyl acetate after the addition of 1N hydrochloric acid (10 ml). The combined organic layers were dried and concentrated, and the obtained residue was purified by silica gel column chromatography (hexane:ethyl acetate=15:1) to obtain (2-m) (28 mg, 30% yield).

¹H NMR (CDCl₃) δ: 0.61 (s, 3 H), 0.99 (d, J=7.6 Hz, 3 H), 1.41 (s, 6 H), 1.54 (s, 3 H), 2.85–2.90 (m, 1 H), 4.01 (s, 1 H), 4.05 (dd, J=5.1, 11.8 Hz, 1 H), 4.32 (t, J=11.8 Hz, 1 H), 5.65 (s, 1 H).

(5) In a nitrogen atmosphere, triphenylphosphine (19 mg) and tris(dibenzylideneacetone)dipalladium (0)-chloroform adduct (9 mg) were dissolved in a mixed solvent of anhydrous toluene (0.5 ml) and diisopropylethylamine (0.5 ml), and the solution was stirred for 15 min at room temperature (Solution A). Further, (3S),(5R)-3,5-bis(t-butyldimethylsilyloxy)-1-octen-7-yne (39 mg) and the above-obtained (2-m) (27 mg) were dissolved in a mixed solvent of anhydrous toluene (0.5 ml) and diisopropylethylamine (0.5 ml), and the solution was added to the above Solution A, and the combined solution was stirred for 3 hr at 100° C. The reaction mixture was extracted with ethyl acetate after the addition of 1N hydrochloric acid (5 ml). The combined organic layers were dried and concentrated, and the obtained residue was roughly purified by short column chromatography of silica gel (hexane:ethyl acetate=20:1 to 10:1) to obtain a crude product of a coupled body. The crude product was dissolved in a mixed solvent of acetonitrile (3 ml) and methylene chloride (1 ml), and the solution was cooled with ice. The solution was stirred for 30 min under cooling with ice after the addition of lithium tetrafluoroborate (20 mg) and one drop of conc. sulfuric acid. The reaction mixture was extracted with ethyl acetate after the addition of a saturated sodium bicarbonate aqueous solution. The combined organic layers were washed with brine, dried and concentrated. The residue was purified by silica gel column chromatography (hexane:ethyl acetate=2:1 and to hexane:ethyl acetate methanol=1:2:0.1) to obtain No. 2110a (7 mg, 26% yield).

¹H NMR (CDCl₃) δ: 0.52 (s, 3 H), 0.79 (d, J=7.3 Hz, 3 H), 1.10–3.50 (m, 22 H), 1.34 (s, 3 H), 2.48–2.59 (m, 1 H), 2.70–2.80 (m, 1 H), 4.02 (s, 1 H), 4.05 (dd, J=5.5, 13.2 Hz, 1 H), 4.20–4.30 (m, 1 H), 4.32 (t, J=13.2 Hz, 1 H), 4.40–4.44 (m, 1 H), 5.00 (s, 1 H), 5.34 (s, 1 H), 6.03 (d, J=11.1 Hz, 1 H), 6.38 (d, J=11.2 Hz, 1 H).

Example 2-5

Production of Compound No. 2110b

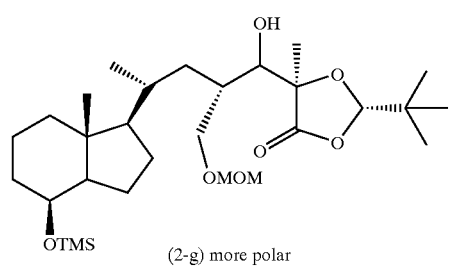

(2-g) more polar

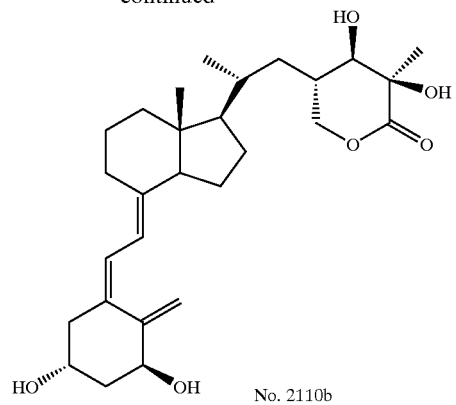

No. 2110b (1) The (2-g) more polar compound obtained in Example 2-2 (1) was treated in the same manner as in Example 2-1 (2) to (7) to obtain No. 2110b.

¹H NMR (CDCl₃) δ: 0.55 (s, 3 H), 1.00 (d, J=5.3 Hz, 3 H), 1.10–3.60 (m, 20 H), 1.52 (s, 3 H), 3.94 (t, J=11.6 Hz, 1 H), 4.15–4.25 (m, 1 H), 4.35–4.50 (m, 2 H), 5.00 (s, 1 H), 5.33 (s, 1 H), 6.01 (d, J=11.2 Hz, 1 H), 6.37 (d, J=11.2 Hz, 1 H).

Example 2-6

Production of Compounds No. 2102a and 2102b

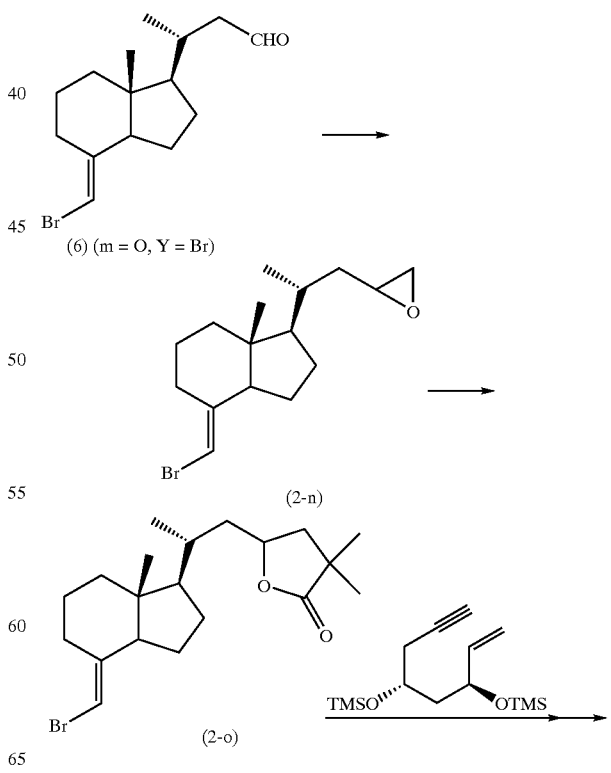

-continued

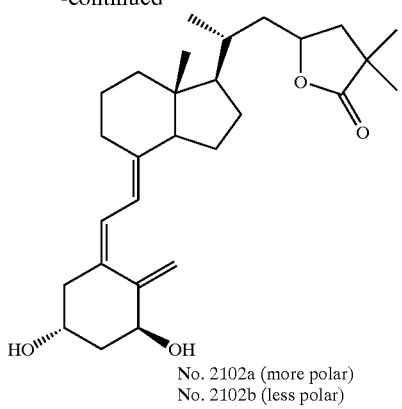

No. 2102a (more polar)
No. 2102b (less polar)

(1) Dry DMSO (6 ml) was added to sodium hydride (117 mg, 8.1 mmol, the sodium hydride kept in oil at 60% was washed with hexane and dried) and trimethylsulfoxonium iodide (1.07 g, 8.11 mmol), and the mixture was stirred for 1.5 hr at room temperature. The solution was cooled with ice, a dry THF solution (5 ml) of the (6) (m=0; Y=Br) (930 mg, 4.06 mmol) obtained in Reference Example 1 was added, and the mixture was stirred for 15 min at room temperature. The reaction mixture was extracted with ethyl acetate after the addition of water. The combined organic layers were washed with brine, dried and concentrated. The residue was purified by silica gel column chromatography (hexane:ethyl acetate=40:1) to obtain (2-n) (392 mg, 31% yield).

$^1$H NMR (CDCl$_3$) δ: 0.59, 0.60 (s, 3 H), 1.07, 1.10 (d, J=6.6 Hz, 3 H), 1.17–1.39 (m, 4 H), 1.43–1.72 (m, 5 H), 1.83–2.06 (m, 3 H), 2.44 (ddd, J=2.8, 5.3, 18.6 Hz, 1 H), 2.77 (dt, J=4.0, 19.0 Hz, 1 H), 2.85–2.95 (m, 2 H), 5.65 (s, 1 H).

(2) Diisopropylamine (305 mg, 3.0 mmol) was added to dry THF (2 ml), and the mixture was cooled with ice. An n-butyllithium solution (1.60 ml, 1.66 M, 2.65 mmol) in hexane was added, and the mixture was stirred for 15 min under cooling with ice. Isobutyric acid (106 mg, 1.21 mmol) was added, and the mixture was stirred for 1 hr under cooling with ice. To the solution was added a dry THF solution (2 ml) of the above-obtained (2-n) (126 mg, 0.4 mmol), and the mixture was stirred for 1 hr under cooling with ice and further for 2 hr at 35° C. The reaction mixture was adjusted to pH 1 by adding 6N hydrochloric acid, and the mixture was stirred for 15 min in this state. The reaction mixture was extracted with ethyl acetate after the addition of water. The combined organic layers were washed with a saturated sodium bicarbonate aqueous solution and with brine, dried and concentrated. The residue was purified by silica gel column chromatography (hexane:ethyl acetate= 20:1 to 5:1) to obtain (2-o) (28 mg, 18% yield).

$^1$H NMR (CDCl$_3$) δ: 0.57, 0.58 (s, 3 H), 1.01, 1.03 (d, J=6.3 Hz, 3 H), 1.20–1.79 (m, 18 H), 1.86–2.04 (m, 3 H), 2.10–2.20 (m, 1 H), 2.85–2.90 (m, 1 H), 4.47–4.58 (m, 1 H), 5.65 (s, 1 H).

(3) In a nitrogen atmosphere, triphenylphosphine (209 mg, 0.80 mmol) and tris(dibenzylideneacetone)dipalladium (0)-chloroform adduct (138 mg, 0.13 mmol) were dissolved in dry toluene (0.7 ml), and the solution was stirred for 30 min at room temperature. The above-obtained (2-o) (255 mg, 0.67 mmol) and a diisopropylamine solution (7 ml) of (3S),(5R)-bis(trimethylsilyloxy)-1-octen-7-yne (378 mg, 1.33 mmol) were added, and the mixture was stirred for 7 hr at 100° C. The reaction mixture was extracted with ethyl acetate after the addition of a saturated potassium hydrogensulfate aqueous solution. The combined organic layers were washed with a saturated sodium bicarbonate aqueous solution and with brine, dried and concentrated to obtain a crudely purified product of a coupled body. This product was dissolved in a mixed solvent of methanol (3 ml) and methylene chloride (1 ml), and the solution was stirred for 4 hr at room temperature after the addition of a micro-spatula of a polymer-supported pyridine p-toluenesulfonate (3.5 mmol/g), and the mixture was stirred for 4 hr at room temperature. The reaction mixture was filtered, and the filtrate was extracted with ethyl acetate. The combined organic layers were washed with brine, dried and concentrated. The residue was purified by silica gel column chromatography (hexane:ethyl acetate=1:1 to 1:3, and to hexane:ethyl acetate:methanol=3:3:1) to obtain an objective-containing fraction (106 mg). This was fractionally purified by HPLC (column:ODS, water:acetonitrile=60:40 to 55:45) to obtain a more polar compound (1.1 mg, No. 2102a, 1.2% yield) and a less polar compound (3.0 mg, No. 2102b, 3.2% yield). These are isomers based on the asymmetric point on the lactone ring.

More Polar Compound, No. 2102a $^1$H NMR (CDCl$_3$) δ: 0.56 (s, 3 H), 1.02 (d, J=6.1 Hz, 3 H), 1.25 (s, 3 H), 1.27 (s, 3 H), 1.42–1.74 (m, 14 H), 1.87–2.05 (m, 5 H), 2.16 (dd, J=5.8, 12.7 Hz, 1 H), 2.32 (dd, J=6.9, 13.4 Hz, 1 H), 2.60 (dd, J=3.6, 13.0 Hz, 1 H), 2.80–2.86 (m, 1 H), 4.24 (br., 1 H), 4.44–4.52 (br., 2 H), 5.00 (s, 1 H), 5.33 (s, 1 H), 6.02 (d, J=11.5 Hz, 1H), 6.37 (d, J=11.4 Hz, 1H).

MS: m/e 443.3 (M+1)$^+$

Less Polar Compound, No. 2102b $^1$H NMR (CDCl$_3$) δ: 0.57 (s, 3 H), 1.01 (d, J=6.4 Hz, 3 H), 1.19–1.39 (m, 4 H), 1.27 (s, 3 H), 1.28 (s, 3 H), 1.42–2.07 (m, 15 H), 2.13 (dd, J=5.8, 12.7 Hz, 1 H), 2.31 (dd, J=6.8, 12.9 Hz, 1 H), 2.60 (dd, J=3.3, 13.5 Hz, 1 H), 2.80–2.85 (m, 1 H), 4.24 (br., 1 H), 4.44 (br., 1 H), 4.49–4.58 (m, 1 H), 5.01 (s, 1 H), 5.34 (s, 1 H), 6.02 (d, J=11.1 Hz, 1 H), 6.38 (d, J=11.2 Hz, 1 H).

MS: m/e 443.3 (M+1)$^+$

Example 2-7

Production of Compounds No. 2105a and 2105b

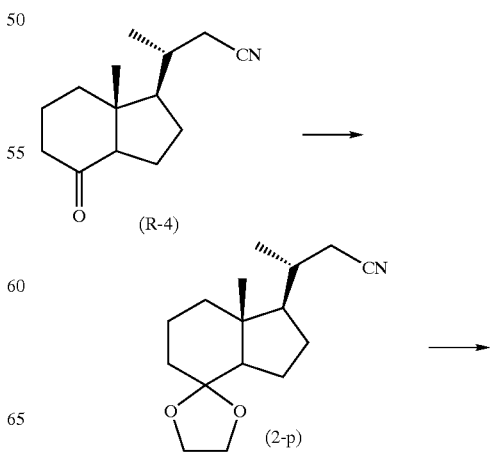

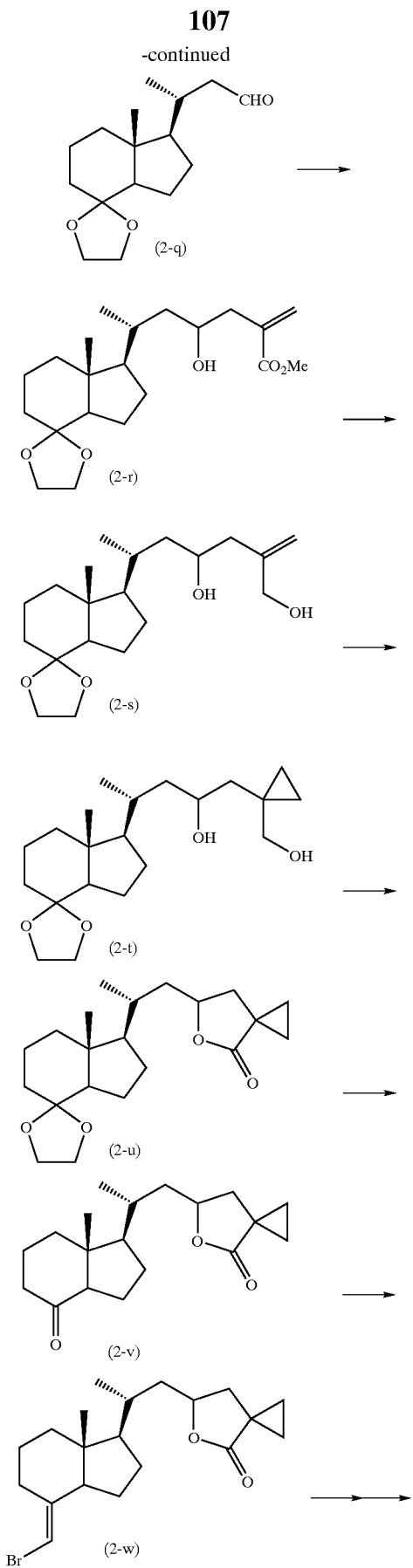

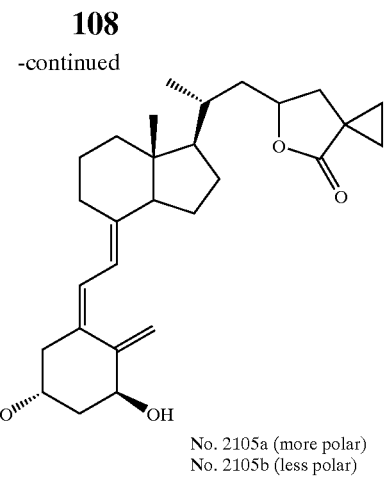

No. 2105a (more polar)
No. 2105b (less polar)

(1) The (R-4) (6.21 g, 28.3 mmol) obtained in Reference Example 1 was dissolved in dry acetonitrile (50 ml), and diethylene glycol (3.51 g, 56.6 mmol), trimethyl orthoformate (4.50 g, 42.4 mmol) and scandium triflate (697 mg, 1.4 mmol) were added, and the mixture was stirred for 6.5 hr at room temperature. The reaction mixture was concentrated, and the residue was extracted with ethyl acetate after the addition of water. The combined organic layers were washed with brine, dried and concentrated. The residue was purified by silica gel column chromatography (hexane:ethyl acetate= 10:1 to 6:1) to obtain (2-p) (7.00 g, 94% yield).

$^1$H NMR (CDCl$_3$) δ: 0.85 (s, 3 H), 1.16 (d, J=6.8 Hz, 3 H), 1.16–1.88 (m, 12 H), 2.17–2.40 (m, 2 H), 3.86–4.01 (m, 4 H).

(2) In a nitrogen atmosphere, the above-obtained (2-p) (7.00 g, 26.6 mmol) was dissolved in dry methylene chloride (150 ml), and the solution was cooled to −70° C. A DIBAL-H solution (39.5 ml, 1.01 M, 39.9 mmol) in toluene was added dropwise over 5 min, and the mixture was stirred for 2 hr in this state. To the reaction mixture was added methanol (15 ml), and subsequently the mixture was warmed up to room temperature. A saturated sodium sulfate aqueous solution (100 ml) was added to the solution, and the mixture was stirred for 1 hr at room temperature. The precipitated solids were filtered off with a glass filter, the filtrate was washed with brine, dried and concentrated. The residue was purified by silica gel column chromatography (hexane:ethyl acetate=10:1 to 8:1) to obtain (2-q) (6.03 g, 85% yield).

$^1$H NMR (CDCl$_3$) δ: 0.88 (s, 3 H), 1.01 (d, J=6.4 Hz, 3 H), 1.00–1.93 (m, 12 H), 2.00–2.21 (m, 2 H), 2.42–2.50 (m, 1 H), 3.86–4.02 (m, 4 H), 9.74–9.76 (m, 1

MS: m/e 267.3 (M+1)$^+$ (3) In a nitrogen atmosphere, the above-obtained (2-q) (3.00 g, 11.3 mmol) was dissolved in dry THF (20 ml), and the solution was cooled with ice. A dry THF solution (10 ml) of methyl bromoacrylate (2.42 g, 13.5 mmol), zinc (1.1 g, 16.9 mmol) and a saturated ammonium chloride solution (20 ml) were added, and the mixture was stirred for 1 hr in this state. After the addition of water, the reaction mixture was extracted twice with ethyl acetate and twice with methylene chloride. The organic layers were washed with brine, dried and concentrated. The residue was purified by silica gel column chromatography (hexane:ethyl acetate=8:1 to 3:1) to obtain (2-r) (4.30 g, including impurities, 104% yield). This sample is a mixture of stereoisomers based on the asymmetric point to which the hydroxyl group is bound.

$^1$H NMR (CDCl$_3$) δ: 0.85 (s, 3 H), 0.95 (d, J=6.4 Hz, 3 H), 1.00–1.97 (m, 16 H), 2.35 (dd, J=8.2, 14.0 Hz, 1 H), 2.51 (dd, J=3.8, 14.0 Hz, 1 H), 3.71–3.79 (m, 1 H), 3.77 (s, 3 H), 3.81–4.02 (m, 4 H), 5.66 (s, 1 H), 6.24 (s, 1 H).

MS: m/e 367.3 (M+1)$^+$ (4) The above-obtained (2-r) (4.30 g, 11.7 mmol) was dissolved in dry methylene chloride (40 ml), and the solution was cooled with ice. A DIBAL-H solution (46.5 ml, 1.01M, 46.9 mmol) in toluene was added dropwise over 20 min, and the mixture was stirred for 3 hr in this state. The reaction mixture was warmed to room temperature after the addition of methanol (20 ml). A saturated sodium sulfate aqueous solution (150 ml) was added, and the mixture was stirred for 1 hr at room temperature. The precipitated solids were filtered off with a glass filter, the solids were washed with methylene chloride and with 0.5N hydrochloric acid. The combined filtrates were extracted twice with methylene chloride and twice with chloroform. The combined organic layers were washed with a saturated sodium bicarbonate aqueous solution and subsequently with brine, dried and concentrated. The residue was purified by silica gel column chromatography (hexane:ethyl acetate=4:1 to 1:3) to obtain (2-s) (1.02 g). The yield was 27% based on (2-q). This sample is a mixture of stereoisomers based on the asymmetric point to which the hydroxyl group is bound.

$^1$H NMR (CDCl$_3$) δ: 0.84 & 0.86 (s, 3 H), 0.95 & 1.01 (d, J=6.3 Hz, 3 H), 1.04–2.46 (m, 19 H), 3.6–3.99 (m, 5 H), 4.11 (s, 2 H), 4.97 & 4.99 (s, 1 H), 5.14 & 5.15 (s, 1 H).

MS: m/e 339.3 (M+1)$^+$ (5) In a nitrogen atmosphere, the above-obtained (2-s) (1.02 g, 3.0 mmol) was dissolved in dry methylene chloride (15 ml), and the solution was cooled with ice. A diethylzinc solution (15.1 ml, 1.0M, 15.1 mmol) in hexane and diiodomethane (4.04 g, 15.1 mmol) were added, and the mixture was stirred for 2.5 hr under cooling with ice and for 2 hr at room temperature. A saturated ammonium chloride solution, a saturated potassium hydrogensulfate solution and a sodium sulfite solution were added, and the mixture was extracted twice with chloroform. The organic layers were dried and concentrated. The residue was purified by silica gel column chromatography (hexane:ethyl acetate=4:1 to 3:2) to obtain (2-t) (691 mg, 65% yield). This sample is a mixture of stereoisomers based on the asymmetric point to which the hydroxyl group is bound.

$^1$H NMR (CDCl$_3$) δ: 0.35–0.45 (m, 1 H), 0.45–0.55 (m, 1 H), 0.82 & 0.86 (s, 3 H), 0.89–2.0 (m, 16 H), 0.95 & 0.96 (d, J=6.6 Hz, 3 H), 2.98 (br, 2 H), 3.19 (dd, J=3.3, 11.4 Hz, 1 H), 3.37–3.78 (m, 2 H), 3.85–3.98 (m, 5 H).

MS: m/e 353.3 (M+1)$^+$ (6) In a nitrogen atmosphere, the above-obtained (2-t) (691 mg, 1.96 mmol) was dissolved in dry benzene (100 ml), Fetizon reagent (AgCO$_3$-celite) (17.6 g, 29.4 mmol) was added, and the mixture was stirred for 3 hr under heating and refluxing. The reaction mixture was filtered with a glass filter on which celite was laid. The filtrate was concentrated, and the residue was purified by silica gel column chromatography (hexane:ethyl acetate=10:1 to 7:1) to obtain (2-u) (525 mg, white solid, 77% yield). This sample is a mixture of stereoisomers based on the asymmetric point on the lactone ring.

$^1$H NMR (CDCl$_3$) δ: 0.83 & 0.85 (s, 3 H), 0.91–2.06 (m, 22 H), 2.25 & 2.29 (dd, J=2.8, 7.1 Hz, 1 H), 3.71–3.79 (m, 1 H), 3.85–4.00 (m, 4H), 4.65–4.72 (m, 1 H).

MS: m/e 349.3 (M+1)$^+$ (7) The above-obtained (2-u) (525 mg, 1.51 mmol) was dissolved in a mixed solvent of acetone (10 ml) and water (1 ml), a polymer-bound pyridinium p-toluenesulfonate (215 mg, 3.5 mmol/g, 0.75 mmol) was added, and the mixture was stirred for 3.5 hr under heating and refluxing. The reaction mixture was filtered with a cotton-packed filter, and the filtrate was concentrated. Ethyl acetate was added to the residue, and the mixture was dried over anhydrous sodium sulfate and concentrated. The resultant residue was purified by silica gel column chromatography (hexane:ethyl acetate= 7:1 to 4:1) to obtain (2-v) (181 mg, 39% yield). The raw material was recovered as much as 113 mg (22%). The recovered raw material was treated in the same manner to obtain (2-v) (87 mg). The total was 268 mg (58% yield). This sample is a mixture of stereoisomers based on the asymmetric point on the lactone ring.

$^1$H NMR (CDCl$_3$) δ: 0.65 & 0.67 (s, 3 H), 0.89–1.00 (m, 2 H), 1.06 & 1.07 (d, J=6.6 Hz, 3 H), 1.18–1.32 (m, 4 H), 1.39–2.16 (m, 11 H), 2.22–2.33 (m, 3 H), 2.42–2.52 (m, 1 H), 4.63–4.75 (m, 1 H).

MS: m/e 305.3 (M+1)$^+$ (8) (Bromomethyl)triphenylphosphonium bromide (342 mg, 0.784 mmol) was dispersed in dry THF (10 ml), and the suspension was cooled to −40° C. A sodium bis (trimethylsilyl)amide solution (0.76 ml, 1.0M, 0.76 mmol) in THF was added dropwise, and the mixture was stirred for 1 hr in this state (Solution A). On the other hand, the above-obtained (2-v) (77 mg, 0.253 mmol) was dissolved in dry THF (2 ml), and the solution was cooled with ice. The above Solution A was added dropwise over about 10 min, and the mixture was stirred for 2.5 hr in this state. The reaction mixture was extracted with ethyl acetate after the addition of a saturated ammonium chloride solution. The organic layers were washed with brine, dried and concentrated. The residue was purified by silica gel column chromatography (hexane:ethyl acetate=20:1 to 5:1) to obtain (2-w) (26 mg, 27% yield). This sample is a mixture of stereoisomers based on the asymmetric point on the lactone ring.

$^1$H NMR (CDCl$_3$) δ: 0.57 & 0.59 (s, 3 H), 0.73–0.97 (m, 2 H), 1.02 & 1.04 (d, J=6.4 Hz, 3 H), 1.18–2.06 (m, 17 H), 2.23–2.32 (m, 1 H), 2.85–2.90 (m, 1 H), 4.63–4.73 (m, 1 H), 5.65 (s, 1 H).

MS: m/e 381.3 (M+1)$^+$ (9) In a nitrogen atmosphere, triphenylphosphine (54 mg, 0.208 mmol) and tris(dibenzylideneacetone)dipalladium (0)-chloroform adduct (36 mg, 0.035 mmol) were dissolved in dry toluene (1.9 ml), and the solution was stirred for 15 min at room temperature. To this solution were added the (2-w) (66 mg, 0.173 mmol) and a triethylamine solution (1.9 ml) of (3S),(5R)-3,5-bis(t-butyldimethylsilyloxy)-1-octen-7-yne (128 mg, 0.346 mmol), and the mixture was stirred for 9 hr at 100° C. The reaction mixture was extracted with ethyl acetate after the addition of a saturated potassium hydrogensulfate aqueous solution. The combined organic layers were washed with a saturated sodium bicarbonate aqueous solution and with brine, dried and concentrated to obtain a crude product of a coupled body. The crude product was dissolved in a mixed solvent of acetonitrile (3 ml) and methylene chloride (1 ml), and the solution was cooled with ice. Lithium tetrafluoroborate (63 mg, 0.67 mmol) and a 1N sulfuric acid-acetonitrile solution (0.2 ml, 0.2 mmol) were added, and the mixture was stirred for 20 min in this state. The reaction mixture was extracted twice with ethyl acetate after the addition of a saturated sodium bicarbonate aqueous solution. The organic layers were washed with brine, dried and concentrated. The residue was roughly purified by silica gel column (hexane:ethyl acetate=10:1 and to hexane:ethyl acetate:methanol=3:3:1), and the crude product was further purified by HPLC fractionation (ODS; acetonitrile:water=60:40) to obtain a more polar compound (12.7 mg, No. 2105a, 8.8% yield) and a less polar compound (7.0 mg, No. 2105b, 4.8% yield). These compounds are isomers based on the asymmetric point on the lactone ring.

More Polar Compound, No. 2105a $^1$H NMR (CDCl$_3$) δ: 0.56 (s, 3 H), 0.88–1.00 (m, 2 H), 1.03 (d, J=6.1 Hz, 3 H), 1.14–1.73 (m, 15 H), 1.88–2.06 (m, 6 H), 2.23–2.35 (m, 2 H), 2.60 (dd, J=3.3, 13.5 Hz, 1 H), 2.80–2.84 (m, 1 H), 4.23 (br., 1 H), 4.43 (br., 1 H), 4.68 (pent, J=7.1 Hz, 1 H), 5.00 (s, 1 H), 5.33 (s, 1 H), 6.02 (d, J=11.4 Hz, 1 H), 6.38 (d, J=11.2 Hz, 1 H).

MS: m/e 441.3 (M+1)$^+$

Less Polar Compound, No. 2105b $^1$H NMR (CDCl$_3$) δ: 0.57 (s, 3 H), 0.80–0.97 (m, 2 H), 1.02 (d, J=6.6 Hz, 3 H), 1.15–1.48 (m, 6 H), 1.47–1.96 (m, 15 H), 2.24–2.35 (m, 2 H), 2.57–2.62 (m, 1 H), 2.80–2.85 (m, 1 H), 4.24 (br., 1 H), 4.43 (br., 1 H), 4.68–4.77 (m, 1 H), 5.00 (s, 1 H), 5.33 (s, 1 H), 6.02 (d, J=11.7 Hz, 1 H), 6.38 (d, J=11.4 Hz, 1 H).

Example 2–8

Production of Compounds No. 2101a and 2101b

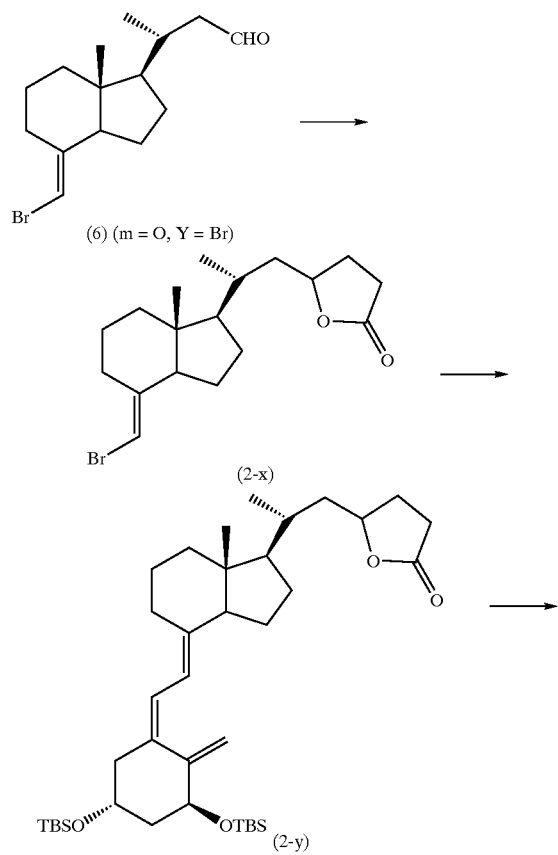

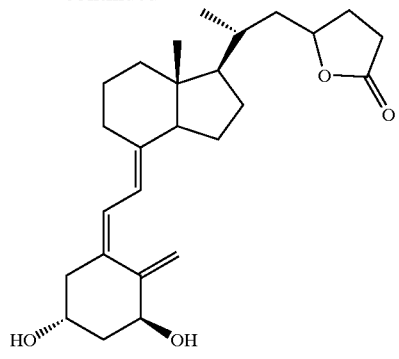

No. 2101a (more polar)
No. 2101b (less polar)

(1) In a nitrogen atmosphere, the (6) (m=0, Y=Br) (0.51 g, 1.70 mmol) obtained according to a method of Reference Example 1 was dissolved in dry methylene chloride (5 ml), and the solution was cooled to −70° C. Titanium tetrachloride (0.64 g, 3.41 mmol) was added, and further a (1-(ethoxycyclopropyl)oxy)trimethylsilane (0.59 g, 3.41 mmol) in dry methylene chloride solution (3 ml) was added dropwise. Subsequently, the mixture was stirred for 1 hr at −70° C., for 1.5 hr under cooling with ice and for 1.5 hr at room temperature. The reaction mixture was extracted with ethyl acetate after the addition of water. The combined organic layers were washed with brine, dried and concentrated. The residue was dissolved in dry THF (4 ml), a TBAF solution (1.0 ml, 1M, 1.0 mmol) in THE was added at room temperature, and the mixture was stirred for 1 hr at room temperature. The reaction mixture was extracted with ethyl acetate after the addition of a saturated potassium hydrogensulfate aqueous solution. The combined organic layers were washed with brine, dried and concentrated. The residue was purified by silica gel column chromatography (hexane:ethyl acetate=20:1 to 5:1) to obtain (2-x) (357 mg, 59% yield). This sample is a mixture of stereoisomers based on the asymmetric point on the lactone ring.

$^1$H NMR (CDCl$_3$) δ: 0.58, 0.58 (s, 3 H), 1.00–1.04 (m, 3 H), 1.20–2.05 (m, 15 H), 2.29–2.38 (m, 1 H), 2.49–2.57 (m, 2 H), 2.85–2.90 (m, 1 H), 4.54–4.62 (m, 1 H), 5.66 (s, 1 H).
MS: m/e 355.3 (M+1)$^+$ (2) In a nitrogen atmosphere, triphenylphosphine (92 mg, 0.35 mmol) and tris(dibenzylideneacetone)dipalladium (0)-chloroform adduct (61 mg, 0.059 mmol) were dissolved in dry toluene (3.2 ml), and the solution was stirred for 1 hr at room temperature. To the solution were added (2-x) (104 mg, 0.29 mmol) and a triethylamine solution (3.2 ml) of (3S),(5R)-3,5-bis(t-butyldimethylsilyloxy)-1-octen-7-yne (216 mg, 0.59 mmol), and the mixture was stirred for 5.5 hr at 100° C. The reaction mixture was extracted with ethyl acetate after the addition of a saturated potassium hydrogensulfate aqueous solution. The combined organic layers were washed with a saturated sodium bicarbonate aqueous solution and with brine, dried and concentrated. The residue was purified by silica gel column chromatography (hexane:ethyl acetate=40:1 to 10:1) to obtain (2-y) (143 mg, 76% yield (containing impurities)). This sample is a mixture of stereoisomers based on the asymmetric point on the lactone ring.

$^1$H NMR (CDCl$_3$) δ: 0.06 (s, 12 H), 0.55–0.56 (m, 3 H), 0.87–0.90 (m, 18 H), 0.96–1.03 (m, 3 H), 1.23–2.56 (m, 22 H), 2.81–2.85 (m, 1 H), 4.19 (br., 1 H), 4.37 (br., 1 H), 4.57–4.60 (m, 1 H), 4.86 (d, J=2.5 Hz, 1 H), 5.17 (s, 1 H), 6.02 (d, J=11.2 Hz, 1 H), 6.24 (d, J=11.2 Hz, 1 H).

MS: m/e 643.8 (M+1)+

(3) The obtained (2-y) (143 mg, 0.222 mmol) was dissolved in a mixed solvent of acetonitrile (4 ml) and methylene chloride (1 ml), and the solution was cooled with ice. Lithium tetrafluoroborate (63 mg, 0.67 mmol) and a 1N sulfuric acid-acetonitrile solution (0.2 ml, 0.2 mmol) were added, and the mixture was stirred for 30 min in this state. The reaction mixture was extracted twice with ethyl acetate after the addition of a saturated sodium bicarbonate aqueous solution. The organic layers were washed with brine, dried and concentrated. The residue was roughly purified by reparative TLC (hexane:ethyl acetate:methanol=3:6:1), and further purified by HPLC fractionation (ODS, acetonitrile:water=50:50) to obtain a more polar compound (13.8 mg, No. 2101a, 15% yield) and a less polar compound (11.0 mg, No. 2101b, 12% yield). These are isomers based on the asymmetric point on the lactone ring.

More Polar Compound, No. 2101a $^1$H NMR (CDCl$_3$) δ: 0.56 (s, 3 H), 1.02 (d, J=6.1 Hz, 3 H), 1.15–2.05 (m, 19 H), 2.27–2.43 (m, 2 H), 2.52 (da, J=6.6, 9.7 Hz, 2H), 2.57–2.63 (m, 1 H), 2.80–2.86 (m, 1 H), 4.19–4.27 (m, 1 H), 4.41–4.46 (m, 1 H), 4.57 (dt, J=6.6, 15.1 Hz, 1 H), 5.00 (s, 1 H), 5.33 (t, J=1.5 Hz, 1 H), 6.02 (d, J=11.2 Hz, 1 H), 6.38 (d, J=11.1 Hz, 1 H).

MS: m/e 415.5 (M+1)+

Less Polar Compound, No. 2101b $^1$H NMR (CDCl$_3$) δ: 0.56 (s, 3 H), 1.01 (d, J=6.6 Hz, 3 H), 1.20–1.36 (m, 4 H), 1.44–2.04 (m, 15 H), 2.26–2.38 (m, 2 H), 2.54 (dd, J=6.6, 9.7 Hz, 2H), 2.57–2.62 (m, 1 H), 2.80–2.85 (m, 1 H), 4.20–4.27 (m, 1 H), 4.41–4.46 (m, 1 H), 4.57–4.66 (m, 1 H), 5.00 (s, 1 H), 5.33 (t, J=1.5 Hz, 1 H), 6.02 (d, J=11.1 Hz, 1 H), 6.37 (d, J=11.2 Hz, 1 H).

MS: m/e 415.5 (M+1)+

Example 3-1

Production of Compounds No. 3505a and 3505b

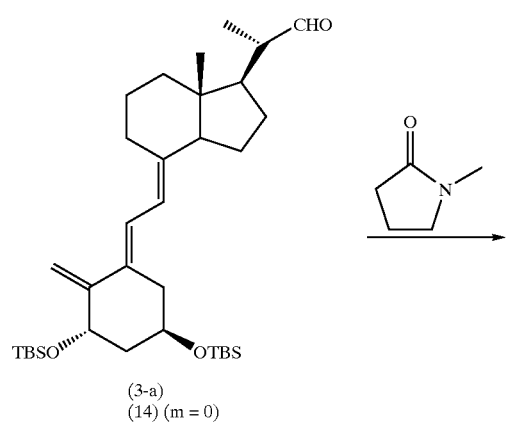

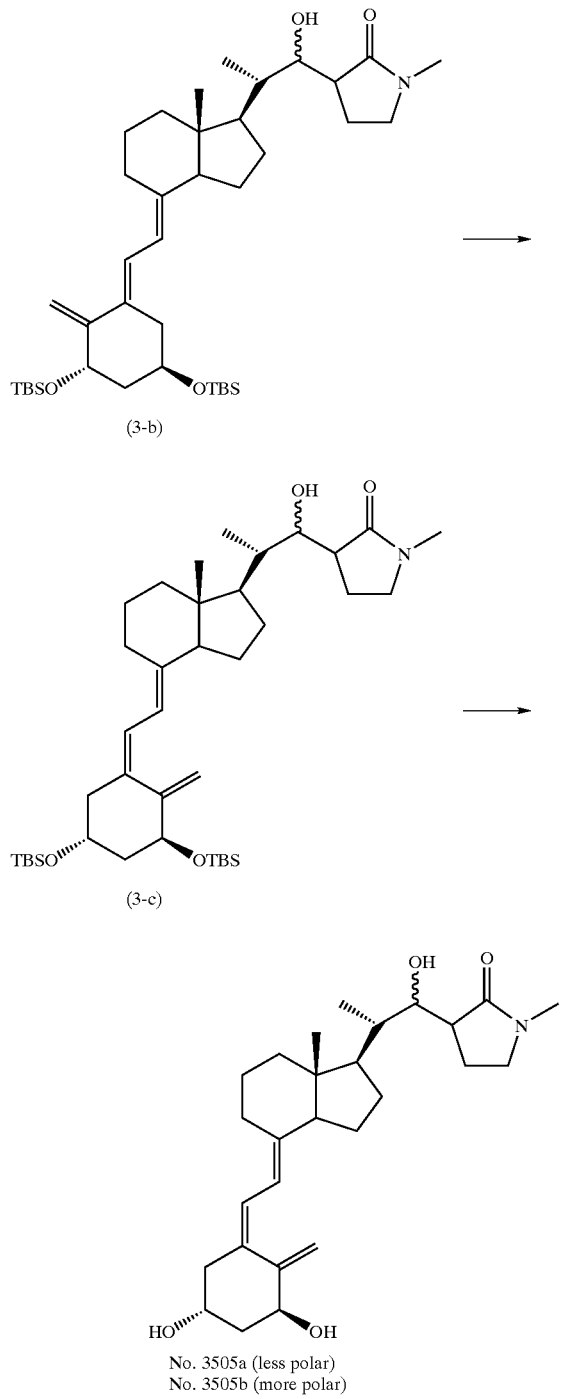

No. 3505a (less polar)
No. 3505b (more polar)

(1) In a nitrogen atmosphere, hexamethyldisilazane (203 mg, 1.26 mmol) was dissolved in dry THF (2 ml), and the solution was cooled with ice. An n-butyilithium solution (0.72 ml, 1.66M, 1.2 mmol) in hexane was added, and the mixture was stirred for 15 min at room temperature. The reaction mixture was cooled to −70 ° C., and a dry THF solution (2 ml) of 1-methyl-2-pyrrolidinone (119 mg, 1.2 mmol) was added. The mixture was stirred for 1.5 hr at −70° C. To the solution was added a dry THF solution (2 ml) of the (3-a) ((14); (m=0)) (343 mg, 0.6 mmol), which can be produced according to a known process (International Patent Publication WO90/09991; Tetrahedron, 20, 4609–4619 (1987)), and the mixture was stirred overnight while it was slowly warmed up to room temperature. The reaction mixture was extracted with ethyl acetate after the addition of a saturated ammonium chloride aqueous solution. The combined organic layers were washed with brine, dried and concentrated. The residue was purified by silica gel column chromatography (hexane:ethyl acetate=6:1 to 1:1) to obtain (3-b) (209 mg, 52% yield). This sample is expected to be a mixture of stereoisomers based on the asymmetric point to which the aldol hydroxyl group is bound.

$^1$H NMR (CDCl$_3$) δ: 0.06 (s, 12 H), 0.54 (s, 3 H), 0.87 (s, 9 H), 0.90 (s, 9 H), 0.88 & 0.97 (d, J=6.8 Hz, 3 H), 1.06–2.07 (m, 17 H), 2.3–2.4 (m, 1 H), 2.52–2.55 (m, 2 H), 2.8–2.9 (m, 1 H), 2.87 (s, 3 H), 3.29–3.37 (m, 2 H), 3.73 & 3.92 (d, J=9.4 Hz, 1 H), 4.22 (br., 1 H), 4.52 (br., 1 H), 4.94 (s, 1 H), 4.99 (s, 1 H), 5.83 (d, J=12.0 Hz, 1 H), 6.46 (d, J=10.1 Hz, 1 H).

(2) The above-obtained (3-b) (214 mg, 0.318 mmol) and anthracene (57 mg, 0.318 mmol) were dissolved in dry toluene (8 ml), and nitrogen gas was bubbled into the solution for 15 min. In a nitrogen atmosphere, the solution was irradiated for 3.5 hr with light by using a high pressure mercury lamp (main wave length of 365 nm). The reaction mixture was concentrated, and the residue was purified by silica gel column chromatography (hexane:ethyl acetate= 20:1 to 3:1) to obtain (3-c) (103 mg, 48% yield). This sample is expected to be a mixture of stereoisomers based on the asymmetric point to which the aldol hydroxyl group is bound.

$^1$H NMR (CDCl$_3$) δ: 0.06 (s, 12 H), 0.53 (s, 3 H), 0.88 (s, 18 H), 0.88 & 0.96 (d, J=6.8 Hz, 3 H), 1.23–2.27 (m, 17 H), 2.42–2.58 (m, 2 H), 2.8–2.9 (m, 1 H), 2.86 (s, 3 H), 3.25–3.36 (m, 2 H), 3.72 & 3.92 (d, J=8.9 & 10.1 Hz, 1 H), 4.20 (br., 1 H), 4.37 (br., 1 H), 4.54 (br., 1 H), 4.86 & 4.87 (s, 1 H), 5.02 & 5.10 (s, 1 H), 6.02 (d, J=11.7 Hz, 1 H), 6.24 (d, J=10.9 Hz, 1 H).

(3) The above-obtained (3-c) (103 mg, 0.153 mmol) and lithium tetrafluoroborate (43 mg, 0.46 mmol) were dissolved in a mixed solvent of acetonitrile (2 ml) and methylene chloride (2 ml), and the solution was cooled with ice. A 1N sulfuric acid-acetonitrile solution (0.14 ml, 0.14 mmol) was added dropwise, and the mixture was stirred for 30 min under cooling with ice. The reaction mixture was extracted with ethyl acetate after the addition of a saturated sodium bicarbonate aqueous solution. The combined organic layers were washed with brine, dried and concentrated. The residue was purified by silica gel column chromatography (hexane:ethyl acetate=2:1, and to hexane:ethyl acetate:methanol=3:3:1) to obtain a fraction (32 mg) containing the objective. This was purified by HPLC fractionation (column, silica gel; methylene chloride:ethanol= 97.5:2.5) to obtain a less polar compound (6.9 mg, No. 3505a, 10% yield) and a more polar compound (10.3 mg, No. 3505b, 15% yield). These are expected to be stereoisomers based on the asymmetric point to which the aldol hydroxyl group is bound.

Less Polar Compound, No. 3505a $^1$H NMR (CDCl$_3$) δ: 0.54 (s, 3 H), 0.88 (d, J=6.8 Hz, 3 H), 1.26–1.70 (m, 13 H), 1.78–2.11 (m, 6 H), 2.31 (dd, J=6.6, 13.4 Hz, 1 H), 2.46–2.63 (m, 2 H), 2.82 (d, J=11.2 Hz, 1 H), 2.86 (s, 3 H), 3.25–3.40 (m, 2 H), 3.92 (d, J=9.9 Hz, 1 H), 4.22 (br., 1 H), 4.43 (br., 1 H), 5.00 (s, 1 H), 5.32 (s, 1 H), 6.02 (d, J=11.4 Hz, 1 H), 6.38 (d, J=11.1 Hz, 1 H).

MS: m/e 444.5 (M+1)$^+$

More Polar Compound, No. 3505b $^1$H NMR (CDCl$_3$) δ: 0.54 (s, 3 H), 0.96 (d, J=6.8 Hz, 3 H), 1.16–1.91 (m, 13 H), 1.92–2.11 (m, 6 H), 2.30 (dd, J=6.8, 13.5 Hz, 1 H), 2.49–2.60 (m, 2 H), 2.81–2.86 (m, 1 H), 2.88 (s, 3 H), 3.27–3.39 (m, 2 H), 3.72 (d, J=11.6 Hz, 1 H), 4.18 (br., 1 M), 4.40 (br., 1 H), 4.99 (s, 1 H), 5.32 (s, 1 H), 6.03 (d, J=11.4 Hz, 1 H), 6.37 (d, J=11.4 Hz, 1 H).

MS: m/e 444.5 (M+1)$^+$

Example 3-2

Production of Compounds No. 3105a, 3105b, 3105c and 3105d

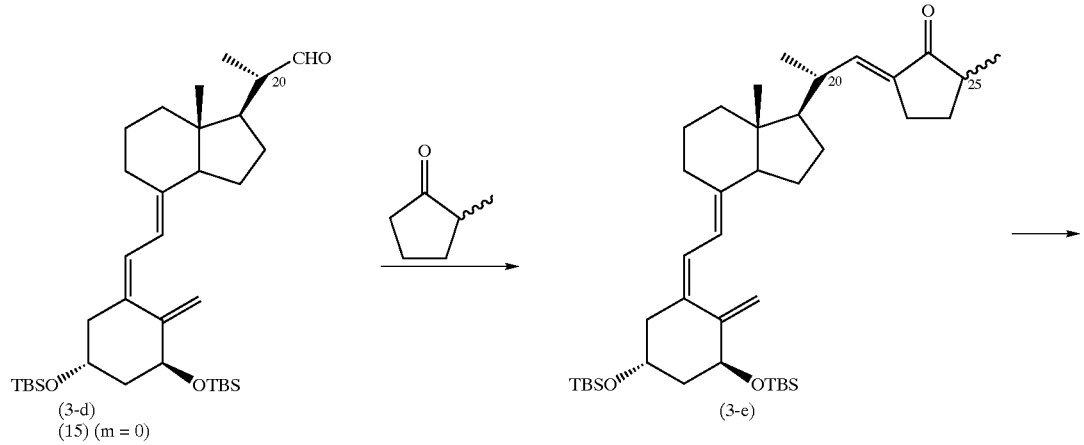

(3-d)
(15) (m = 0)

(3-e)

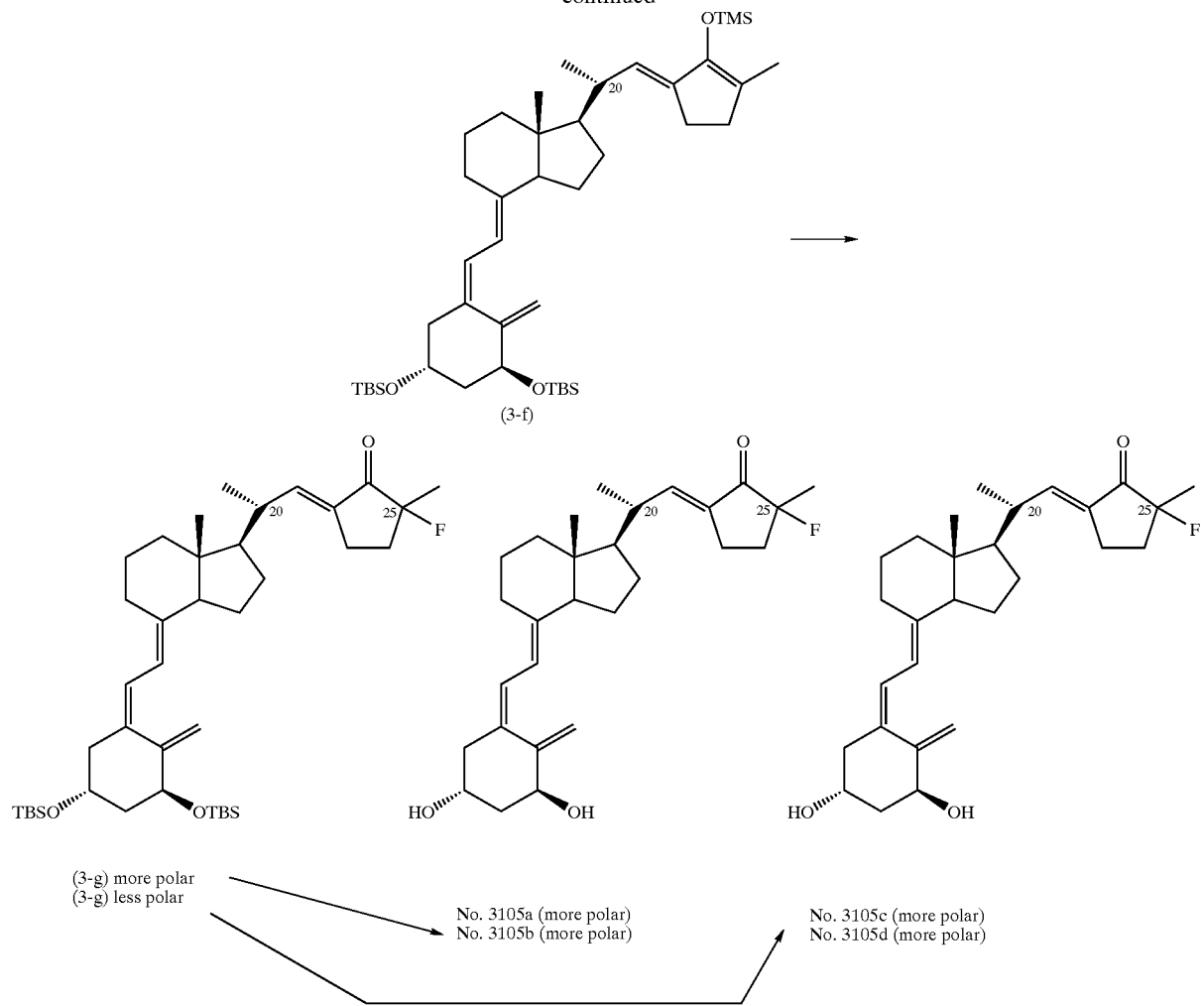

(1) In a nitrogen atmosphere, diisopropylamine (2 ml) was added to dry THF (15 ml), and the mixture was cooled with ice. An n-butyllithium solution (1.54 M) in hexane was added, and the mixture was stirred for 15 min at the same temperature. The solution was cooled to −70 °C., 2-methylcyclopentanone (1.6 ml) was added, and the mixture was stirred for 1 hr. At the same temperature, a THF solution (2 ml) of the (3-d) (a mixture of stereoisomers based on the asymmetric point of the 20-position), which can be produced according to a known process (International Patent Publication WO90/09991; Tetrahedron, 20, 4609–4619 (1987)), was added dropwise, and the mixture was stirred overnight while the temperature of the mixture was allowed to rise spontaneously to room temperature. The reaction mixture was extracted with ethyl acetate after the addition of an 1N hydrochloric acid aqueous solution. The combined organic layers were washed with a saturated sodium bicarbonate aqueous solution and condensed, and the residue was purified by silica gel column chromatography to obtain (3-e) (2.3 g, 70% yield). This sample is a mixture of stereoisomers based on the asymmetric points at the 20-position and the 25-position.

(2) The above-obtained (3-e) (653 mg) was dissolved in dichloromethane (3 ml), and 1,8-diazabicyclo-[5,4,0]-7-undecene (228 mg) and trimethylchlorosilane (152 μl) were added at room temperature. The solution was stirred for 1 hr under heating and refluxing. The reaction mixture was extracted with hexane-ethyl acetate (10:1) after the addition of brine. The combined organic layers were washed with a saturated sodium bicarbonate aqueous solution and concentrated, and the residue was purified by silica gel column chromatography to obtain (3-f) (620 mg, 92% yield). This sample is a mixture of stereoisomers based on the asymmetric point at the 20-position.

$^1$H NMR (CDCl$_3$) δ: 0.05 (s, 12 H), 0.19 (s, 9 H), 0.44 (s, 3 H), 0.55 (s, 3 H), 0.70–3.50 (m, 21 H), 0.88 (s, 18 H), 0.98 (d, J=6.6 Hz, 3 H), 1.66 (s, 3 H), 4.16 (br., 1 H), 4.36 (br., 1 H), 4.85 (br., 1 H), 5.00 (dd, J=9.6, 19.6 Hz, 1 H), 5.17 (br., 1 H), 6.00 (d, J=11.4 Hz, 1 H), 6.23 (d, J=11.4 Hz, 1 H).

(3) The above-obtained (3-f) (437 mg) was dissolved in dichloromethane (6 ml), N-fluoropyridinium triflate (163 mg) was added at room temperature, and the mixture was stirred for 2 hr at room temperature. To the reaction mixture was added dichloromethanewater (50 ml-50 ml), the organic layer was washed with a saturated sodium bicarbonate aqueous solution and concentrated. The residue was purified by silica gel column chromatography to obtain (3-g) more polar compound (56 mg), (3-g) less polar compound (98 mg) and a mixture (89 mg) of both the compounds. The total yield was 60%. These compounds are stereoisomers based on the asymmetric points at the 20-position and the 25-position.

(3-g) more polar compound

¹H NMR (CDCl₃) δ: 0.06 (s, 12 H), 0.40 (s, 3 H), 0.56 (s, 3 H), 0.88 (s, 18 H), 1.00–3.00 (m, 21 H), 1.46 (d, J=22.3 Hz, 3 H), 4.13 (br., 1 H), 4.37 (br., 1 H), 4.85 (br., 1 H), 5.18 (br., 1 H), 6.00 (d, J=12.4 Hz, 1 H), 6.22 (d, J=12.5 Hz, 1 H), 6.60 (d, J=10.7 Hz, 1 H), 6.70 (d, J=10.7 Hz, 1 H).

(3-g) less polar compound

¹H NMR (CDCl₃) δ: 0.06 (s, 12 H), 0.40 (s, 3 H), 0.56 (s, 3 H), 0.88 (s, 18 H), 1.00–3.00 (m, 21 H), 1.46 (d, J=22.3 Hz, 3 H), 4.13 (br., 1 H), 4.37 (br., 1 H), 4.85 (br., 1 H), 5.18 (br., 1 H), 6.00 (d, J=12.4 Hz, 1 H), 6.22 (d, J=12.5 Hz, 1 H), 6.60 (d, J=10.7 Hz, 1 H), 6.70 (d, J=10.7 Hz, 1 H).

(4) The above-obtained (3-g) less polar compound (98 mg) was dissolved in a mixed solvent of acetonitrile (3 ml) and dichloromethane (1 ml), lithium tetrafluoroborate (41 mg) and further a 1N sulfuric acid-acetonitrile solution (0.13 ml) were added dropwise at room temperature, and the mixture was stirred for 10 min at room temperature. The reaction mixture was extracted with ethyl acetate after the addition of a saturated sodium bicarbonate aqueous solution. The combined organic layers were concentrated, and the residue was purified by silica gel column chromatography to obtain a fraction containing the objective. The product was purified by HPLC fractionation (column, ODS; acetonitrile water=75:25) to obtain a more polar compound (26 mg, No. 3105c, 40% yield) and a less polar compound (25 mg, No. 3105d, 38% yield). These compounds are stereoisomers based on the asymmetric points at the 20-position and the 25-position.

More Polar Compound, No. 3105c

¹H NMR (CDCl₃) δ: 0.41 (s, 3 H), 0.96 (d, J=6.7 Hz, 3 H), 1.00–3.00 (m, 21 H), 1.44 (d, J=22.4 Hz, 3 H), 4.21 (br., 1 H), 4.41 (br., 1 H), 4.97 (s, 1 H), 5.31 (s, 1 H), 5.98 (d, J=11.6 Hz, 1 H), 6.34 (d, J=11.6 Hz, 1 H), 6.68 (d, J=10.8 Hz, 11H).

Less Polar Compound, No. 3105d

¹H NMR (CDCl₃) δ: 0.57 (s, 3 H), 1.00–3.00 (m, 21 H), 1.07 (d, J=6.7 Hz, 3 H), 1.46 (d, J=22.4 Hz, 3 H), 4.23 (br., 1 H), 4.43 (br., 1 H), 4.98 (s, 1 H), 5.32 (s, 1 H), 5.99 (d, J=10.8 Hz, 1 H), 6.37 (d, J=10.8 Hz, 1 H), 6.66 (d, J=10.5 Hz, 1 H).

(5) The above-obtained (3-g) more polar compound (56 mg) was subjected to the deprotection reaction in the same manner to obtain a more polar compound (16 mg, No. 3105a, 43% yield) and a less polar compound (8 mg, No, 3105b, 22% yield). These compounds are stereoisomers based on the asymmetric points at the 20-position and the 25-position.

More Polar Compound, No. 3105a

¹H NMR (CDCl₃) δ: 0.41 (s, 3 H), 0.96 (d, J=6.7 Hz, 3 H), 1.00–3.00 (m, 21 H), 1.44 (d, J=22.4 Hz, 3 H), 4.21 (br., 1 H), 4.41 (br., 1 H), 4.97 (s, 1 H), 5.31 (s, 1 H), 5.98 (d, J=11.6 Hz, 1 H), 6.34 (d, J=11.6 Hz, 1 H), 6.68 (d, J=10.8 Hz, 1H).

Less Polar Compound, No. 3105b

¹H NMR (CDCl₃) δ: 0.57 (s, 3 H), 1.00–3.00 (m, 21 H), 1.07 (d, J=6.7 Hz, 3 H), 1.46 (d, J=22.4 Hz, 3 H), 4.23 (br., 1 H), 4.43 (br., 1 H), 4.98 (s, 1 H), 5.32 (s, 1 H), 5.99 (d, J=10.8 Hz, 1 H), 6.37 (d, J=10.8 Hz, 1 H), 6.66 (d, J=10.5 Hz, 1 H).

Example 3-3

Production of Compound No. 3405

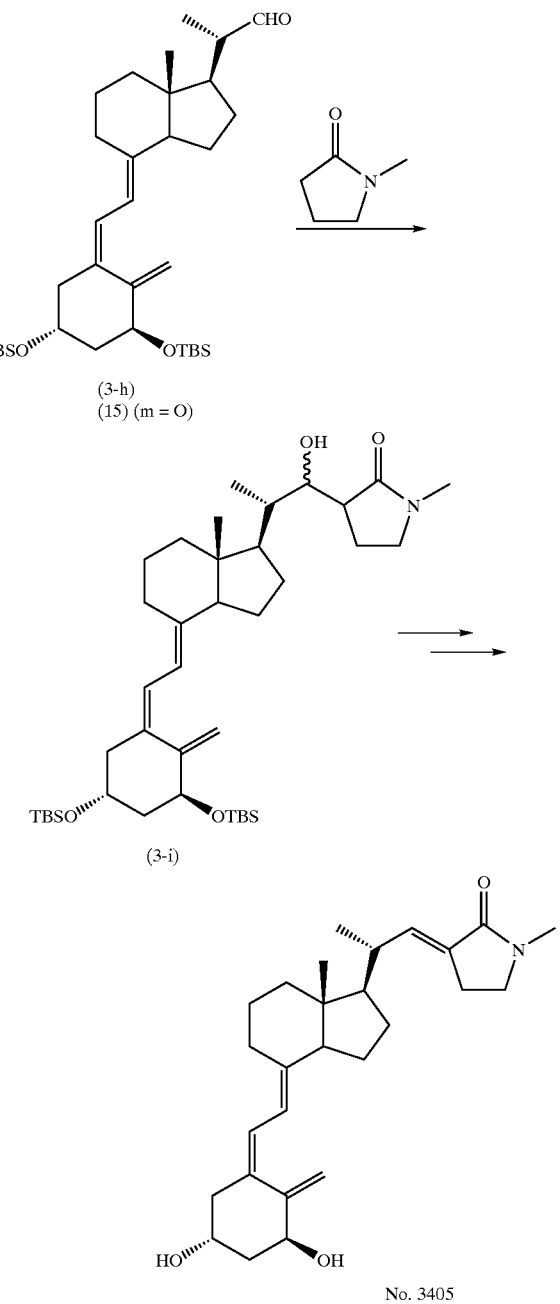

(1) In a nitrogen atmosphere, 1-methyl-2-pyrrolidinone (149 mg, 1.5 mmol) was added to dry THF (3 ml), and the mixture was cooled to −78° C. A lithium bis(trimethylsilyl) amide solution (1.5 ml, 1.0 M, 1.5 mmol) in THF was added dropwise, and the mixture was stirred for 40 min at the same temperature (Solution A). In another flask, the (3-h) (286 mg, 1.0 mmol), which can be produced according to a known process (International Patent Publication WO90/09991; Tetrahedron, 20, 4609–4619 (1987)), was dissolved in dry THF (3 ml). After the solution was cooled to −78° C., boron trifluoride-diethyl ether complex (85 mg, 0.6 mmol) was added. Further, the solution of the complex was added dropwise to the above-mentioned Solution A, and the mixture was stirred for 30 min at −78° C. The reaction mixture was extracted with ethyl acetate after the addition of a saturated ammonium chloride aqueous solution (10 ml). The combined organic layers were concentrated, and the residue was purified by silica gel column chromatography (hexane:ethyl acetate=1:1 to 1:2) to obtain (3-i) (177 mg, 53% yield).

$^1$H NMR (CDCl$_3$) δ: 0.07 (s, 12 H), 0.49 (s, 3 H), 0.81 (s, 18 H), 2.80(s, 3 H), 3.68 (d, J=13.5 Hz, 1 H), 4.10 (br., 1 H), 4.30 (br., 1 H), 4.82 (s, 1 H), 5.03 (s, 1 H), 5.10 (s, 1 H), 5.96 (d, J=11.2 Hz, 1 H), 6.19 (d, J=11.2 Hz, 1 H).

(2) Phosphorus oxychloride (37 mg) and HMPA (0.215 ml) were mixed, the mixture was heated for about 1 hr at 50° C., and then it was dried for 10 min under reduced pressure using a vacuum pump. To the solution were added the above-obtained (3-i) (67 mg) and pyridine (0.5 ml), and the mixture was stirred overnight at 60° C. The reaction mixture was extracted with ethyl acetate after the addition of 1N hydrochloric acid. The combined organic layers were concentrated to obtain a crude product sample of a dehydrated body. The sample was dissolved in a mixed solvent of acetonitrile (3 ml) and dichloromethane (1 ml), and lithium tetrafluoroborate (28 mg) and a 1N sulfuric acid-acetonitrile solution were added, and the mixture was stirred for 30 min at room temperature. The reaction mixture was extracted with ethyl acetate after the addition of a saturated sodium bicarbonate aqueous solution. The combined organic layers were concentrated, and the obtained crude product was purified by HPLC fractionation (column, ODS; acetonitrile:water=50:50) to obtain No. 3405 (7 mg, 16% yield).

$^1$H NMR (CDCl$_3$) δ: 0.57 (s, 3 H), 1.04 (d, J=6.6 Hz, 3 H), 2.92 (s, 3 H), 3.38 (t, J=7.1 Hz, 2 H), 4.23 (br., 1 H), 4.42 (br., 1 H), 4.99 (s, 1 H), 5.32 (s, 1 H), 6.00 (d, J=11.2 Hz, 1 H), 6.26 (d, J=10.4 Hz, 1 H), 6.37 (d, J=11.2 Hz, 1 H).

Example 3-4

Production of Compound No. 3401

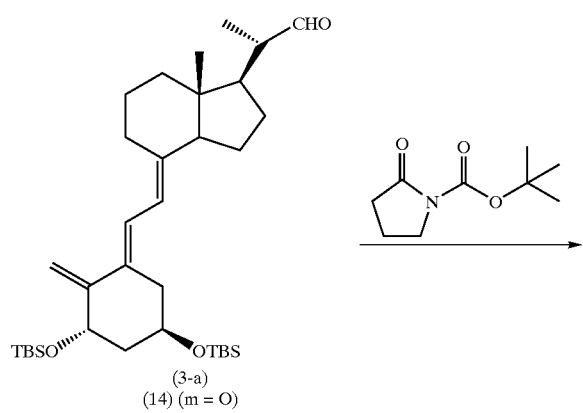

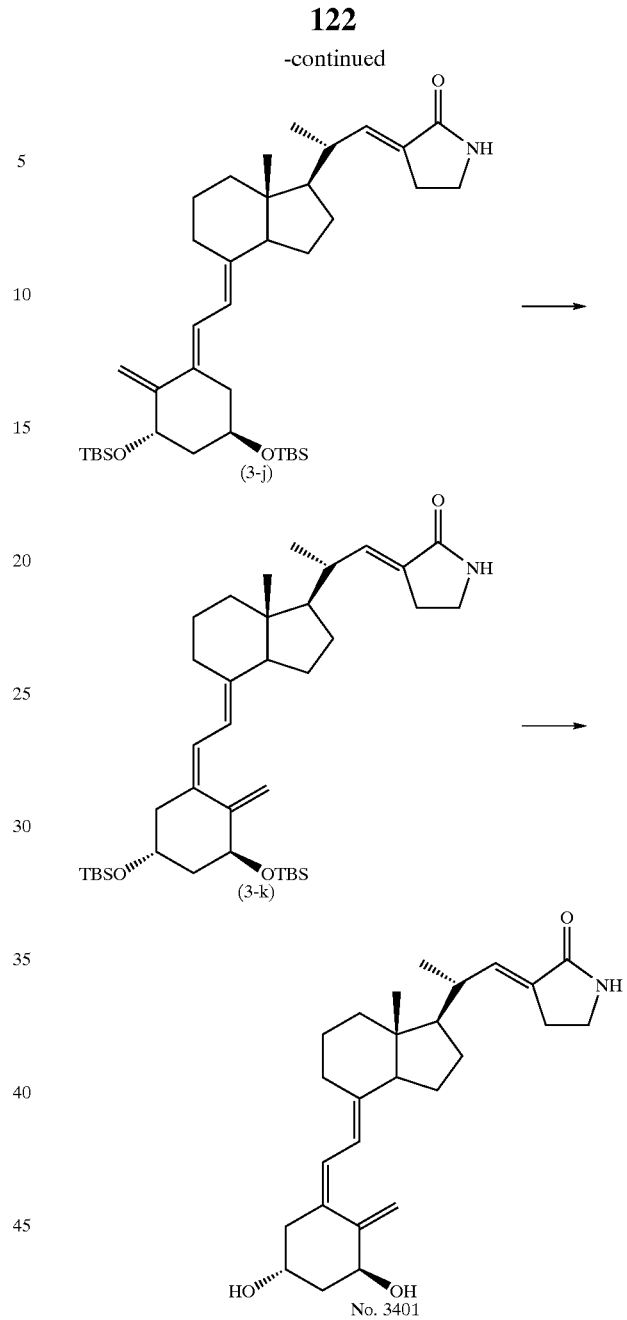

(1) By employing substantially the same process as in Example 3-1 (1), but using 1-(t-butoxycarbonyl)-2-pyrrolidinone in place of 1-methyl-2-pyrrolidinone, (3-j) was obtained (66 mg, 21% yield).

$^1$H NMR (CDCl$_3$) δ: 0.07 (s, 12 H), 0.58 (s, 3 H), 0.87 (s, 9 H), 0.90 (s, 9 H), 1.06 (d, J=6.6 Hz, 3 H), 1.10–2.08 (m, 13 H), 2.30–2.34 (m, 2 H), 2.55 (dd, J=5.1, 14.2 Hz, 1 H), 2.76–2.80 (m, 2 H), 2.87–2.91 (m, 1 H), 3.45 (t, J=6.8 Hz, 2 H), 4.22 (br., 1 H), 4.53–4.55 (m, 1 H), 4.95 (s, 1 H), 4.99 (s, 1 H), 5.82 (d, J=11.4 Hz, 1 H), 6.30 (d, J=10.4 Hz, 1 H), 6.46 (d, J=11.4 Hz, 1 H), 7.11 (br., 1 H).
MS: m/e 640.8 (M+1)$^+$ (2) The (3-j) (66 mg, 0.103 mmol) was dissolved in dry toluene (3 ml), anthracene (18 mg, 0.103 mmol) was added, and nitrogen gas was bubbled into the mixture for 20 min. Subsequently, the solution was sealed tightly and irradiated with light (mercury lamp, 100 W) for 1.5 hr at room temperature. The reaction mixture was concentrated, to the residue was added methanol (3 ml), insoluble matter was filtered, and the filtrate was concentrated. The residue was purified by silica gel column chromatography (hexane:ethyl acetate=20:1 to 1:2) to obtain (3-k) (60 mg, 91% yield).

¹H NMR (CDCl₃) δ: 0.06 (s, 12 H), 0.57 (s, 3 H), 0.87 (s, 18 H), 1.04–1.07 (m, 3 H), 1.23–2.03 (m, 13 H), 2.23–2.41 (m, 3H), 2.76 (br., 3 H), 3.44 (t, J=6.6 Hz, 2 H), 4.18 (br., 1 H), 4.37 (br., 1 H), 4.86 (d, J=2.5 Hz, 1 H), 5.18 (s, 1 H), 6.01 (d, J=11.1 Hz, 1 H), 6.21–6.30 (m, 2 H), 7.01 (br., 1 H).

MS: m/e 640.8 (M+1)⁺

(3) The raw material (3-k) (60 mg, 0.094 mmol) was treated in the same manner as in Example 3–1 (3) to obtain No. 3401 (17.5 mg, 47%).

¹H NMR (CDCl₃) δ: 0.58 (s, 3 H), 1.06 (d, J=6.4 Hz, 3 H), 1.11–2.06 (m, 15 H), 2.24–2.35 (m, 2 H), 2.58–2.61 (m, 1 H), 2.76–2.86 (m, 3 H), 3.44 (t, J=6.9 Hz, 2 H), 4.22–4.25 (m., 1 H), 4.41–4.45 (m, 1 H), 4.98 (s, 1 H), 5.32 (s, 1 H), 6.01 (d, J=11.2 Hz, 1 H), 6.30 (dt, J=2.8, 10.4 Hz, 1 H), 6.37 (d, J=11.2 Hz, 1 H), 6.50 (br., 1 H).

MS: m/e 412.5 (M+1)⁺

Example 3-5
Production of Compounds No. 3513a and 3513b

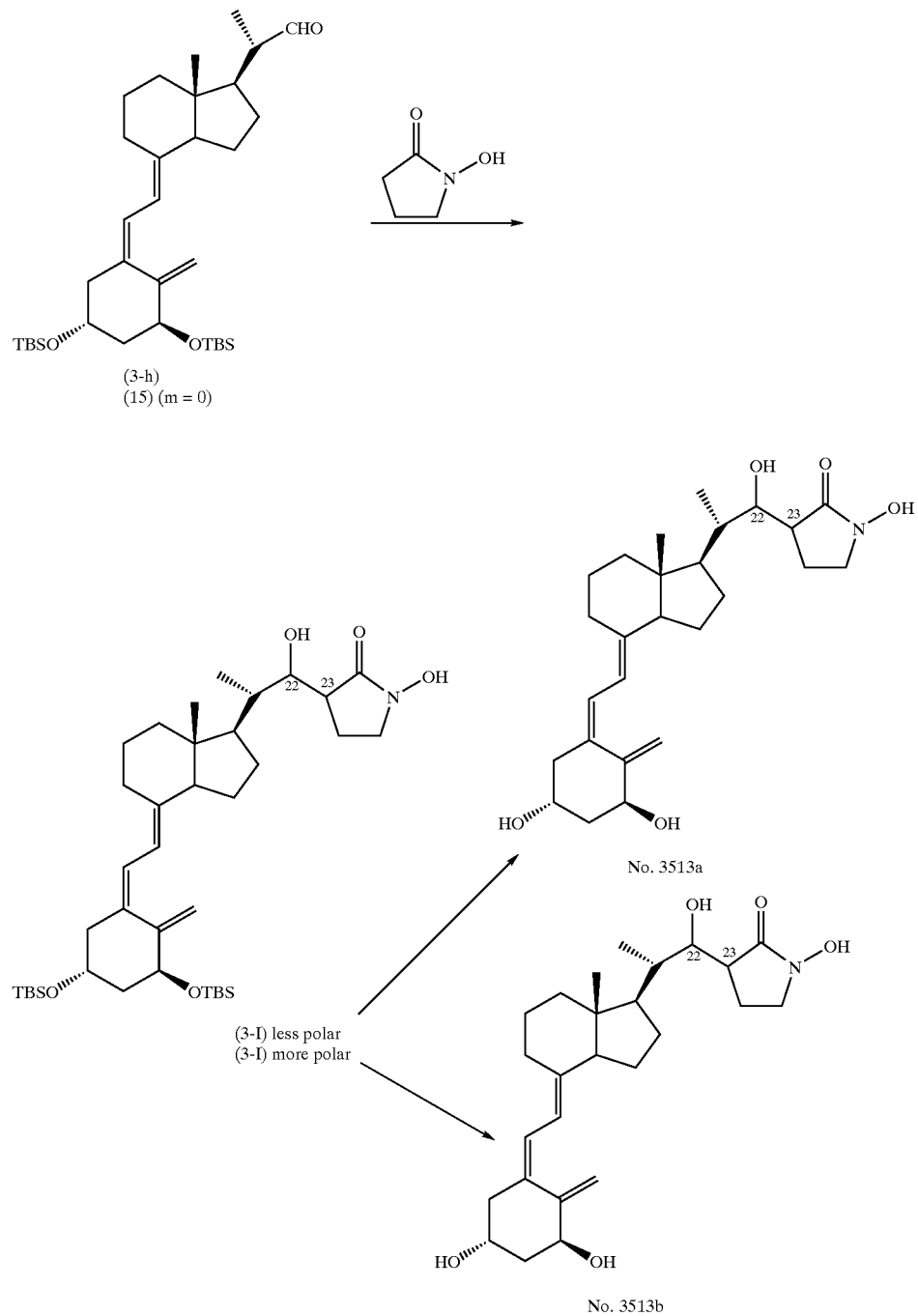

(1) Hexamethyldisilazane (355 mg, 2.2 mmol) was dissolved in dry THF (5 ml), the solution was cooled with ice, an n-butyllithium solution (1.43 ml, 1.47 M, 2.1 mmol) in hexane was added dropwise, and the mixture was stirred for 15 min in this state. To the solution was added a dry THF solution (2 ml) of 1-hydroxy-2-pyrrolidinone (101 mg, 1.0 mmol), which can be produced according to a known process (for example, JP-A 3-68553), and the mixture was stirred for 1 hr under cooling with ice. A dry THF solution (1.5 ml) of the (3-h) (258 mg, 0.45 mmol), which can be produced according to a known process (International Patent Publication WO90/09991; Tetrahedron, 20, 4609–4619 (1987)), was added dropwise, and the mixture was stirred for 1.5 hr under cooling with ice. The reaction mixture was extracted with ethyl acetate after the addition of a saturated ammonium chloride aqueous solution. The combined organic layers were washed with brine, dried and concentrated. The residue was purified by silica gel column chromatography (hexane:ethyl acetate=20:1, and to ethyl acetate:methanol=2:1), and subsequently by preparative TLC (hexane:ethyl acetate=1:2) to obtain (3-1) less polar compound (24 mg, 7.9% yield) and (3-1) more polar compound (9.9 mg, 14% yield). These compounds are expected to be stereoisomers based on asymmetric points of the 22-position and the 23-position.

(3-1) Less Polar Compound $^1$H NMR (CDCl$_3$) δ: 0.06 (s, 12 H), 0.53 (s, 3 H), 0.88 (s, 18 H), 0.93–2.05 (m, 21 H), 2.12–2.25 (m, 1 H), 2.42–2.47 (m, 1 H), 2.58–2.62 (m, 1 H), 2.80–2.85 (m, 1 H), 3.59 (d, J=7.8 Hz, 2 H), 3.72–3.76 (m, 1 H), 4.18–4.19 (m, 1 H), 4.37 (br., 1 H), 4.86 (s, 1 H), 5.17 (s, 1 H), 6.02 (d, J=10.9 Hz, 1 H), 6.24 (d, J=11.1 Hz, 1H).

MS: m/e 674.8 (M+1)$^+$ (3-1) More Polar Compound $^1$H NMR (CDCl$_3$) δ: 0.06 (s, 12 H), 0.55 (s, 3 H), 0.88 (s, 18 H), 0.89–1.96 (m, 21 H), 2.18–2.25 (m, 1 H), 2.42–2.47 (m, 1 H), 2.56 (br., 1 H), 2.80–2.84 (m, 1 H), 3.58 (br., 2 H), 4.11–4.26 (m, 1 H), 4.35–4.37 (m, 1 H), 4.86 (d, J=2.3 Hz, 1 H), 5.18 (s, 1 H), 6.02 (d, J=11.59 Hz, 1 H), 6.23 (d, J=11.2 Hz, 1 H).

MS: m/e 674.8 (M+1)$^+$ (2) According to the same process as in Example 3–1 (3), the (3-1) less polar compound (24 mg, 0.036 mmol) was converted to No. 3513a (13.1 mg, 83% yield). This sample is expected to be a mixture of stereoisomers based on the asymmetric point of the 22-position or the 23-position.

$^1$H NMR (CDCl$_3$+CD$_3$OD) δ: 0.54, 0.56 (s, 3 H), 0.86–1.07 (m, 3 H), 0.94 (d, J=6.9 Hz, 3 H), 1.20–2.21 (m, 17 H), 2.30 (dd, J=6.9, 12.9 Hz, 1 H), 2.55–2.59 (m, 2 H), 2.81–2.86 (m, 1 H), 3.54 (br., 2 H), 3.69–3.82 (m, 1 H), 4.11–4.18 (m, 1 H), 4.37–4.39 (m, 1 H), 4.98 (s, 1 H), 5.32 (s, 1 H), 6.04 (d, J=11.9 Hz, 1 H), 6.36 (d, J=10.9 Hz, 1 H).

MS: m/e 446.3 (M+1)$^+$ (3) According to the same process as in Example 3-1 (3), by using the (3-1) more polar compound (9.9 mg, 0.015 mmol) as the raw material, No. 3513b was obtained (7.5 mg, 115% yield). This sample is expected to be a mixture of stereoisomers based on the asymmetric point of the 22-position or the 23-position.

$^1$H NMR (CDCl$_3$+CD$_3$OD) δ: 0.56, 0.58 (s, 3 H), 0.74–0.99 (m, 6 H), 1.26–2.33 (m, 17 H), 2.53–2.58 (m, 3 H), 2.81–2.86 (m, 1 H), 3.51 (br., 2 H), 4.06 (br., 1 H), 4.17–4.20 (m, 1 H), 4.31–4.41 (m, 1 H), 4.98 (s, 1 H), 5.32 (s, 1 H), 6.05 (d, J=11.2 Hz, 1 H), 6.35 (d, J=10.9 Hz, 1 H).

MS: m/e 446.2 (M+1)$^+$

Example 4-1

Production of Compounds No. 4101a and 4101b

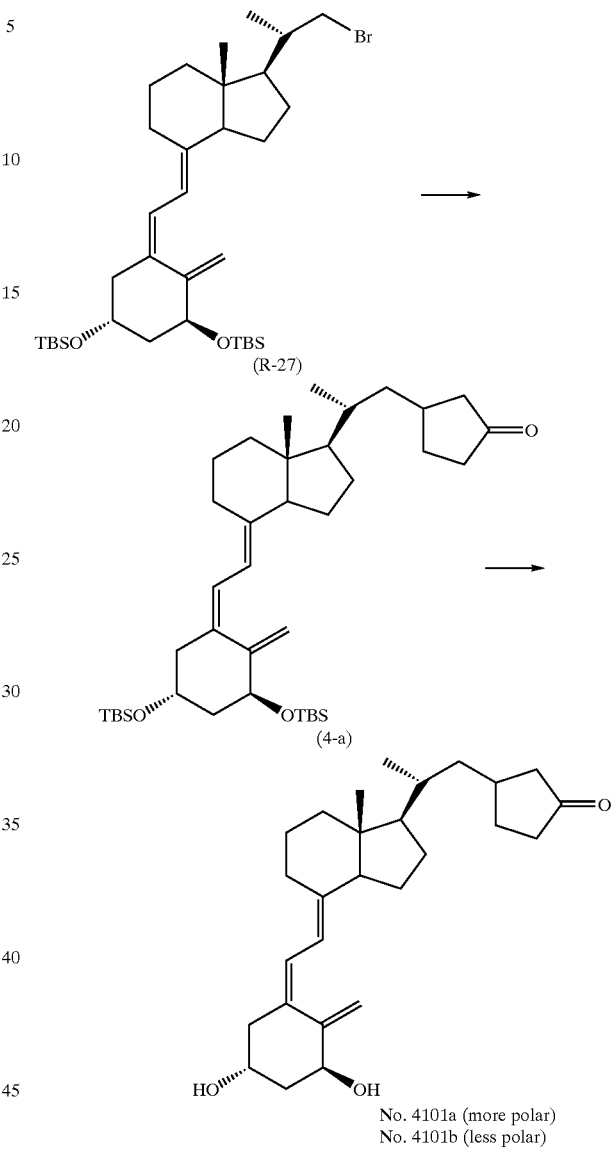

No. 4101a (more polar)
No. 4101b (less polar)

(1) The (R-27) (461 mg, 0.724 mmol) obtained in Reference Example 6 was dissolved in dry THF (2 ml), and the solution was cooled to −78° C. A t-butyllithium solution (0.55 ml, 1.57M, 0.87 mmol) in n-pentane was added dropwise, and the mixture was stirred for 20 min at −78° C. without elevating the temperature (Solution A). In another container, a copper (I) bromide-dimethyl sulfide complex (74 mg, 0.362 mmol) solution in dry THF was placed and cooled to −40° C., to the solution was added dropwise the Solution A, and the mixture was stirred for 30 min at −40° C. Subsequently, the temperature of the mixture was lowered to −78° C., HMPA (302 μl, 1.74 mmol) was added, and the mixture was stirred for 15 min. Then, chlorotrimethylsilane (220 μl, 1.74 mmol) and 2-cyclopenten-1-one (49 μl, 0.58 mmol) were added, and the mixture was stirred for 3.5 hr at −78° C. The reaction mixture was extracted with ethyl acetate after the addition of a saturated ammonium chloride aqueous solution. The combined organic layers were dried over anhydrous sodium sulfate and concentrated. The residue was purified by silica gel column chromatography (hexane:ethyl acetate=9:1) to obtain (4-a) (141 mg, 21% yield). This sample is a mixture of stereoisomers based on the asymmetric point on the cyclopentanone ring.

(2) The above-obtained compound (4-a) (35 mg) was dissolved in a mixed solvent of dichloromethane (2 ml) and acetonitrile (2 ml), and the solution was cooled with ice. Lithium tetrafluoroborate (65 mg, 0.69 mmol) and a 1N sulfuric acid-acetonitrile solution (0.2 ml) were added, and the mixture was stirred for 30 min under cooling with ice. The reaction mixture was extracted with ethyl acetate after the addition of a saturated sodium bicarbonate aqueous solution. The combined organic layers were dried over anhydrous sodium sulfate and concentrated. The residue was purified by silica gel column chromatography (hexane:ethyl acetate=2:1), and further the obtained sample was purified by HPLC fractionation (column, ODS; acetonitrile:water= 70:30) to obtain a more polar compound (9 mg, No. 4101a, 40% yield) and a less polar compound (10 mg, No. 4101b, 44% yield). These are stereoisomers based on the asymmetric point on the cyclopentanone ring.

More Polar Compound, 4101a $^1$H-NMR (CDCl$_3$) δ: 0.57 (s, 3 H), 0.97 (d, J=6 Hz, 3 H), 2.41–1.19 (m, 25 H), 2.60 (dd, J=4, 12 Hz, 1 H), 2.83 (dd, J=4, 12 Hz, 2 H), 4.23 (m, 1 H), 4.43 (m, 1 H), 5.00 (s, 1 H), 5.33 (s, 1 H), 6.02 (d, J=11 Hz, 1 H), 6.38 (d, J=11 Hz, 1 H).

MS: m/e 413.2 (M+1)$^+$, 395.3 (M—H$_2$O+1)$^+$

UV/vis λ=213 nm, 266 nm

Less Polar Compound, 4101b $^1$H-NMR (CDCl$_3$) δ: 0.55 (s, 3 H), 0.95 (d, J=6 Hz, 3 H), 2.41–1.19 (m, 25 H), 2.60 (dd, J=4, 12 Hz, 1 H), 2.83 (dd, J=4, 12 Hz, 2 H), ,4.23 (m, 1 H), 4.43 (m, 1 H), 5.00 (s, 1 H), 5.33 (s, 1 H), 6.02 (d, J=11 Hz, 1 H), 6.38 (d, J=11 Hz, 1 H).

MS: m/e 413.2 (M+1)$^+$, 395.3 (M—H$_2$O+1)$^+$

UV/vis λ=213 nm, 266 nm

Example 4-2

Production of Compounds No. 4102a, 4102b, 4107a and 4107b

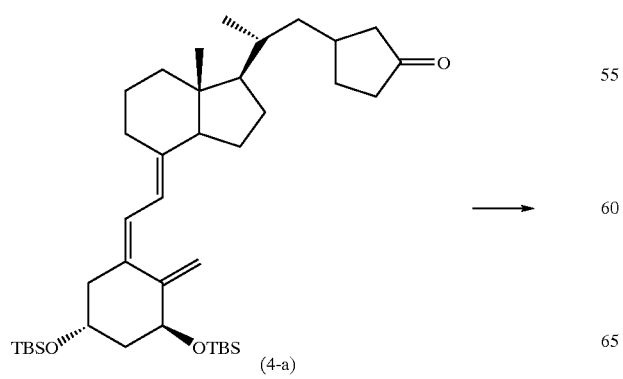

(1) The (4-a) (130 mg, 0.20 mmol) obtained in Example 4-1 was dissolved in dry THF (3 ml), and N-methylaninium trifluoroacetate (106 mg, 0.48 mmol) and paraformaldehyde (18 mg) were added. The mixture was heated and refluxed for 1 hr, and the obtained reaction mixture was extracted with water-ethyl acetate. The combined organic layers were washed serially with 1N hydrochloric acid, a saturated sodium bicarbonate aqueous solution and brine, dried over anhydrous sodium sulfate and concentrated. The residue was purified by preparative TLC (hexane:ethyl acetate=95:5) to obtain two fractions (the more polar compound is expressed by F1, and the less polar compound by F2). These are mixtures of (4-b) and (4-c).

(2) The above-obtained F1 was dissolved in a mixed solvent of dichloromethane (1 ml) and acetonitrile (1 ml), lithium tetrafluoroborate (33 mg, 0.35 mmol) and conc. sulfuric acid (20 mg) were added, and the mixture was stirred for 45 min at 0° C. The reaction mixture was extracted with ethyl acetate after the addition of a saturated sodium bicarbonate aqueous solution. The combined organic layers were washed with brine, dried over anhydrous sodium sulfate and concentrated. The residue was purified by silica gel column chromatography (hexane:ethyl acetate:methanol=5:4:1), and further by HPLC fractionation (column, ODS; solvent, acetonitrile:water:ethanol=75:25:3) to obtain 1.4 mg (No. 4102a), 3.3 mg (No. 4107a) and 1.8 mg (No. 4102b) in the order from the more polar compound. No. 4102a and No. 4102b are stereoisomers based on the asymmetric point on the cyclopentanone ring.

No. 4102a
$^1$H-NMR (CDCl$_3$) δ: 0.59 (s, 3 H), 1.01 (d, J=6 Hz, 3 H), 2.40–1.26 (m, 23 H), 2.60 (dd, J=4, 12 Hz, 1 H), 2.83 (dd, J=4, 12 Hz, 2 H), 4.23 (m, 1 H), 4.43 (m, 1 H), 5.00 (s, 1 H), 5.28 (s, 1 H), 5.33 (s, 1 H), 6.00 (s, 1 H), 6.02 (d, J=11 Hz, 1 H), 6.38 (d, J=11 Hz, 1 H).
MS: m/e 425.4 (M+1)$^+$, 407.4 (M—H$_2$O+1)$^+$

No. 4107a
$^1$H-NMR (CDCl$_3$) δ: 0.57 (s, 3 H), 0.96 (d, J=6 Hz, 3 H), 2.34–1.20 (m, 22 H), 2.50 (dd, J=7, 18 Hz, 1 H), 2.60 (dd, J=4, 12 Hz, 1 H), 2.83 (dd, J=4, 12 Hz, 2 H), 4.23 (m, 1 H), 4.43 (m, 1 H), 5.00 (s, 1 H), 5.28 (s, 1 H), 5.33 (s, 1 H), 5.96 (s, 1 H), 6.02 (d, J=11 Hz, 1 H), 6.38 (d, J=11 Hz, 1 H).
MS: m/e 425.4 (M+1)$^+$, 407.4 (M—H$_2$O+1)$^+$

No. 4102b
$^1$H-NMR (CDCl$_3$) δ: 0.56 (s, 3 H), 1.03 (d, J=6 Hz, 3 H), 2.37–1.14 (m, 23 H), 2.60 (dd, J=4, 12 Hz, 1 H), 2.83 (dd, J=4, 12 Hz, 2 H), 4.23 (m, 1 H), 4.43 (m, 1 H), 5.00 (s, 1 H), 5.26 (s, 1 H), 5.33 (s, 1 H), 6.00 (s, 1 H), 6.02 (d, J=11 Hz, 1 H), 6.38 (d, J=11 Hz, 1 H).
MS: m/e 425.4 (M+1)$^+$, 407.4 (M—H$_2$O+1)$^+$ (3) In the same manner, No. 4107b (0.7 mg) was obtained from the above-obtained F2. No. 4107a and No. 4107b are stereoisomers based on the asymmetric point on the cyclopentanone ring.

No. 4107b
$^1$H-NMR (CDCl$_3$) δ: 0.55 (s, 3 H), 0.95 (d, J=6 Hz, 3 H), 2.34–1.23 (m, 22 H), 2.50 (dd, J=7, 18 Hz, 1 H), 2.60 (dd, J=4, 12 Hz, 1 H), 2.83 (dd, J=4, 12 Hz, 2 H) 4.23 (m, 1 H), 4.43 (m, 1 H), 5.00 (s, 1 H) 5.27 (s, 1 H), 5.33 (s, 1 H), 5.95 (s, 1 H), 6.02 (d, J=11 Hz, 1 H), 6.38 (d, J=11 Hz, 1 H).
MS: m/e 425.4 (M+1)$^+$, 407.4 (M—H$_2$O+1)$^+$

Example 4-3
Production of Compound No. 4601

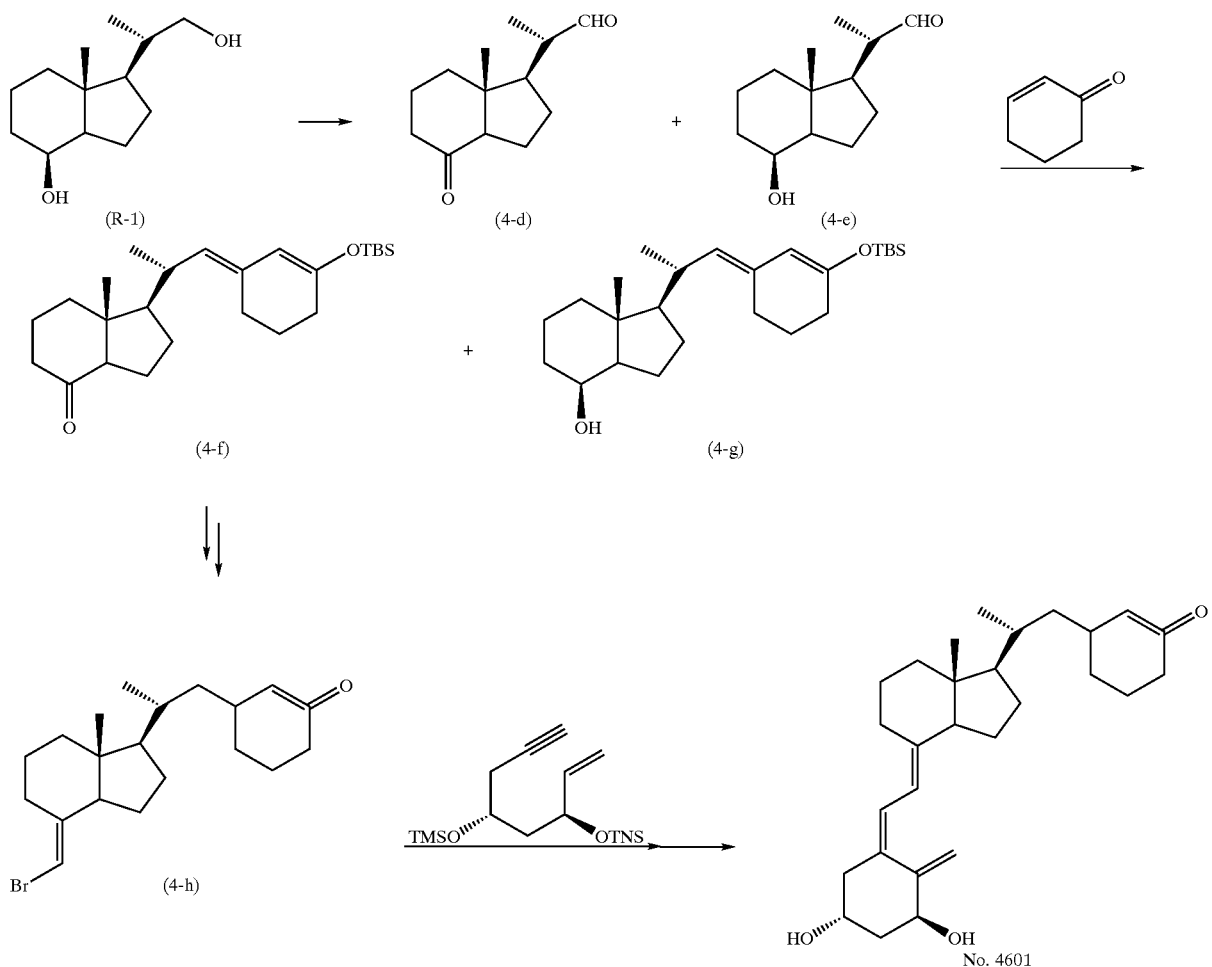

(1) To anhydrous acetone (300 ml) were added anhydrous magnesium sulfate powder (3 g), further the (R-i) (5.3 g), which can be produced from vitamin D2 according to a known process (for example, J. Org. Chem., 51, 1264–1269 (1986)), 4-methylmorpholine-N-oxide (8.8 g) and dichlorotris(trifluorophosphine)ruthenium (II) (240 mg). The reaction mixture was stirred for 1.5 hr at room temperature, subsequently hexane (100 ml) was added, and acetone was removed under reduced pressure. The obtained hexane-containing residue was extracted with ethyl acetate after the addition of 1N hydrochloric acid (50 ml). The combined organic layers were washed with brine (100 ml), with a saturated sodium hydrogensulfite aqueous solution (100 ml) and further with a saturated sodium bicarbonate aqueous solution (100 ml). The organic layer was concentrated, the residue was purified by silica gel column chromatography (hexane:ethyl acetate=2:1) to obtain a mixture (3.8 g) of (4-d) and (4-e).

(2) In a nitrogen atmosphere, triphenylphosphine (1.6 g) was dissolved in dry THF (20 ml), and t-butyldimethylsilyltrifluoromethane-sulfonate (1.4 ml) was added at room temperature. After the mixture was stirred for 10 min, cyclohexanone (0.586 ml) was added, and the mixture was stirred for 1.5 hr at room temperature. This reaction solution was cooled to −78° C., an n-butyllithium solution (3.6 ml) in hexane was slowly added dropwise, and they were stirred for 15 min at the temperature. A dry THF solution (3 ml) of the above-obtained mixture (1.03 g) of (4-d) and (4-e) was slowly added, the mixture was stirred for 30 min at −78° C., and subsequently, it was warmed up to room temperature by taking out the cooling bath. After the addition of hexane (150 ml) and anhydrous magnesium sulfate (6 g), the reaction mixture was stirred for 30 min at room temperature, it was filtered by glass filter, the filtrate was concentrated, and the residue was purified by silica gel chromatography (hexane:ethyl acetate-10:1) to obtain (4-f) (1.2 g) and (4-g) (448 mg).
(4-f)
$^1$H-NMR (CDCl$_3$) δ: 0.00 (s, 6 H), 0.51 (s, 3 H), 0.76 (s, 9 H), 0.84 (d, J=6.6 Hz, 3 H), 1.0–2.5 (m, 19 H), 4.63 (d, J=9.9 Hz, 1 H), 5.17 (s, 1 H).

(3) (Bromomethyl)triphenylphosphonium bromide (3.7 g) was dissolved in dry THF (75 ml), and the solution was cooled to −40° C. Subsequently, a sodium bis(trimethylsilyl) amide solution (8.2 ml, 1M) in THF was added, and the mixture was stirred for 40 min. A dry THF solution (25 ml) of the above-obtained (4-f) (1.1 g) was added, the mixture was stirred for 1 hr at −40° C., subsequently slowly warmed up to room temperature, and further stirred overnight. The reaction mixture was extracted with ethyl acetate after the addition of 1N hydrochloric acid (50 ml). The solvent was concentrated to obtain a crude product of the silylenol body of bromomethylene. The sample of the crude product was dissolved in a mixed solvent of acetonitrile (50 ml) and dichloromethane (10 ml), the solution was cooled to 0° C., and lithium tetrafluoroborate (380 mg) was added. Subsequently, a 1N sulfuric acid-acetonitrile solution (2 ml) was added dropwise, and the mixture was stirred for 20 min in this state. The reaction mixture was extracted with ethyl acetate after the addition of a saturated ammonium chloride aqueous solution (50 ml). The combined organic layers were washed with a saturated sodium bicarbonate aqueous solution and concentrated. The residue was purified by silica gel chromatography (hexane:ethyl acetate=3:1) to obtain (4-h) (500 mg, 50% yield).

$^1$H-NMR (CDCl$_3$) δ: 0.60 (s, 3 H), 0.88 (d, J=6.3 Hz, 3 H), 1.2–3.0 (m, 21 H), 5.65 (s, 1 H), 5.85 (s, 1 H).

(4) In a nitrogen atmosphere, triphenylphosphine (62.9 mg) and tris(dibenzylideneacetone)dipalladium (0)-chloroform adduct (20.7 mg) were dissolved in a mixed solvent of anhydrous toluene (2 ml) and diisopropylethylamine (2 ml), and the solution was stirred for 15 min at room temperature (solution A). Both of (3S),(5R)-3,5-bis(trimethylsilyloxy)-1-octen-7-yne (114 mg) and the above-obtained (4-h) (73 mg) were dissolved in a mixed solvent of anhydrous toluene (2.8 ml) and diisopropylethylamine (2 ml), the solution was added to the above Solution A, and the mixture was stirred for 3 hr at 90° C. The reaction mixture was extracted with ethyl acetate after the addition of 1N hydrochloric acid (10 ml). The combined organic layers were concentrated, and the residue was roughly purified by silica gel chromatography (hexane:ethyl acetate=3:1) to obtain a crude product of a coupled body. The crude product was dissolved in THF (6 ml), the solution was cooled to 0° C., subsequently 1N hydrochloric acid (1 ml) was added, and the mixture was stirred for 1 hr at the same temperature. The reaction mixture was extracted with ethyl acetate after the addition of a saturated sodium bicarbonate aqueous solution (5 ml). The combined organic layers were concentrated, and the residue was purified by silica gel chromatography (hexane:ethyl acetate:methanol=5:5:0.8), and the obtained sample was further purified by HPLC fractionation (column, ODS; acetonitrile water=60:40) to obtain No. 4601 (16 mg, 19% yield).

$^1$H-NMR (CDCl$_3$) δ: 0.58 (s, 3 H), 0.87 (d, J=6.3 Hz, 3 H), 1.0–3.0 (m, 25 H), 4.15–4.30 (m, 1 H), 4.35–4.45 (m, 1 H), 5.00 (s, 1 H), 5.33 (s, 1 H), 5.86 (s, 1 H), 6.02 (d, J=11.2 Hz, 1 H), 6.37 (d, J=11.2 Hz, 1 H).

Example 4-4

Production of Compound No. 4301

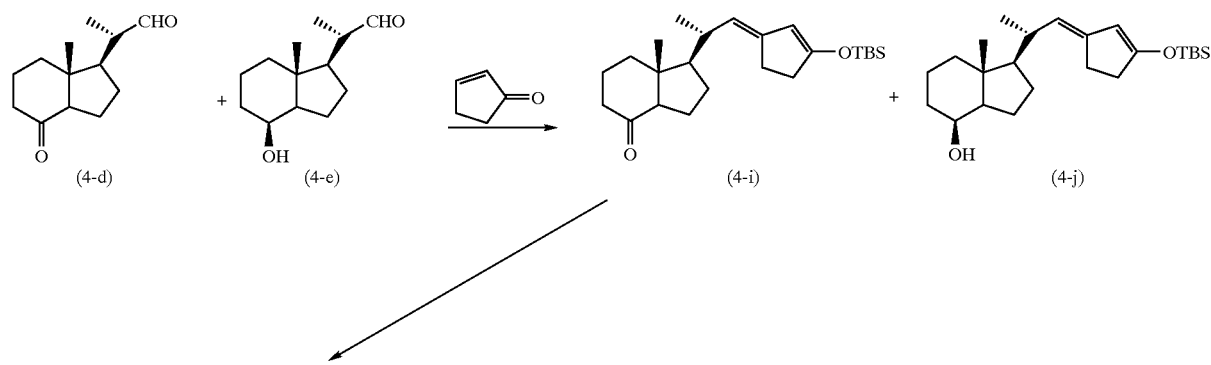

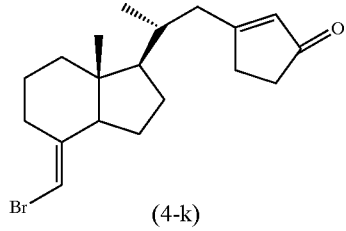

(4-k)

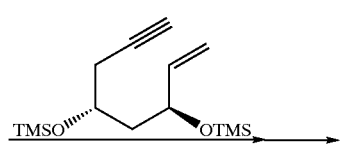

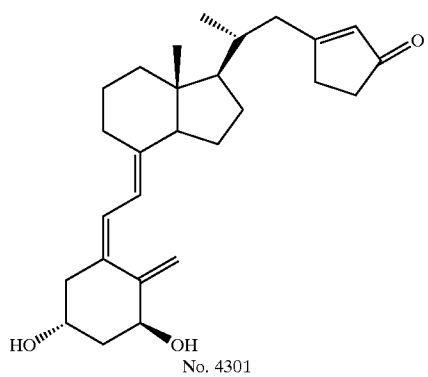

No. 4301

(1) The mixture (1.03 g) of (4-d) and (4-e) which were obtained in Experiment 4-3 (1), and cyclopentanone (0.506 ml) were treated in the same manner as in Example 4-3 (2) to obtain (4-i) (0.75 g) and (4-j) (368 mg).

(4-i)

$^1$H-NMR (CDCl$_3$) δ: 0.16 (s, 6 H), 0.67 (s, 3 H), 0.90 (s, 9 H), 0.97 (d, J=6.6 Hz, 3 H), 1.5–2.5 (m, 17 H), 4.77 (d, J=9.6 Hz, 1 H), 5.12 (s, 1 H).

(2) The above-obtained (4-i) (700 mg) was treated in the same manner as in Example 4-3 (3) to obtain (4-k) (136 mg, 22% yield).

$^1$H-NMR (CDCl$_3$) δ: 0.61 (s, 3 H), 0.93 (d, J=6.6 Hz, 3 H), 1.2–2.8 (m, 19 H), 2.80–2.95 (m, 1 H), 5.67 (s, 1 H), 5.95 (s, 1 H).

(3) The above-obtained (4-k) (25 mg) was treated in the same manner as in Example 4-3 (4) to obtain No. 4301 (10 mg, 22% yield).

$^1$H-NMR (CDCl$_3$) δ: 0.61 (s, 3 H), 0.93 (d, J=6.6 Hz, 3 H), 1.0–3.0 (m, 23 H), 4.15–4.30 (m, 1 H), 4.35–4.45 (m, 1 H), 5.00 (s, 1 H), 5.33 (s, 1 H), 5.95 (s, 1 H), 6.02 (d, J=11.2 Hz, 1 H), 6.37 (d, J=11.2 Hz, 1 H).

Example 4-5

Production of Compounds No. 4306a and 4306b

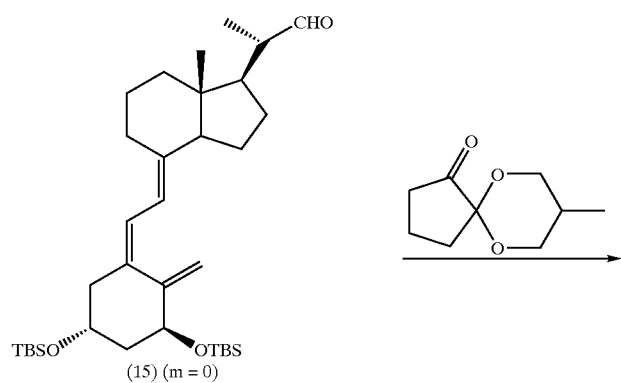

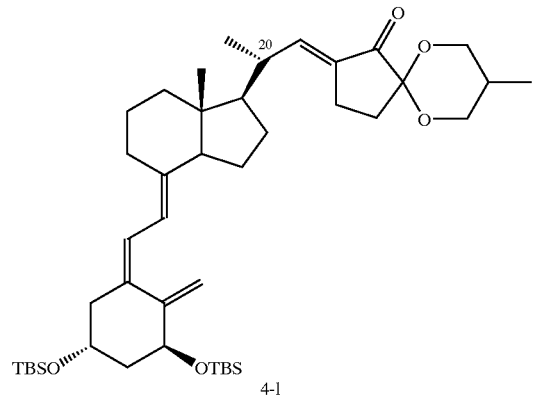

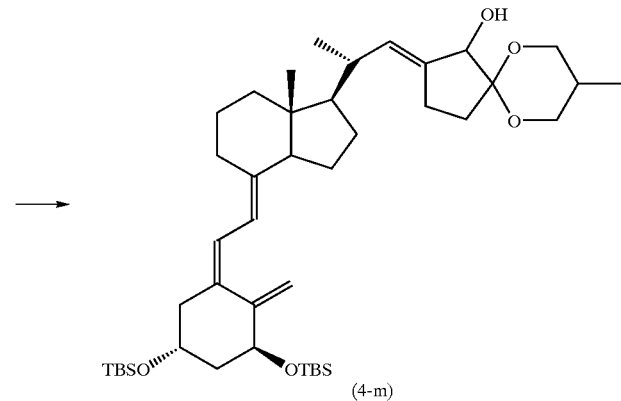

(4-m)

+

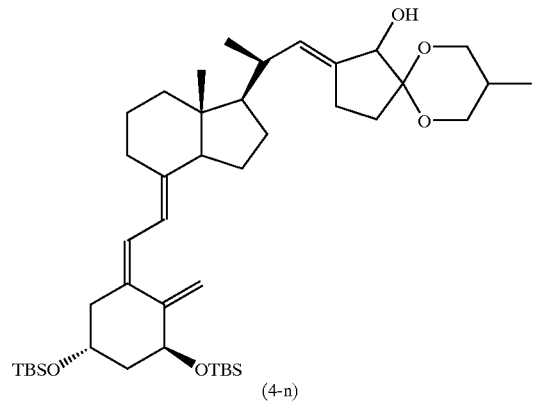

(4-n)

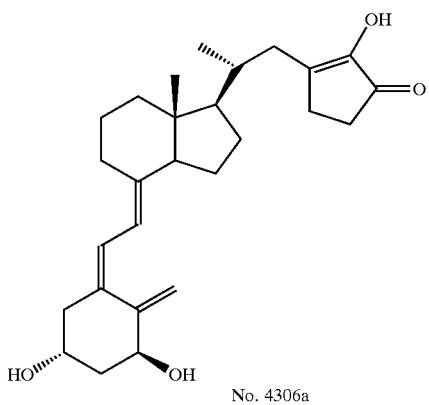
No. 4306a

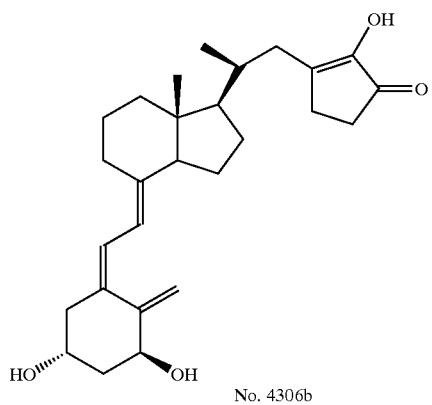
No. 4306b (1) Both of 8-methyl-6,10-dioxospiro[4,5]decan-1-one (70 mg, 0.41 mmol) and the (15) (m=0) (257 mg, 0.45 mmol), which can be obtained according to a known process (International Patent Publication WO90/09991; Tetrahedron, 20, 4609–4619 (1987)), were dissolved in ethanol (5 ml), and sodium ethylate (109 mg, 1.6 mmol) was added. The mixture was stirred for 16 hr at room temperature and evaporated under reduced pressure. The residue was extracted with water-ethyl acetate, and the organic layer was dried and concentrated to obtain (4-1) (132 mg, 43% yield). The sample is a mixture of stereoisomers based on the asymmetric point based on the 20-position.

(2) The above-obtained (4-1) (106 mg, 0.15 mmol) was dissolved in a mixed solvent of dichloromethane (0.5 ml) and methanol (1 ml), and cerium chloride (heptahydrate) (149 mg, 0.4 mmol) and sodium borohydride (5.7 mg, 0.15 mmol) were added, and the mixture was stirred for 10 min at room temperature. The reaction mixture was evaporated under reduced pressure, the residue was purified by preparative TLC (hexane:ethyl acetate=4:1) to obtain a less polar compound (40 mg, (4-m), 38% yield) and a more polar compound (25 mg, (4-n), 24% yield).

(3) The above-obtained (4-m) (40 mg, 0.055 mmol) was dissolved in a mixed solvent of dichloromethane (1 ml) and acetonitrile (1 ml), and lithium tetrafluoroborate (33 mg, 0.35 mmol) and a 1N-surfuric acid-acetonitrile solution (0.2 ml) were added, and the mixture was stirred for 45 min under cooling with ice. The reaction mixture was extracted with ethyl acetate after the addition of a saturated sodium bicarbonate aqueous solution. The combined organic layers were dried over anhydrous sodium sulfate and concentrated. The residue was purified by preparative TLC (hexane:ethyl acetate:methanol=4:5:1), and the obtained sample was further purified by HPLC fractionation (column, ODS; acetonitrile:water:methanol=70:30:3) to obtain No. 4306a (2.2 mg, 9.4% yield).

$^1$H-NMR (CDCl$_3$) δ: 0.62 (s, 3 H), 0.82 (d, J=7 Hz, 3 H), 2.05–1.26 (m, 14 H), 2.52–2.17 (m, 7 H), 2.61 (d, J=13 Hz, 2 H), 2.85 (d, J=12 Hz, 1 H), 4.23 (m, 1 H), 4.43 (m, 1 H), 5.01 (s, 1 H), 5.20 (br., 1 H, C=C-OO, 5.33 (s, 1 H), 6.03 (d, J=11 Hz, 1 H), 6.38 (d, J=11 Hz, 1 H).

(4) The (4-n) was treated in the same manner as in Example 4-5 (3) to obtain No. 4306b.

$^1$H-NMR (CDCl$_3$) δ: 0.59 (s, 3 H), 0.91 (d, J=7 Hz, 3 H), 2.52–1.23 (m, 22 H), 2.61 (d, J=13 Hz, 1 H), 2.85 (d, J=12 Hz, 1 H), 4.44 (m, 1 H), 4.24 (m, 1 H), 5.01 (s, 1 H), 5.20 (br., 1 H), 5.33 (s, 1 H), 6.03 (d, J=11 Hz, 1 H), 6.38 (d, J=11 Hz, 1 H).

Example 4-6

Production of Compounds No. 4203a, 4203b, 4203c and 4203d

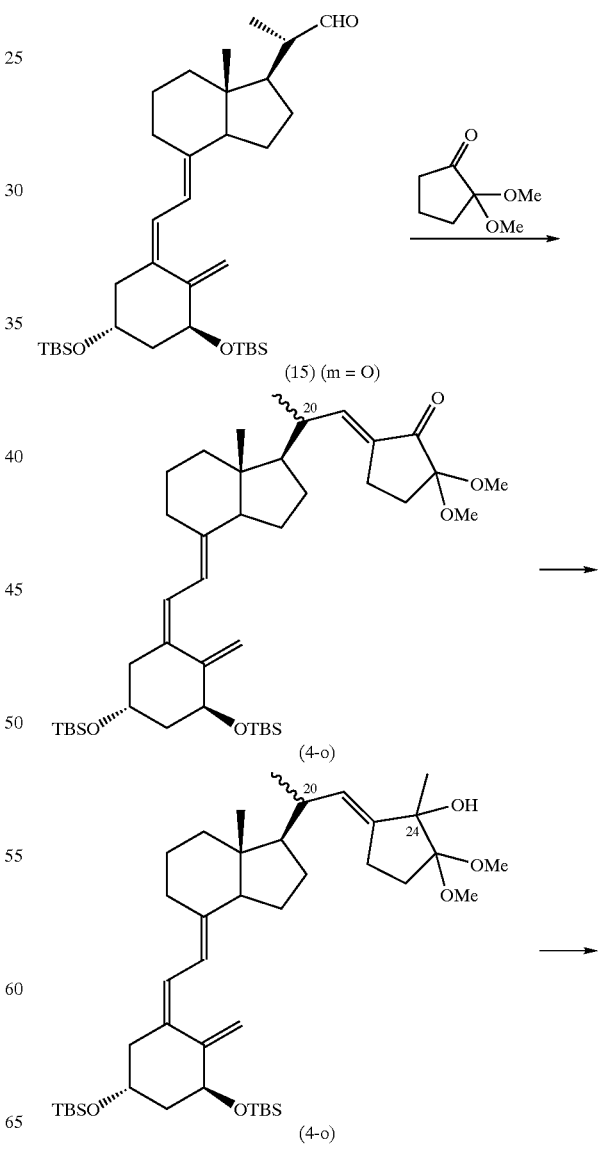

-continued

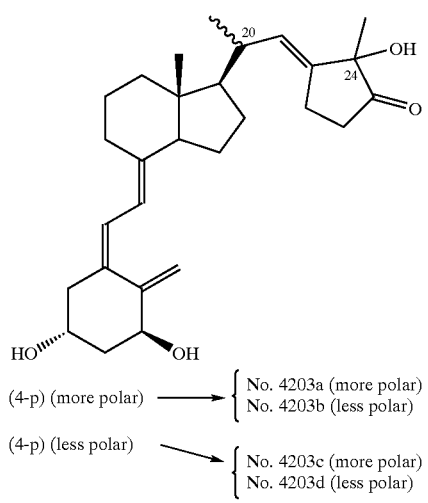

(4-p) (more polar) ⟶ { No. 4203a (more polar)
                       No. 4203b (less polar)

(4-p) (less polar) ⟶ { No. 4203c (more polar)
                       No. 4203d (less polar)

(1) The (15) (m=0) (646 mg, 1.13 mmol), which can be produced according to a known process (International Patent Publication WO90/09991; Tetrahedron, 20, 4609–4619 (1987)) and 2,2-dimethoxycyclopentan-1-one (140 mg, 1.03 mmol) were dissolved in ethanol (10 ml), sodium ethylate (272 mg, 4.0 mmol) was added to the solution, and the mixture was stirred for 15 hr at room temperature. The solvent was removed under reduced pressure, and the residue was purified by silica gel column chromatography (hexane:ethyl acetate=4:1) to obtain (4-o) (240 mg, 33% yield). The sample is a mixture of stereoisomers based on the asymmetric point of the 20-position.

(2) In a nitrogen atmosphere, the above-obtained (4-o) (47 mg, 0.067 mmol) was dissolved in dry THF (2 ml), and the solution was cooled to −78° C. A methyllithium solution (66 μl, 1.06M, 0.07 mmol) in diethyl ether was added dropwise, and the mixture was stirred for 30 min without raising the temperature. The reaction mixture was extracted with ethyl acetate after the addition of a saturated ammonium chloride aqueous solution. The combined organic layers were washed with brine, dried over anhydrous sodium sulfate and concentrated. The residue was purified by preparative TLC (hexane:ethyl acetate=9:1) to obtain (4-p) more polar compound and (4-p) less polar compound. The total was 40 mg (83% yield). These compounds are stereoisomers based on the asymmetric points at the 20-position and the 24-position. Each compound contains two kinds of stereoisomers.

(3) The above-obtained (4-p) more polar compound (18 mg, 0.025 mmol) was dissolved in a mixed solvent of methanol (1 ml) and dichloromethane (0.5 ml), a polymer-bound pyridinium p-toluenesulfonate (20 mg, 3.5 mmol/g-resin, 0.07 mmol) was added, and the mixture was stirred for 6 hr at room temperature. The polymer was removed by filtration, and the filtrate was evaporated under reduced pressure. The residue was purified by preparative TLC (hexane:ethyl acetate:methanol=4:5:1), and the obtained sample was further purified by HPLC fractionation (column, ODS; acetonitrile:water:methanol=60:40:3) to obtain a more polar compound (2.2 mg, No. 4203a, 20% yield) and a less polar compound (1.3 mg, No. 4203b, yield 12%). These compounds are stereoisomers based on the asymmetric point at the 20-position or the 24-position.

More Polar Compound, 4203a
$^1$H-NMR (CDCl$_3$,) δ: 0.48 (s, 3 H), 0.91 (d, J=7 Hz, 3 H), 1.2–2.8 (m, 23 H), 4.23 (m, 1 H), 4.44 (m, 1 H), 5.00 (s, 1 H), 5.33 (s, 1 H), 5.59 (d, J=10 Hz, 1 H), 6.02 (d, J=11 Hz, 1 H), 6.38 (d, J=11 Hz, 1 H).

Less Polar Compound, 4203b
$^1$H-NMR (CDCl$_3$) δ: 0.59 (s, 3 H), 1.01 (d, J=7 Hz, 3 H), 1.2–2.9 (m, 23 H), 4.23 (m, 1 H), 4.44 (m, 1 H), 5.00 (s, 1 H), 5.33 (s, 1 H), 5.52 (d, J=10 Hz, 1 H), 6.02 (d, J=11 Hz, 1 H), 6.38 (d, J=11 Hz, 1 H).

(4) The (4-p) less polar compound (52 mg) was treated in the same manner as in Example 4–6 (3) to obtain a more polar compound (4.1 mg, No. 4203c, 13% yield) and a less polar compound (3.0 mg, No. 4203d, yield 9.4%). These compounds are stereoisomers based on the asymmetric point at the 20-position or the 24-position.

More Polar Compound, 4203c
$^1$H-NMR (CDCl$_3$) δ: 0.41 (s, 3 H), 0.93 (d, J=7 Hz, 3 H), 1.2–2.8 (m, 23 H), 4.23 (m, 1 H), 4.42 (m, 1 H), 4.99 (s, 1 H), 5.32 (s, 1 H), 5.62 (d, J=10 Hz, 1 H), 6.00 (d, J=11 Hz, 1 H), 6.37 (d, J=11 Hz, 1 H).

Less Polar Compound, 4203d
$^1$H-NMR (CDCl$_3$) δ: 0.58 (s, 3 H), 1.02 (d, J=7 Hz, 3 H), 1.2–2.9 (m, 23 H), 4.23 (m, 1 H), 4.43 (m, 1 H), 4.99 (s, 1 H), 5.32 (s, 1 H), 5.53 (d, J=10 Hz, 1 H), 6.00 (d, J=11 Hz, 1 H), 6.38 (d, J=11 Hz, 1 H).

Example 5-1

Production of Compounds 5107 and 5109

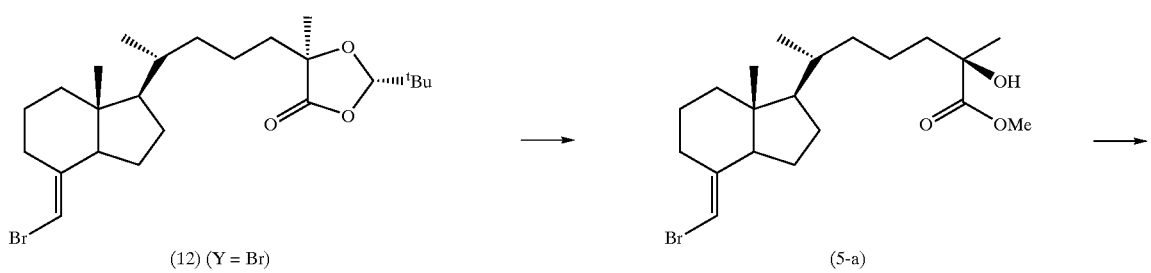

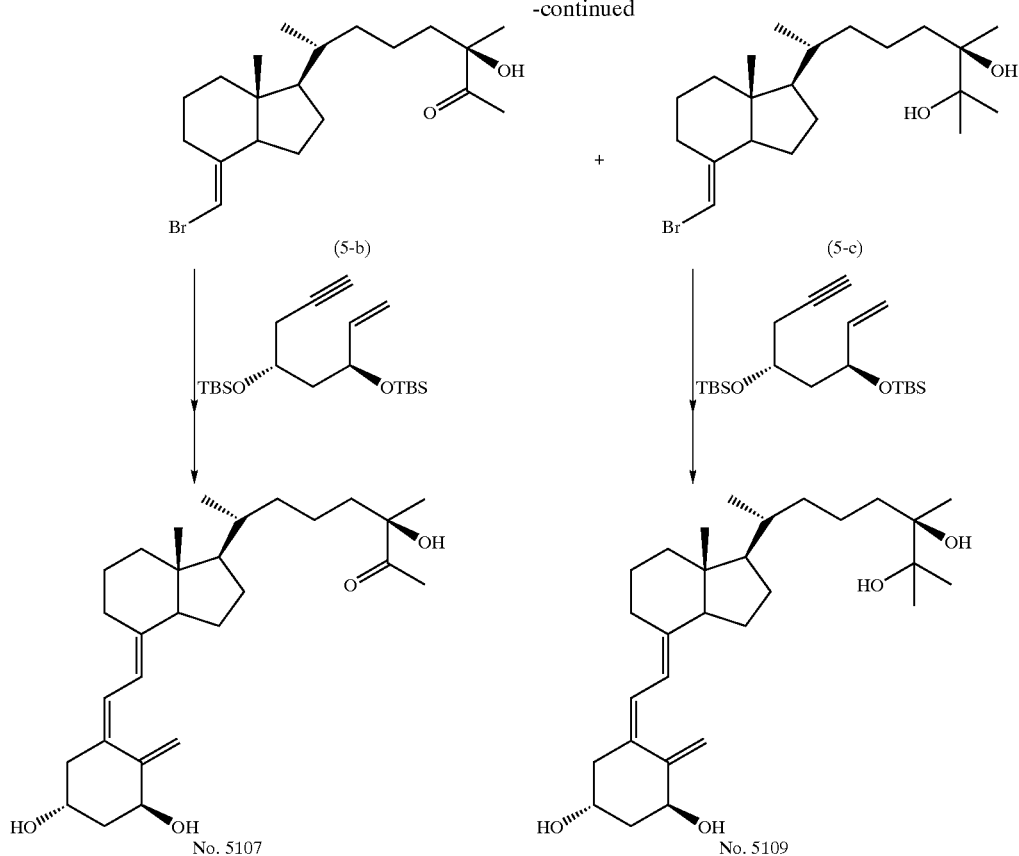

No. 5107        No. 5109

(1) The (12) (Y=Br) (49.5 mg, 0.067 mmol), which can produced according to a known process (for example, International Patent Publication WO95/33716), was dissolved in a mixed solvent of methanol (2 ml) and methylene chloride (1 ml), and the solution was cooled with ice. Sodium methoxide (39.1 mg, 28% methanol solution, 0.203 mmol) was added, and the mixture was stirred for 1 hr under cooling with ice, and further for 1 hr at room temperature. The reaction mixture was extracted with ethyl acetate after the addition of a saturated potassium hydrogensulfate aqueous solution. The combined organic layers were washed with a saturated potassium hydrogensulfate aqueous solution, with water and with brine, dried over anhydrous magnesium sulfate and evaporated under reduced pressure. The residue was purified by silica gel column chromatography (hexane:ethyl acetate=9:1) to obtain (5-a) (33 mg, 73% yield).

$^1$H NMR (CDCl$_3$) δ: 0.55 (s, 3 H), 0.90 (d, J=6.6 Hz, 3 H), 0.81–2.01 (m, 18 H), 1.40 (s, 3 H), 2.84–2.88 (m, 1 H), 3.79 (s, 3 H), 5.64 (s, 1 H).

(2) A lithium bis(trimethylsilyl)amide solution (0.51 ml, 1M, 0.51 mmol) in THF and a methylmagnesium chloride solution (0.087 ml, 3M, 0.26 mmol) in THF were mixed at −10° C., the mixture was added at −20° C. to a toluene solution (2 ml) of the above-obtained (5-a) (31 mg, 0.079 mmol) in toluene, and the mixture was stirred for 15 min without raising temperature and subsequently at 0° C. for 4 hr. The reaction mixture was extracted with ethyl acetate after the addition of a saturated ammonium chloride aqueous solution. The organic layers were washed with brine, dried over anhydrous magnesium sulfate and evaporated under reduced pressure. The residue was purified by silica gel column chromatography (hexane:ethyl acetate=5:1 to 1:1) to obtain (5-b) (20 mg, 65% yield) and (5-c) (8 mg, 25% yield).

(5-b)

$^1$H NMR (CDCl$_3$) δ: 0.55 (s, 3 H), 0.90 (d, J=6.6 Hz, 3 H), 1.00–2.01 (m, 18 H), 1.37 (s, 3 H), 2.21 (s, 3 H), 2.82–2.90 (m, 1 H), 5.64 (s, 1 H).

(5-c)

$^1$H NMR (CDCl$_3$) δ: 0.56 (s, 3 H), 0.95 (d, J=6.6 Hz, 3 H), 0.85–2.05 (m, 18 H), 1.17 (s, 3 H), 1.22 (s, 3 H), 1.23 (s, 3 H), 2.84–2.89 (m, 1 H), 5.64 (s, 1 H).

(3) In a nitrogen atmosphere, triphenylphosphine (26.5 mg, 0.10 mmol) and tris(dibenzylideneacetone)dipalladium (0)-chloroform adduct (10.6 mg, 10.2 μmol) were dissolved in dry toluene (0.5 ml), and the solution was stirred for 20 min at room temperature. A solution of the above-obtained (5-b) (39 mg, 0.10 mmol) and (3S),(5R)-3,5-bis(t-butyldimethylsilyloxy)-1-octen-7-yne (56 mg, 0.15 mmol) in a mixed solvent of diisopropylethylamine (1 ml) and toluene (1 ml) was added, and the mixture was stirred for 3 hr at 110–120° C. The reaction mixture was extracted with ethyl acetate after the addition of a saturated potassium hydrogensulfate. The combined organic layers were washed with a saturated sodium bicarbonate aqueous solution and with brine, dried and concentrated. The residue was purified by silica gel column chromatography (hexane:ethyl acetate= 8:1) to obtain a coupled body (34 mg, 50% yield). The coupled body was dissolved in a mixed solvent of acetonitrile (2 ml) and methylene chloride (1 ml), and lithium tetrafluoroborate (59 mg, 0.63 mmol) and subsequently a 1N sulfuric acid-acetonitrile solution (0.1 ml) were added under cooling with ice, and the mixture was stirred for 20 min in this state. The reaction mixture was extracted with ethyl acetate after the addition of a saturated sodium bicarbonate aqueous solution. The combined organic layers were washed with brine, dried and concentrated. The residue was purified by silica gel column chromatography (hexane:ethyl acetate=1:2) to obtain a fraction containing the objective. The fraction was further purified by HPLC fractionation (column, ODS; acetonitrile:water=60:40) to obtain No, 5107 (1.9 mg, 8.5% yield).

$^1$H NMR (CDCl$_3$) δ: 0.53 (s, 3 H), 0.90 (d, J=6.3 Hz, 3 H), 0.81–2.02 (m, 20 H), 1.37 (s, 3 H), 2.22 (s, 3 H), 2.28–2.35 (m, 1 H), 2.57–2.63 (m, 1 H), 2.79–2.85 (m, 1 H), 4.23 (br., 1 H), 4.43 (br., 1 H), 5.00 (s, 1 H), 5.33 (s, 1 H), 6.01 (d, J=11.5 Hz, 1 H), 6.38 (d, J=11.5 Hz, 1 H).

(4) The above-obtained (5-c) (9.5 mg) was treated in the same manner as in Example 5-1 (3) to obtain No. 5109 (1.8 mg, 28% yield).

$^1$H NMR (CDCl$_3$) δ: 0.54 (s, 3 H), 0.95 (d, J=5.9 Hz, 3 H), 0.85–2.05 (m, 20 H), 1.17 (s, 3 H), 1.22 (s, 3 H), 1.23 (s, 3 H), 2.28–2.35 (m, 1 H), 2.58–2.63 (m, 1 H), 2.80–2.85 (m, 1 H), 4.23 (br., 1 H), 4.43 (br., 1 H), 5.01 (s, 1 H), 5.33 (s, 1 H), 6.02 (d, J=10.9 Hz, 1 H), 6.38 (d, J=11.6 Hz, 1 H).

Example 5-2

Production of Compound No. 5102

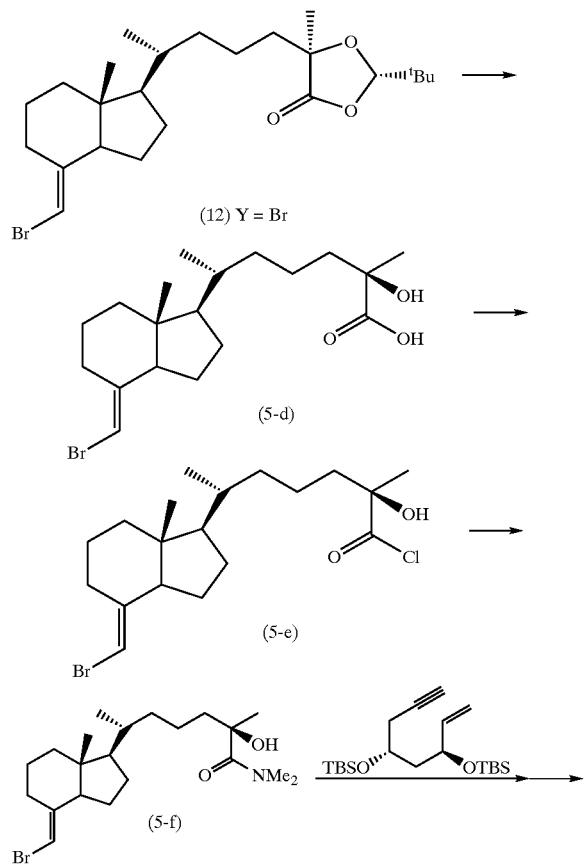

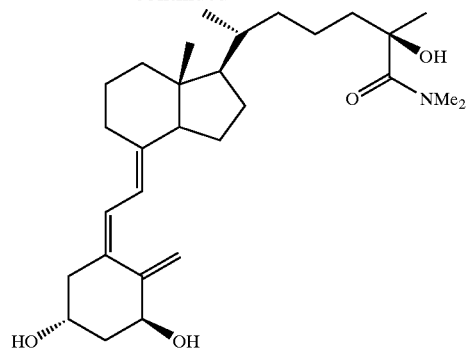

No. 5102

(1) The (12) (Y=Br) (75 mg), which can be obtained according to a known method (for example, International Patent Publication WO95/33716) was dissolved in a mixed solvent of 1,2-dimethoxyethane (6 ml) and water (2 ml), a 4N lithium hydroxide aqueous solution (2 ml) was added, and the mixture was stirred for 2 hr at room temperature. The reaction mixture was extracted with ethyl acetate after the addition of 1N hydrochloric acid (10 ml). The combined organic layers were concentrated to obtain a crude product of (5-d). This was used in the next reaction without applying any treatment.

(2) In a nitrogen atmosphere, the above-obtained crude product of (5-d) was dissolved in dry dichloromethane (10 ml), and oxalyl chloride (0.043 ml) and dimethylformamide (0.013 ml) were added, and the mixture was stirred for 1 hr at room temperature. The reaction mixture was concentrated to obtain a crude product of (5-e). The product was used in the next reaction without applying any treatment.

(3) The above-obtained (5-e) was dissolved in dry dichloromethane (6 ml), and dimethylamine hydrochloric acid salt (41 mg), and further triethylamine (0.23 ml) were added, and the mixture was stirred for 1 hr at room temperature. The reaction mixture was extracted with ethyl acetate after the addition of a saturated ammonium chloride aqueous solution (10 ml). The combined organic layers were dried and concentrated. The residue was purified by silica gel column chromatography (hexane:ethyl acetate=1:1) to obtain (5-f) (50 mg, 73%).

$^1$H NMR (CDCl$_3$) δ: 0.55 (s, 3 H), 0.90 (d, J=6.2 Hz, 3 H), 1.00–2.50 (m, 19 H), 1.47 (s, 3 H), 3.09 (s, 6 H), 4.88 (br., 1 H), 5.64 (s, 1 H).

(4) The (5-f) (50 mg) was treated in the same manner as in Example 5-1 (3) to obtain No. 5102 (20 mg, yield 35%).

$^1$H NMR (CDCl$_3$) δ: 0.53 (s, 3 H), 0.90 (d, J=5.9 Hz, 3 H), 1.00–2.50 (m, 23 H), 1.50 (s, 3 H), 3.09 (s, 6 H), 4.25–4.35 (m, 1 H), 4.35–4.45 (m, 1 H), 4.87 (s, 1 H), 5.00 (sept, J=6.3 Hz, 1 H), 5.23 (s, 1 H), 6.01 (d, J=11.5 Hz, 1 H), 6.37 (d, J=11.5 Hz, 1 H).

Example 5-3

Production of Compound No. 5106

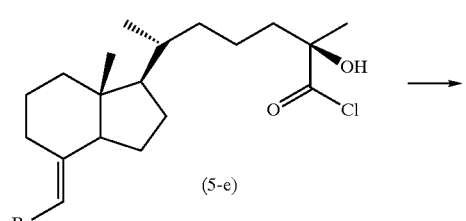

(5-e)

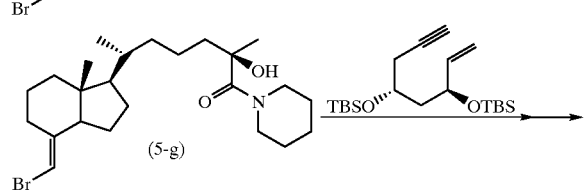

(5-g)

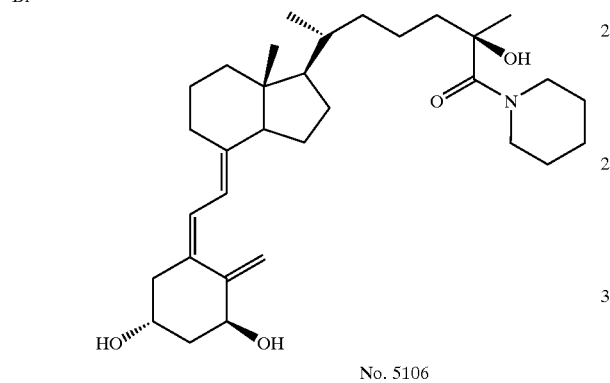

No. 5106

(1) Employing substantially the same process as in Example 5-2 (3), but reacting piperidine in place of dimethylamine hydrochloric acid salt, the (5-e) was converted to (5-g) (55 mg, 55% yield).

$^1$H NMR (CDCl$_3$) δ: 0.55 (s, 3 H), 0.91 (d, J=6.3 Hz, 3 H), 0.80–2.10 (m, 28 H), 2.75–2.90 (m, 1 H), 3.58 (br., 4 H), 5.00 (s, 1 H), 5.63 (s, 1 H).

(2) The above-obtained (5-g) (55 mg) was treated in the same manner as in Example 5-1 (3) to obtain No. 5106 (10 mg, 16% yield).

$^1$H NMR (CDCl$_3$) δ: 0.53 (s, 3 H), 0.90 (d, J=6.3 Hz, 3 H), 0.80–2.10 (m, 29 H), 2.20–2.35 (m, 1 H), 2.50–2.65 (m, 1 H), 2.75–2.85 (m, 1 H), 3.58 (br., 4 H), 4.15–4.25 (br., 1 H), 4.35–4.45 (br., 1 H), 5.00 (s, 1 H), 5.03 (s, 1 H), 5.32 (s, 1 H), 6.38 (d, J=11.2 Hz, 1 H).

Example 5-4

Production of Compound No. 5103

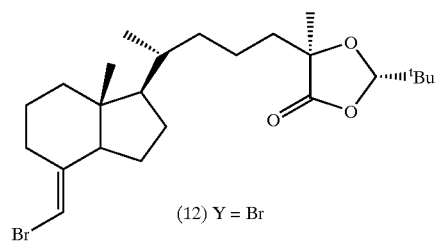

(12) Y = Br

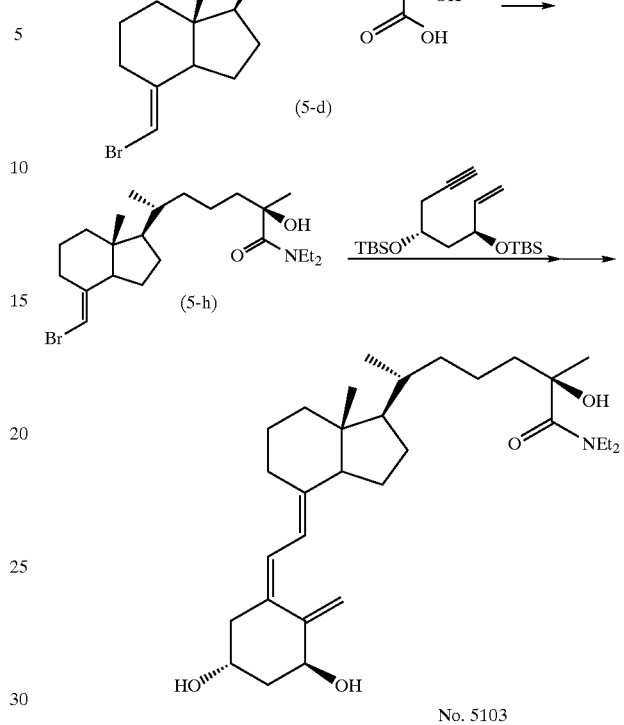

No. 5103

(1) The (12) (Y=Br) (23 mg) was treated in the same manner as in Example 5-2 (1) to produce (5-d). The product was dissolved in THF (3 ml), and diethylamine (0.015 ml) and diisopropylethylamine (0.051 ml) were added, and the mixture was stirred for 15. min at room temperature. Further, diethyl cyanophosphate (0.023 ml) was added, and the mixture was stirred overnight at room temperature. The reaction mixture was extracted with ethyl acetate after the addition of a saturated ammonium chloride aqueous solution. The combined organic layers were dried and concentrated. The residue was purified by silica gel column chromatography (hexane:ethyl acetate=1:1) to obtain (5-h) (12 mg, 65% yield).

$^1$H NMR (CDCl$_3$) δ: 0.55 (s, 3 H), 0.90 (d, J=6.3 Hz, 3 H), 1.00–3.80 (m, 19 H), 1.33 (t, J=6.9 Hz, 6 H), 1.74 (s, 3 H), 4.00–4.20 (m, 4 H), 5.63 (s, 1 H).

(2) The above-obtained (5-h) (12 mg) was treated in the same manner as in Example 5-1 (3) to obtain No. 5103 (3.7 mg, 27% yield).

$^1$H NMR (CDCl$_3$) δ: 0.52 (s, 3 H), 0.88 (d, J=5.1 Hz, 3 H), 1.00–3.80 (m, 23 H), 1.33 (t, J=5.4 Hz, 6 H), 1.74 (s, 3 H), 4.05–4.18 (m, 4 H), 4.20–4.30 (br., 1 H), 4.40–4.50 (br., 1 H), 5.00 (s, 1 H), 5.32 (s, 1 H), 6.00 (d, J=11.0 Hz, 1 H), 6.37 (d, J=11.0 Hz, 1 H).

Example 6-1

Neutrophilic Infiltration Suppressing Effect Assayed by Using Hamster LPS-induced Pneumonia Model A male golden hamster was placed in an inhalation chamber (volume: 12 liter) and allowed to inhale LPS (nebulizer filled concentration: 2.0 mg/ml) generated by an ultrasonic nebulizer for 30 min to cause pneumonia. Just after the inhalation of the LPS, a treating agent of the present invention was administered infratracheally at a dosage of 1 to 20 μg/kg under halothane anesthesia. After 24 hr, tracheal branches and pulmonary alveoli were washed, and the number of neutrophils in the washing was determined. Using the number of neutrophils obtained in the absence of the treating agent of the present invention as the control, the decreasing rates of the numbers of neutrophils were expressed in terms of percent suppression based on the control. The results are shown in Table 6-1.

TABLE 6-1

Neutrophilic infiltration suppressing effect assayed by using hamster LPS-induced pneumonia model

| % Suppression | Compound No. (dose: μg/kg) |
|---|---|
| >40% | 1101a (20), 1101b (20), 1125 (4), 2102a (4), 2105a (4), 3105d (4), 3405 (4), 5102 (20), 5107 (20) |
| 20–40% | 1113 (20), 1207b (4), 4101a (4), 4102b (1), 4203b (4), 5106 (20), 5109 (20) |
| <20% | 1107b (4), 4301 (20) |

This model is widely used as an inflammatory pulmonary disease model (Esbenshade, et al., J. Appl. Physiol., 53, 967–976 (1982)), and it has been reported that the model exhibits a morbid state of acute aggravation of an inflammatory pulmonary disease (Hurlar, et al., J. Appl. Physiol., 54, 1463–1468 (1983)).

From the results of the present examples, it was found that treating agents of the present invention have neutrophilic infiltration suppressing effect in the model. These results have demonstrated that treating agents of the present invention are effective for treating inflammatory respiratory diseases.

Example 6-2
Vitamin $D_3$ Antagonistic Effect Expressed by the Parameter of Differentiation Induction Effect on HL-60 Cell Caused by 1α,25-dihydroxyvitamin $D_3$ (1) HL-60 cell line which had been purchase (Japanese Cancer Research Resource Bank, Cell No: JCRB0085) was used. The cell line was stored as a frozen storage stock to prevent the change of cell characteristics attributable to successive cultivations. Prior to the initiation of experiments, the cells were defrosted and successive culturing was stared, and such cells were used. For the experiments, cells whose successive culturing was from one month to about a half year were used. The successive culturing was carried out by centrifugally collecting cells which were in the state of suspension culture, and diluting the collected cell concentrate with a fresh culture medium at a ratio of about 1/100 (1–2×10⁴ cells/ml). As the culture medium, an RPMI-1640 medium containing 10% fetal bovine serum was used.

(2) The cells which were being in the successive culturing in the above process (1) were centrifugally collected, and they were dispersed in a culture medium at the cell concentration of 2×10⁴ cells/ml. The dispersion was seeded into a 24-well culture schale at 1 ml/well. In this system, 1α,25-dihydroxyvitamin $D_3$, and compounds of the present invention, No. 4102a, No. 4107a and No. 4102b were each separately treated, and also the combinations of 1α,25-dihydroxyvitamin $D_3$ and one of the compounds of the present invention, No. 4102a, No. 4107a and No. 4102b were subjected to simultaneous treatments. 1α,25-dihydroxyvitamin $D_3$, and compounds, No. 4102a, No. 4107a and No. 4102b were each dissolved in ethanol to prepare ethanol solutions having a concentration of $1\times10^{-6}$M to $1\times10^{-3}$M, and the solutions were each added at 1 μl/well. For the control, ethanol was added at 1 μl/well. After culturing at 37° C. for 4 days in the presence of 5% $CO_2$, the cells were centrifugally collected.

(3) As the parameter of differentiation induction effect on HL-60 cells, the induction of nitroblue tetrazonium (henceforth, NBT) reduction activity was used. The measurement of the NBT reduction activity was carried out according to the following procedure. That is, centrifugally collected cells were suspended in a fresh culture medium, and NBT and 12-O-tetradecanoylphorbol-13-acetate were added so that their concentrations became 0.1% and 100 nM, respectively. After the mixed suspension was incubated at 37° C. for 25 min, a cytospin sample was prepared. After air drying, it was stained with Kernechtrot, and the ratio of the positive cells of NBT reduction activity was determined under an optical microscope.

(4) The NBT reduction activities of the cells singly treated by the compounds of the present invention, No. 4102a, No. 4107a and No. 4102b are shown in Table 6-2. In the cells which were singly treated with each of these compounds of the present invention, the induction of NBT reduction activity was not recognized at all.

TABLE 6-2

Effect on NBT reduction activity in HL-60 cells (singly by a compound of the present invention)

| Compound No. | Concentration (M) | % of Positive cell of NBT Reduction Activity (N = 3) Average ± SD |
|---|---|---|
| control |  | 1.17 ± 0.35 |
| 4102a | $10^{-9}$ | 1.00 ± 0.10 |
|  | $10^{-8}$ | 0.57 ± 0.15 |
|  | $10^{-7}$ | 0.63 ± 0.15 |
|  | $10^{-6}$ | 1.03 ± 0.15 |
| 4107a | $10^{-9}$ | 0.87 ± 0.31 |
|  | $10^{-8}$ | 0.87 ± 0.15 |
|  | $10^{-7}$ | 0.67 ± 0.12 |
|  | $10^{-6}$ | 0.37 ± 0.06 |
| 4102b | $10^{-9}$ | 0.80 ± 0.10 |
|  | $10^{-8}$ | 0.80 ± 0.20 |
|  | $10^{-7}$ | 1.05 ± 0.34 |
|  | $10^{-6}$ | 0.50 ± 0.17 |

(5) The NBT reduction activities of the cells treated simultaneously by 1α, 25-dihydroxyvitamin $D_3$ and each of the compounds of the present invention, No. 4102a, No. 4107a and No. 4102b are shown in Table 6-3. It was recognized that the NBT reduction activity induced by 1α, 25-dihydroxyvitamin $D_3$ ($10^{-8}$M) was suppressed dose dependently by a compound of the present invention which was simultaneously added.

TABLE 6-3

Effect on NBT reduction activity in HL-60 cells (simultaneous addition of 1 α, 25-dihydroxyvitamin $D_3$ and a compound of the present invention)

| Compound No. | Concentration (M) | % of Positive cell of NBT Reduction Activity (N = 3) Average ± SD |
|---|---|---|
| control (no additive) |  | 1.17 ± 0.35 |
| control(1 α, 25-(OH)$_2$VD$_3$ only) | $10^{-8}$ | 61.93 ± 3.25 |
| 1 α, 25-(OH)$_2$VD$_3$ ($10^{-8}$M) + No. 4102a | $10^{-9}$ | 61.13 ± 1.26 |
|  | $10^{-8}$ | 46.27 ± 2.37 |
|  | $10^{-7}$ | 10.80 ± 0.26 |
|  | $10^{-6}$ | 9.60 ± 1.65 |
| 1 α, 25-(OH)$_2$VD$_3$ ($10^{-8}$M) + No. 4107a | $10^{-9}$ | 62.63 ± 1.04 |
|  | $10^{-8}$ | 58.67 ± 1.20 |
|  | $10^{-7}$ | 52.53 ± 1.11 |

TABLE 6-3-continued

Effect on NBT reduction activity in HL-60 cells (simultaneous addition of 1 α, 25-dihydroxyvitamin $D_3$ and a compound of the present invention)

| Compound No. | Concentration (M) | % of Positive cell of NBT Reduction Activity (N = 3) Average ± SD |
|---|---|---|
| 1 α, 25-$(OH)_2VD_3$ ($10^{-8}$M) + No. 4102b | $10^{-6}$ | 10.73 ± 1.40 |
| | $10^{-9}$ | 58.83 ± 0.80 |
| | $10^{-8}$ | 41.30 ± 1.32 |
| | $10^{-7}$ | 12.53 ± 1.17 |

As shown in the examples, the compounds of the present invention did not exhibit differentiation induction effect on HL-60 cells by single treatment, but they suppressed the differentiation induction effect induced by 1α,25-dihydroxyvitamin $D_3$. That is, it was shown that compounds of the present invention acted as antagonists to 1α,25-dihydroxyvitamin $D_3$. From the above findings it is found that compounds of the present invention are effective as treating agents for diseases attributable to the overactivity of vitamin $D_3$.

Example 7-1
Production of Tablets
Tablets, which were composed of the following components, were produced.

| | |
|---|---|
| Compound No. 1207b | 5 μg |
| Lactose | 230 mg |
| Potato starch | 80 mg |
| Polyvinylpyrrolidone | 11 mg |
| Magnesium stearate | 5 mg |

The compound (Compound No. 1207b) of the present invention, lactose and potato starch were mixed. The mixture was homogeneously wetted with 20% solution of polyvinylpyrrolidone in ethanol, passed through a 20-mesh sieve, dried at 45° C. and passed again through a 15-mesh sieve. To thus obtained granules was added magnesium stearate, and the mixture was compressed to tablets.

Industrial Field of Application

Medicines containing a vitamin $D_3$ derivative of the present invention expressed by the above formula (1) or (3) as an active ingredient can be used for treating inflammatory respiratory diseases.

Further, medicines containing a vitamin $D_3$ derivative of the present invention expressed by the above formula (1) which is a compound having antagonistic effect to vitamin $D_3$ as an active ingredient can be used for treating diseases attributable to overactivity of vitamin $D_3$.

On the other hand, the blood calcium level-elevation effects of vitamin $D_3$ derivatives of the present invention are extremely reduced compared with that of 1α,25-dihydroxyvitamin $D_3$.

Furthermore, vitamin $D_3$ derivatives of the present invention expressed by the above formula (1) have immunosuppressive effects such as the stimulation of maturation and differentiation of a cell, and the inhibition of interleukin 2 production, and the derivatives further have effects for stimulating the production of microbicidal oxygen metabolite and the chemotactic reaction of a leukocyte as immunological synergistic effect. Medicines containing vitamin $D_3$ derivatives of the present invention expressed by the above formula (1) as active ingredients can therefore be the following: treating agents for malignant tumors, psoriasis, rheumatoid arthritis, inflammatory diseases such as dermatitis, and autoimmune diseases; supplementary agents in chemotherapy for infections; and treating agents in other therapeutic phases to which mononuclear phagocytes are associated.

Besides these, medicines containing vitamin $D_3$ derivatives of the present invention expressed by the above formula (1) as active ingredients can be used for treating hypertension, for treating diabetes mellitus, for stimulating hair growth, and for treating acne and osteoporosis.

What is claimed is:

1. A method for treating an inflammatory respiratory disease comprising administering to a subject a therapeutically effective amount of a vitamin $D_3$ compound expressed by the following general formula (1) or pharmaceutically permissible solvates thereof,

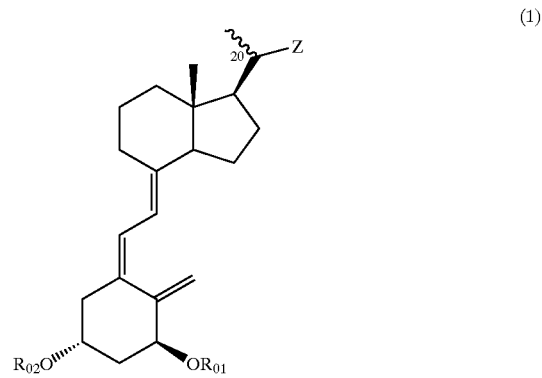

(1)

wherein, $R_{01}$ and $R_{02}$ are each independently a hydrogen atom, a trimethylsilyl group, a triethylsilyl group, a t-butyldimethylsilyl group, an acetyl group, a methoxymethyl group or a tetrahydro-4H-pyran-2-yl group;

Z is one out of the following formulae (1-1), (1-2), (1-3), (1-4) or (1-5),

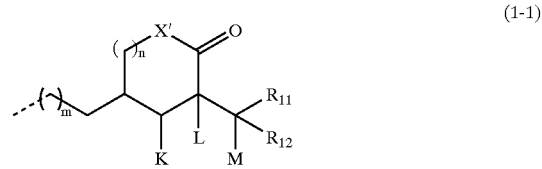

(1-1)

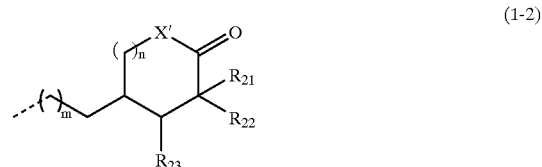

(1-2)

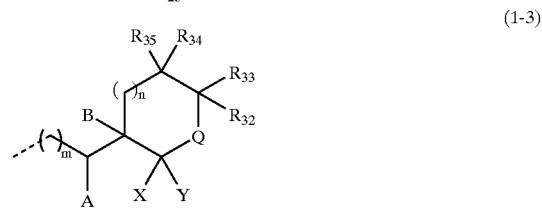

(1-3)

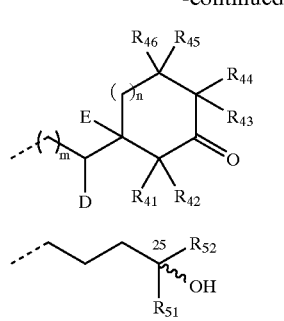

(1-4)

(1-5)

in the above formulae (1-1) to (1-5), m is an integer of 0 to 2;

n is an integer of 0 to 2;

X' is an oxygen atom or NH;

$R_{11}$ and $R_{12}$ are identical to or different from each other, and express a hydrogen atom or a $C_1$–$C_4$ alkyl group;

K, L and M are each a hydrogen atom; M is a hydrogen atom, and K and L together express a single bond and express a double bond in cooperation with the single bond already shown in the formula; or K is a hydrogen atom, and L and M together express a single bond and express a double bond in cooperation with the single bond already shown in the formula;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or $R_{21}$ and $R_{22}$ together may express a $C_3$–$C_6$ cyclic alkyl group in cooperation with the carbon atom to which they are bonded;

Q expresses >C(—F—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which maybe substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and F express each a hydrogen atom, D is a hydroxy group and E expresses a hydrogen atom, D and E together express a single bond and express a double bond in cooperation with the single bond already shown in the formula, or E and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

$R_{51}$ expresses —$CONR_{511}R_{512}$, —$C(OH)R_{513}$ or —$C(OH)R_{514}R_{515}$, wherein $R_{511}$ and $R_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{44}$, and $R_{45}$ and $R_{46}$ are both hydroxy groups, both alkyloxy groups, or a hydroxy group and an alkyloxy group, (b) a compound expressed by the above formula (1) in which Z is the following formula (1-6),

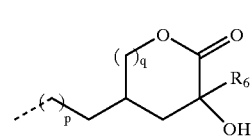

(1-6)

wherein, p and q are each 0 or the integer 1; $R_6$ is a hydrogen atom or a $C_1$–$C_4$ alkyl group, and

151

(c) a compound of the following formula (2),

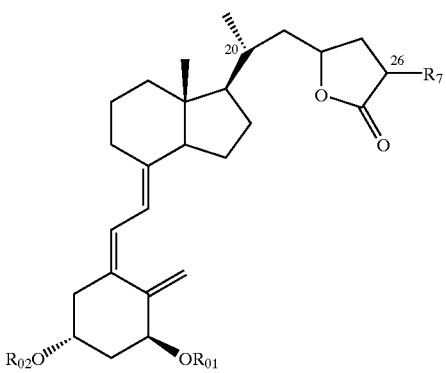

(2)

wherein, $R_{01}$ and $R_{02}$ are defined in the same manner as in the above formula (1); the configuration of the carbon atom at the 20-position is (R)-configuration; $R_7$ is a methyl group or a methylene group; when $R_7$ is a methylene group, the bond between $R_7$ and the carbon atom at the 26-position is double bond.

2. The method according to claim 1, wherein the inflammatory respiratory disease is one or not less than two kinds of inflammatory respiratory diseases selected from a group consisting of acute upper airway infection, chronic sinusitis, allergic rhinitis, chronic lower airway infection, pulmonary emphysema, pneumonia, bronchial asthma, tuberculosis sequela, acute respiratory distress syndrome, cystic fibrosis and pulmonary fibrosis.

3. The method according to claim 2, wherein the acute upper airway infection is one or not less than two kinds of diseases selected from a group consisting of common cold, acute pharyngitis, acute rhinitis, acute sinusitis, acute tonsillitis, acute pharyngitis, acute epiglottitis and acute bronchitis.

4. The method according to claim 2, wherein the chronic lower airway infection is one or not less than two kinds of diseases selected from a group consisting of chronic bronchitis, diffuse panbronchiolitis and bronchiectasis.

5. A method for treating one or not less than two kinds of inflammatory respiratory diseases selected from a group consisting of chronic bronchitis, diffuse panbronchiolitis, bronchiectasis, bronchial asthma, pulmonary emphysema, tuberculosis sequela and cystic fibrosis comprising administering to a subject a therapeutically effective amount of a vitamin $D_3$ compound expressed by the following formula (1) or pharmaceutically permissible solvate thereof:

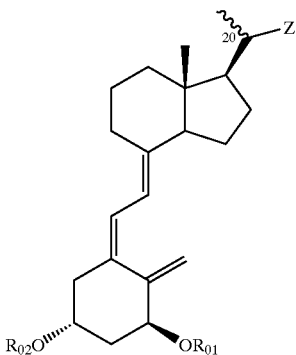

(1)

wherein, $R_{01}$ and $R_{02}$ are each independently a hydrogen atom, a trimethylsilyl group, a triethylsilyl group, a

152 t-butyldimethylsilyl group, an acetyl group, a methoxymethyl group or a tetrahydro-4H-pyran-2-yl group;

Z is one out of the following formulae (1-1), (1-2), (1-3), (1-4) or (1-5),

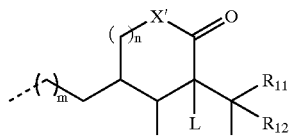

(1-1)

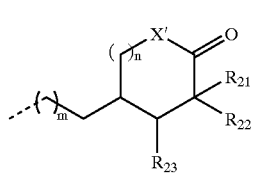

(1-2)

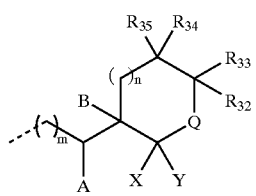

(1-3)

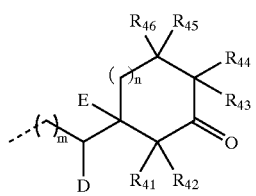

(1-4)

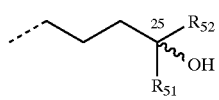

(1-5)

in the above formulae (1-1) to (1-5), m is an integer of 0 to 2;

n is an integer of 0 to 2;

X' is an oxygen atom or NH;

$R_{11}$ and $R_{12}$ are identical to or different from each other, and express a hydrogen atom or a $C_1$–$C_4$ alkyl group;

K, L and M are each a hydrogen atom; M is a hydrogen atom, and K and L together express a single bond and express a double bond in cooperation with the single bond already shown in the formula; or K is a hydrogen atom, and L and M together express a single bond and express a double bond in cooperation with the single bond already shown in the formula;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a alkyloxy group, or $R_{21}$ and $R_{22}$ together may express a $C_3$–$C_6$ cyclic alkyl group in cooperation with the carbon atom to which they are bonded;

Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and E express each a hydrogen atom, D is a hydroxy group and E expresses a hydrogen atom, D and E together express a single bond and express a double bond in cooperation with the single bond already shown in the formula, or E and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

$R_{51}$ expresses —$CONR_{511}R_{512}$, —$COR_{513}$ or —$C(OH)R_{514}R_{515}$, wherein $R_{511}$ and $R_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{44}$ and $R_{45}$ and $R_{46}$ are both hydroxy groups, both alkyloxy groups, or a hydroxy group and an alkyloxy group, (b) a compound expressed by the above formula (1) in which Z is the following formula (1-6),

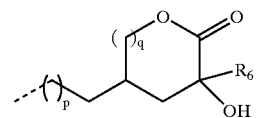

(1-6)

wherein, p and q are each 0 or the integer 1; $R_6$ is a hydrogen atom or a $C_1$–$C_4$ alkyl group, and (c) a compound of the following formula (2),

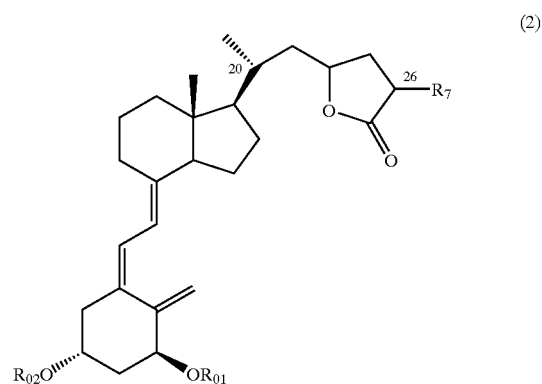

(2)

wherein, $R_{01}$, and $R_{02}$ are defined in the same manner as in the above formula (1); the configuration of the carbon atom at the 20-position is (R)-configuration; $R_7$ is a methyl group or a methylene group; when $R_7$ is a methylene group, the bond between $R_7$ and the carbon atom at the 26-position is double bond.

6. A method for treating a disease selected from a group consisting of malignant tumors, rheumatoid arthritis, osteoporosis, diabetes mellitus, hypertension, alopecia, acne, psoriasis and dermatitis comprising administering to a subject a therapeutically effective amount of a vitamin $D_3$ compound expressed by the following formula (1) or pharmaceutically permissible solvate thereof:

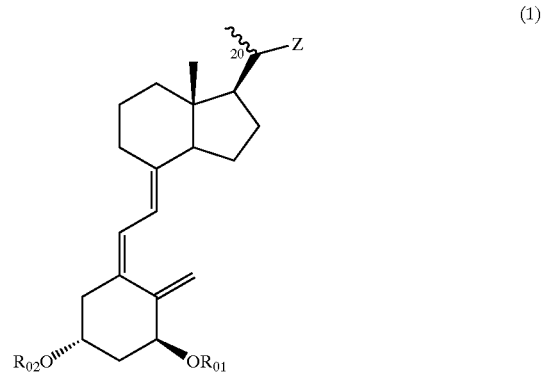

(1)

wherein, $R_{01}$ and $R_{02}$ are each independently a hydrogen atom, a trimethylsilyl group, a tnethylsilyl group, a t-butyldimethylsilyl group, an acetyl group, a methoxymethyl group or a tetrahydro-4H-pyran-2-yl group;

Z is one out of the following formulae (1-1), (1-2), (1-3), (1-4) or (1-5),

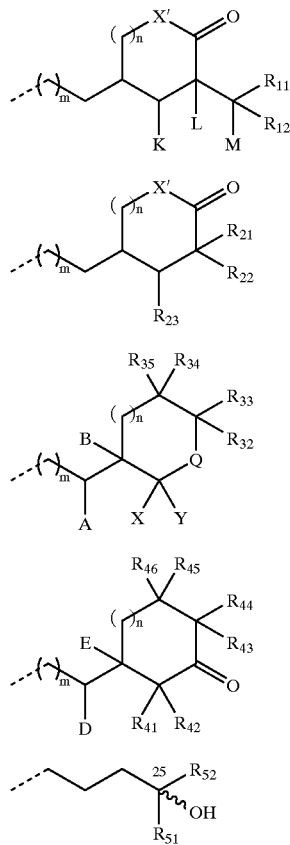

in the above formulae (1-1) to (1-5), m is an integer of 0 to 2;

n is an integer of 0 to 2;

X' is an oxygen atom or NH;

$R_{11}$ and $R_{12}$ are identical to or different from each other, and express a hydrogen atom or a $C_1$–$C_4$ alkyl group;

K, L and M are each a hydrogen atom; M is a hydrogen atom, and K and L together express a single bond and express a double bond in cooperation with the single bond already shown in the formula; or K is a hydrogen atom, and L and M together express a single bond and express a double bond in cooperation with the single bond already shown in the formula;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or $R_{21}$ and $R_{22}$ together may express a $C_3$–$C_6$ cyclic alkyl group in cooperation with the carbon atom to which they are bonded;

Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and E express each a hydrogen atom, D is a hydroxy group and E expresses a hydrogen atom, D and E together express a single bond and express a double bond in cooperation with the single bond already shown in the formula, or E and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

$R_{51}$ expresses —CONR$_{511}$R$_{512}$, —COR$_{513}$ or —C(OH)R$_{514}$R$_{515}$, wherein $R_{511}$ and $R_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{45}$, and $R_{45}$ and $R_{46}$ are both hydroxy groups, both alkyloxy groups, or a hydroxy group and an alkyloxy group, (b) a compound expressed by the above formula (1) in which Z is the following formula (1-6),

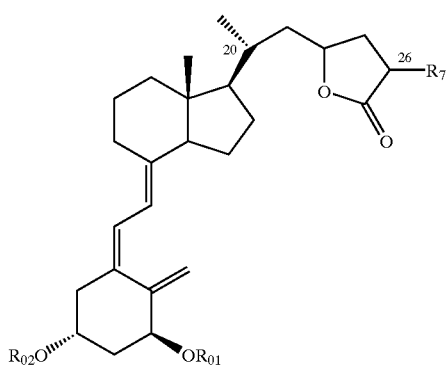

(1-6)

wherein, p and q are each 0 or the integer 1; $R_6$ is a hydrogen atom or a $C_1$–$C_4$ alkyl group, and (c) a compound of the following formula (2),

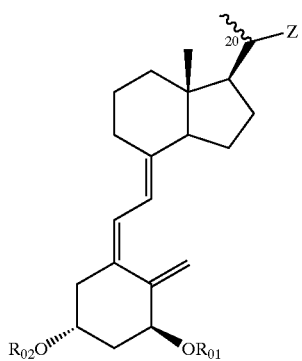

(2)

wherein, $R_0$, and $R_{02}$ are defined in the same manner as in the above formuLa (1); the configuration of the carbon atom at the 20-position is (R)-configuration; $R_7$ is a methyl group or a methylene group; when $R_7$ is a methylene group, the bond between $R_7$ and the carbon atom at the 26-position is double bond.

7. A method for treating hypercalcemia attributable to vitamin D excess comprising administering to a subject a therapeutically effective amount of a vitamin $D_3$ compound of the following Formula (1) or pharmaceutically permissible solvate thereof,

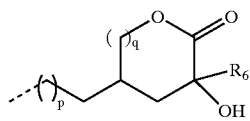

(1)

wherein, $R_{01}$ and $R_{02}$ are each independently a hydrogen atom, a trimethylsilyl group, a triethylsilyl group, a t-butyldimethylsilyl group, an acetyl group, a methoxymethyl group or a tetrahydro-4H-pyran-2-yl group;

Z is one out of the following formulae (1-2), (1-3), (1-4) or (1-5),

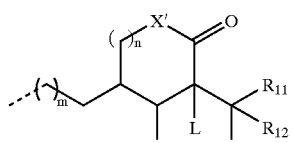

(1-1)

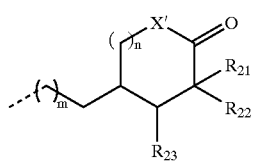

(1-2)

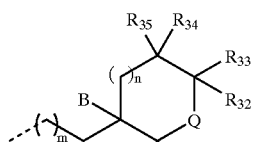

(1-3)

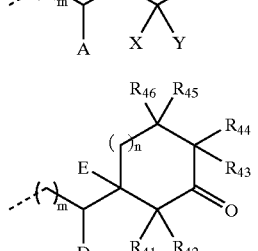

(1-4)

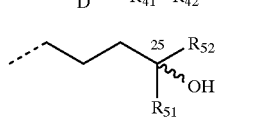

(1-5)

in the above formulae (1-2) to (1-5), m is an integer of 0 to 2;

n is an integer of 0 to 2;

X' is an oxygen atom or NH;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or $R_{21}$ and $R_{22}$ together may express a $C_3$–$C_6$ cyclic alkyl group in cooperation with the carbon atom to which they are bonded;

Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and E express each a hydrogen atom, D is a hydroxy group and E expresses a hydrogen atom, D and E together express a single bond and express a double bond in cooperation with the single bond already shown in the formula, or E and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

$R_{51}$ expresses —$CONR_{511}R_{512}$, —$COR_{513}$ or —$C(OH)R_{514}R_{515}$, wherein $R_{511}$ and $R_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{44}$, and $R_{45}$ and $R_{46}$ are both hydroxy groups, both alkyloxy groups, or a hydroxy group and an alkyloxy group, (b) a compound expressed by the above formula (1) in which Z is the following formula (1-6),

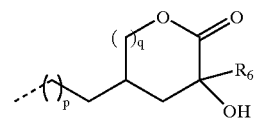

(1-6)

wherein, p and q are each 0 or the integer 1; $R_6$ is a hydrogen atom or a $C_1$–$C_4$ alkyl group, and (c) a compound of the following formula (2),

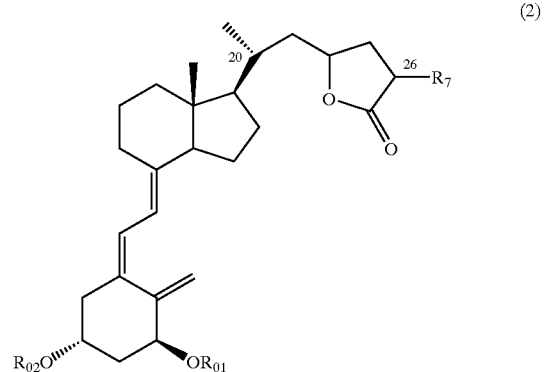

(2)

wherein, $R_{01}$ and $R_{02}$ are defined in the same manner as in the above formula (1); the configuration of the carbon atom at the 20-position is (R)-configuration; $R_7$ is a methyl group or a methylene group; when $R_7$ is a methylene group, the bond between $R_7$ and the carbon atom at the 26-position is double bond.

8. A method for treating hypoparathyroidism comprising administering to a subject a therapeutically effective amount of a vitamin $D_3$ compound of the following Formula (1) or pharmaceutically permissible solvate thereof,

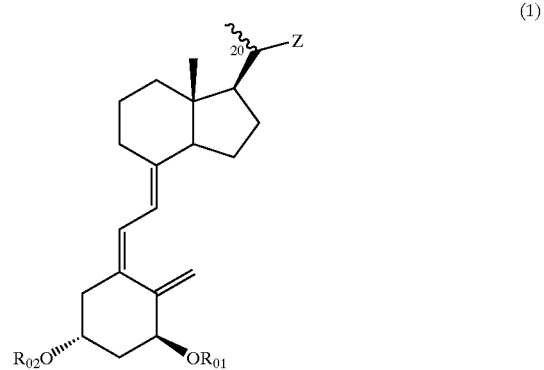

(1)

wherein, $R_{01}$ and $R_{02}$ are each independently a hydrogen atom, a trimethylsilyl group, a triethylsilyl group, a t-butyldimethylsilyl group, an acetyl group, a methoxymethyl group or a tetrahydro-4H-pyran-2-yl group;

Z is one out of the following formulae (1-2), (1-3), (1-4) or (1-5),

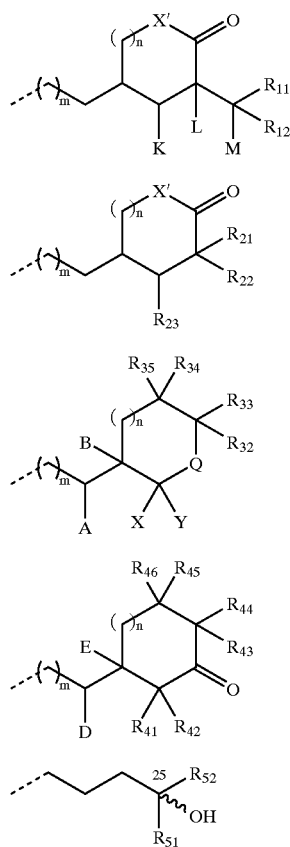

in the above formulae (1-2) to (1-5), m is an integer of 0 to 2;

n is an integer of 0 to 2;

X' is an oxygen atom or NH;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or $R_{21}$ and $R_{22}$ together may express a $C_3$–$C_6$ cyclic alkyl group in cooperation with the carbon atom to which they are bonded;

Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and E express each a hydrogen atom, D is a hydroxy group and E expresses a hydrogen atom, D and B together express a single bond and express a double bond in cooperation with the single bond already shown in the formula, or B and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

$R_{51}$ expresses —$CONR_{511}R_{512}$, —$COR_{513}$ or —$C(OH)R_{514}R_{515}$, wherein $R_{511}$ and $R_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{44}$, and $R_{45}$ and $R_{46}$ are both hydroxy groups, both alkyloxy groups, or a hydroxy group and an alkyloxy group, (b) a compound expressed by the above formula (1) in which Z is the following formula (1-6),

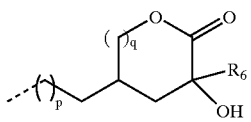
(1-6)

wherein, p and q are each 0 or the integer 1; $R_6$ is a hydrogen atom or a $C_1$–$C_4$ alkyl group, and (c) a compound of the following formula (2),

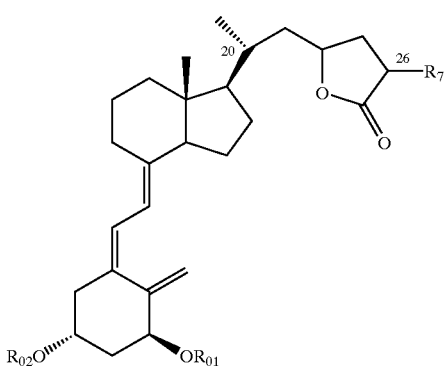
(2)

wherein, $R_{01}$ and $R_{02}$ are defined in the same manner as in the above formula (1); the configuration of the carbon atom at the 20-position is (R)-configuration; $R_7$ is a methyl group or a methylene group; when $R_7$ is a methylene group, the bond between $R_7$ and the carbon atom at the 26-position is double bond.

9. A method for treating metabolic disorder of cartilage comprising administering to a subject a therapeutically effective amount of a vitamin $D_3$ compound of the following Formula (1) or pharmaceutically permissible solvate thereof,

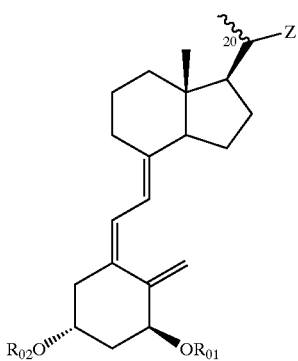
(1)

wherein, $R_{01}$ and $R_{02}$ are each independently a hydrogen atom, a trimethylsilyl group, a triethylsilyl group, a t-butyldimethylsilyl group, an acetyl group, a methoxymethyl group or a tetrahydro-4H-pyran-2-yl group;

Z is one out of the following formulae (1-2), (1-3), (1-4) or (1-5),

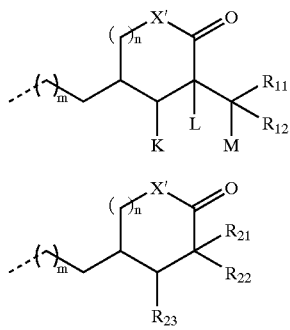
(1-1)

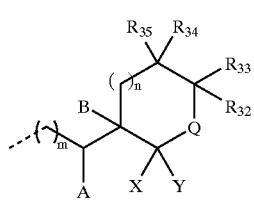
(1-2)

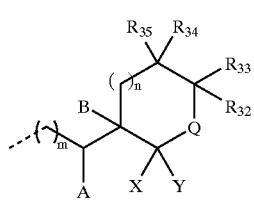
(1-3)

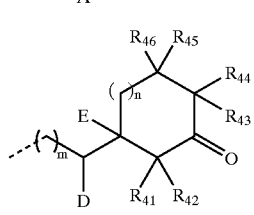
(1-4)

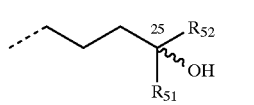
(1-5)

in the above formulae (1-2) to (1-5), m is an integer of 0 to 2;

n is an integer of 0 to 2;

X' is an oxygen atom or NH;

$R_{21}$, $R_{22}$ and $R_{23}$ are identical to or different from each other, and they are a hydrogen atom, a hydroxy group, a carboxyl group, a trifluoromethyl group, a pentafluoroethyl group, a $C_1$–$C_4$ alkyloxycarbonyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or $R_{21}$ and $R_{22}$ together may express a $C_3$–$C_6$ cyclic alkyl group in cooperation with the carbon atom to which they are bonded;

Q expresses >C(—F)—$R_{31}$ or >N—$R_{31}$, and herein $R_{31}$ is a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxy group, a $C_2$–$C_5$ acyloxy group or a $C_1$–$C_4$ alkyloxy group;

$R_{32}$, $R_{33}$, $R_{34}$ and $R_{35}$ are identical to or different from each other, and they are a hydrogen atom, a hydroxyl group, a $C_1$–$C_4$ alkyl group or a $C_2$–$C_5$ acyloxy group;

A and B are identical to or different from each other, and they express a hydrogen atom or a hydroxyl group, or together express a single bond and form a double bond in cooperation with the single bond already shown in the formula;

X and Y together express a carbonyl group in cooperation with the carbon atom to which they are bonded, one of them is a hydrogen atom and the other is a hydroxyl group, or one of them is a hydrogen atom and the other is a $C_2$–$C_5$ acyloxy group;

$R_{41}$ and $R_{42}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or they express a $C_3$–$C_6$ cyclic alkyl group in cooperation with the carbon atom to which they are bonded;

$R_{43}$ and $R_{44}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group, or both the members together express a $C_1$–$C_5$ alkylidene group, or express a $C_3$–$C_6$ cyclic alkyl group in cooperation with the carbon atom to which they are bonded;

$R_{45}$ and $R_{46}$ are identical to or different from each other, and they express a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

D and B express each a hydrogen atom, D is a hydroxy group and E expresses a hydrogen atom, D and E together express a single bond and express a double bond in cooperation with the single bond already shown in the formula, or E and $R_{41}$ together express a single bond and express a double bond in cooperation with the single bond already shown in the formula, wherein D expresses a hydrogen atom or a hydroxy group; and $R_{42}$ expresses a hydrogen atom, a hydroxyl group, a trifluoromethyl group, a pentafluoroethyl group, a $C_2$–$C_5$ acyloxy group, a $C_1$–$C_4$ alkyloxy group or a $C_1$–$C_4$ alkyl group which may be substituted with a hydroxyl group, a $C_2$–$C_5$ acyloxy group or a $C_1$–$C_4$ alkyloxy group;

$R_{51}$ expresses —$CONR_{511}R_{512}$, —$COR_{513}$ or —$C(OH)R_{514}R_{515}$, wherein $R_{511}$ and $R_{512}$ are identical to or different from each other, and they are a hydrogen atom or a $C_1$–$C_4$ alkyl group, or both the members together express a nitrogen-containing $C_3$–$C_8$ alkyl ring or a morpholino group in cooperation with the nitrogen atom to which they are bonded; and $R_{513}$, $R_{514}$ and $R_{515}$ are identical to or different from each other, and they express a $C_1$–$C_4$ alkyl group;

$R_{52}$ expresses a methyl group, an ethyl group, a trifluoromethyl group or a pentafluoroethyl group, with the proviso that the following compounds (a), (b) and (c) are excluded, (a) a compound in which the groups of one combination out of $R_{21}$ and $R_{22}$, $R_{32}$ and $R_{33}$, $R_{34}$ and $R_{35}$, $R_{41}$ and $R_{42}$, $R_{43}$ and $R_{44}$, and $R_{45}$ and $R_{46}$ are both hydroxy groups, both alkyloxy groups, or a hydroxy group and an alkyloxy group, (b) a compound expressed by the above formula (1) in which Z is the following formula (1-6),

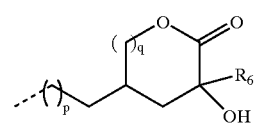

(1-6)

wherein, p and q are each 0 or the integer 1; $R_6$ is a hydrogen atom or a $C_1$–$C_4$ alkyl group, and (c) a compound of the following formula (2),

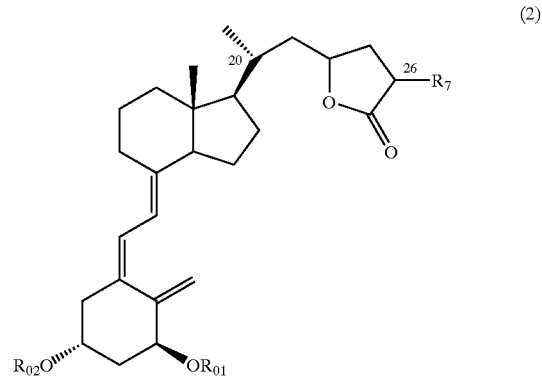

(2)

wherein, $R_{01}$ and $R_{02}$ are defined in the same manner as in the above formula (1); the configuration of the carbon atom at the 20-position is (R)-configuration; $R_7$ is a methyl group or a methylene group; when $R_7$ is a methylene group, the bond between $R_7$ and the carbon atom at the 26-position is double bond.

* * * * *